US 12,426,818 B2
Sep. 30, 2025

(12) United States Patent
Herrera et al.

(54) PACKAGING ASSEMBLY AND METHOD OF PREPARING SENSING DEVICE FOR INSERTION INTO A BODY CAVITY TO PRESERVE STERILITY

(71) Applicant: Bright Uro, Inc., Irvine, CA (US)

(72) Inventors: Derek Herrera, San Clemente, CA (US); Tracy Maahs, Foothill Ranch, CA (US); Peman Montazemi, Aliso Viejo, CA (US); Teresa Nguyen, Cypress, CA (US); Bryan Nowroozi, Laguna Beach, CA (US); Hamed Shamkhalichenar, Irvine, CA (US); Kevin Arnal, Minneapolis, MN (US); Jordan Burich, Minneapolis, MN (US); Morgan Wendl, Minneapolis, MN (US)

(73) Assignee: Bright Uro, Inc., Irvine, CA (US)

( * ) Notice: Subject to any disclaimer, the term of this patent is extended or adjusted under 35 U.S.C. 154(b) by 0 days.

(21) Appl. No.: 18/967,503

(22) Filed: Dec. 3, 2024

(65) Prior Publication Data
US 2025/0090065 A1    Mar. 20, 2025

Related U.S. Application Data

(63) Continuation-in-part of application No. 18/739,024, filed on Jun. 10, 2024, now Pat. No. 12,186,084, (Continued)

(51) Int. Cl.
A61B 5/20 (2006.01)
A61B 5/00 (2006.01)
(Continued)

(52) U.S. Cl.
CPC .............. *A61B 5/205* (2013.01); *A61B 5/07* (2013.01); *A61B 5/168* (2013.01); *A61B 5/6852* (2013.01);
(Continued)

(58) Field of Classification Search
CPC .......... A61B 5/205; A61B 5/07; A61B 5/168; A61B 5/6852; A61B 5/7275;
(Continued)

(56) References Cited

U.S. PATENT DOCUMENTS

| 5,964,732 A | 10/1999 | Willard |
| 6,712,772 B2 | 3/2004 | Cohen et al. |

(Continued)

FOREIGN PATENT DOCUMENTS

| CN | 110215310 B | 7/2021 |
| GB | 2413769 | 9/2005 |

(Continued)

OTHER PUBLICATIONS

Systems and Methods for Urological Sensing, U.S. Appl. No. 18/476,963, U.S. Pat. No. 12,036,023.

(Continued)

*Primary Examiner* — Jennifer Robertson
*Assistant Examiner* — Jonathan Drew Moroneso
(74) *Attorney, Agent, or Firm* — Knobbe, Martens, Olson & Bear, LLP

(57) ABSTRACT

Various packaging assemblies and methods for preserving sterility of a sensing device prior to insertion into a body cavity of a subject are described herein. Some implementations of a packaging assembly include: a bag comprising an interior, the bag at least partially comprising a transparent material; and a tray configured to be positioned within the interior of the bag and configured to retain and protect the sensing device, wherein the tray comprises an opening configured to allow a button of the sensing device to be engaged via a portion of the bag, thereby allowing the sensing device to be transitioned from a non-operational state to an operational state when retained by the tray and positioned within the interior of the bag. Such operational (Continued)

state can be one in which the sensing device can be wirelessly paired with a separate electronic device, for example, to enable wireless data transmission.

25 Claims, 86 Drawing Sheets

Related U.S. Application Data which is a continuation of application No. 18/476,963, filed on Sep. 28, 2023, now Pat. No. 12,036,023, which is a continuation of application No. PCT/US2023/024881, filed on Jun. 8, 2023.

(60) Provisional application No. 63/606,031, filed on Dec. 4, 2023, provisional application No. 63/350,305, filed on Jun. 8, 2022, provisional application No. 63/447,765, filed on Feb. 23, 2023.

(51) Int. Cl.
| | |
|---|---|
| A61B 5/07 | (2006.01) |
| A61B 5/154 | (2006.01) |
| A61B 5/16 | (2006.01) |
| A61L 29/02 | (2006.01) |
| A61M 25/00 | (2006.01) |
| B01L 3/00 | (2006.01) |
| A61B 5/15 | (2006.01) |

(52) U.S. Cl.
CPC ............ *A61B 5/7275* (2013.01); *A61L 29/02* (2013.01); *A61B 5/150351* (2013.01); *A61B 5/154* (2013.01); *A61B 5/16* (2013.01); *A61B 5/20* (2013.01); *A61B 5/202* (2013.01); *A61B 5/68* (2013.01); *A61B 5/6846* (2013.01); *A61B 5/6847* (2013.01); *A61B 5/72* (2013.01); *A61B 5/7271* (2013.01); *A61B 2560/0214* (2013.01); *A61B 2562/02* (2013.01); *A61B 2562/0247* (2013.01); *A61B 2562/164* (2013.01); *A61B 2562/166* (2013.01); *A61M 25/002* (2013.01); *B01L 3/50825* (2013.01); *B01L 2200/06* (2013.01); *B01L 2300/04* (2013.01); *B01L 2300/044* (2013.01); *B01L 2300/046* (2013.01); *B01L 2300/14* (2013.01)

(58) Field of Classification Search
CPC ..... A61B 5/150351; A61B 5/154; A61B 5/16; A61B 5/20; A61B 5/202; A61B 5/68; A61B 5/6846; A61B 5/6847; A61B 5/72; A61B 5/7271; A61B 2560/0214; A61B 2562/02; A61B 2562/0247; A61B 2562/164; A61B 2562/166; A61L 29/02; A61M 25/002; B01L 3/50825; B01L 2200/06; B01L 2300/04; B01L 2300/044; B01L 2300/046; B01L 2300/14
See application file for complete search history.

(56) References Cited

U.S. PATENT DOCUMENTS

| | | | |
|---|---|---|---|
| 7,074,178 | B2 | 7/2006 | Connors et al. |
| 10,143,391 | B2 | 12/2018 | Damaser et al. |
| 10,478,113 | B2 | 11/2019 | Damaser et al. |
| 11,207,013 | B2 | 12/2021 | Damaser et al. |
| 11,382,155 | B2 | 7/2022 | Daniels |
| 11,419,533 | B2 | 8/2022 | Damaser et al. |
| 12,036,023 | B2 | 7/2024 | Herrera et al. |
| 12,161,469 | B2 | 12/2024 | Herrera et al. |
| 12,186,084 | B2 | 1/2025 | Herrera et al. |
| 2003/0100839 | A1 | 5/2003 | Cohen et al. |
| 2003/0229263 | A1 | 12/2003 | Conners et al. |
| 2005/0177067 | A1 | 8/2005 | Tracey et al. |
| 2006/0095079 | A1 | 5/2006 | Gerber |
| 2006/0247723 | A1 | 11/2006 | Gerber et al. |
| 2009/0149833 | A1 | 6/2009 | Cima et al. |
| 2009/0152148 | A1* | 6/2009 | Scheurer ............ A61B 50/3001 |
| | | | 206/365 |
| 2010/0331770 | A1 | 12/2010 | Lee et al. |
| 2011/0152839 | A1 | 6/2011 | Cima et al. |
| 2012/0089121 | A1 | 4/2012 | Lee et al. |
| 2013/0205528 | A1* | 8/2013 | Jungnickel ........... B65D 75/322 |
| | | | 15/167.1 |
| 2014/0228943 | A1 | 8/2014 | Stigall et al. |
| 2014/0303551 | A1 | 10/2014 | Germain et al. |
| 2014/0364766 | A1* | 12/2014 | Devgon ........... A61B 5/150396 |
| | | | 600/581 |
| 2015/0164401 | A1 | 6/2015 | Toth et al. |
| 2015/0223745 | A1 | 8/2015 | Wille et al. |
| 2015/0305671 | A1 | 10/2015 | Yoon et al. |
| 2016/0228676 | A1* | 8/2016 | Glithero ................. A61B 42/00 |
| 2016/0374576 | A1 | 12/2016 | Ziaie et al. |
| 2018/0199816 | A1 | 7/2018 | Kalt et al. |
| 2019/0380628 | A1 | 12/2019 | Routh et al. |
| 2021/0196203 | A1 | 7/2021 | Damaser et al. |
| 2022/0032295 | A1 | 2/2022 | Kirkpatrick et al. |
| 2023/0041528 | A1 | 2/2023 | Damaser et al. |
| 2023/0121584 | A1 | 4/2023 | Damaser et al. |
| 2023/0157603 | A1 | 5/2023 | Shin et al. |
| 2023/0329851 | A1* | 10/2023 | Lam ...................... B65D 25/10 |
| 2024/0156383 | A1 | 5/2024 | Sawada |
| 2024/0324927 | A1 | 10/2024 | Herrera et al. |

FOREIGN PATENT DOCUMENTS

| | | |
|---|---|---|
| JP | H07120336 A | 5/1995 |
| JP | 2002369810 A | 12/2002 |
| KR | 20120016442 A | 2/2012 |
| WO | WO 1999/64099 A1 | 12/1999 |
| WO | WO 2005/115245 A1 | 12/2005 |
| WO | WO 2016/176590 A1 | 11/2016 |
| WO | WO 2016/191479 A1 | 12/2016 |
| WO | WO 2017/136212 A1 | 8/2017 |
| WO | WO 2023/014785 A1 | 2/2023 |
| WO | WO 2023239883 A1 | 12/2023 |

OTHER PUBLICATIONS

Systems and Methods for Urological Sensing, U.S. Appl. No. 18/739,024, 2024/0324927 A1.
Systems and Methods for Urological Sensing, U.S. Appl. No. 18/738,946, U.S. Pat. No. 12,161,469.
Systems and Methods for Urological Sensing, U.S. Appl. No. 18/926,956.
Systems and Methods for Urological Sensing, U.S. Appl. No. 18/959,442.
Clark et al., "Effect of transducer diaphragm movement on pressure probe measurements". Chemical Engineering Science, 52. 1301-1306, Apr. 1997.
Coleman et al., "A Gel filled intravaginal transducer for extended measurements of intra-abdominal pressure," 2010 Annual International Conference of the IEEE Engineering in Medicine and Biology, Buenos Aires, Argentina, 2010, pp. 1852-1855, doi: 10.1109/IEMBS,2010.5625987. (Year: 2010).
Kim et al., "A Generic packaging technique using fluidic isolation or low-drift implantable pressure sensors" 2015 Transducers, 2015 18$^{th}$ International Conference on Solid State Sensors, Actuators and Microsystems, IEEE, 21, pp. 476-479.
PCT International Search Report and Written Opinion for International Application No. PCT/US2023/024881, mailed Jan. 18, 2024 in 13 pages.

* cited by examiner

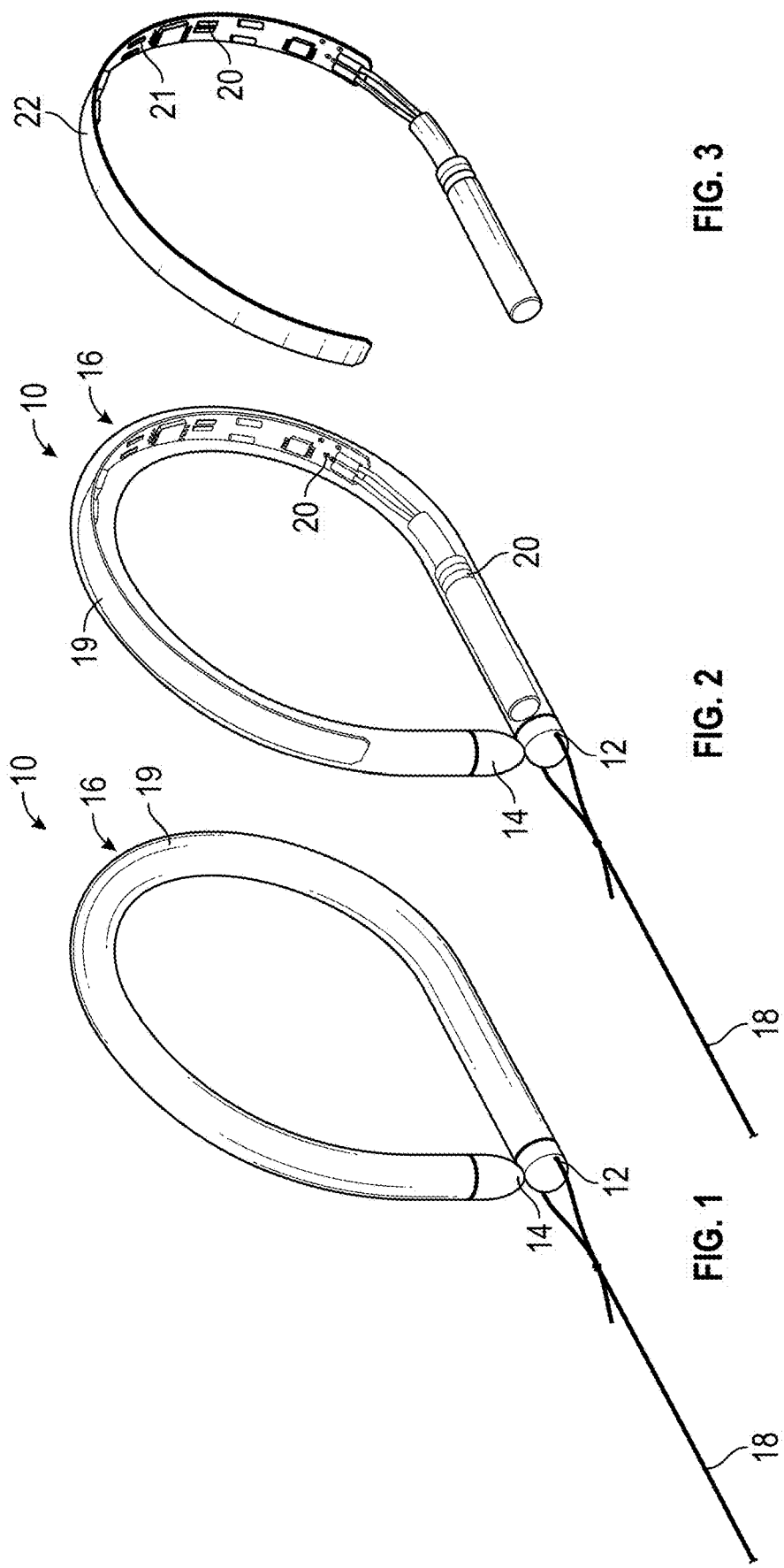

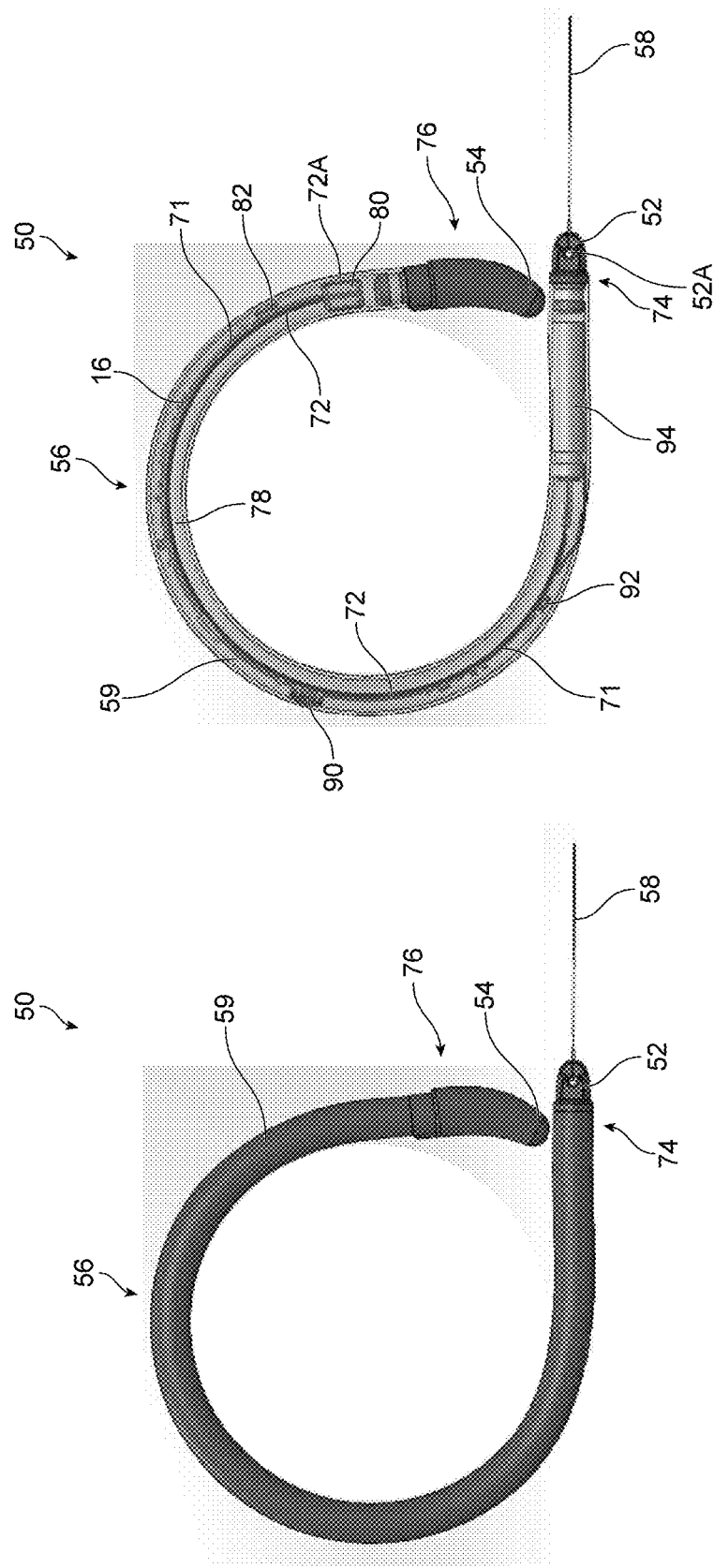

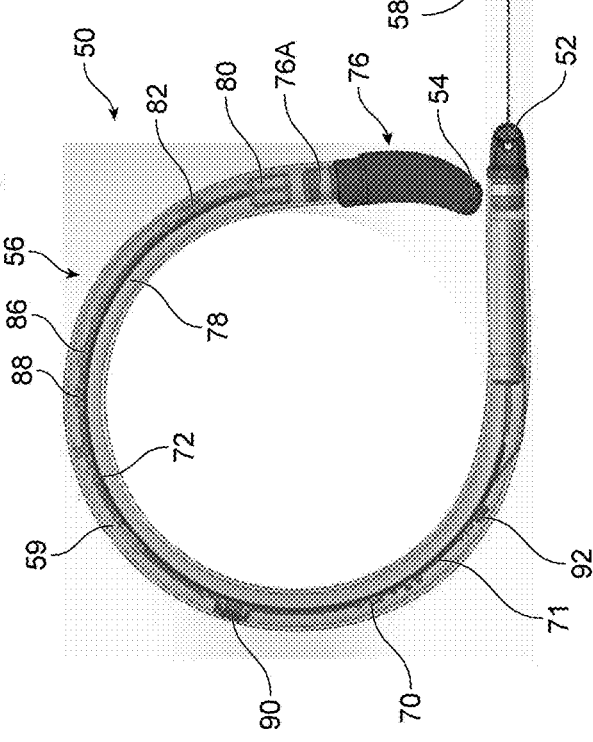
FIG. 21
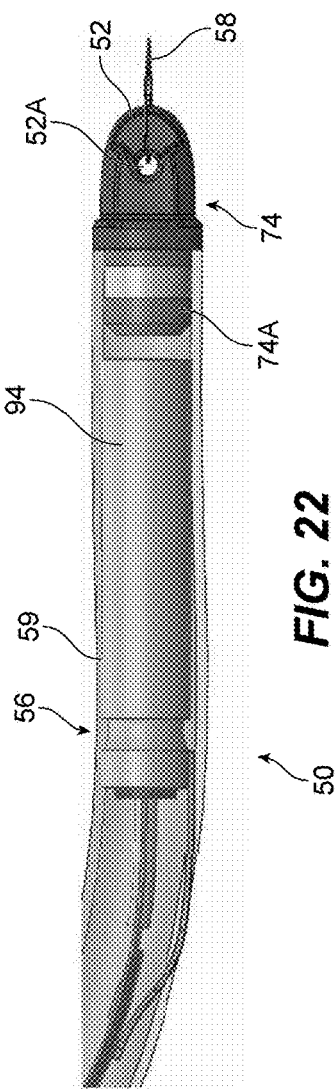
FIG. 22
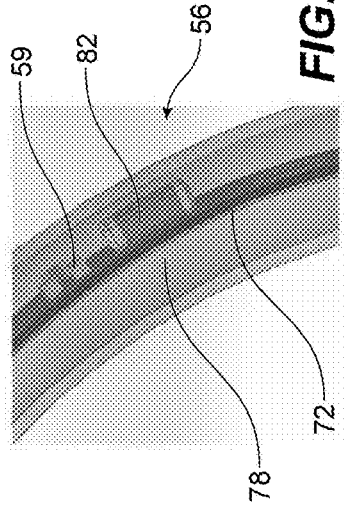
FIG. 18
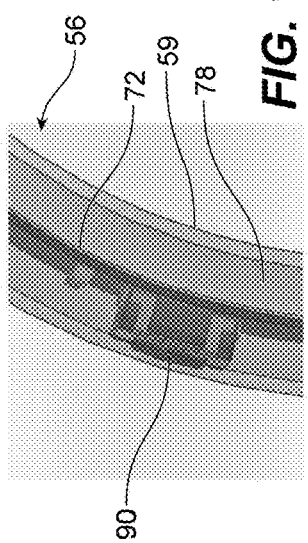
FIG. 19
FIG. 20

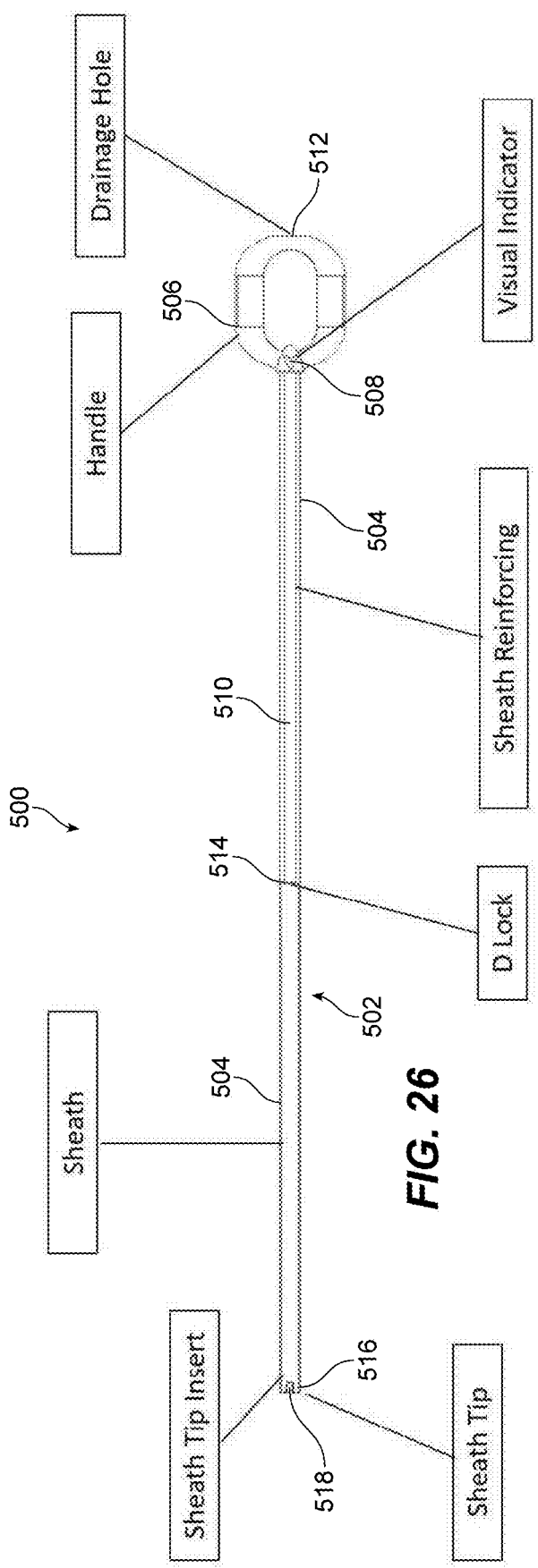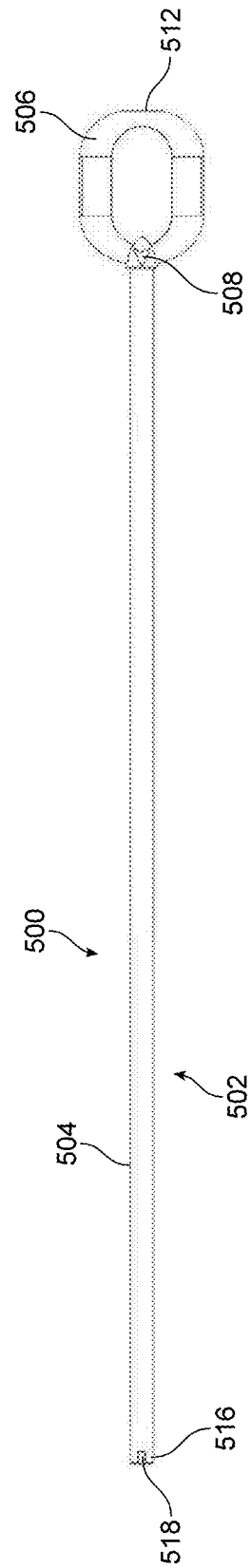

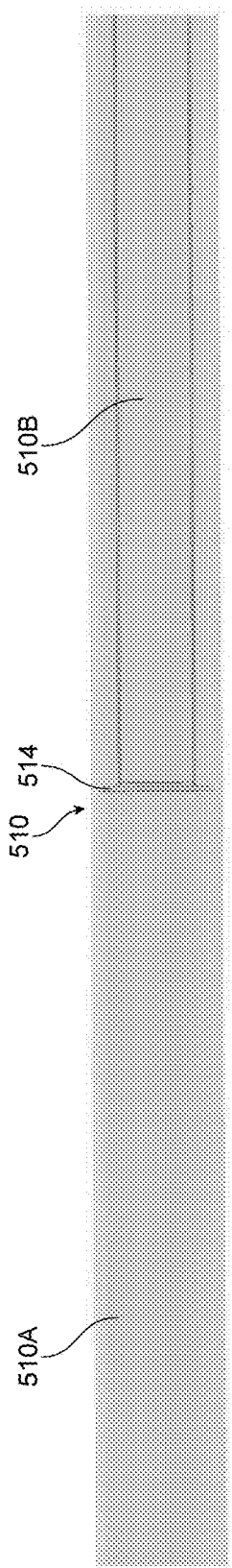
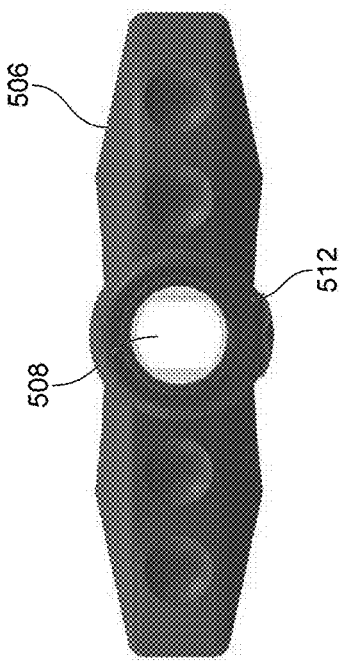
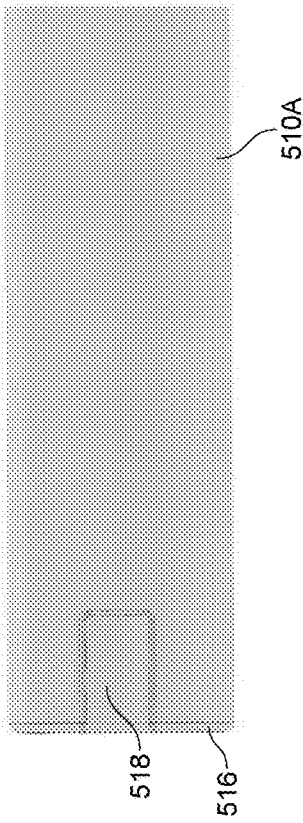
FIG. 29
FIG. 30
FIG. 28

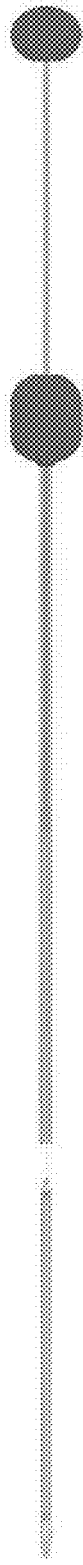
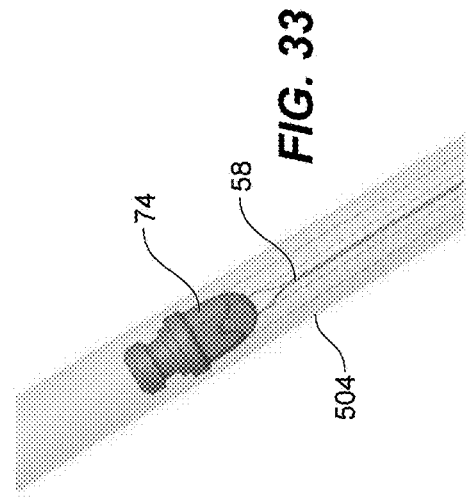
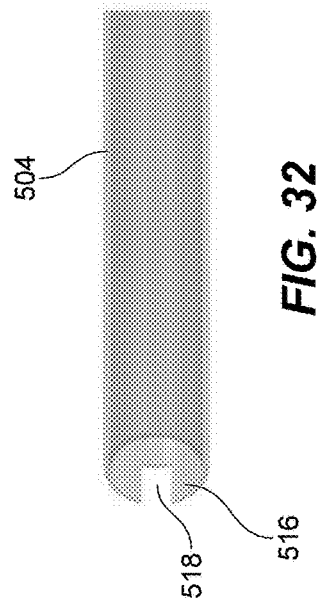
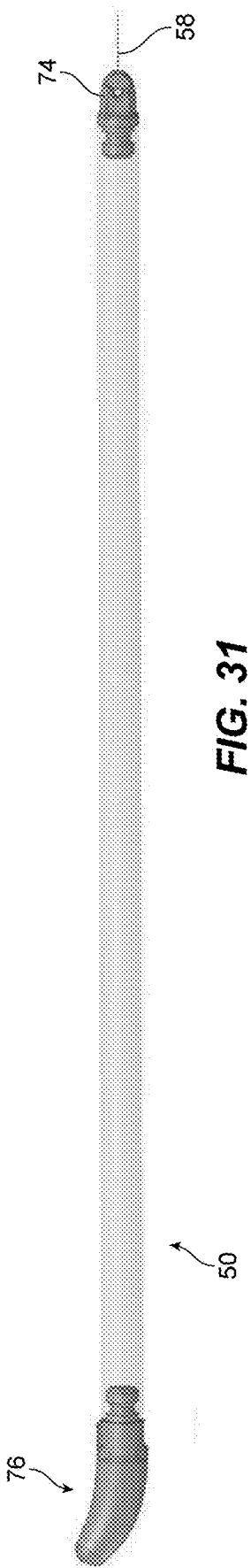

Test Protocol

- Three BU sensors was fabricated using the following:
  - Flex PCB Rev 2, Firmware V3.0.3
  - Silicone end caps and septa
  - RTV adhesive
  - Curved Spine not welded to the battery and no spacer.
  - Double lumen tubes and Silicone Oil
- During injection of silicone oil, the pressure was adjusted to the following
  - Sensor 1: 1142 cmH2O
  - Sensor 2: 918 cmH2O
  - Sensor 3: 836 cmH2O

- Tested in Human Bladder model
  - Step 0 to 320 and 320 to 0 cmH2O (3 s width)
  - Step 320 to 0 cmH2O 5 cmH2O intervals
  - Sweep 0 – 30 Hz
  - Square 0.1 Hz and amplitude 200 cmH2O

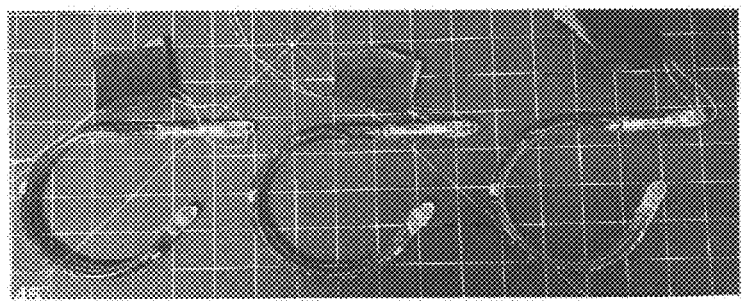

FIG. 35

Test Protocol (Air Injection)

- After Testing the sensors as described in the previous section, air was injected to the sensor until the pressure measured by the sensor reaches the following values:
  - Sensor 1: 1237 cmH2O
  - Sensor 2: 1223 cmH2O
  - Sensor 3: 1203 cmH2O
- Considering the initial pressure of the sensors, Sensor 1 has the least amount of air bubbles and Sensor 3 has the most.

- Tested in Human Bladder model (Results in Previous section)
  - Step 0 to 320 and 320 to 0 cmH2O (3 s width)
  - Step 320 to 0 cmH2O 5 cmH2O intervals
  - Sweep 0 – 30 Hz
  - Square 0.1 Hz and amplitude 200 cmH2O
  - UDS simulation

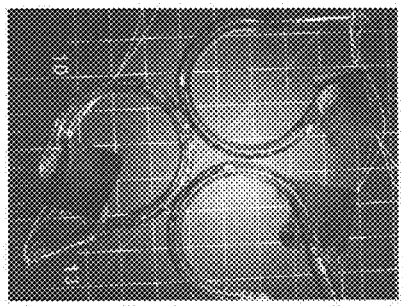

FIG. 36

Test Protocol (Pressure Drift After Fabrication)

- After Testing the sensors as described in the previous section, silicone oil was injected to Sensor air was injected to the Sensor 3 until the pressure measured by the sensor reaches the following values:
  - Sensor 1: 1381 cmH2O
  - Sensor 3: 1332 cmH2O
- The sensors was left over night (~16 hrs) at room temperature while recording the pressure.

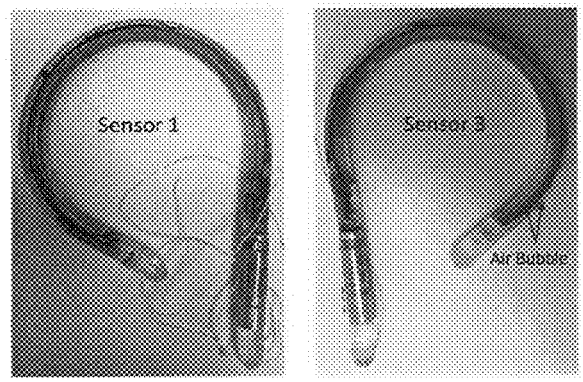

FIG. 37

Test Protocol (High Pressure)

- Three BU sensors was fabricated using the following:
  - Flex PCB Rev 2, Firmware V3.0.2
  - Silicone end caps and septa
  - RTV adhesive
  - Curved Spine not welded to the battery and no spacer.
  - Double lumen tubes and Silicone Oil
- During injection of silicone oil, the pressure was adjusted to the following
  - Sensor 4: 1232 cmH2O
  - Sensor 5: 1191 cmH2O
  - Sensor 6: 1129 cmH2O

- Tested in Human Bladder model
  - Step 0 to 320 and 320 to 0 cmH2O (3 s width) (Note: Sensor 5 stopped working after this test)
  - Step 320 to 0 cmH2O 5 cmH2O intervals
  - Sweep 0.1 – 3 Hz
  - Square 0.1 Hz and amplitude 200 cmH2O
  - Simulated UDS

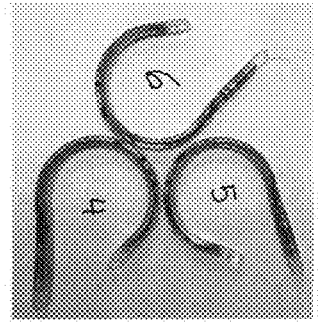

FIG. 38

Test Protocol (Temperature Change)

- After the previous test (1 day) sensor 4 and 6 these sensor was used for temperature effect testing.
- The pressure was measured on the bench as:
  - Sensor 4: 1263 cmH2O
  - Sensor 6: 1109 cmH2O
- Needs to be identified why the pressure of the sensors was increased after the previous testing.

- Tested in Human Bladder model
  - @ Room Temperature
    - Step 0 to 320 and 320 to 0 cmH2O (3 s width) (Note: Sensor 5 stopped working after this test)
    - Step 320 to 0 cmH2O 5 cmH2O intervals
    - Sweep 0.1 – 15 Hz
    - Square 0.1 Hz and amplitude 200 cmH2O
  - @ 37 C
    - Step 0 to 320 and 320 to 0 cmH2O (3 s width) (Note: Sensor 5 stopped working after this test)
    - Step 320 to 0 cmH2O 5 cmH2O intervals
    - Sweep 0.1 – 15 Hz
    - Square 0.1 Hz and amplitude 200 cmH2O
- Temperature ramp from room temperature to 37 C. The HBM valve was left open
  - Constant open HBM pressure (Only Sensor 6)

*FIG. 39*

Test Protocol (Temperature Change, Repeat)

- a BU sensors was fabricated using the following:
  - Flex PCB Rev 2, Firmware V3.0.6
  - Silicone end caps and septa
  - RTV adhesive
  - Curved Spine not welded to the battery and no spacer.
  - Single lumen tubes and Silicone Oil
- During injection of silicone oil, the pressure was adjusted to the following
  - Sensor 8: 1259 cmH2O

- Temperature ramp from room temperature to 37 C. The HBM valve was left open. Next the heater was turned off until HBM cools down to 29 C.

*FIG. 40*

Test Protocol (Temperature Change, Repeat, Cycles)

- a BU sensors was fabricated using the following:
  - Flex PCB Rev 3, Firmware V3.0.7
  - Silicone end caps and septa
  - RTV adhesive
  - Curved Spine not welded to the battery and no spacer.
  - Single lumen NuSil tubes and Silicone Oil Med-460
- During injection of silicone oil, the pressure was adjusted to the following
  - Sensor 10: 1264 cmH2O

- Temperature ramp from room temperature (23 C) to 37 ± 1 C. Stayed at 37 ± 1 C for 20 minutes. Next the heater was turned off until HBM cools down to 27 ± 1 C. Again, the Temperature was turned on to reach 37 ± 1 C, stayed at 37 ± 1 C for 20 minutes, and turned off. The HBM valve was left open through out the experiment.

*FIG. 41*

Test Protocol (Temperature Cycle Hotplate)

- A BU sensors was fabricated using the following:
  - Flex PCB Rev 3, Firmware V3.0.7
  - Silicone end caps and septa
  - RTV adhesive
  - Curved Spine not welded to the battery and no spacer.
  - Single lumen NuSil tubes and Silicone Oil Med-460
- During injection of silicone oil, the pressure was adjusted to the following
  - Sensor 12: 1255 cmH2O

- The sensor was placed inside a beaker filled with water on a hotplate. The temperature raised to ~40 C and brout back to room temperature 3 times.

- Bubbles formed after increasing the temperature.

*FIG. 42*

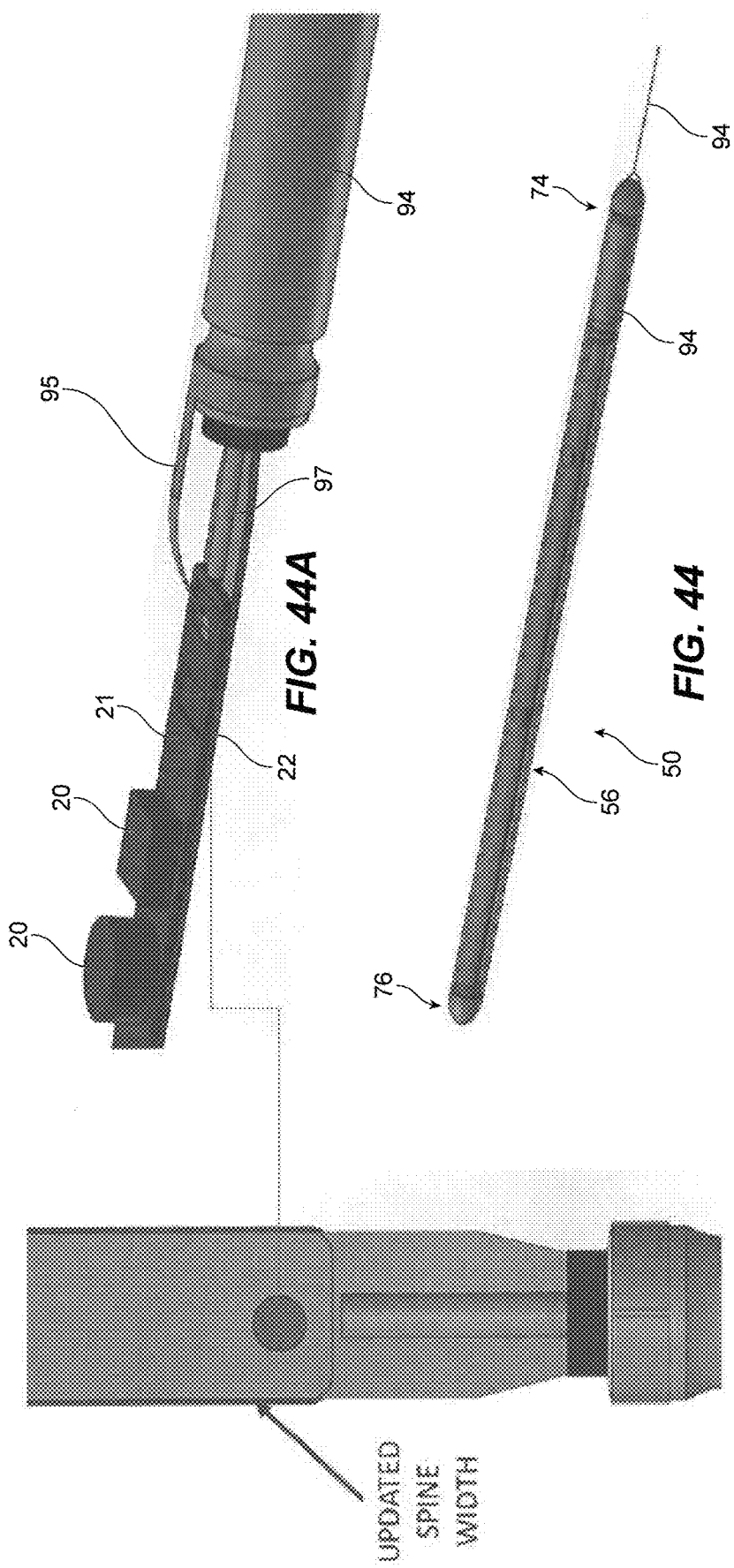

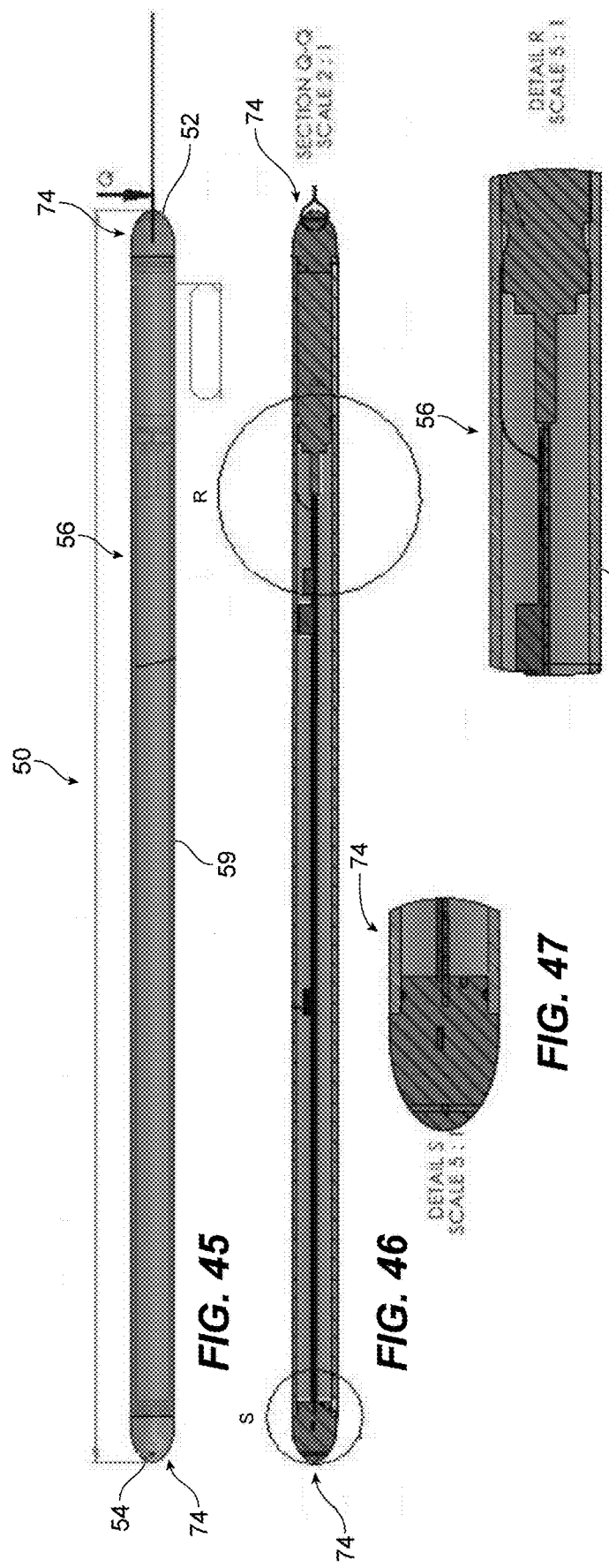

Silicone Extrusions
- Single Lumen
- Dual Lumen
- Pre-cut to length

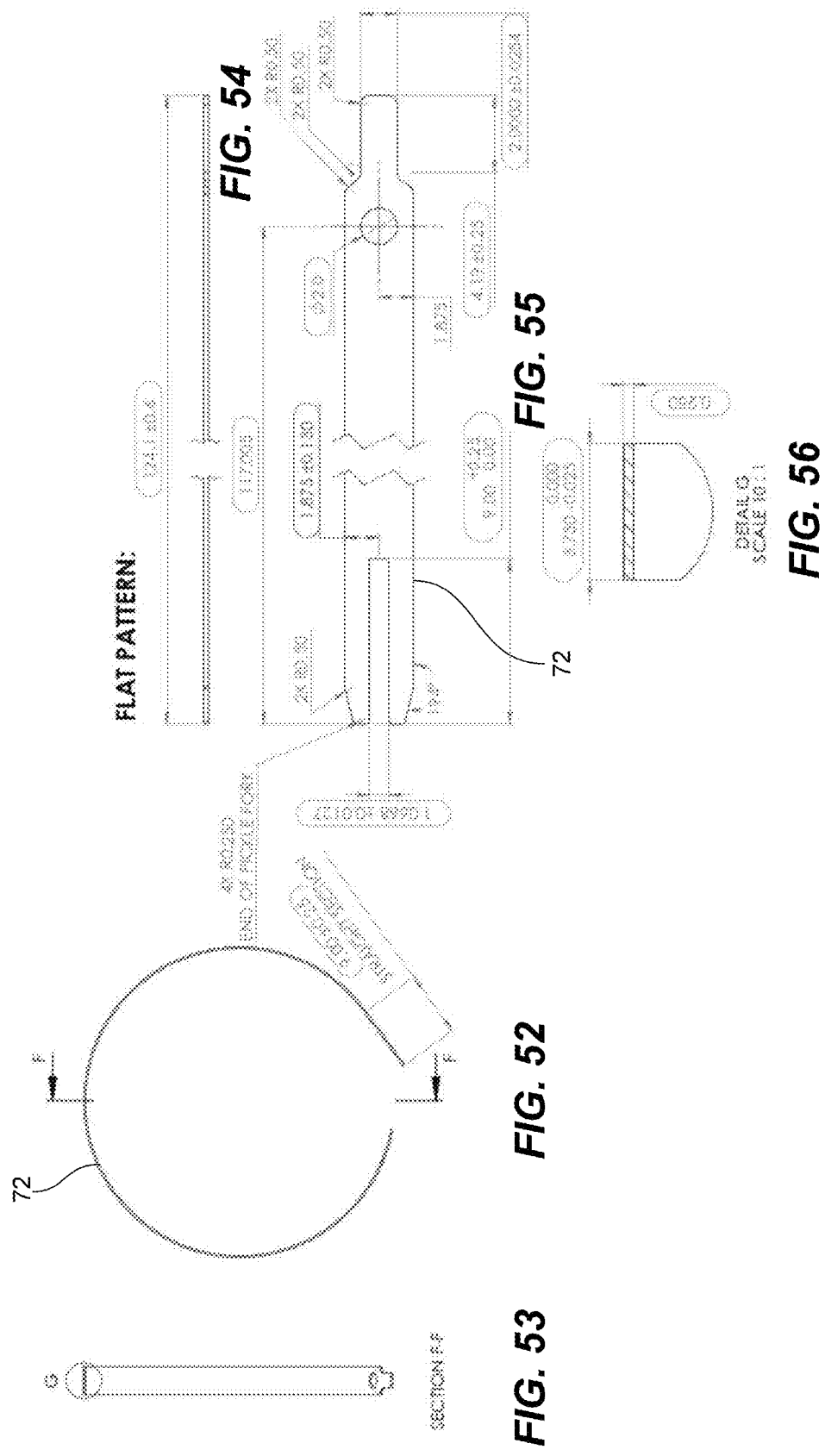

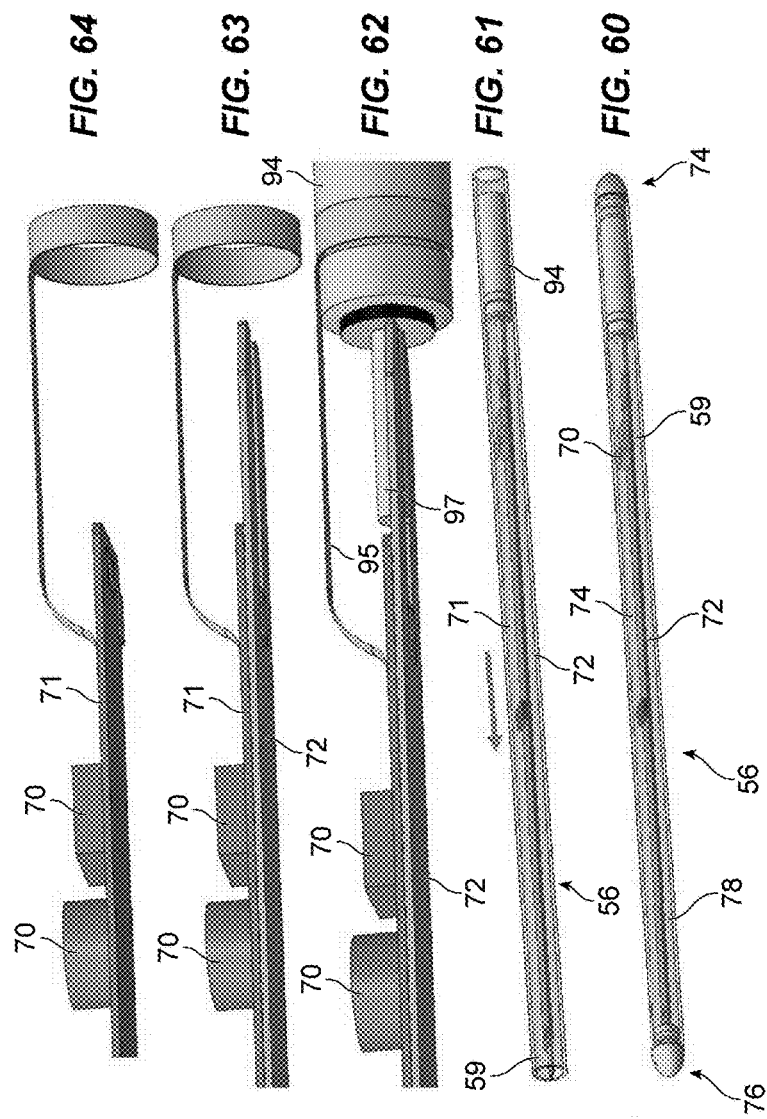

|  | Sample 1 | Sample 2 | Sample 3 |
|---|---|---|---|
| Needle to inject mineral oil | 25 Ga | 22 Ga | 22 Ga |
| Needle to let air escape | 30 Ga | 25 Ga | 25 Ga |
| Pressure Change? | No pressure change | Pressure change | N/A (did not sit overnight) |
| Leak? | No leak | Leak | Leak |
| Pictures | 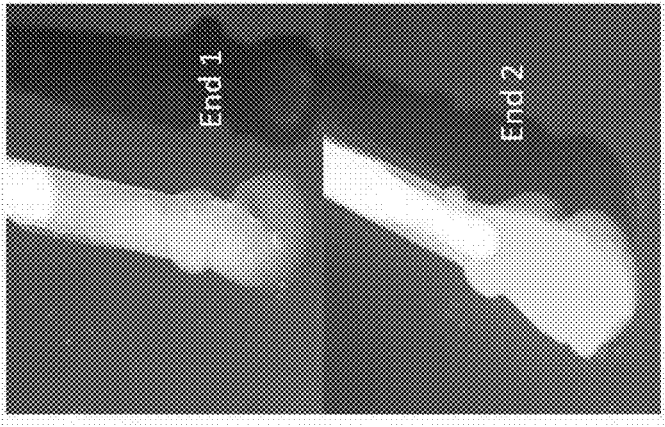 End 1 / End 2 | 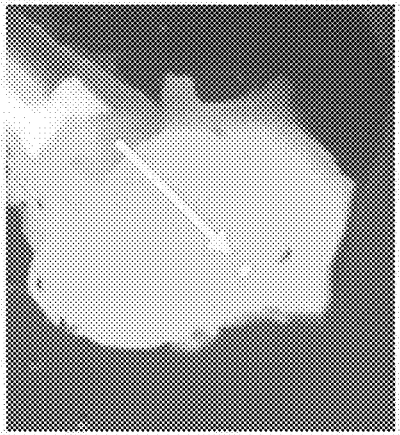 Leak one end only | 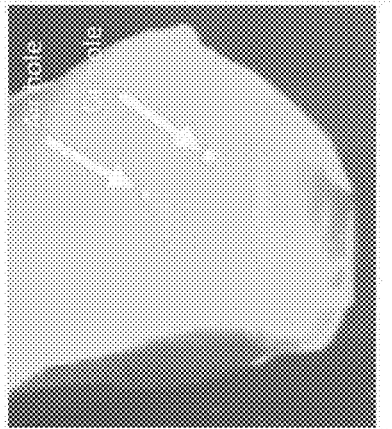 Leak one end only |
FIG. 69

Catheter Flexibility

Tipping

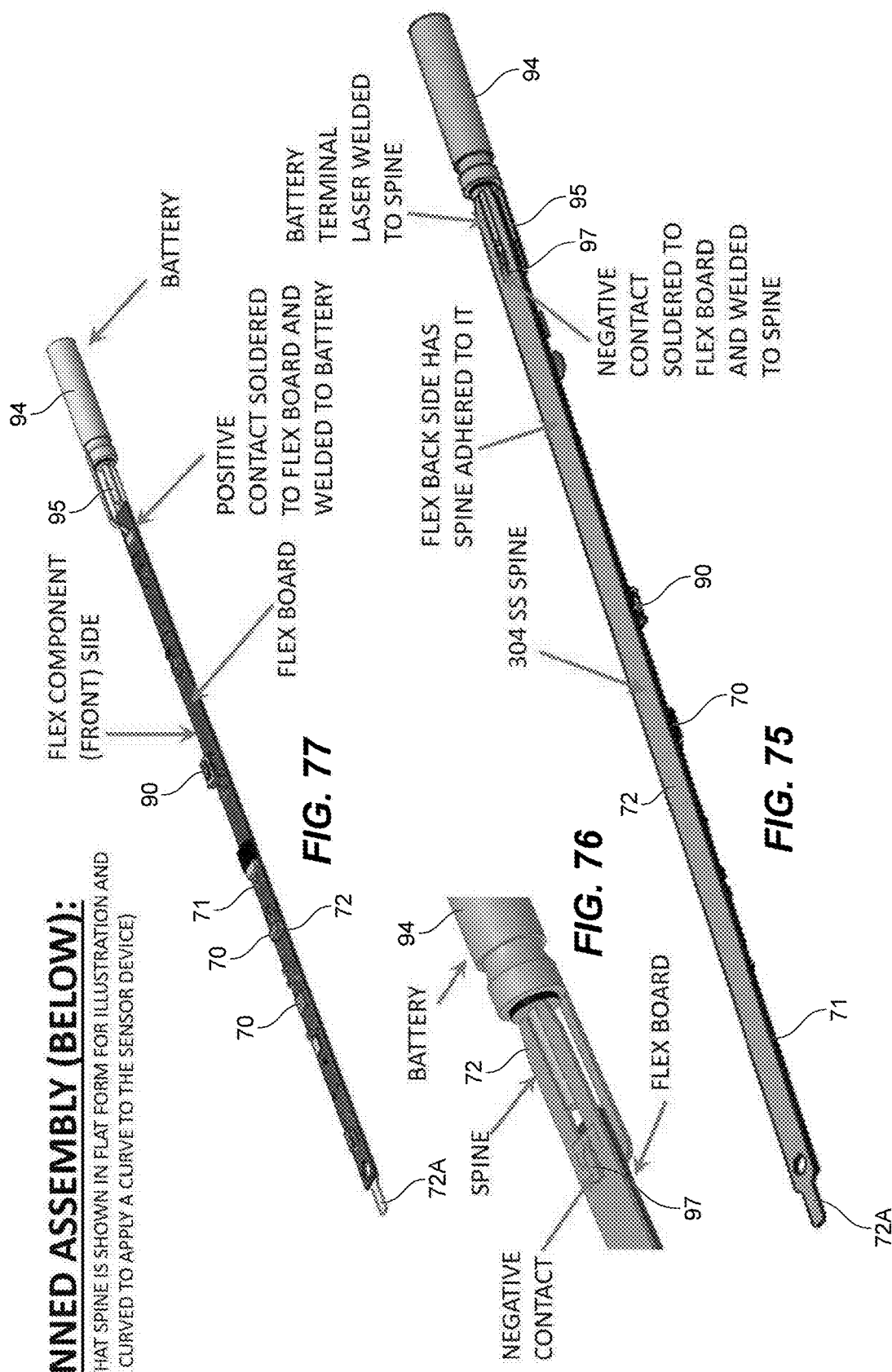

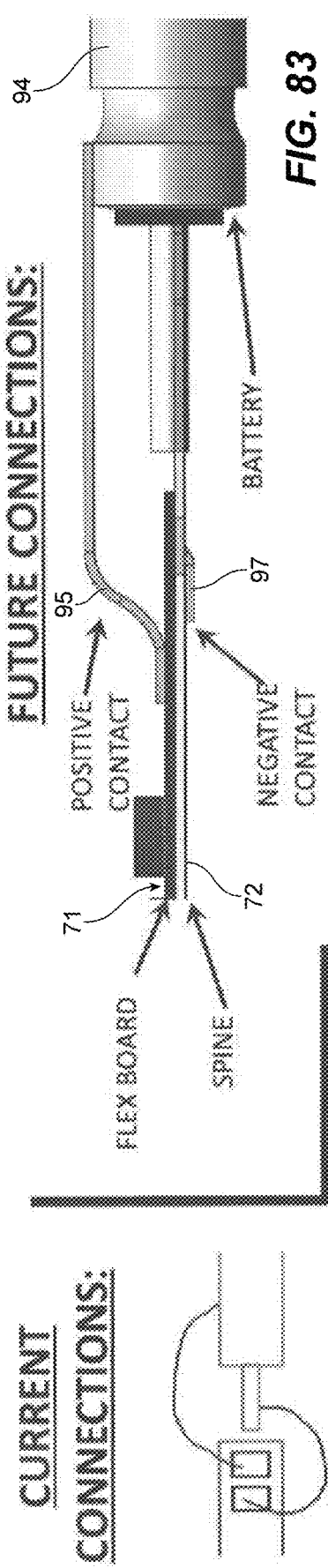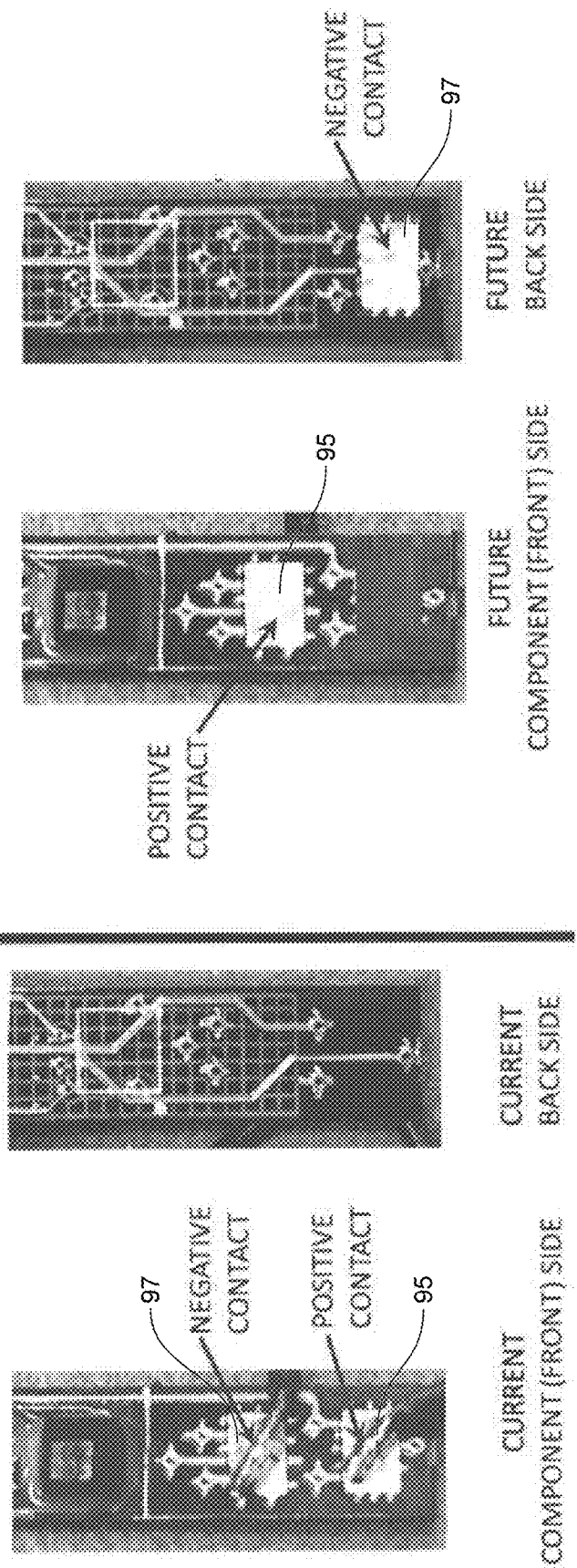
FIG. 83
FIG. 82
FIG. 81
FIG. 80
FIG. 79

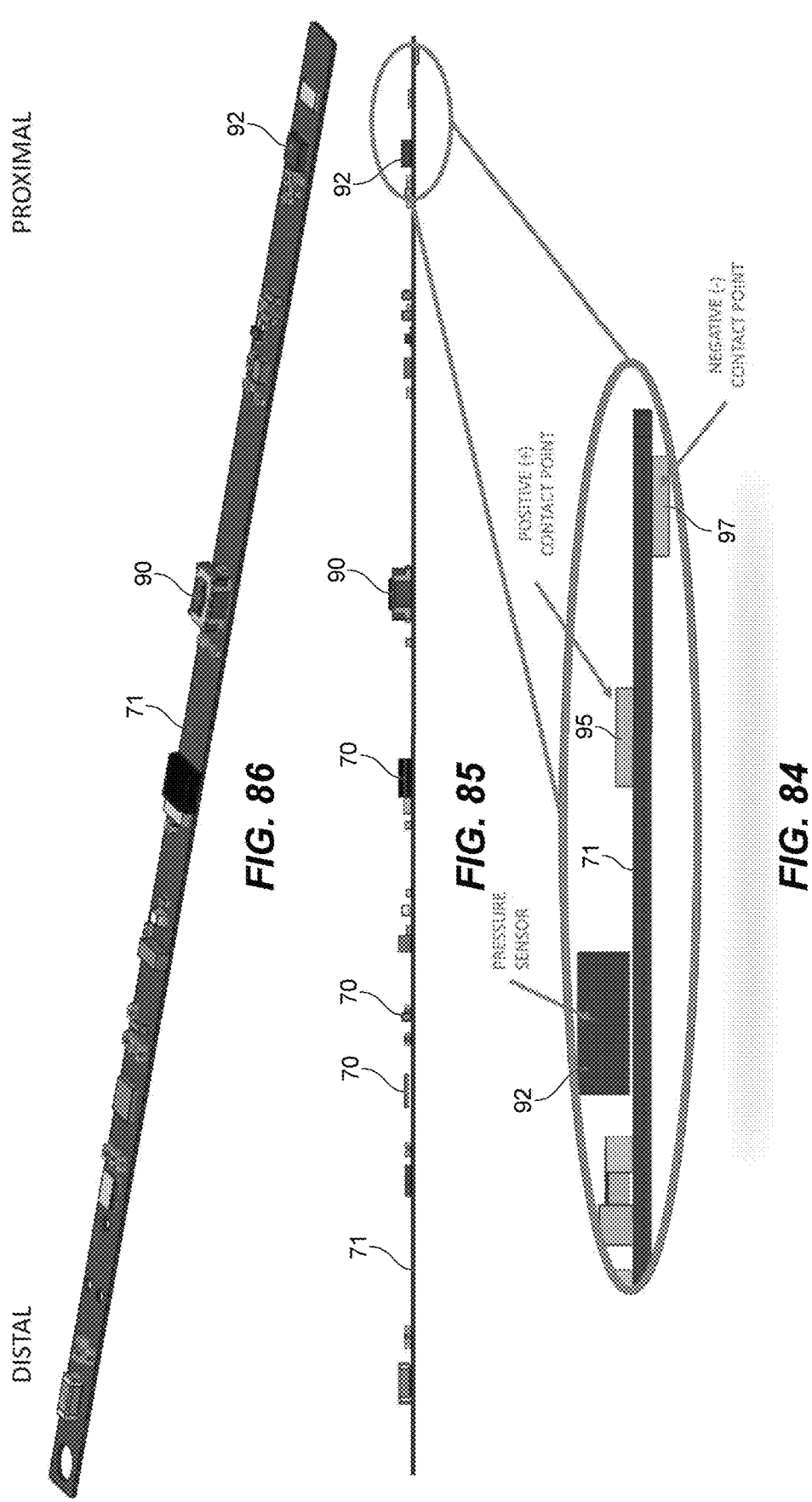

FIG. 87 Soldering Positive(+) Contact

WELDING BATTERY AND SPINE

PLACE DISTAL ENDCAP PARTIALLY ONTO THE SILICONE EXTRUSION

APPLY SILICONE ADHESIVE COMPLETELY AROUND THE ENDCAP VALLEY

PUSH ON DISTAL ENDCAP UNTIL IT HITS A HARD STOP AND LEAVE TO DRY FOR 24H OR PLACE IN OVEN AT 150°F FOR 2 HOURS

Septas
- Fill in mineral oil most of the way with large needle (curved configuration)
- Glue in bottom piece of endcap
- Let dry (fully sealed)
- Glue in septa
- Glue in top piece of endcap
- Fill the rest of the way with smaller needle
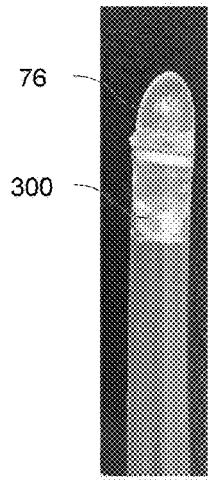
76
300
FIG. 98
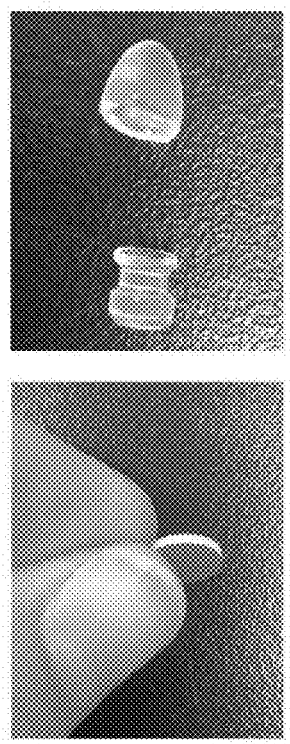
FIG. 99
Fluid Testing
- Mineral Oil:
  - Citation 200
    - Viscosity: 207.4
- Silicone Oil
  - MED-460
    - Viscosity: 350
 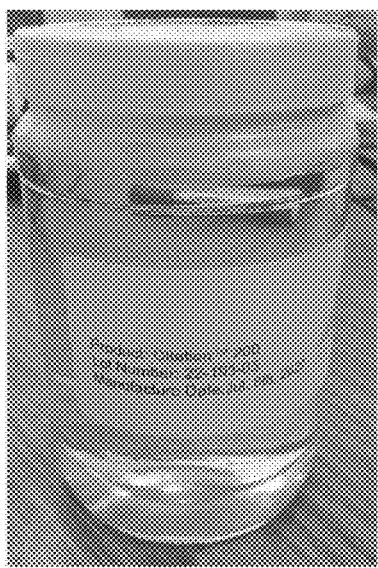
FIG. 100     FIG. 101

Sensor inside the Insertion Tools

Procedure Forces

- Force to pull Sensor into the Insertion Tool (Using KY Jelly Lubricant)
  - Average Force: 1.18 lbf
- Force to push Sensor out of the Insertion Tool
  - Average Force: 0.83 lbf
- Force to Pull Sensor out of the bladder model
  - Average Force: 0.36 lbf

Spine Flexion Analysis

Sample #2 (0.010" Thick) @ 5min in Insertion Tool

Sample #1 (0.010" Thick) @ 20 min in Insertion Tool

No leakage found when using Septa w/ 18G Needle

Fill Analysis

| Gauge Needle | Fill Ratio (mL/sec) | PSI |
|---|---|---|
| 18 | 1.750 | 30 |
| 20 | 0.333 | 30 |
| 22 | 0.120 | 30 |
| 23 | 0.058 | 30 |
| 25 | 0.017 | 30 |
| 25 | 0.037 | 50 |

BRAIDED INSERTION TOOL

20 PPI Braid Wire

35 PPI Braid Wire

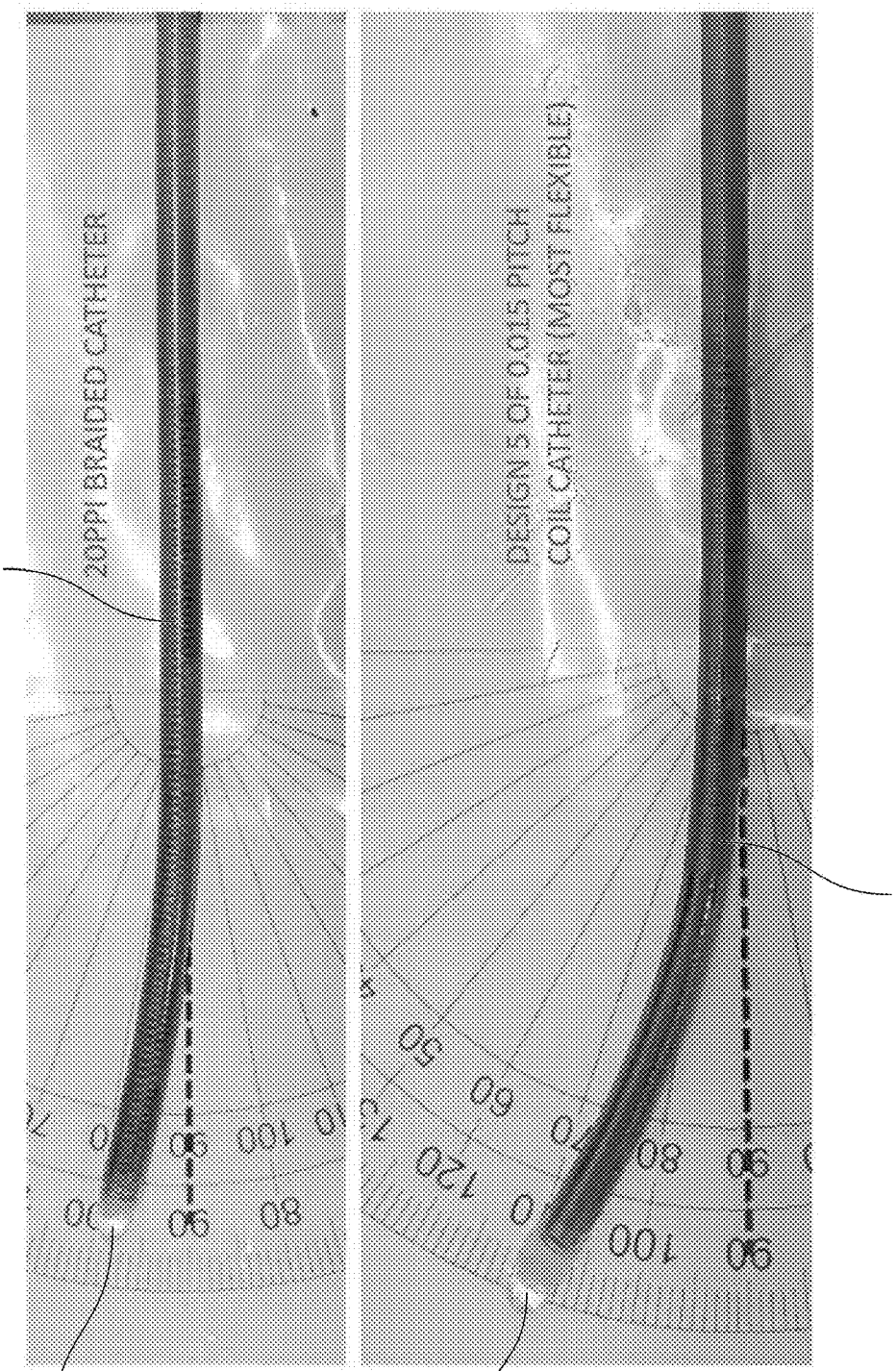

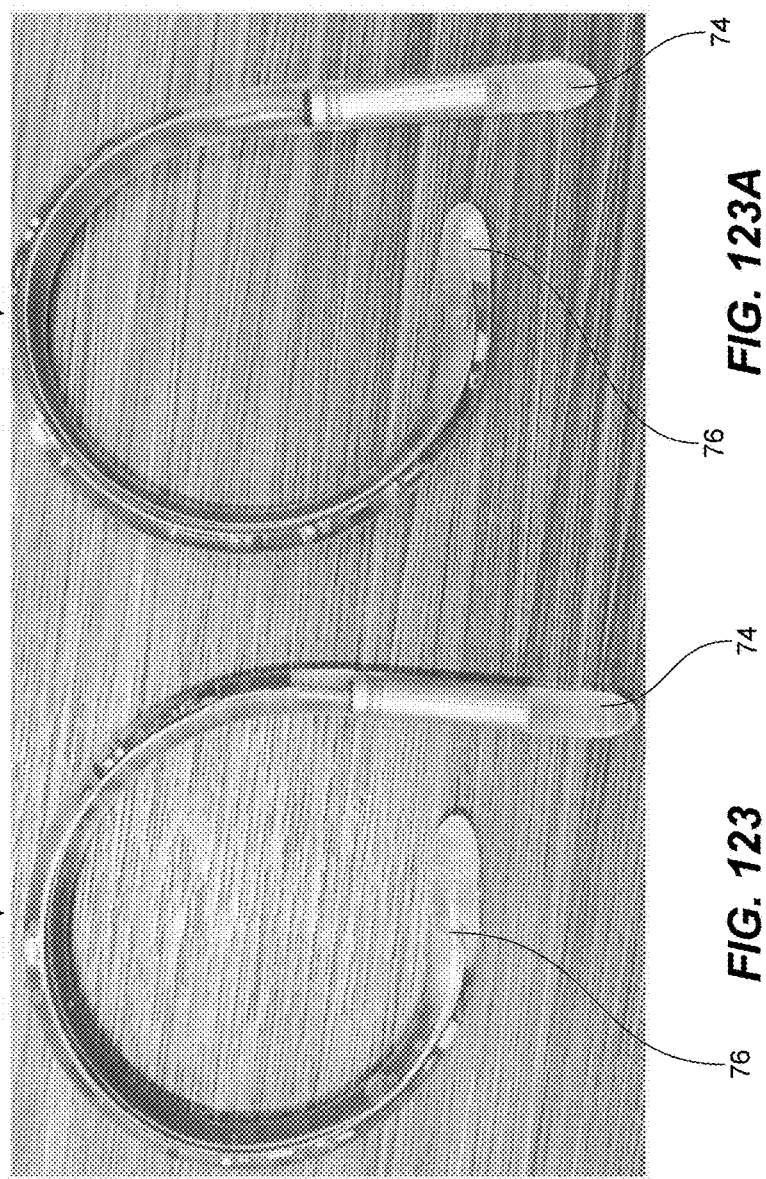

Tip Design

- Spiked tip on the distal end of the spine
- Heat-stake spine into the Distal Tip Spacer

FIG. 124

FIG. 125 DISTAL SPACER

FIG. 126 SPIKED SPINE

Spines from Universal Formations

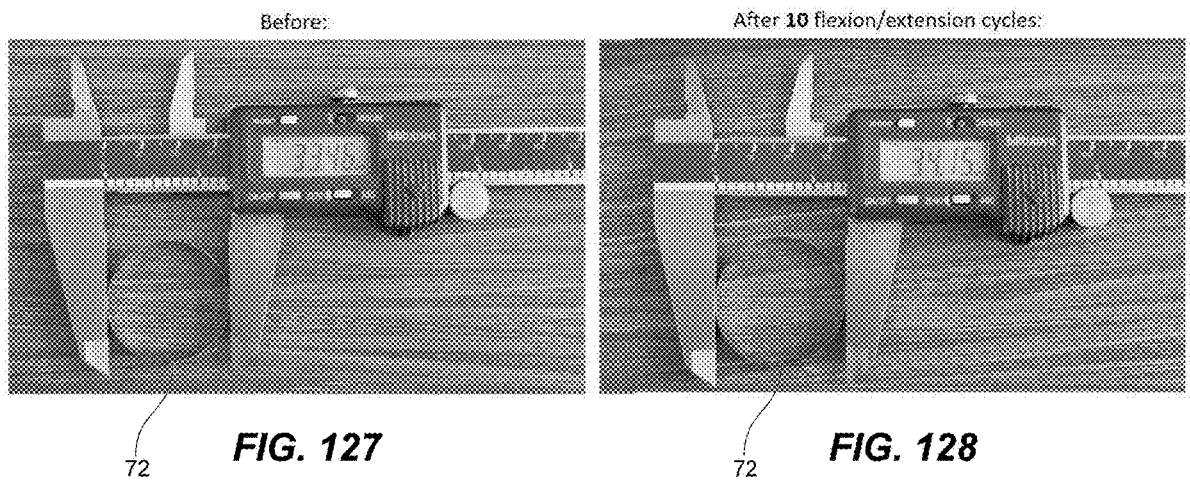

Material/ Oil Testing (in mm)

| Sample # | Material | Soaking Media (14 hours @ 37 C) | Before Immersion | | After Immersion | | Delta | |
|---|---|---|---|---|---|---|---|---|
| | | | OD | Length | OD | Length | Delta OD | Delta Length |
| 1 | 80A Pellethane | Mineral Oil | 2.78 | 150.75 | 2.81 | 151.5 | 0.91% | 0.50% |
| 2 | 70A Pellethane Thin Wall | Mineral Oil | 2.45 | 150.5 | 2.48 | 152 | 1.04% | 1.00% |
| 3 | 90A Pellethane (Fluid Tubing) | Mineral Oil | 3.59 | 150.5 | 3.59 | 151 | 0.14% | 0.33% |
| 4 | 55D Pellethane (Blue) | Mineral Oil | 4.06 | 150.5 | 4.06 | 151 | 0.00% | 0.33% |
| 5 | Qflex (Hard) | Mineral Oil | 4.74 | 151 | 4.74 | 151.5 | 0.00% | 0.33% |
| 6 | Dual Lumen Silicone Tube | Mineral Oil | 4.97 | 150.25 | 5.06 | 155.75 | 1.74% | 3.66% |
| 7 | 35D Pebax | Mineral Oil | 6.10 | 150.25 | 6.08 | 155.25 | N/A* | 3.33% |
| 8 | Nylon 12 | Mineral Oil | 6.03 | 150 | 5.86 | 150.5 | N/A* | 0.33% |
| 9 | Silicone Tube | MED-400 | 4.99 | 150.5 | 5.01 | 150.5 | 0.31% | 0.00% |

FIG. 129

Septa vs. No-Septa Leakage Results

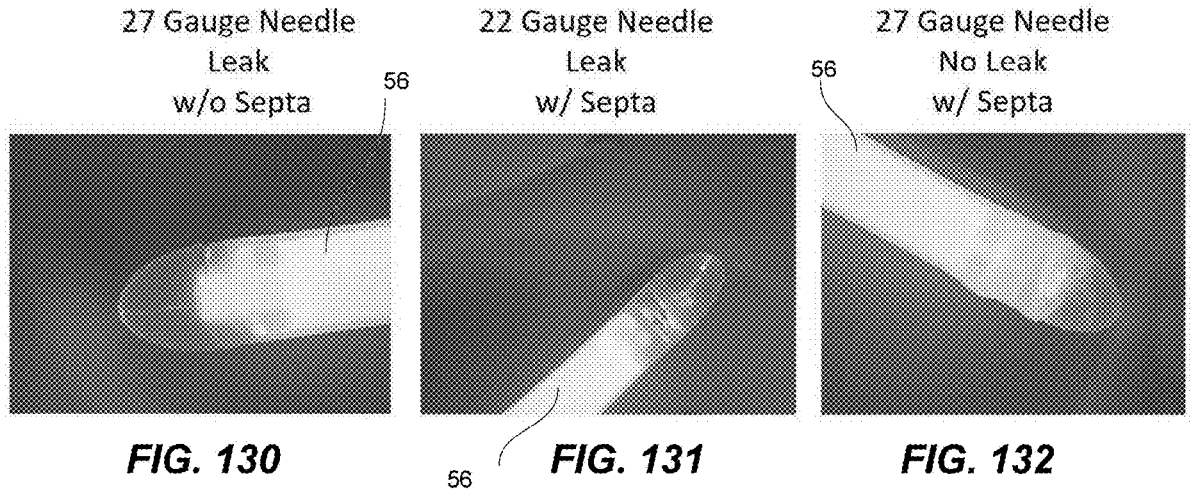

27 Gauge Needle Leak w/o Septa — FIG. 130

22 Gauge Needle Leak w/ Septa — FIG. 131

27 Gauge Needle No Leak w/ Septa — FIG. 132

- Three 27 Ga needle holes were tested through septa without leakage
- 27-30 Ga needle did not leak w/ septa
- Testing with additional needle to optimize filling

Needle Size Analysis

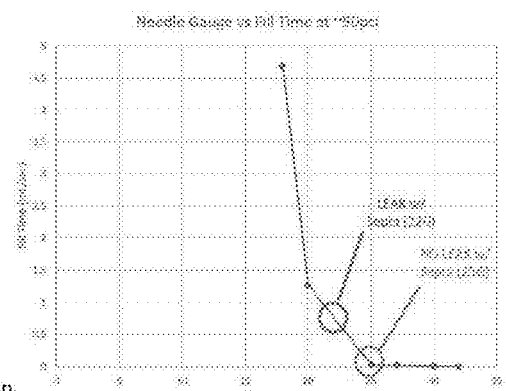

- With the septa, leakage occurred with a 22G needle
- 27G needle
  - W/ septa – no leakage occurred
  - W/O septa – Leakage occurred
- Used square tipped needles which may cause coring in endcap
- Hypodermic needles ordered to reduce leakage caused by coring of endcap

*FIG. 133*

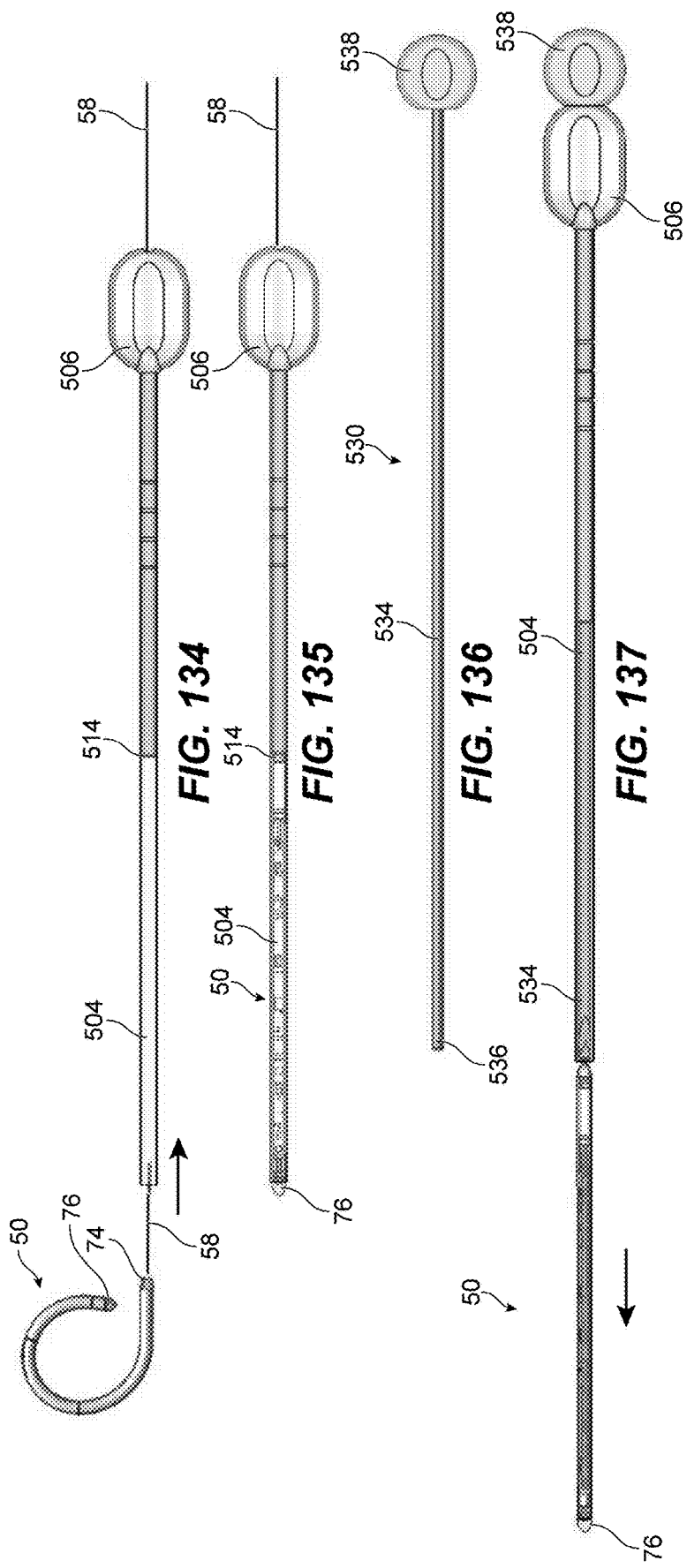

Distal Spacer for Spine

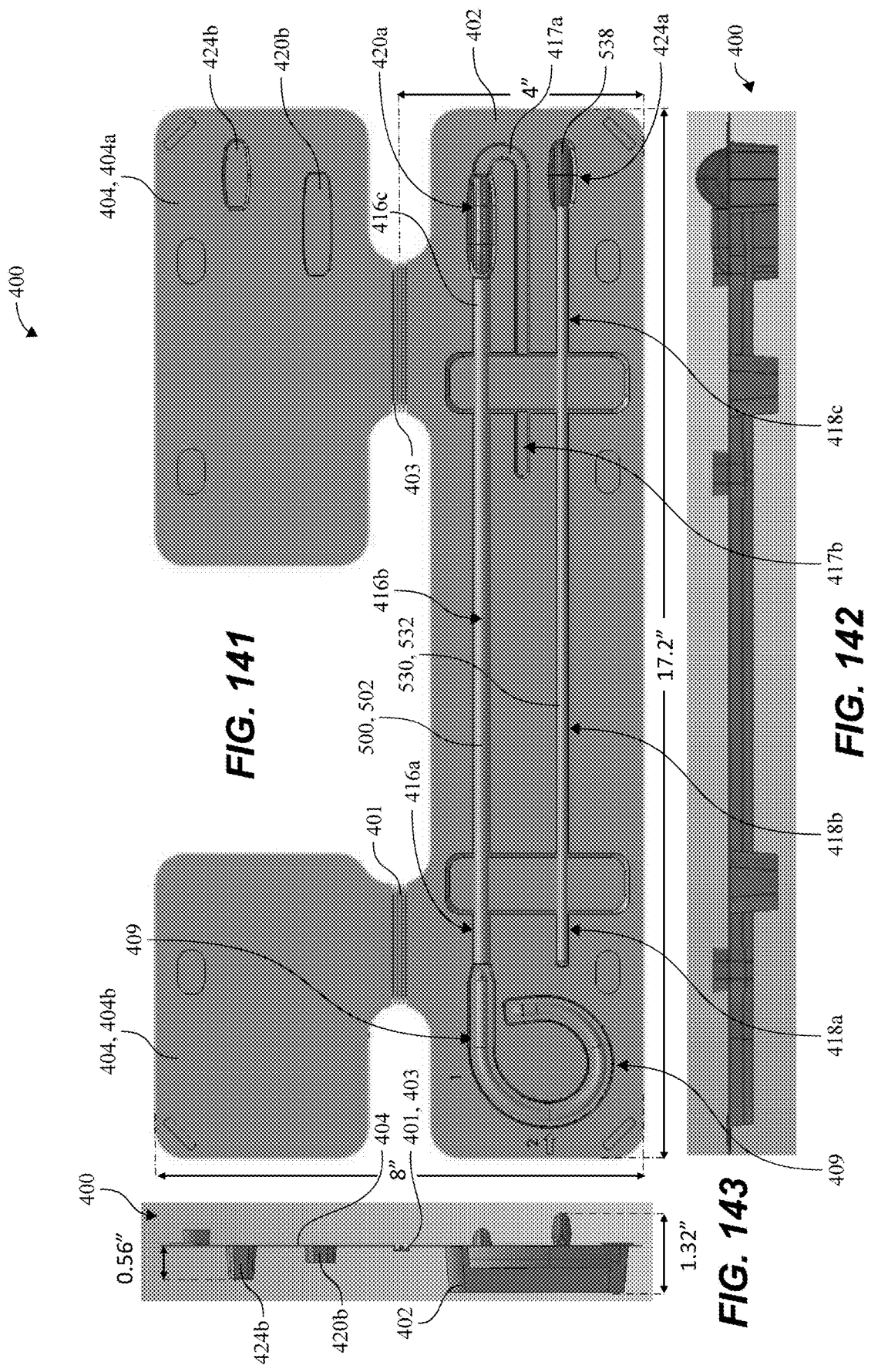

Updated Proximal Tip Design

Updated to allow cystoscopic forceps to grip onto tip (if necessary)

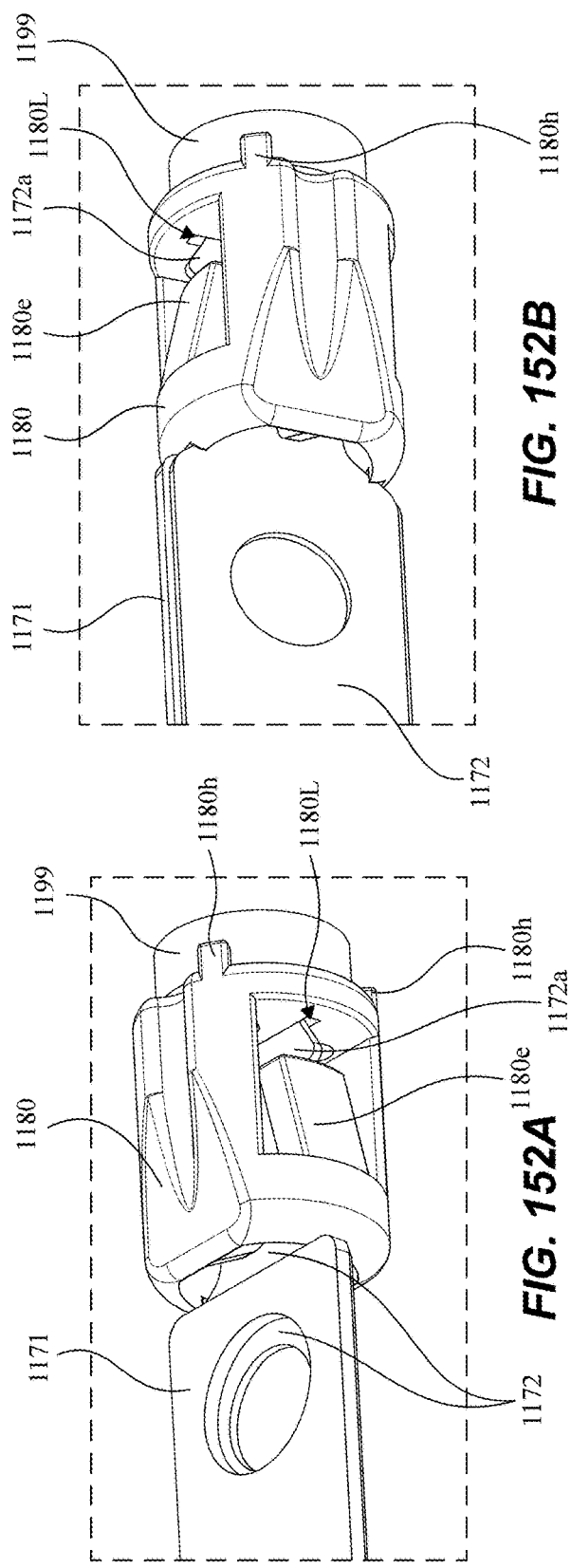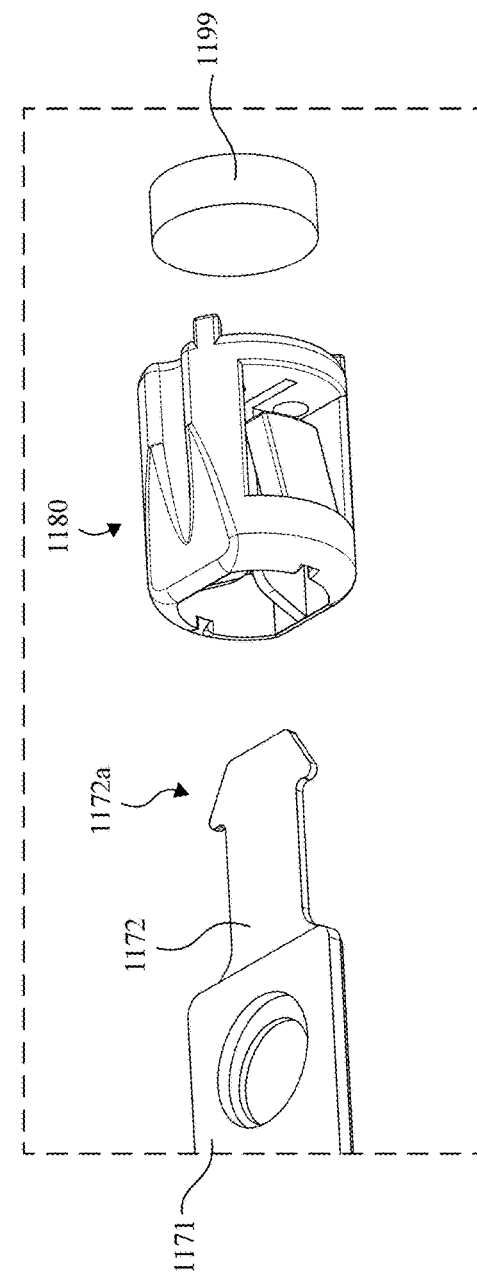
FIG. 152A  FIG. 152B  FIG. 152C

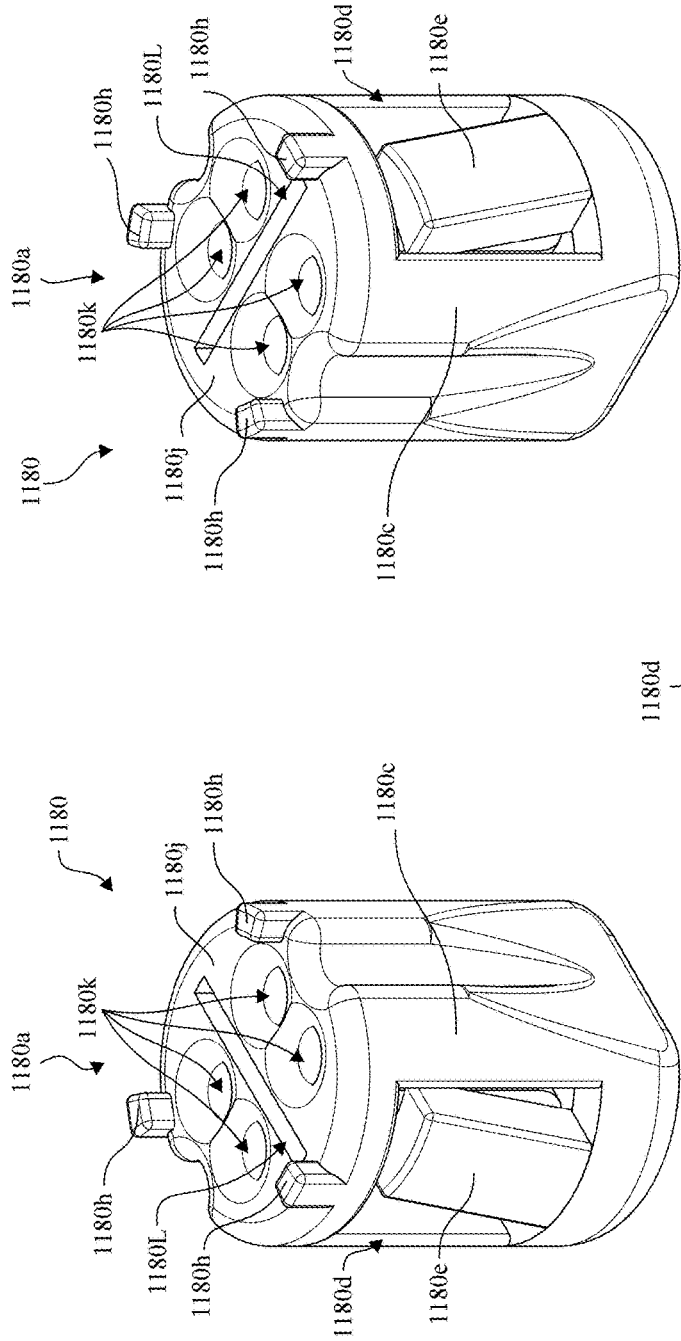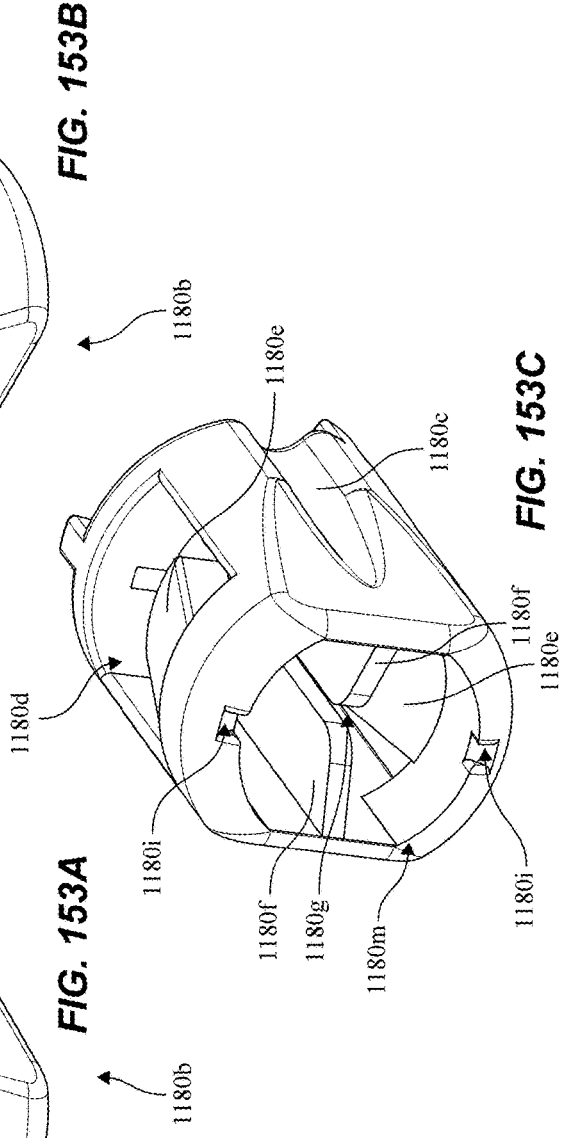

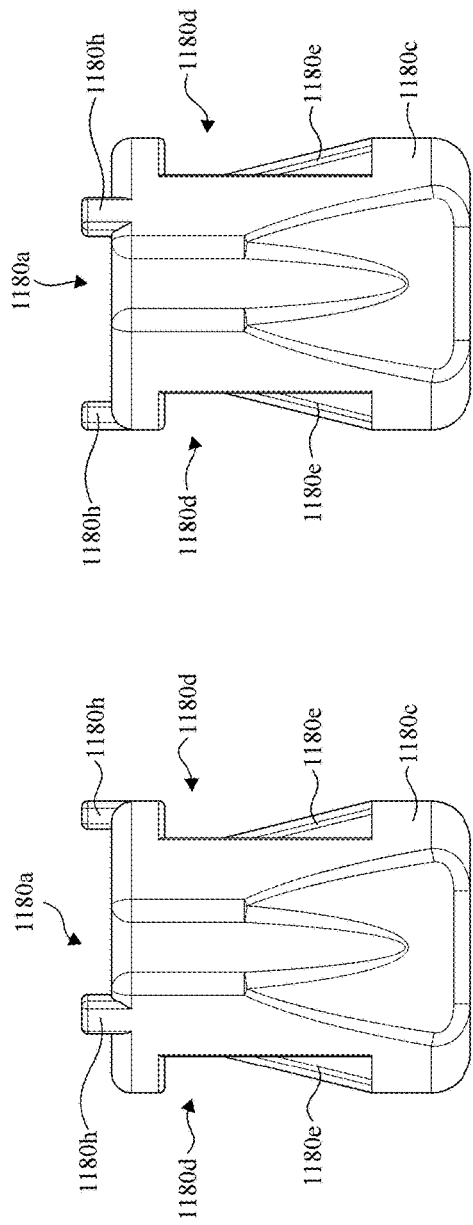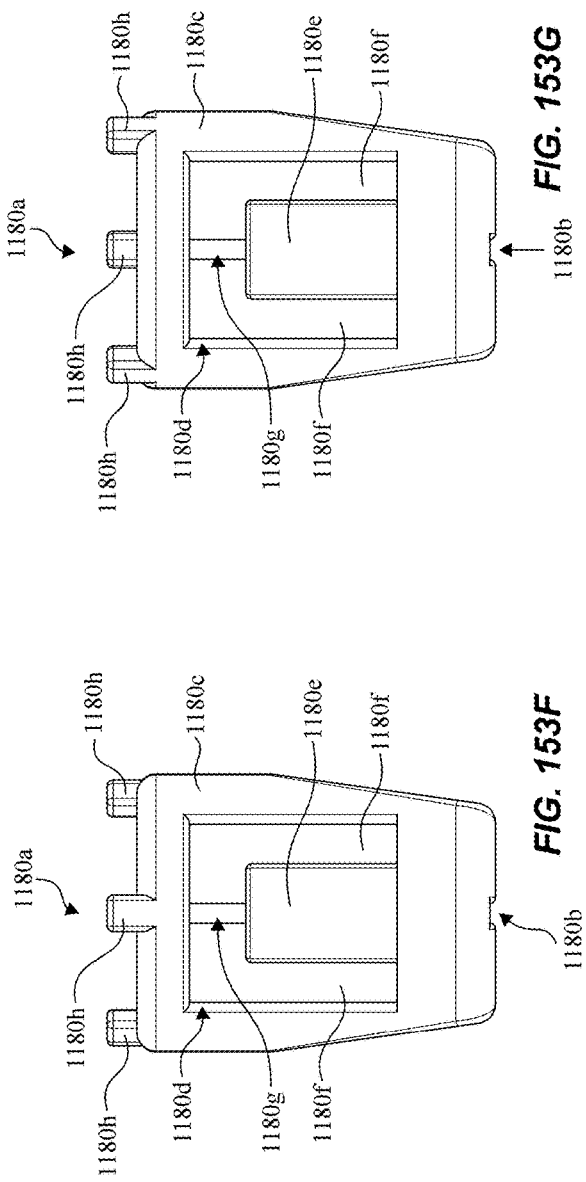

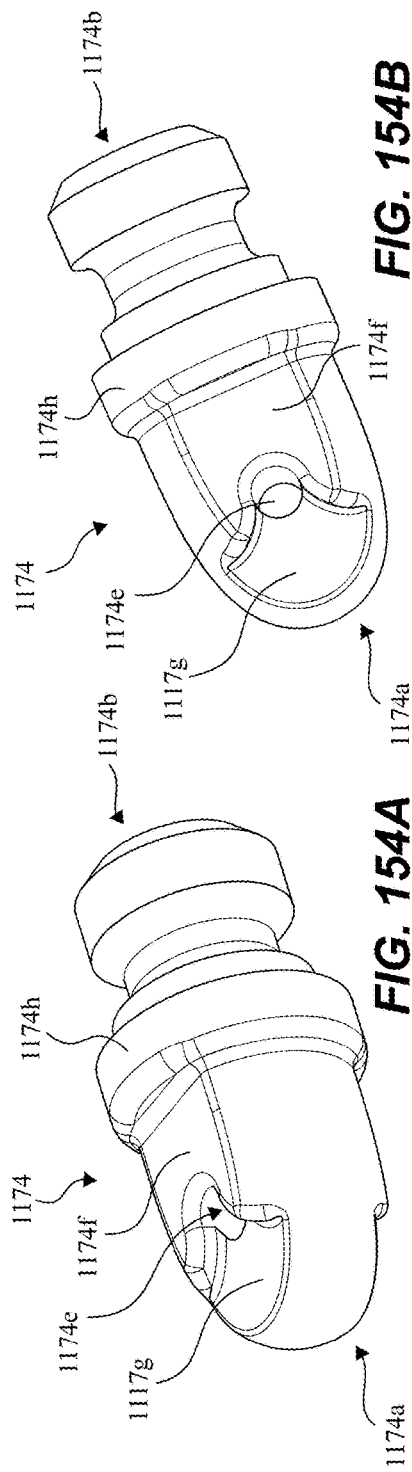
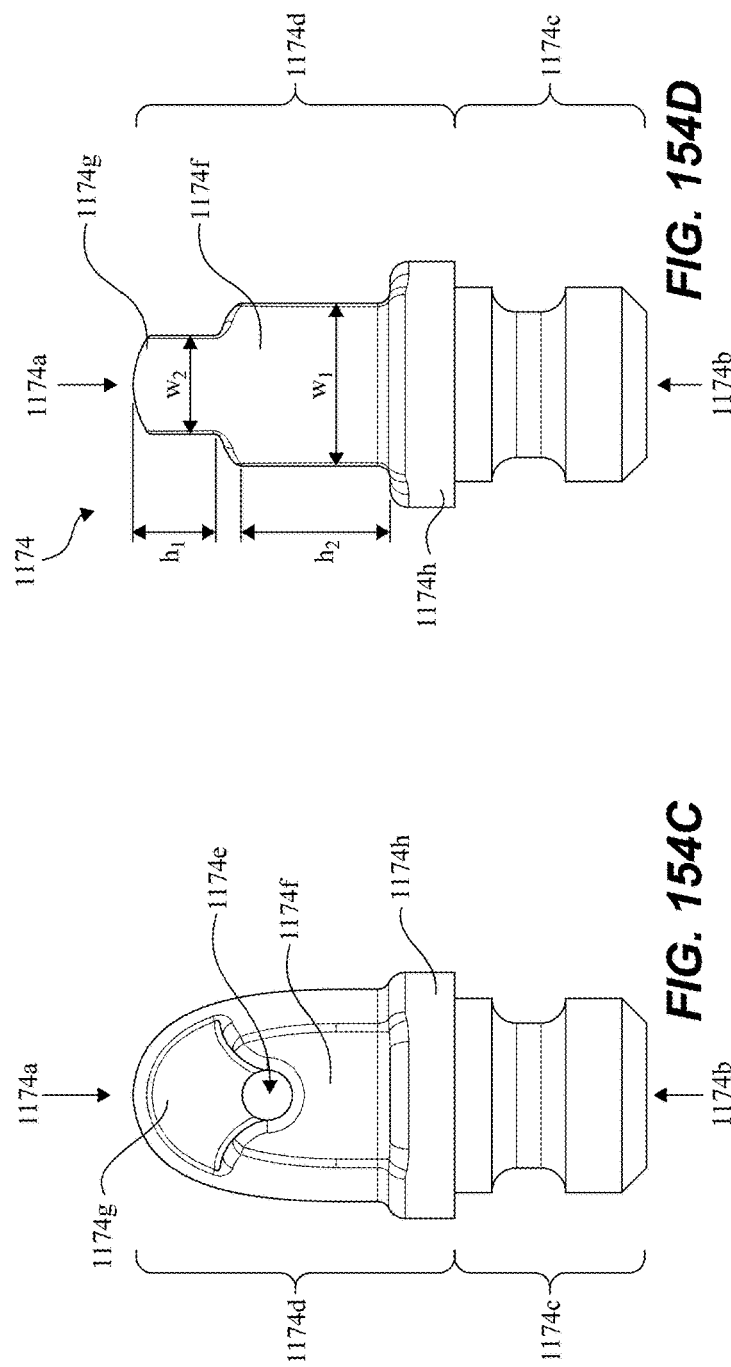
FIG. 154A  FIG. 154B  FIG. 154C  FIG. 154D

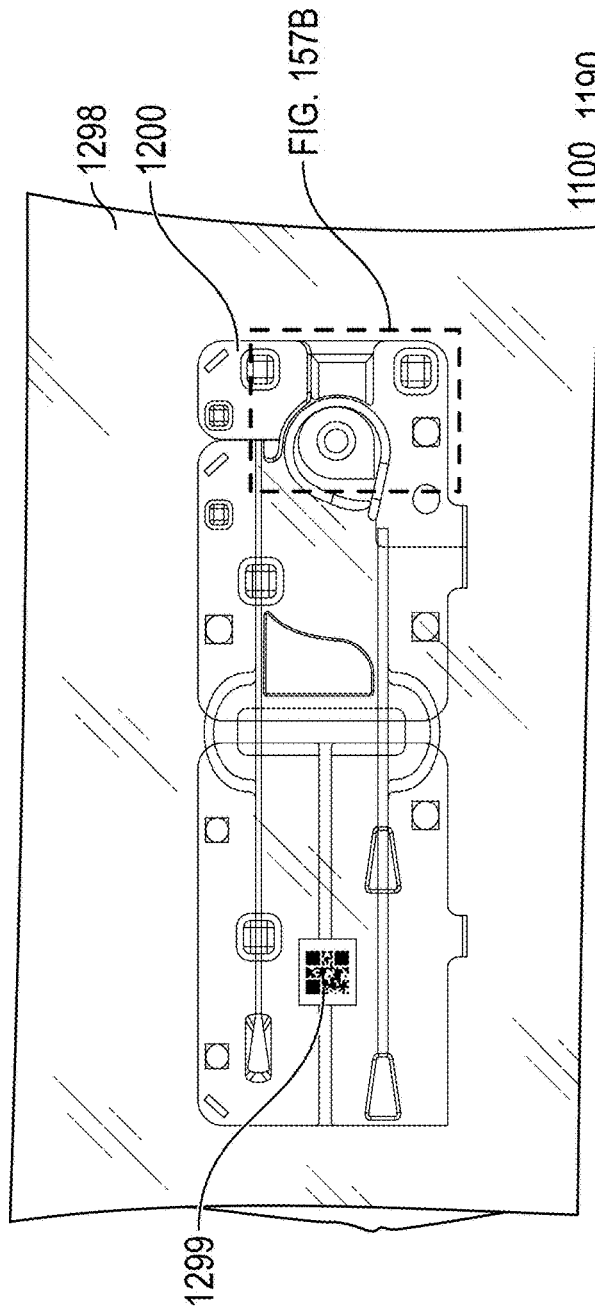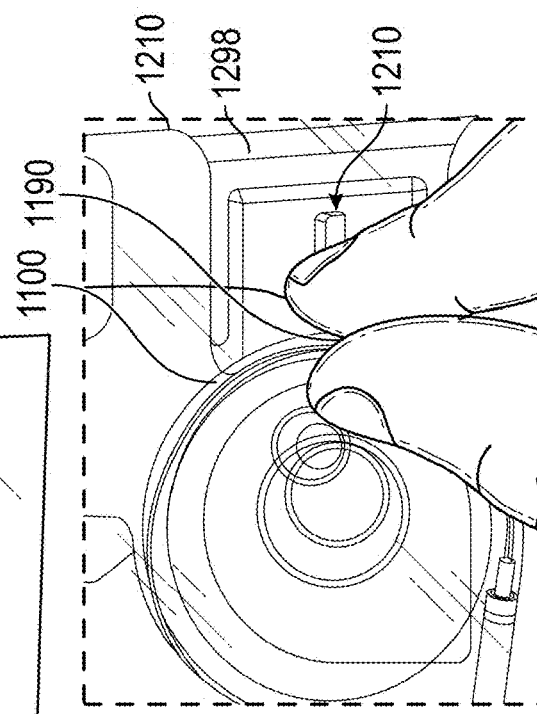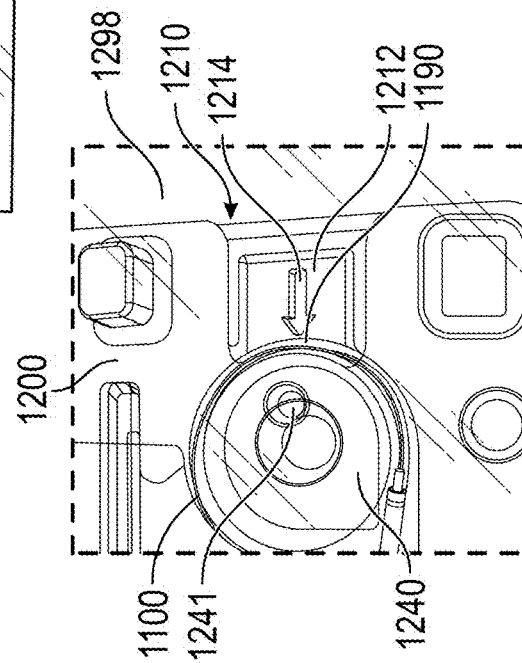

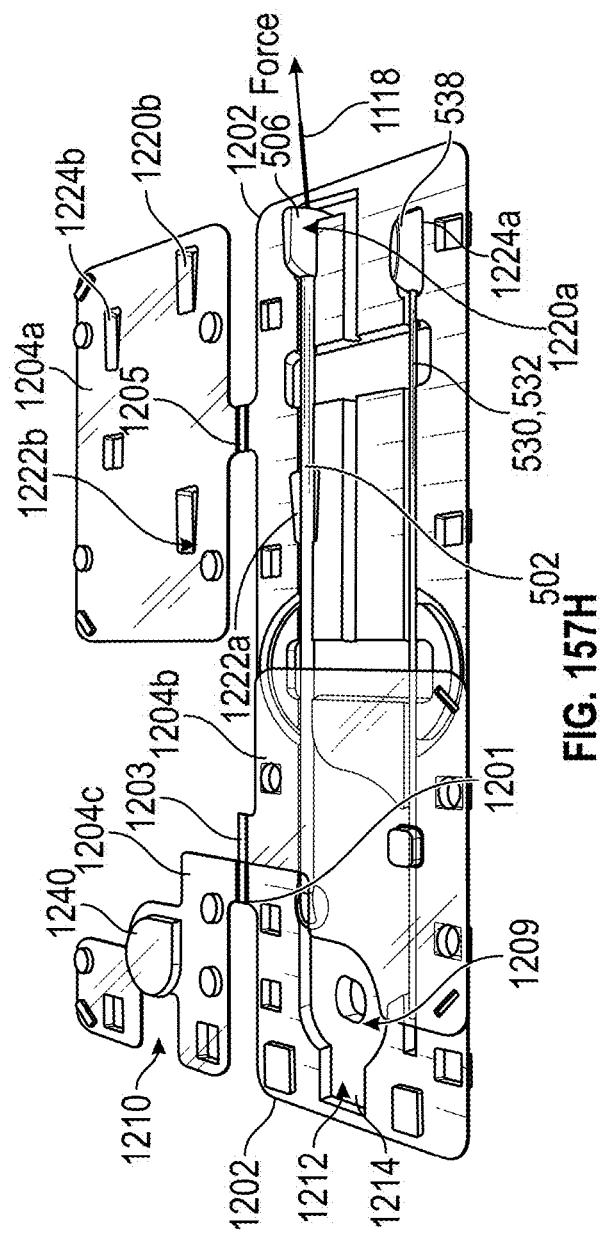
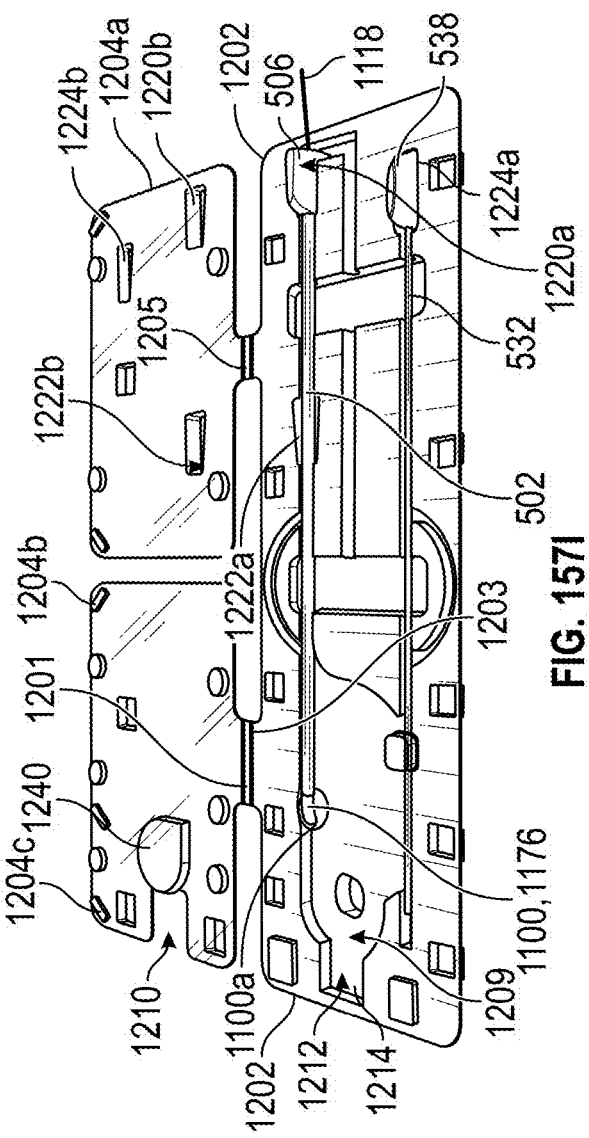

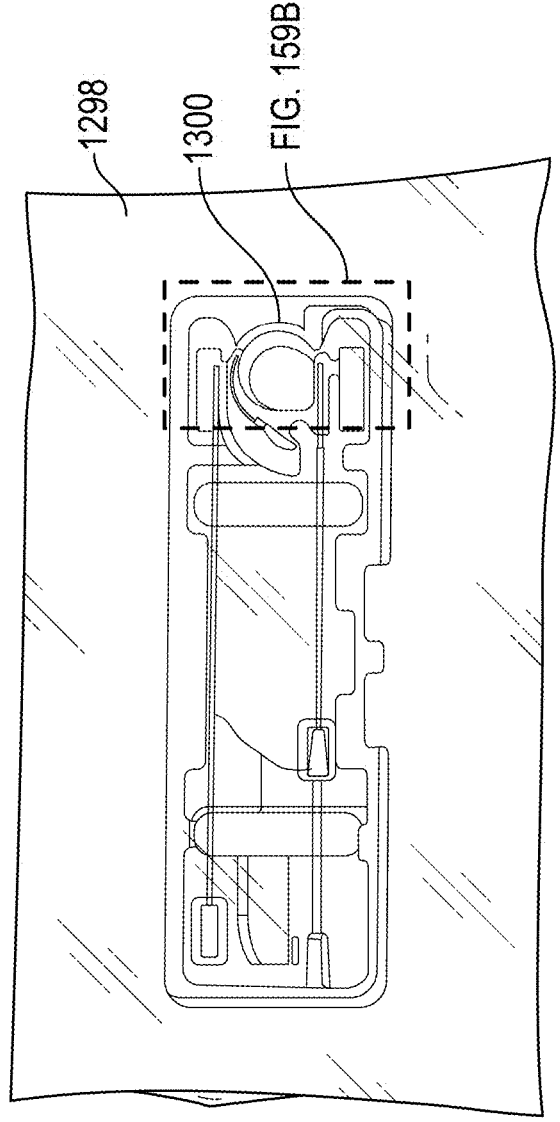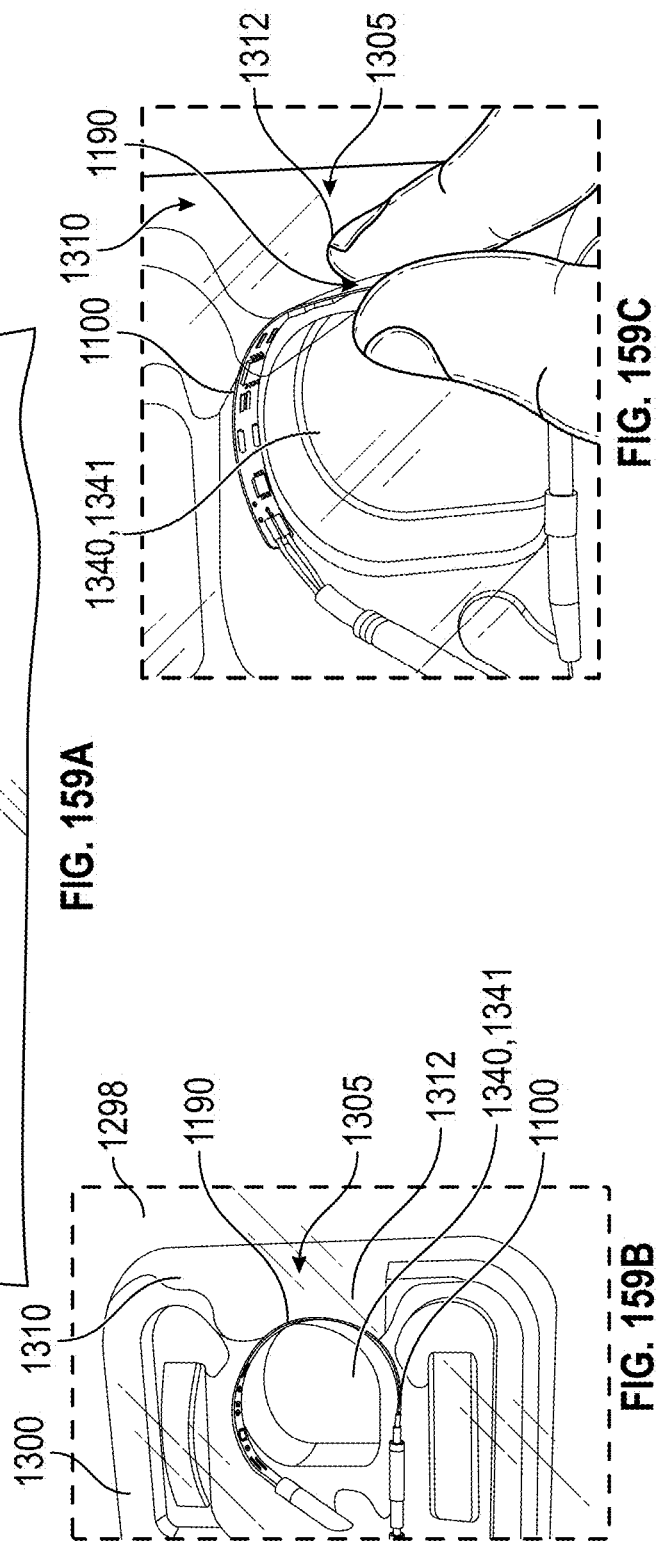
FIG. 159A
FIG. 159B
FIG. 159C

PACKAGING ASSEMBLY AND METHOD OF PREPARING SENSING DEVICE FOR INSERTION INTO A BODY CAVITY TO PRESERVE STERILITY

CROSS REFERENCE TO RELATED APPLICATIONS

This application is a continuation-in-part of U.S. application Ser. No. 18/739,024, filed Jun. 10, 2024, entitled "Systems and Methods for Urological Sensing," which is a continuation of U.S. application Ser. No. 18/476,963, filed Sep. 28, 2023, entitled "Systems and Methods for Urological Sensing," which is a continuation of PCT/US2023/024881, filed Jun. 8, 2023, titled "Systems and Methods for Urological Sensing", which claims priority to U.S. Provisional Patent App. Ser. No. 63/350,305, entitled "Systems and Methods for Urological Sensing," filed Jun. 8, 2022, and also claims priority to U.S. Provisional Patent App. Ser. No. 63/447,765, entitled "Sensors and Software for Urodynamics," filed Feb. 23, 2023. This application also claims priority to U.S. Provisional Patent App. Ser. No. 63/606,031, entitled "Systems and Methods for Urological Sensing," filed Dec. 4, 2023. All of the above-listed applications and any and all applications for which a foreign or domestic priority claim is identified in the Application Data Sheet as filed with the present application are hereby incorporated by reference under 37 CFR 1.57.

BACKGROUND

Sensors for urological sensing that are positioned in the bladder are known. Yet there are areas in which these can be improved.

SUMMARY

Disclosed herein is a kit including a sensing device and a packaging assembly for preserving sterility of the sensing device prior to insertion into a body cavity of a subject. The sensing device can be configured for sensing one or more physiological conditions inside the subject's body cavity and can comprise a housing, one or more electronic components contained within the housing, and a button arranged within the housing and configured to transition the sensing device from a non-operational state to an operational state in which the sensing device can be paired with a separate electronic device. The housing can comprise a transparent and flexible material to allow the button to be located and engaged via a portion of the housing. The packaging assembly can comprise: a bag comprising an interior, the bag at least partially comprising a transparent material; and a tray positioned within the interior of the bag and configured to retain and protect the sensing device, wherein the tray is further configured to enclose only a portion of the sensing device to allow the portion of the housing and the button to be engaged via a portion of the bag, thereby allowing the sensing device to be transitioned to said operational state while retained by the tray and positioned within the interior of the bag.

In some implementations: the tray comprises a base and a cover that is pivotably connected to the base via one or more hinges and configured to pivot between an open position and a closed position; and the tray comprises an opening configured to allow the portion of the housing and the button to be engaged via a portion of the bag when the cover is in said closed position. In some implementations, the cover comprises said opening. In some implementations, the base comprises a perimeter and a wall extending along at least a portion of said perimeter, and wherein the wall comprises said opening of the tray. In some implementations, the opening of the tray is defined by a portion of the cover and a portion of the base. In some implementations, the cover comprises: a top surface and a bottom surface, the bottom surface configured to face toward the base when the cover is in the closed position; and a protrusion extending from the bottom surface and forming a cavity on the top surface, the protrusion having an at least partially cylindrical shape and being at least partially surrounded by the sensing device when the sensing device is retained by the tray. In some implementations: the protrusion is arranged adjacent said opening of the tray; and the opening of the tray and the cavity formed by the protrusion of the cover provide access for fingers of a user to press the portion of the housing and the button against the protrusion, thereby allowing the sensing device to be transitioned to said operational state.

In some implementations, the kit further comprises: an insertion tool configured to facilitate insertion of the sensing device into the subject's body cavity, the insertion tool comprising a sheath configured to receive a portion of the sensing device; and a string coupled to the sensing device and configured to extend through the sheath, the string configured to allow the portion of the sensing device to be pulled into the sheath. In some implementations, the tray is further configured to retain and limit movement of the insertion tool when the portion of the sensing device is pulled into the sheath via the string. In some implementations: the insertion tool further comprises a handle connected to the sheath; the tray comprises a cavity configured to receive at least a portion of the handle; and the cavity is configured to limit movement of the handle, and in turn the sheath, when the portion of the sensing device is pulled into the sheath via the string. In some implementations, the tray comprises a base and a cover that is pivotably connected to the base and configured to pivot between an open position and a closed position, and wherein the base comprises said cavity.

In some implementations: the sheath of the insertion tool further comprises a first mating feature and the sensing device further comprises a second mating feature, the first and second mating features configured to engage one another and inhibit rotation of the sensing device relative to the insertion tool when the portion of the sensing device is positioned within the sheath; and the cavity is configured to limit rotation of the handle, and in turn, the sheath, when the at least the portion of the sensing device is pulled into the sheath via the string, thereby facilitating alignment of the first and second mating features with one another. In some implementations: the first mating feature is arranged at an end of the sheath; and the sensing device further comprises a first endcap secured to a first end of the housing, a second endcap secured to a second end of the housing, said first mating feature arranged on the first endcap. In some implementations, said cavity is configured to limit a degree of rotation of the handle to be less than 45 degrees relative to an axis extending through the handle and the sheath. In some implementations: the sheath of the insertion tool comprises a first end, a second end, and a sheath lumen extending between the first and second ends and configured to receive the portion of the sensing device; the string is configured to allow the portion of the sensing device to be pulled through the first end of the sheath and into the sheath lumen; and the tray comprises a channel configured to receive and operably position the first end of the sheath when the portion of the sensing device is pulled through the first end of the sheath and into the sheath lumen.

In some implementations: the insertion tool further comprises a first mating feature arranged at the first end of the sheath; the sensing device comprises a first endcap secured to a first end of the housing, a second endcap secured to a second end of the housing, and a second mating feature arranged on the first endcap; the first and second mating features are configured to engage one another and inhibit rotation of the sensing device relative to the insertion tool when the portion of the sensing device is positioned within the sheath lumen; the tray comprises an inner wall at least partially defining said channel and a bump arranged on said inner wall within said channel; and said bump is configured to contact the second endcap of the sensing device when the sensing device is pulled through the first end of the sheath to align the second endcap with the sheath lumen, thereby inhibiting interference of the second endcap with the first mating feature at the first end of the sheath.

Disclosed herein is a packaging assembly for preserving sterility of a sensing device prior to insertion into a body cavity of a subject, the packaging assembly comprising: a bag comprising an interior, the bag at least partially comprising a transparent material; and a tray configured to be positioned within the interior of the bag and configured to retain and protect the sensing device, wherein the tray comprises an opening configured to allow a button of the sensing device to be engaged via a portion of the bag, thereby allowing the sensing device to be transitioned from a non-operational state to an operational state when retained by the tray and positioned within the interior of the bag.

In some implementations, the tray comprises a base and a cover that is pivotably connected to the base via one or more hinges and configured to pivot between an open position and a closed position, and wherein said opening is configured to allow the button to be engaged via the portion of the bag when the cover is in said closed position. In some implementations, the cover comprises said opening. In some implementations, the base comprises a recessed portion arranged proximate to the opening of the cover when the cover is in the closed position, the recessed portion of the base and the opening of the cover providing access to allow the button to be engaged via the portion of the bag when the sensing device is retained by the tray and positioned within the interior of the bag. In some implementations, the base comprises a perimeter and a wall extending along at least a portion of said perimeter, and wherein the wall comprises said opening of the tray. In some implementations, the opening of the tray is defined by a portion of the cover and a portion of the base.

In some implementations, the cover comprises: a top surface and a bottom surface, the bottom surface configured to face toward the base when the cover is in the closed position; and a protrusion extending from the bottom surface and forming a cavity on the top surface, the protrusion having an at least partially cylindrical shape and being at least partially surrounded by the sensing device when the sensing device is retained by the tray. In some implementations: the protrusion is arranged adjacent said opening of the tray; and the opening of the tray and the cavity formed by the protrusion of the cover provide access for fingers of a user to engage the button of the sensing device and a portion of the protrusion, thereby allowing the sensing device to be transitioned to said operational state.

In some implementations, the base of the tray comprises a channel configured to receive a sheath of an insertion tool, the insertion tool configured to receive a portion of the sensing device. In some implementations: the tray comprises an inner wall at least partially defining said channel and a bump arranged on said inner wall within said channel; and said bump is configured to contact and align an end of the sensing device with a lumen of the sheath when the portion of the sensing device is inserted into the sheath. In some implementations, said channel comprises a first channel of the base, and wherein the base further comprises a second channel that is configured to receive a push rod that is configured to be inserted into the sheath of the insertion tool and push the sensing device out of the sheath and into the subject's body cavity.

In some implementations, the base of the tray comprises a cavity configured to receive at least a portion of a handle of an insertion tool that is configured to receive a portion of the sensing device, said cavity configured to limit movement of the insertion tool when the portion of the sensing device is inserted into the insertion tool. In some implementations, the tray comprises an identification tag comprising information associated with the sensing device, said identification tag configured to allow a user to electronically pair the sensing device with a patient monitoring device. In some implementations, the tray comprises a transparent material.

Disclosed herein is a tray configured to retain and protect a sensing device, the sensing device configured to be inserted into a body cavity of a subject, the tray comprising: a base; a cover pivotably connected to the base via one or more hinges and configured to pivot between an open position and a closed position; and an opening configured to allow a button of the sensing device to be engaged when the cover is in the closed position, thereby allowing the sensing device to be transitioned from a non-operational state to an operational state when retained by the tray.

In some implementations, the cover comprises said opening. In some implementations, the base comprises a recessed portion arranged proximate to the opening of the cover when the cover is in the closed position, the recessed portion of the base and the opening of the cover providing access to allow the button of the sensing device to be engaged when the sensing device is retained by the tray. In some implementations, the base comprises a perimeter and a wall extending along at least a portion of said perimeter, and wherein the wall comprises said opening of the tray. In some implementations, the opening of the tray is defined by a portion of the cover and a portion of the base. In some implementations, the cover comprises: a top surface and a bottom surface, the bottom surface configured to face toward the base when the cover is in the closed position; and a protrusion extending from the bottom surface and forming a cavity on the top surface, the protrusion having an at least partially cylindrical shape and being at least partially surrounded by the sensing device when the sensing device is retained by the tray. In some implementations: the protrusion is arranged adjacent said opening of the tray; and the opening of the tray and the cavity formed by the protrusion of the cover provide access for fingers of a user to engage the button of the sensing device and a portion of the protrusion, thereby allowing the sensing device to be transitioned to said operational state.

In some implementations, the base of the tray comprises a channel configured to receive a sheath of an insertion tool that is configured to receive a portion of the sensing device. In some implementations: the tray comprises an inner wall at least partially defining said channel and a bump arranged on said inner wall within said channel; and said bump is configured to contact and align an end of the sensing device with a lumen of the sheath when the portion of the sensing device is inserted into the sheath. In some implementations, said channel comprises a first channel of the base, and wherein the base further comprises a second channel that is configured to receive a push rod that is configured to be inserted into the sheath of the insertion tool and push the sensing device out of the sheath and into the subject's body cavity. In some implementations, the base of the tray comprises a cavity configured to receive at least a portion of a handle of an insertion tool that is configured to receive a portion of the sensing device, said cavity configured to limit movement of the insertion tool when the portion of the sensing device is inserted into the insertion tool. In some implementations, the tray comprises an identification tag comprising information associated with the sensing device, said identification tag configured to allow a user to electronically pair the sensing device with a patient monitoring device.

Disclosed herein is a method of preparing a sensing device for insertion into a body cavity of a subject to preserve sterility, the method comprising: obtaining a bag and a tray positioned within an interior of the bag, wherein said sensing device is retained by the tray, said sensing device configured for sensing one or more physiological conditions inside the subject's body cavity and comprising a housing, one or more electronic components contained within the housing, and a button arranged within the housing and configured to transition the sensing device from a non-operational state to an operational state, wherein the tray comprises an opening; pressing a portion of the bag against a portion of the housing via said opening to engage the button, thereby transitioning the sensing device to said operational state; and wirelessly pairing the sensing device with a patient monitoring device after the sensing device is transitioned to said operational state.

In some implementations, the method further comprises opening the bag and emptying the tray onto a surface without touching the tray after the sensing device is wirelessly paired to the patient monitoring device. In some implementations, said tray is further configured to retain an insertion tool that is configured to facilitate insertion of the sensing device into the subject's body cavity, and wherein the method further comprises inserting at least a portion of the sensing device into a sheath of the insertion tool. In some implementations, a string is connected to the sensing device and extends through the sheath of the insertion tool, and wherein said inserting the at least the portion of the sensing device into the sheath of the insertion tool comprises pulling the string. In some implementations, the method further comprises applying a lubricating material to the sensing device prior to inserting the at least the portion of the sensing device into the sheath of the insertion tool. In some implementations: the tray comprises a base configured to provide a support surface for the sensing device and the insertion tool and a cover pivotably connected to the base via one or more hinges and configured to pivot between an open position and a closed position; and the method further comprises pivoting the cover to the open position prior to applying the lubricating material to the sensing device.

In some implementations: the sensing device further comprises a first mating feature and the insertion tool further comprises a second mating feature; and the method further comprises engaging the first and second mating features together such that rotation of the sensing device relative to the insertion tool is inhibited. In some implementations, the first mating feature comprises a projection on an exterior portion of the sensing device and wherein the second mating feature comprises a slot on an end of the sheath, the slot sized and shaped to receive the projection. In some implementations, the sensing device comprises an end having a coude shape, and wherein said first mating feature is arranged proximate said end. In some implementations, said inserting the at least the portion of the sensing device into the sheath of the insertion tool is performed without touching the sensing device and/or without touching the insertion tool. In some implementations: the tray comprises an identification tag comprising information associated with the sensing device; and said wirelessly pairing the sensing device with the patient monitoring device comprises scanning the identification tag with said patient monitoring device or a mobile device configured to wirelessly communicate with said patient monitoring device.

Disclosed herein is a method of preparing a sensing device for insertion into a body cavity of a subject to preserve sterility, the method comprising: obtaining a bag that includes a sensing device within an interior of the bag, the sensing device configured for sensing one or more physiological conditions inside the subject's body cavity and comprising a housing, one or more electronic components contained within the housing, and a button arranged within the housing and configured to transition the sensing device from a non-operational state to an operational state, wherein at least a portion of the bag and the housing is transparent to allow the button to be located; pressing a portion of the bag against a portion of the housing to engage the button, thereby transitioning the sensing device to said operational state; and wirelessly pairing the sensing device with a patient monitoring device after the sensing device is transitioned to said operational state.

In some implementations, said pressing the portion of the bag against the portion of the housing to engage the button is performed by a user without wearing a glove. In some implementations, said wirelessly pairing the sensing device with the patient monitoring device is performed by a user without wearing a glove. In some implementations, the method further comprises breaking a seal of the bag and removing the sensing device from the interior after the sensing device is wirelessly paired to the patient monitoring device. In some implementations, said breaking the seal of the bag is performed by a user without wearing a glove. In some implementations, the bag further includes a tray configured to retain and protect the sensing device, the tray comprising an opening, and wherein said pressing comprises pressing the portion of the bag against the portion of the housing via the opening of the tray. In some implementations, the method further comprises removing the sensing device from the interior of the bag by emptying the tray onto a surface without touching the tray and/or the sensing device.

BRIEF DESCRIPTION OF THE DRAWINGS

FIG. 1 is a side, perspective view of a sensor device according to this disclosure.

FIG. 2 is a side, perspective view of a sensor device of FIG. 1 with the electronics visible through the outer sheath.

FIG. 3 is a side, perspective view of the sensor device of FIG. 1 with the outer sheath removed and showing the electronics and spine.

FIGS. 8-8B show side views of the sensors of FIGS. 1-3.

FIGS. 13-14 are alternate, top views of the sensor of FIG. 12.

FIGS. 18-20 are close-up, partial top views of the sensor of FIGS. 12-17.

FIG. 21 is an alternate view of the sensor of FIG. 12.

FIG. 22 is a partial, enlarged view of the sensor of FIG. 21.

FIG. 25 is a side view of an insertion sheath and handle used to implant a sensor of this disclosure into a bladder.

FIG. 26 is a side view of a push rod with various components labeled.

FIG. 28 is a partial, close-up, side view of the distal end of an insertion tool (or sheath) according to this disclosure showing a keyway configured to receive a key on the distal end of a sensor.

FIG. 29 is a rear view of a handle according to this disclosure, which shows an opening through which the push rod is inserted, wherein the opening leads to a lumen that has a rounded top and rounded bottom and straight sides.

FIG. 30 is a partial, side, cut away view of an insertion tool stem according to this disclosure showing a lumen with a first, distal portion having a first diameter and a second, proximal portion having a second diameter that is less than the first diameter.

FIG. 31 is a side view of the sensor of FIGS. 21-24 showing the proximal tip with removal string attached and the distal tip with coude design and not showing the electronics.

FIG. 32 is a partial, side perspective view of the distal end of an insertion sheath according to this disclosure showing a keyway configured to receive a key on the distal end of a sensor.

FIG. 33 is a partial, side view of an insertion tool with the proximal end of the sensor with a removal string attached positioned therein and extending into the lumen of the insertion tool.

FIG. 34 is a partial, assembled device according to this disclosure with a sensor positioned in an insertion sheath and a push rod extending from a housing.

FIG. 35 shows a test protocol and top views of sensors 1-3 that were used to perform the tests using the protocol.

FIG. 36 shows a test protocol and a top view of sensors 1-3 that were used to perform the tests according to the protocol.

FIG. 37 shows a test protocol and a top view of sensors 1 and 3 that were used to perform the tests according to the protocol.

FIG. 38 shows a test protocol and a top view of sensors 4-6 that were used to perform the tests according to the protocol.

FIG. 39 shows a test protocol run using sensors 4 and 6.

FIG. 40 shows a test protocol run on a sensor 8.

FIG. 41 shows a test protocol run on a sensor 10.

FIG. 42 shows a test protocol run on a sensor 12 and a side view of a beaker with water showing bubbles forming.

FIGS. 44-44B show internal components of a sensor according to this disclosure.

FIG. 45 is a side view of a sensor according to this disclosure.

FIG. 46 is a cross-sectional view of the sensor of FIG. 45 taken through lines Q-Q.

FIG. 47 is an enlarged view of the tip shown in detail S of FIG. 46.

FIG. 48 is an enlarged view of the section shown in detail T of FIG. 46.

FIGS. 52-56 show various views of a sensor spine according to this disclosure.

FIGS. 60-64 show side, perspective views of aspects of the assembly process for a sensor according to this disclosure.

FIG. 69 illustrates three examples of using needles to inject oil, to allow oil to escape, and recording pressure changes and leaks.

FIGS. 75-77 show side, perspective views of the assembly of some internal components of a sensor according to this disclosure.

FIGS. 79-83 show various views of electrical contacts for use in a sensor according to this disclosure.

FIGS. 84-86 show side views, and a side perspective view of some internal components of a sensor according to this disclosure.

FIGS. 87-89 show various views of electrical components and soldering locations for a sensor according to this disclosure.

FIGS. 98-99 show views of an example distal end of a sensor according to this disclosure that has a septum.

FIGS. 100-101 show mineral oil and silicone oil used in testing.

FIGS. 121-122 show side views of a sensor inside of insertion tools with no kinking detected.

FIGS. 123 and 123A show side views of sensors that include an alternate spine that is a waterjet cut spine.

FIGS. 124-126 show side, partial perspective views of a sensor with a distal tip, wherein the distal end of the spine is positioned in a soft spacer to avoid damage to the outer sheath.

FIGS. 127-128 include top views of a spine showing the change in diameter after 10 flexion/extension cycles.

FIG. 129 is a chart of material/oil testing using the mineral oil and silicone oil of FIGS. 100-101.

FIGS. 130-132 includes side views of distal ends of sensors with a septum and including leakage results.

FIG. 133 shows leakage results for sensor distal ends with and without a septum using different gauge needles.

FIGS. 134-137 show side views of a sensor, an insertion tool, and a push rod.

FIGS. 141-143 show an open, top view (FIG. 141) of a case for retaining a sensor, insertion tool, and push rod according to this disclosure, a side view (FIG. 143) of the case and a bottom view (FIG. 142) of the case.

FIGS. 152A-152B illustrate enlarged views of an end of a flexible circuit board of a sensing device, and FIG. 152C shows an exploded view of such end.

FIGS. 153A-153B illustrate top perspective views, and FIG. 153C illustrates a bottom perspective view, of a spacer of a sensing device, and FIGS. 153D-153I show front, rear, side, top, and bottom views (respectively) of such spacer.

FIGS. 154A-154B illustrate perspective views, and FIGS. 154C-154D illustrate side views, of a proximal end cap of a sensing device.

FIGS. 157A-157I illustrate an example method of preparing a sensing device for insertion into a body cavity of a subject in accordance with aspects of the disclosure.

FIGS. 159A-159F illustrate an example method of preparing a sensing device for insertion into a body cavity of a subject in accordance with aspects of the disclosure.

DETAILED DESCRIPTION

Sensor and Insertion Tool Example 1

Figure 3A:
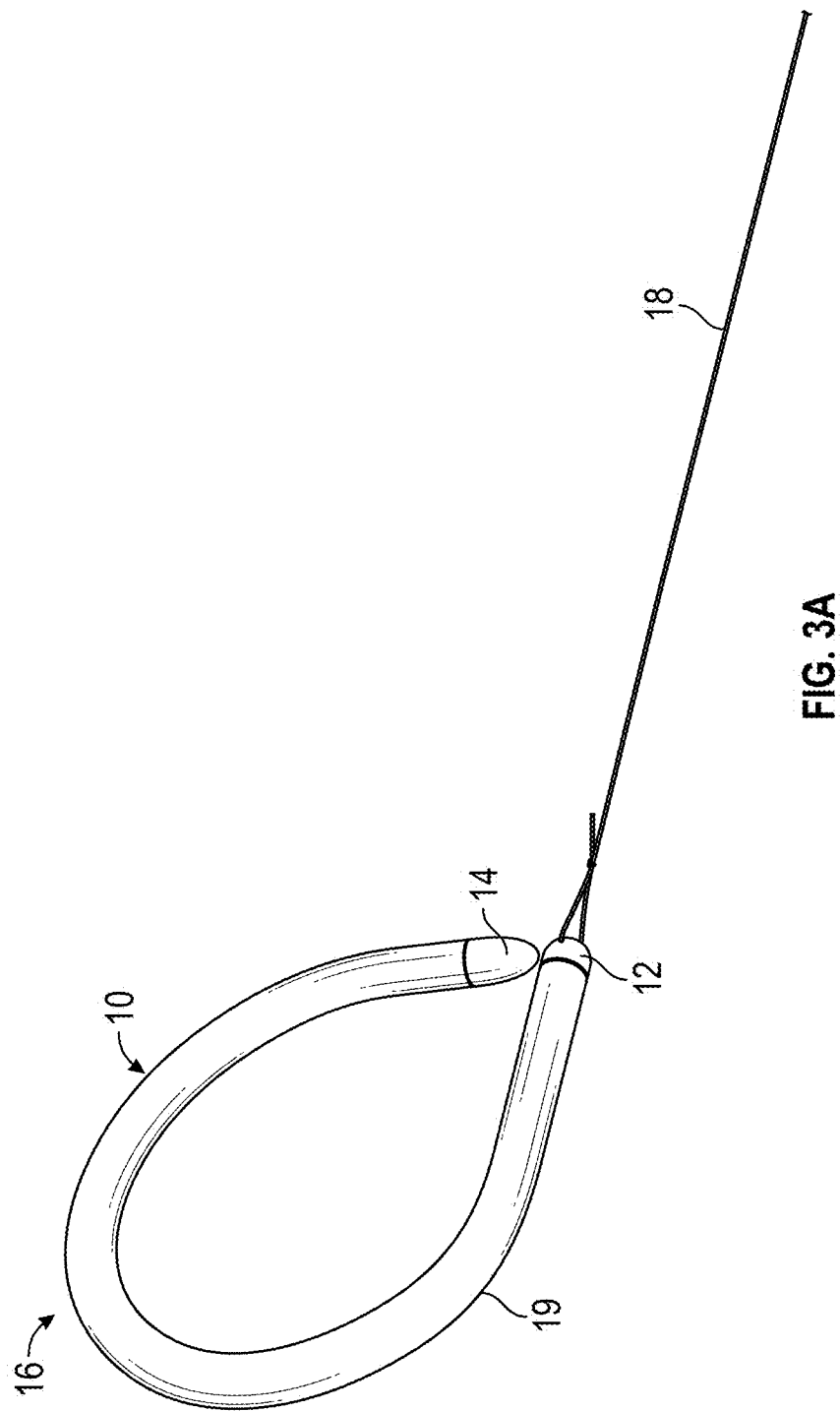
FIG. 3A is an alternate, side perspective view of the sensor of FIG. 1 with a removal string attached.

Disclosed is a urodynamics system that may include one or more of the following components, as well as additional components: (1) a sensor as shown in FIGS. 1-2, and 9-10, which is in one embodiment a flexible silicone rubber tube with electronics inside, as shown in FIG. 3, to sense pressure and volume, (2) an insertion tool to deliver the sensor through the urethra and into the bladder.

FIGS. 1-3A illustrate a sensor 10 according to this disclosure. Sensor 10 has a proximal end 12, which is closest to the clinician prior to being inserted, a distal end 14, which is farthest from the clinician when inserted into a bladder and is the end of first inserted into the bladder. Sensor 16 has a tubular body 16 that includes tube wall, or over sheath 19. A string 18 is connected to proximal end 12 and configured to (1) be pulled to pull sensor 10 into an insertion tool, and (2) be pulled to pull sensor 10 out of a bladder. When sensor 10 is deployed in a bladder, string 18 preferably remains outside of the patient's body.

Sensor 10 also includes internal electronics 20 positioned on and attached to a flexible circuit board 21 and a spine 22 connected to the back of flexible circuit board 21 (i.e., the side of flexible circuit board 21 opposite electronics 20). Spine 22 is connected to flexible circuit board 21 preferably by welding. Spine (or shape memory spring) 22 is biased to a first, curved position and biases sensor to a first, curved position, as shown in FIGS. 1-3.

Figure 4:
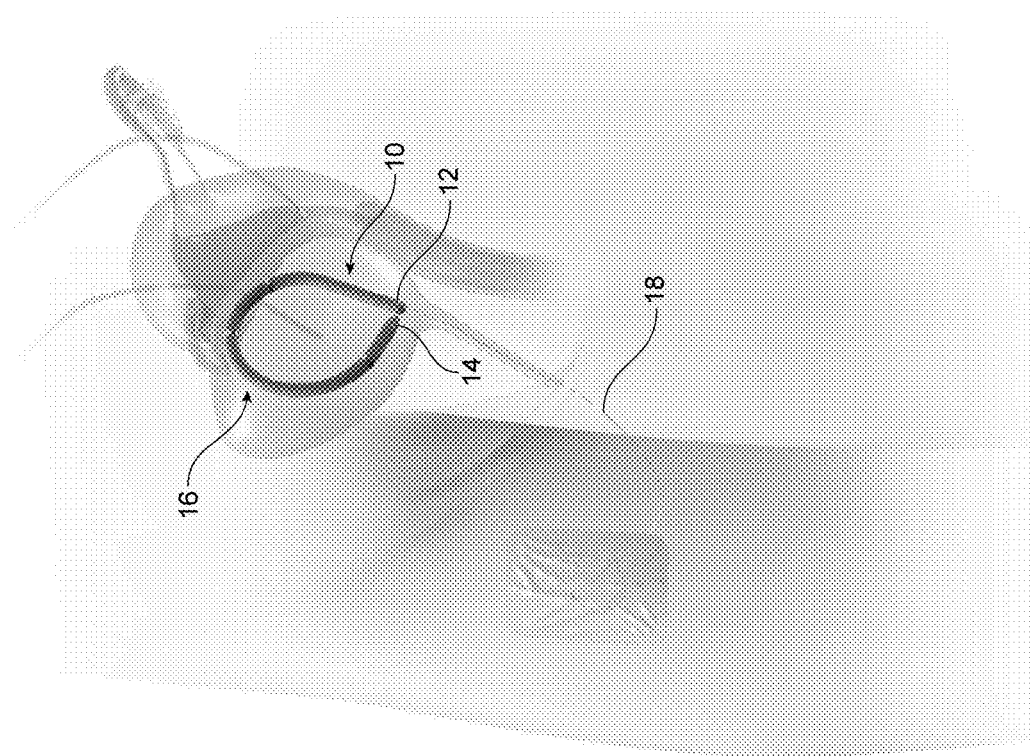
FIG. 4 is a partial side, perspective view of the sensor of FIG. 1 positioned in a human female bladder with the removal string secured to a patient's leg.
Figure 5:
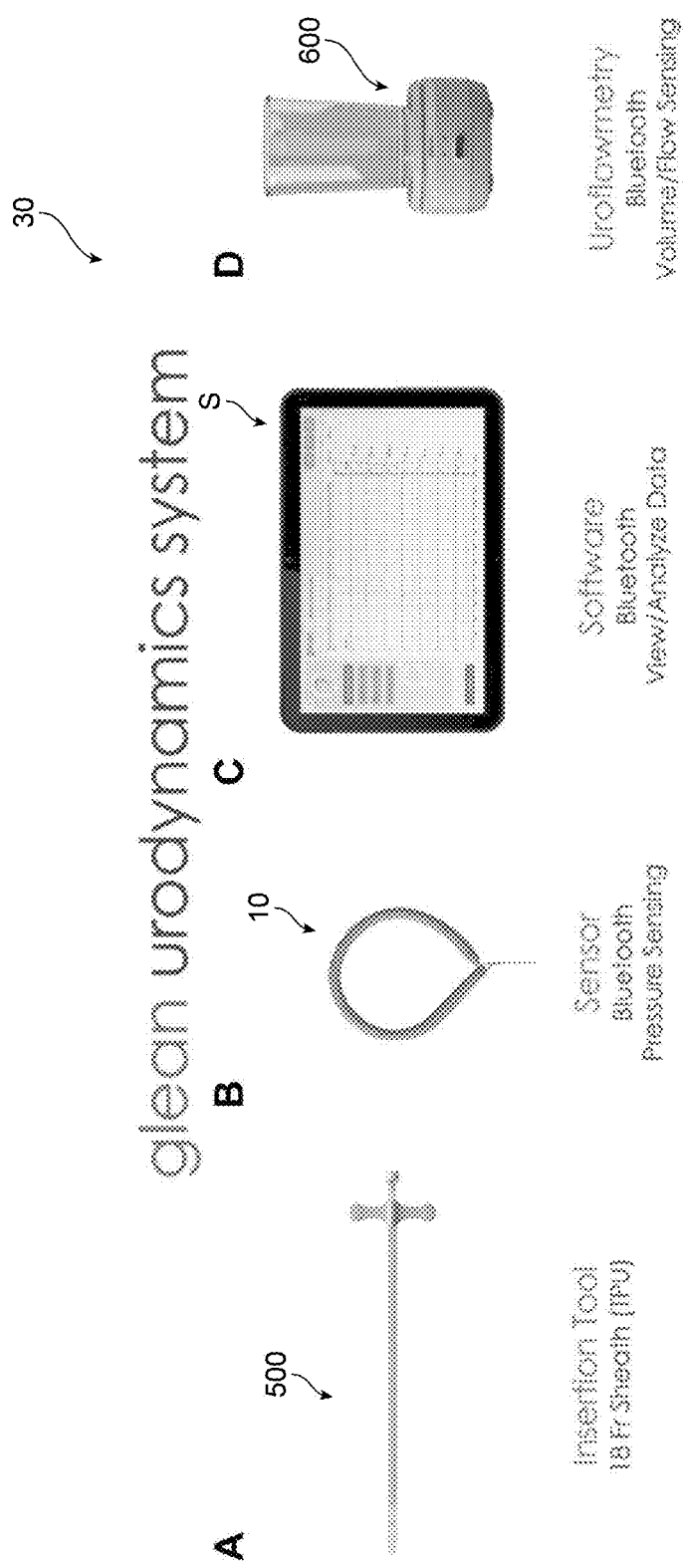
FIG. 5 illustrates a urodynamic sensor system and display according to this disclosure.

FIG. 4 shows sensor 10 in the bladder of a female human. FIG. 5 shows components a system 30 that comprises an insertion tool 500 (discussed herein) for inserting a sensor 10 into a bladder, a screen S to project data using a computer system 1000 (discussed herein) according to this disclosure, and a uroflow device 600 (discussed herein).

Figure 6:
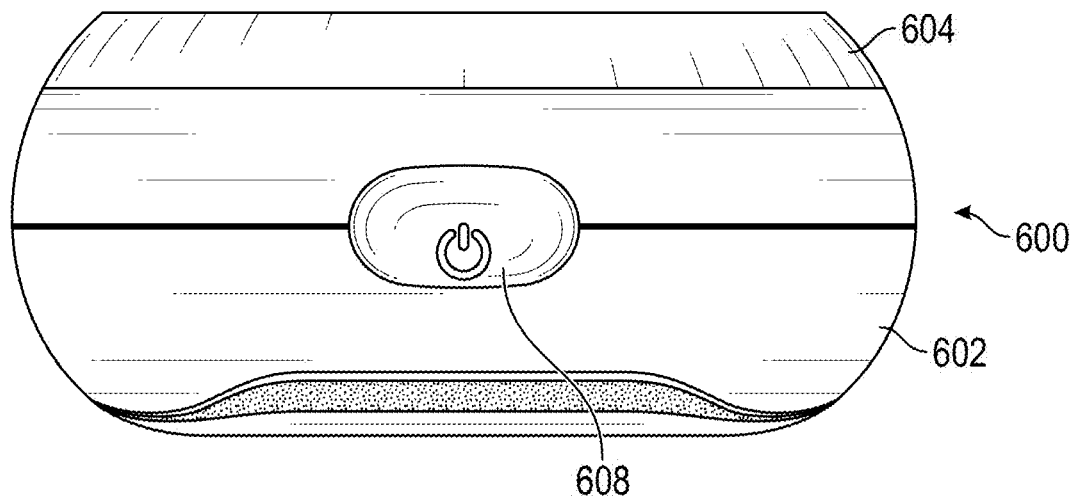
FIG. 6 is a front view of a uroflowmeter according to this disclosure.
Figure 7:
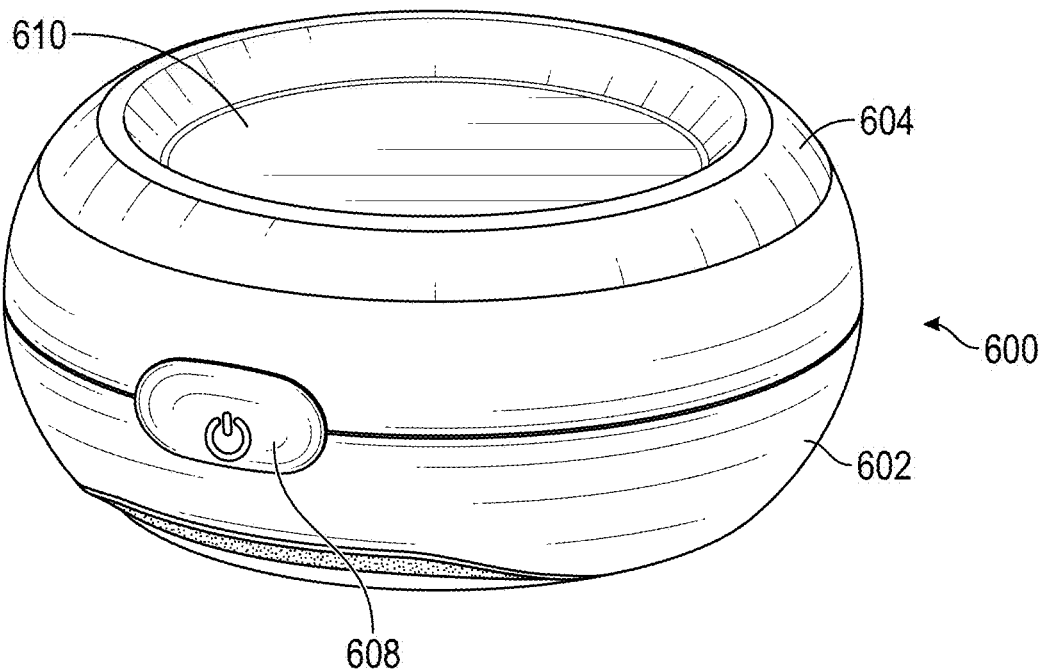
FIG. 7 is a top, perspective view of the uroflowmeter of FIG. 6.

FIGS. 6-7 show, respectively a side view and a top, perspective view of a uroflowmeter 600, which is a scale that has electronics configured to convert weight to volume. Uroflowmeter 600 has a body 602, a top 604, and an off/on indicator 608. As best seen in FIG. 7, the top 604 has a depression 610 configured to hold a beaker or other container that holds urine. Uroflowmeter 600 weighs the urine, which assists clinicians in analyzing a urine void event.

Figure 8:
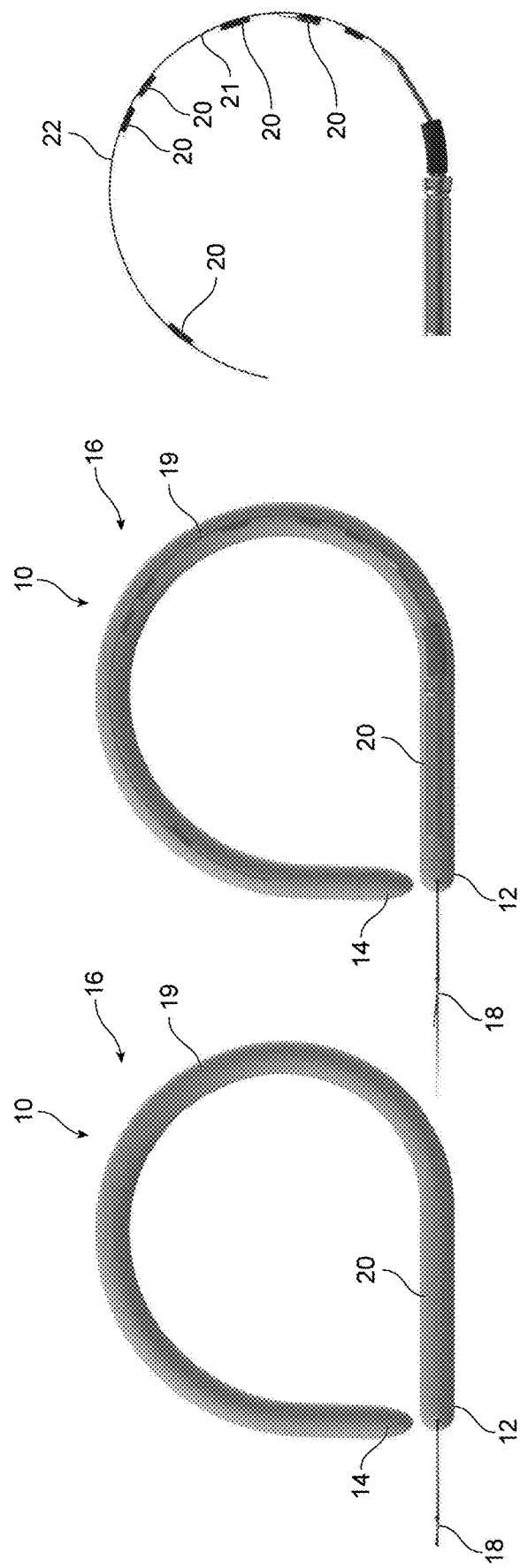
Figures 9, 9A, 9B:
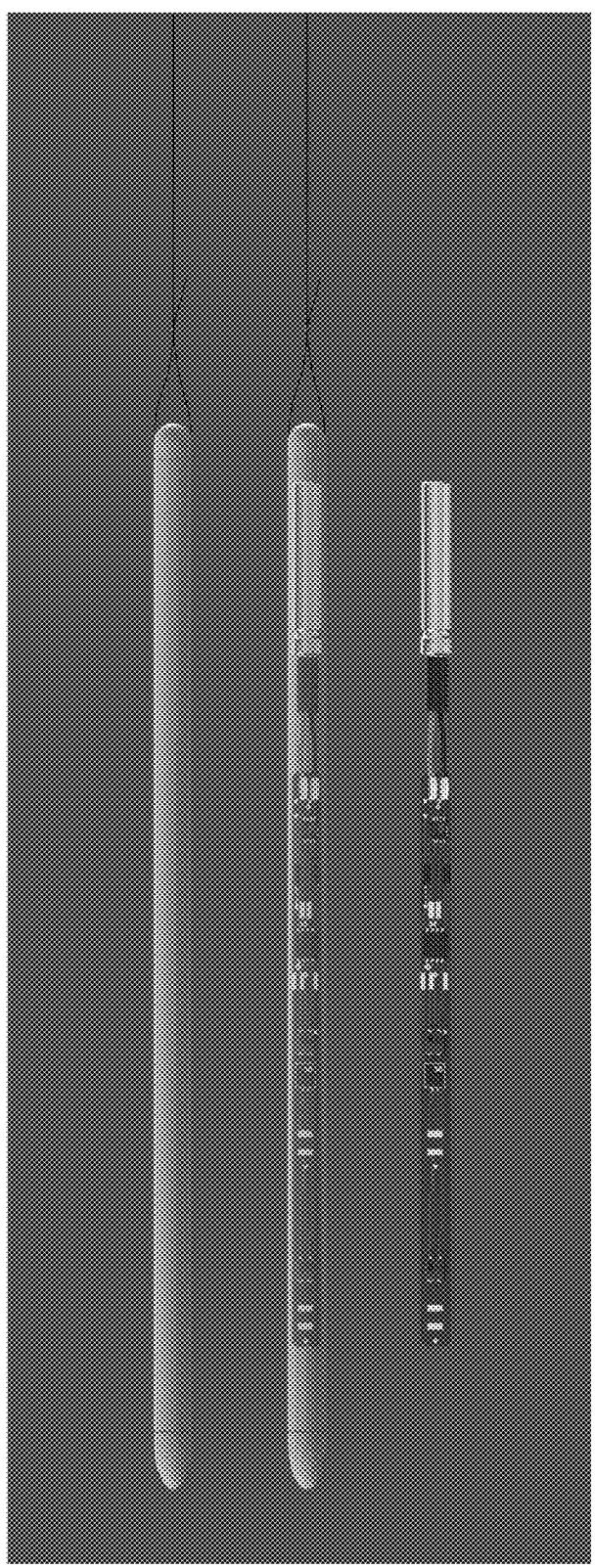
FIGS. 9-9B are top views of the sensors of FIGS. 1-3 in a straight position.

FIGS. 8, 8A, and 8B are side views, respectively, of the sensor of FIGS. 1, 2, and 3. FIGS. 9, 9A, and 9B are side views, respectively of the sensor of FIGS. 1, 2, and 3 moved to its second, straight position.

Figure 11:
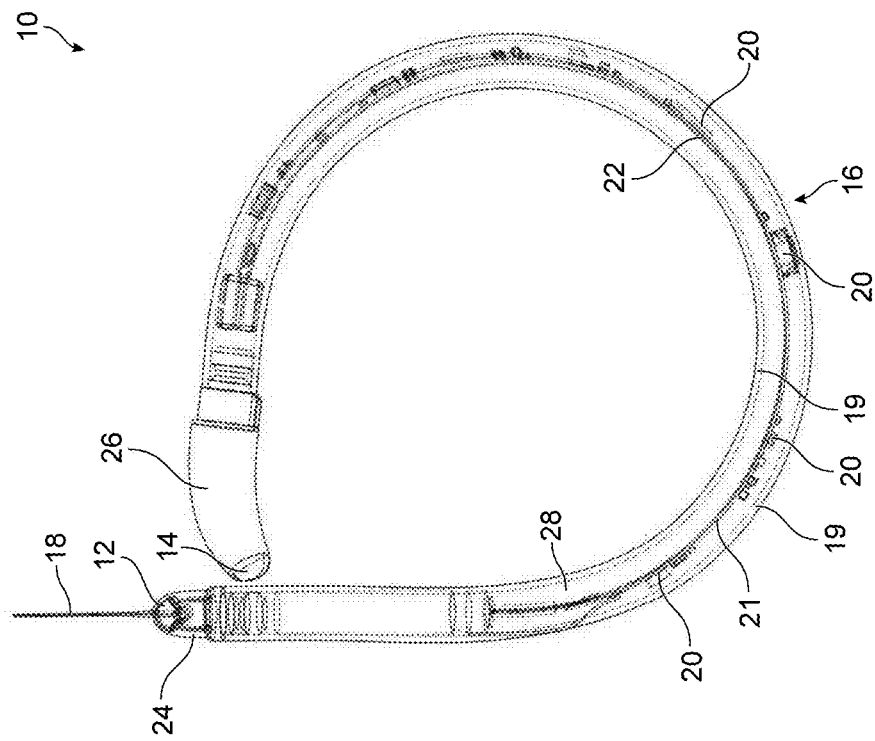
FIG. 11 shows the sensor of FIG. 10 with a clear outer wall so the internal components are visible.
Figure 10:
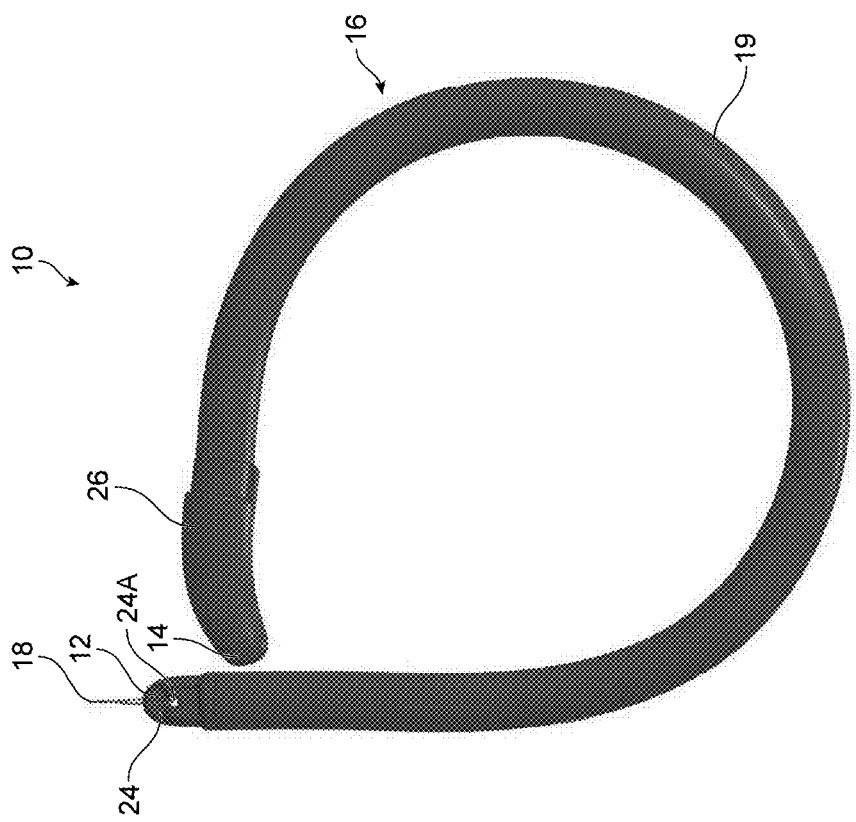
FIG. 10 is a top view of a sensor according to this disclosure with a removal string attached to its proximal end.

FIG. 10 is a top view of the sensor of FIGS. 1, 8, and 9 in its first, curved position. FIG. 11 is also a top view of the sensor of FIGS. 1, 8, and 9 in its first, curved position and depicting the outer sheath as clear so the internal electronics can be seen. In FIGS. 10 and 11 proximal end cap 24 and distal end cap 26 can more readily be seen. Proximal end cap 24 and distal end cap 24 are attached to tube, or outer sheath 19, such as by pressing them into cavity 28 with adhesive to secure them. Proximal end cap 24 has an aperture 24A for attaching to string 18. Distal end cap 26 preferably has a coude shape (e.g., curved) for easier insertion into a bladder.

A uroflowmeter 600 used to measure voided urine volume and changes to volume (flow).

Sensor 10

One embodiment of the sensor 10 may include:

A tubular outer housing (or "tube" or "outer housing" or "outer cover") preferably comprised of silicone elastomer or rubber, although any suitable material may be used, wherein the tube has a lumen (or "cavity") therethrough.

A flexible circuit board 21 with electronic components positioned inside of the tube.

A power source, such as a battery, positioned in the tube and preferably connected to the flexible circuit board.

One or more electronic parameter sensors, such as pressure and/or volume sensors, positioned in the tube and preferably on the circuit board, where they receive power from the power source.

In some embodiments, fluid, such as silicone oil, fills the cavity between the tubular outer housing and internal components. The fluid is preferably incompressible and electrically non-conductive.

A shape memory spring 22 that is positioned on the inside, part of, or outside of the tube and that is comprised of either steel, plastic, or other suitable material or some combination of materials. In one embodiment the shape memory spring 22 is welded to the bottom of the (i.e., the side that does not include circuitry) flexible circuit board 21. So, instead of, for example, using nitinol wire or injection molding to create a shape memory elastic housing, the flexible circuit board with the shape memory spring creates the specific shape for the sensor. In this case, the sensor has a generally circular or curved shape that prevents it from inadvertently being voided or discharged from the bladder. In some embodiments the spring 22 may be rectangular in cross-sectional profile to provide the appropriate profile for pushability and translation of force in a linear manner. This also provides additional support and rigidity for protection of the flexible electronic circuit board.

Endcaps 24, 26 for the tube are comprised of steel, plastic, silicone, or other suitable material. There is a distal end cap 26 and a proximal end cap 24.

A removal string 18 for pulling the sensor 10 and removing it from the bladder. The removal string may or may not be attached to an end cap and is preferably attached to the proximal end cap.

This sensor design enables reliable, low-cost manufacturing because the extruded sensor tubing is simple and inexpensive to make as compared to injection molding or nitinol hand assemblies. This sensor design also provides reliability and strength because the shape memory spring 22 is designed to provide sufficient torsional rigidity and hence increases the durability of the flexible circuit board (FCB) 21 and any electronic components attached to the FCB via soldering or other means.

The shape memory of the sensor 10 should preferably be sufficient to enable the sensor to be straightened for delivery through the urethra. Once delivered inside of the bladder, the sensor 10 springs back, or returns, to its original circular or curved shape. To achieve this a combination of manufacturing methods may be utilized including heat-treating, forming, and/or cold-rolling of the spring.

An additional benefit of the sensor 10 design is that the shape memory spring 22 may be flat and designed to mate with one or both endcaps and with the tube by creating the desired geometric configuration in each part. For example, the endcap mating could be used to provide additional stability and pushability in support of delivery. Side cutouts in the sensor housing would be used to provide reliable manufacturing and stability of the circuit as well.

This technique may be used with both endcaps whereby the spring is able to travel the entire length of the sensor housing, or from one endcap to a rigid or semi-rigid battery which is mechanically coupled to the battery. In this embodiment, the force may be transferred from one endcap to the battery to the spring to the other endcap.

In one embodiment, the shape memory spring 22 could translate force between each of the endcaps 24, 26 and act as a backbone or spine for the sensor 10. In another embodiment, the shape memory spring 22 could translate force from one endcap 24 or 26 to one or multiple components in the lumen of the tube. These embodiments are unique because they enable pushability and enable safe passage of the catheter through the urethra of the patient. Additionally, the rigidity of the spring 22 enables optimal mechanical properties that would otherwise be impossible to accomplish without drastically increasing the overall outer diameter of the sensor. By using the spring 22 the outer housing 16 of the sensor 10 can be reduced in overall outer diameter and also maintain flexibility. Ultimately, this design provides the optimal combination of soft material on the exterior coupled with mechanical strength for pushability which results in the best performance for any sensor insertion through the urethra of a patient.

The shape memory spring 22 could either be made using a manufacturing process to create a "flat spring," such as a leaf spring. Such a process could use either heat treating of the spring 22 to form, or use work hardening, each of which is known in the art. Work hardening of the shape memory spring is less likely to induce magnetic properties to the spring, and is most preferred in this disclosure.

In some embodiments, the shape memory spring (or simply "spring") 22 may be totally or partially coated with a material that prevents electrical contact with other components and prevents interaction with the circuit board. The coating material may also enable the shape memory spring to resist corrosion to increase the spring's reliability. This coating may be a material that is resistant to oils such as mineral oil. The coating may be applied using any suitable method, including spray or dip coating.

In another embodiment, shape memory may be obtained by using nitinol to provide the optimal mechanical properties for reliable configuration of the sensor.

Another option is to create the tube 16 using injection molding. To accomplish this, the mechanical properties and geometries of the materials used in the injection molding should be selected such that they can provide the proper amount of rigidity and flexibility while withstanding the tube's requirements for repeated actuation, i.e., repeated straightening and springing back to a circular or curved shape. This may be similar to a "living hinge" method of manufacturing.

The endcaps 24, 26 could be made from either a metal, rigid plastic, semi-rigid plastic, elastomer, soft rubber, silicone, or any suitable material. The endcaps may also be comprised of some combination of these materials. The endcaps could be of various shapes as long as they support insertion of the sensor using the insertion tool as described herein.

In some embodiments, the spring may be covered using a sheet of adhesive. The adhesive sheet may be comprised of a non-conductive material to prevent electrical interaction with the circuit board. This adhesive sheet may be cut in any suitable manner, such as by using laser cutting or a punch method. This is beneficial because it is desirable to leave some portion of the flexible circuit board free from attachment to the spring to ensure reliability and protection of the circuit. If the circuit board is fully attached to the spring with adhesive when in a circular configuration, when the sensor is straightened the circuit board would be compressed, which would create interference with the adhesive. This could result in either delamination of the circuit from the spring 22, damage to the electrical components on the circuit board 21, or other undesirable reactions.

In addition to the coating, a double-sided adhesive sheet made of electrically non-conductive material may also prevent electrical interference between the spring and the FCB 21. In some cases this may be manufactured in a method to streamline assembly including partial scoring which could enable select portions of the sheet to be prepared for adhesion while other parts remain non-adherent.

The adhesive may comprise materials that are resistant to solvents, oils, or other harmful fluids. For example, mineral or silicone oil may be used as lubrication because of its biocompatibility, but mineral oil and silicone oil can dissolve certain latex, plastics, and other rubber substances.

Attachment of the spring 22 to the flexible circuit 21 may also be accomplished using a mechanical process. In such an embodiment, the spring 22 may contain features designed to interact with the circuit board to provide a mechanical integration and enable reliable attachment with or without adhesive. This may improve flexibility of the sensor 10 and reduce bunching (or compressing) of the circuit board when attached to the spring and straightened. These mechanical features may be vias or other holes that are designed and created as part of the electronic circuit board and pegs that may be molded into the spring.

Insertion Tool

The insertion tool (or "tool" or "insertion device") 500, discussed in more detail below, delivers the sensor 10 to the bladder through the urethra and is generally comprised of the following components: an outer housing 504 with a handle 506; and a pushrod 530 with a handle.

The outer housing includes a channel or lumen through which the sensor can be delivered to the bladder. The outer housing also includes a tip 516, which could be of any suitable design including: a straight tip; a coude tip; a sheath tip; or a sheath tip with sensor endcap interaction.

In addition to the sensor endcap interaction at the distal end of the sheath, the proximal sensor endcap may be designed in a symmetric or asymmetric pattern to enable locking and translation of force rotationally through an interaction with a second lumen inside the sheath of the insertion tool. This would provide two methods of interaction to translate force rotationally and enable successful insertion of the sensor.

Both the straight and coude tip are similar to urological catheter tips, but include an angled tip with a key near the tip of the outer housing to enable the sensor to be delivered into the bladder. The angled tip design for the coude tip may offer greater advantage through column strength and mechanical rigidity or pushability when inserting into the urethra of a patient. This is because an angled tip that is on the top of the outer housing is directly on plane and may buckle from any force associated with the coude or straight tip during insertion. In this manner there could be advantages to the side port for certain patient anatomies such as a tight sphincter.

The sheath tip leverages the sensor endcap to perform the function of the tool tip. In this manner, the sensor endcap may also be designed as a straight or coude tip and constructed in a manner to simplify the insertion process. This could integrate two separate components designed to provide the optimal properties for insertion in the urethra such as pushability or navigation through challenging anatomies, such as bladder outlet obstruction and may be valuable for both female and male anatomies.

The sheath tip could also provide an added benefit because if the sensor is deployed before the tool is positioned properly in the bladder, then it would be unlikely to cause trauma to the tissue of the urethra. In this case, the sensor would essentially function as a urological catheter and be pushed through the urethra and into the bladder.

Regardless of the tip design, the material properties are selected to enable proper performance characteristics of the tool. This includes pushability, rigidity, trackability, and flexibility. The outer housing of the tool may be extruded from TPU, TPE, other similar materials, or any suitable material. To reinforce the pushability of the tube the tool may be reinforced with braided or coiled wire using stainless steel or similar materials.

The outer housing of the tool may also be marked with one or more markings to aid clinicians in understanding placement of the device using depth of the insertion. The markings could correspond to different sizes to incorporate either the anatomical requirements of that patient or using an average of multiple patients to determine the ideal depth of insertion for the device.

In some embodiments this may include a lower bound and upper bound based on the reported urethral lengths and statistical analysis from published literature. This would aid the clinician in understanding proper positioning of the sensor in the bladder.

The outer housing of the insertion tool may be optimized with the dimensions and mechanical properties of the sensor housing and pushrod to obtain optimal device performance. This allows for simple and easy insertion while reducing the outer diameter of the outer housing. This could also enable the outer housing to be extruded and maintain kinkability and pushability with very small tubing dimensions. This greatly reduces cost and complexity for the device because extrusion is much cheaper than braided or coiled tubing and requires less money and time to manufacture.

In some embodiments the sheath may be designed with a total length and flexibility such that the tool may be inserted completely until the handle of the tool reaches the urethral opening. With the optimal flexibility the sheath and sensor are unlikely to injure the patient's bladder. This is optimal to simplify the training for the clinician and ensure they are in the bladder when the sensor is deployed.

In some embodiments, the pushrod may be injection molded from a semi-rigid plastic or elastomer. This could also be molded in an asymmetric or non-uniform shape to obtain the optimal mechanical properties of the device.

To prepare the tool and sensor for insertion, the sensor is inserted into a first lumen of the outer housing (or "over sheath") of the tool. In some embodiments, the removal string may be pre-positioned such that the clinician only needs to lubricate the sensor and pull the string until it locks in the insertion tool.

Once the sensor is in place, the sheath and sensor are prepared for insertion into the urethra of the patient. The sheath and sensor will be inserted until the sensor tip reaches the bladder. The clinician will then use the pushrod to deploy the sensor into the bladder. In some implementations, urine may flow around the pushrod and out of the sheath. For example, in some implementations, the push rod (for example, a stem of the push rod) has an outer diameter that is smaller than an inner diameter of the sheath such that urine can flow around the push rod and through the sheath. The pushrod may also contain a lumen to enable flow of urine through the pushrod. This is particularly helpful for the clinician to confirm proper placement of the sensor in the bladder.

Depth markings or length measurements may be (such as by being pad printed) on the outer housing tubing to help clinicians confirm proper placement of the sensor in the bladder.

In another embodiment, the outer housing may incorporate a second lumen configured for urine to flow therethrough once a certain portion of the tool has reached the bladder. This could aid in proper placement of the sensor because a user would know the tool is in proper position for insertion into the bladder. The second lumen could also be temporarily filled by a wire or other structure to ensure reliable flow of urine by preventing lubricant from clogging the second lumen. The wire or other structure would be removed when the user felt the tool was in the bladder to permit the passage of urine through the second lumen.

One embodiment of the insertion tool may be designed in a manner to further improve the pushability of the sensor and insertion tool. This embodiment is similar to the sheath design but by using an expanded sensor endcap that overlaps the sheath inner diameter (ID) the design transfers force directly from the sheath to the endcap, whereas the sensor in the sheath design previously described has no such ability and relies on the transfer of force from the pushrod to the sensor. In this embodiment, it may be possible to decrease the outer diameter (OD) of the sheath by leveraging this interaction between the sensor endcap and the sheath of the insertion tool.

In another embodiment of the over sheath with endcap interaction, the endcap may be designed in a manner to provide accurate rotational positioning of the sensor endcap and the sheath. One manner to accomplish this is to provide one or more keys and keyways in the end of the sheath and one or more corresponding, mating features on the sensor endcap that would enable precise rotational positioning of the sensor and the tool. This would enable the translation of rotational force between the handle of the insertion tool sheath to the sensor endcap. This could be valuable because in some instances, the patient anatomy may be challenging for insertion and require a coude or rounded tip. This version of our device would allow clinicians to control the rotational orientation of the sensor endcap (i.e., the tip) as it advances through the urethra.

The rotational positioning may be indicated to the clinician through one or more markings, such as one or more features molded into the handle of the sheath or lines or other markings on the insertion tool sheath, which can be added in any suitable manner, such as by co-extrusion or pad printing.

This embodiment would also enable the sensor to be loaded into the insertion tool by the string pulling it through instead of the sensor being pushed into the sheath by the pushrod. The string may also be secured to the proximal end of the pushrod to prevent any movement or premature deployment of the sensor.

Sensor and Insertion Tool Example 2

Sensor Endcap (or Tip) Integration with the Insertion Tool

The sensor and insertion tool of this Example 2 is the same as the sensor and insertion tool of Example 1 except as noted herein. Sensor distal tip (or insert, or end cap) integration with the insertion tool sheath allows for rotational orientation of the sensor using the handle or sheath of the insertion tool by gripping and rotating the insertion tool handle, which in turn rotates the sensor including its distal tip. In this manner a user can rotate the sensor by the same amount as the insertion tool is rotated and locate the distal tip of the sensor at the proper position for insertion into the bladder. Then the sensor is pushed, using a push rod out of the insertion tool and into the bladder without (or with minimal) trauma to the patient.

Figure 12:
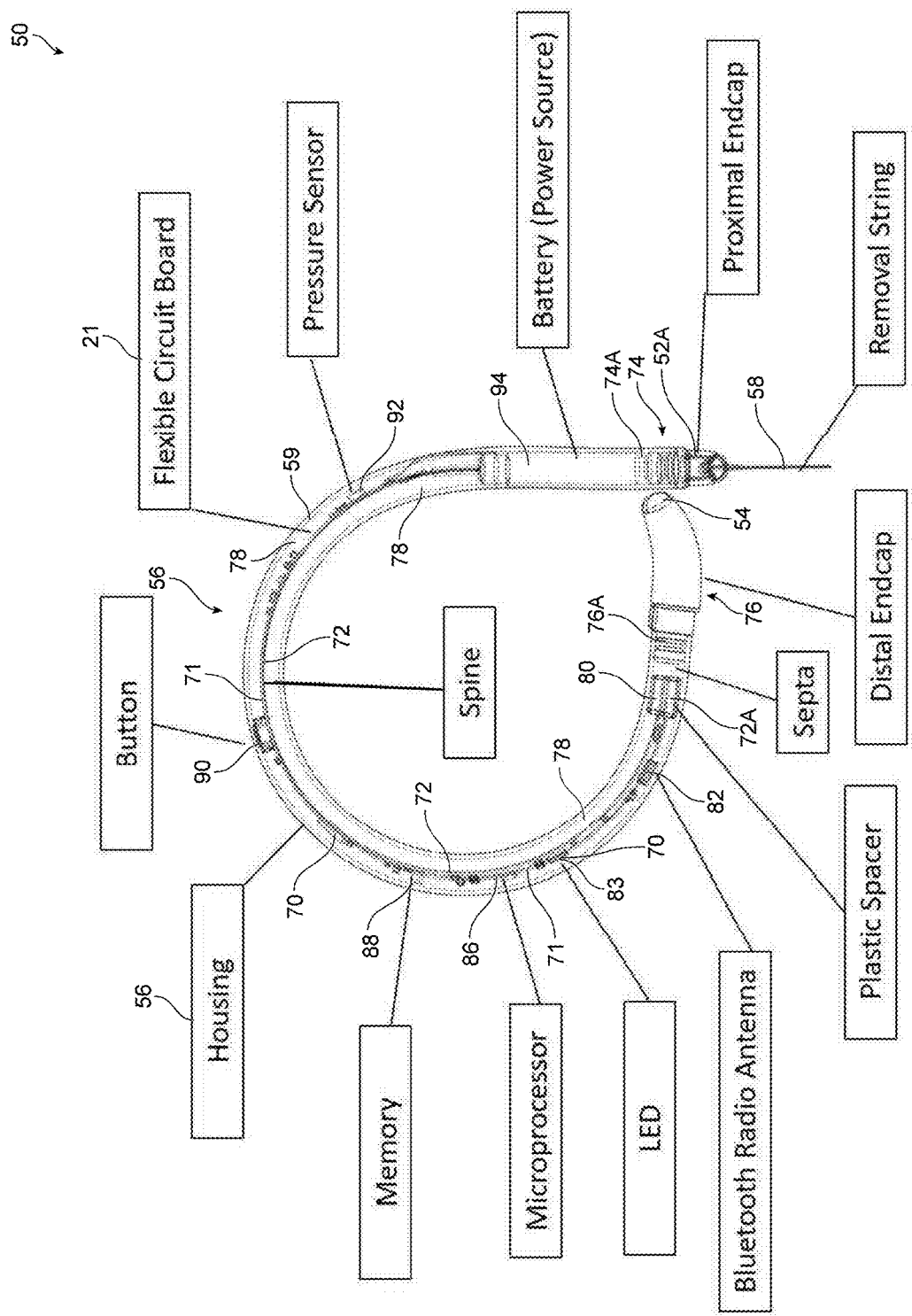
FIG. 12 shows a side view of an alternate sensor with various components labeled.

FIG. 12 shows an alternate embodiment of a sensor 50 according to this disclosure. Sensor 50 has a proximal end 52, a distal end 54, a body 56 with an outer wall (or tube or outer sheath) 59 that is comprised of silicone rubber (or elastomer). Proximal end cap 74 has an aperture 52A that attaches to removal string 58. Removal string 58 is used in the same manner as previously described string 18. Proximal end cap 74 and distal end cap 76 are attached to tube 56 in the same manner as previously described end caps 24, 26 and tube 16. As shown, proximal end cap 74 has a narrow section 74A that fits in the cavity 78 of tube 56 and distal end cap 76 has a narrow section 76A that fits inside the cavity 78 of tube 56.

A flexible circuit 71 retains electronics 70 and a spine 72 is attached to flexible circuit board 71 on the side opposite electronics 70, preferably by welding spine 72 to flexible circuit board 71. Spine 72 is biased to a first, curved position, which biases sensor 50 to its first, curved position.

A spacer 80 is preferably comprised of plastic or other soft material and covers end 72A of spine 72. This protects the inner wall of tube 56 from being torn by end 72A.

The electronics on this version of sensor 50 include a Bluetooth radio antenna 82, and LED 83, a microprocessor 86, a memory 88, a button 90 configured to turn sensor 50 off and on, and a pressure sensor 92, which measures the pressure of urine in the bladder when sensor 50 is positioned in a bladder. A power source 94, such as a buttery, is positioned in tube (or housing) 56 and supplies power to the electronic components 70 through flexible circuit board 71.

Figure 17:
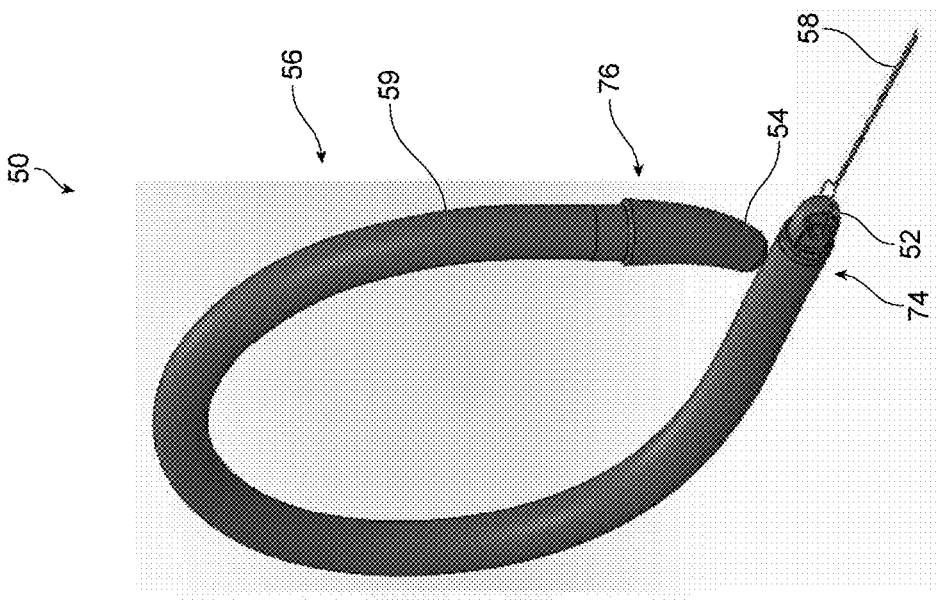
FIGS. 15-17 are side, isometric views of the sensor of FIGS. 12-14.
Figure 16:
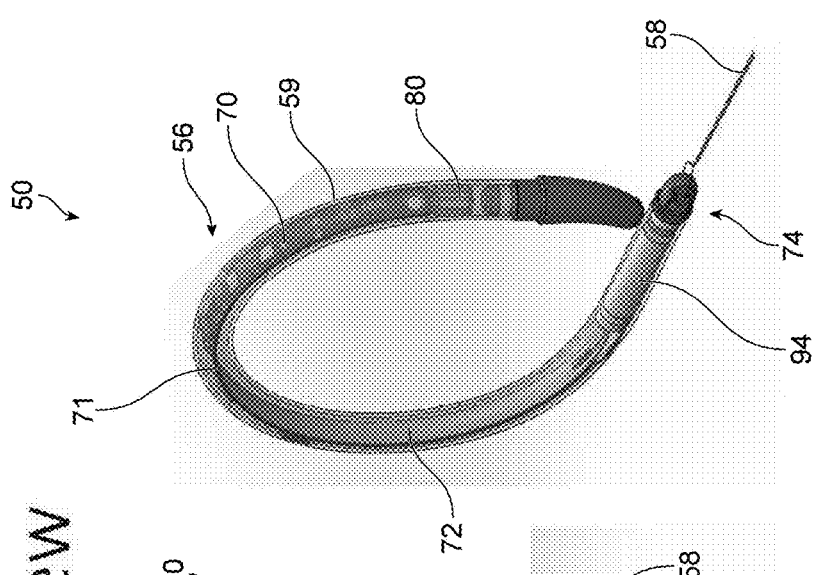
Figure 15:
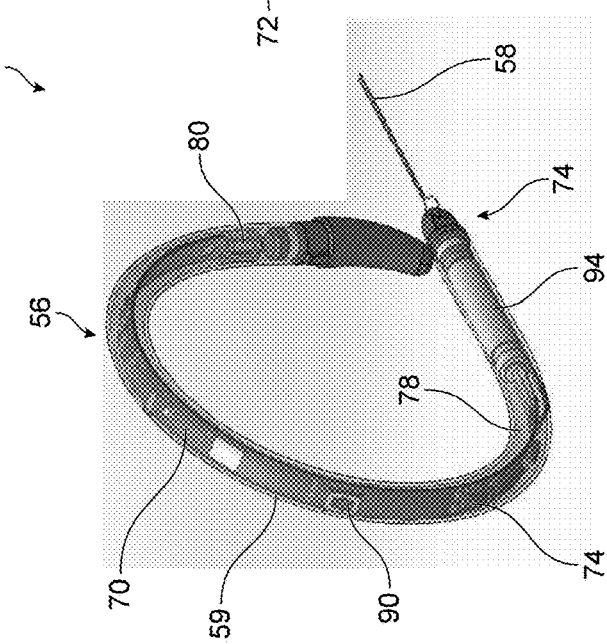

FIGS. 13 and 14 are top views of sensor 50. FIGS. 15-17 are isometric views of sensor 50 with FIGS. 15-16 showing the tube as clear so the internal components of sensor 50 can be better seen.

FIGS. 18-22 show close-up views of some internal components of sensor 50 with tube 56 being shown as clear.

Figure 24:
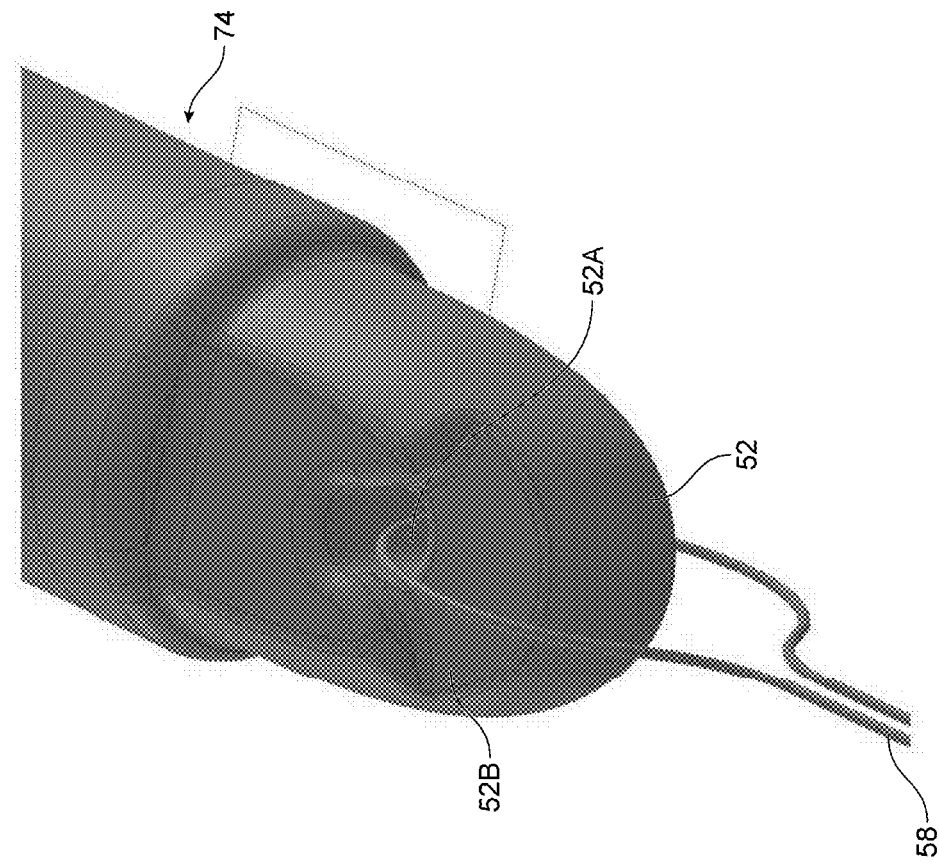
FIG. 24 is a close-up, partial view of the proximal tip of the sensor of FIG. 21 with the removal string attached.
Figure 23:
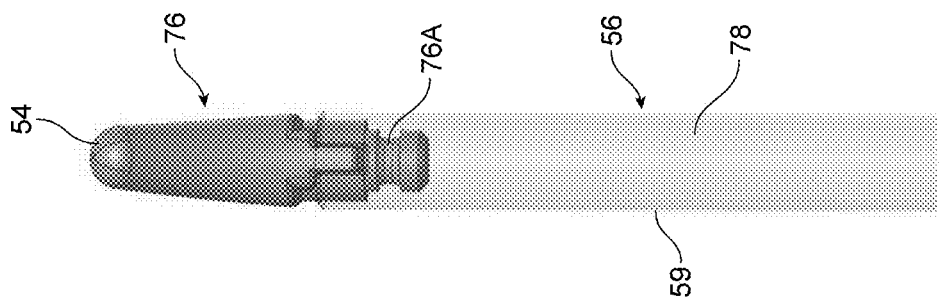
FIG. 23 is a partial, top view of the distal end of the sensor of FIG. 21 showing the distal tip.

FIG. 23 shows a front view of a distal end cap of sensor 50 with the curve, or coude tip, facing forwards with narrow portion 76A inside of cavity 78 of tube 56. FIG. 24 is a close-up view of proximal end cap 74. Opening 52A, which connects to removal string 58 can be seen as can dual-flat connective portion 52B. Dual-flat connective portion 52B is on each side of proximal end cap 74 and is configured so a clinician can grasp proximal end cap 74 with a tool, such as forceps, and pull it out of a bladder.

FIGS. 25 and 26 show an insertion tool 500 according to this disclosure. Insertion tool 500 has an elongated body or sheath 502 with an outer wall 504, a sheath reinforcement 504 at its proximal portion, which is the portion of sheath 502 nearest the handle 506. A visual indication 508 that enables a clinician to see inside of lumen 510, a drainage hole 512 through with a push rod will pass and permits drainage of urine from the bladder through drainage hole 512 when a sensor, such as sensor 50, is properly positioned in a bladder.

A D-lock 514 is a structure of, or in, lumen 510 that mates with or otherwise connects to the proximal end cap, such as proximal end cap 74, to prevent sensor 50 from advancing any farther into lumen 510 and to engage proximal end cap 74 in order to translate rotational force to sensor 50 when handle 506 and insertion tool 500 are rotated. Insertion tool 500 further has a distal end (or sheath tip) 516 having a sheath tip insert 518. Sheath tip insert 518 is where a sensor, such as sensor 50, is inserted into sheath 502 prior to insertion into a bladder. When sensor 50 is inserted its proximal end cap 74 is blocked from advancing by D-lock 514. Distal end cap 76 has a protruding structure, such as a key or other projection, that is received in sheath key insert 518, which as shown is a slot or keyway. Distal end cap 76 extends outward from sheath tip 516 and rotational force is transmitted to it by sheath tip insert 518 when handle 506 and insertion tool 500 are rotated. In this manner, a clinician can rotate the distal end cap 76 until it is aligned with the bladder opening. In some implementations, sheath 502 does not include D-lock 514. In some implementations, sheath 502 does not include a lock structure that is configured to engage end cap 74 when end cap 74 is arranged within the sheath 502. In some implementations, sheath 502 comprises a single cross-section throughout its length.

Figure 27:
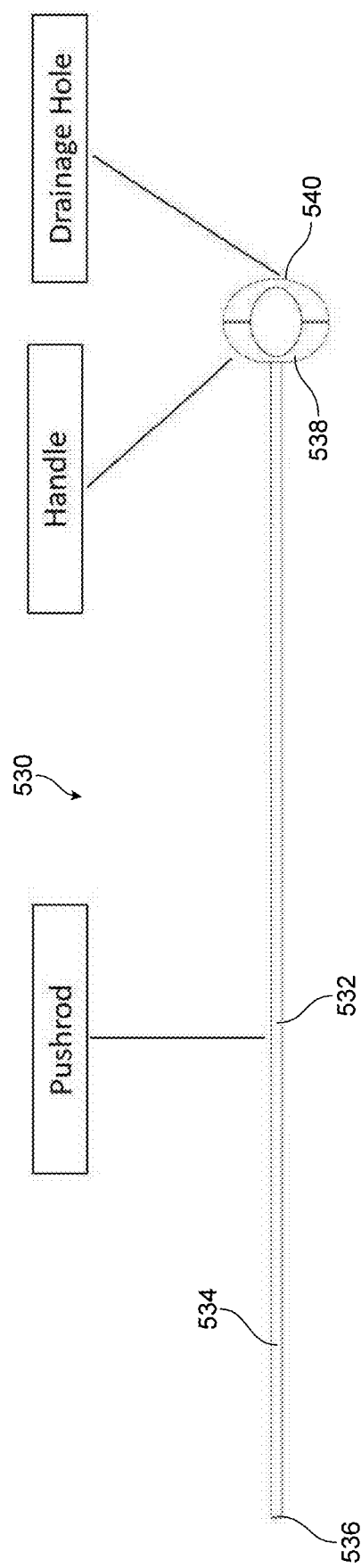
FIG. 27 is a side view of the handle with push rod to be used with the sheath of FIGS. 25-26.
Figure 43:
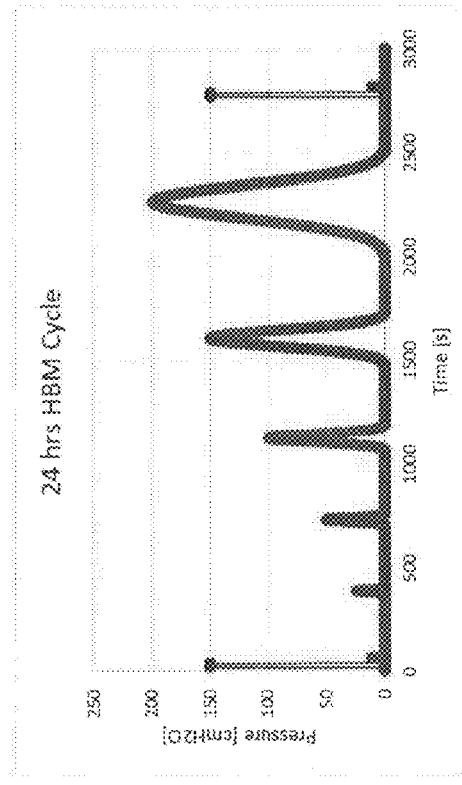
FIG. 43 shows a test protocol run on a sensor 12.

FIG. 27 shows a push rod 530 that is used with insertion tool 500. Push rod 530 pushes a sensor, such as sensor 50, out of lumen 510 and into a bladder. Push rod 530 has a stem 532 with a tip 536 and preferably a lumen 534 through which urine can pass. Stem 532 is connected to a handle 538 that preferably has a drainage hole 540. In some implementations, stem 532 does not include a lumen.

When a sensor, such as sensor 50, is in insertion tool 500 and properly positioned to be deployed, tip 536 and stem 532 of push rod 530 are pushed by a clinician through drainage hole 540 and into lumen 510 of insertion tool 500. This pushes sensor 50 out of lumen 510 and into the bladder. Urine moving through lumen 534 (if utilized) indicates that sensor 50 is fully positioned in a bladder. In some implementations, the urine may flow around the pushrod stem 532 and out of the lumen 510 of sheath 502. For example, in some implementations, the stem 532 of push rod 530 has an outer diameter that is smaller than an inner diameter of the sheath 502 such that urine can flow around the stem 532 and through the sheath 502.

FIG. 30 is a close-up view showing the lumen 510 and D-lock 514. As shown, lumen 510 has a large-diameter section 510A and a narrower-diameter section 510B through which the proximal end cap 74 of sensor 50 cannot pass. FIG. 28 is a close-up view showing sheath tip insert 518.

FIG. 29 is an end view of handle 506 in which drainage hole 512 and visual indicator 508 are visible. As can be seen, portion 510B of lumen 510 has a curved top, curved bottom, and flat sides.

FIG. 31 shows a side view of sensor 50 in its straight position when moved into insertion tool 500. FIG. 32 is a close up view of sheath tip 516 of insertion device 500 showing sheath tip insert 518. FIG. 33 is a close-up view showing the proximal end cap 74 and retrieval string 58 of sensor 50 positioned in the sheath of insertion tool 500.

FIG. 35 is a test protocol on identified sensors 1, 2, and 3. FIG. 36 shows a test protocol used on identified sensors 1, 2, and 3. FIG. 37 shows a test protocol on identified sensors 1 and 3 FIG. 38 shows a test protocol run on identified sensors 4, 5, and 6.

FIG. 39 shows a test protocol run on identified sensors 4 and 6. FIG. 40 shows a test protocol run on a sensor designated as sensor 8. FIG. 41 shows a test protocol run on a sensor identified as sensor 10.

FIG. 42 shows a test protocol run on a sensor identified as sensor 12.

FIGS. 44-44B show a sensor 50 and a battery 94 with its positive and negative connections, 95 and 97, respectively.

Figure 49:
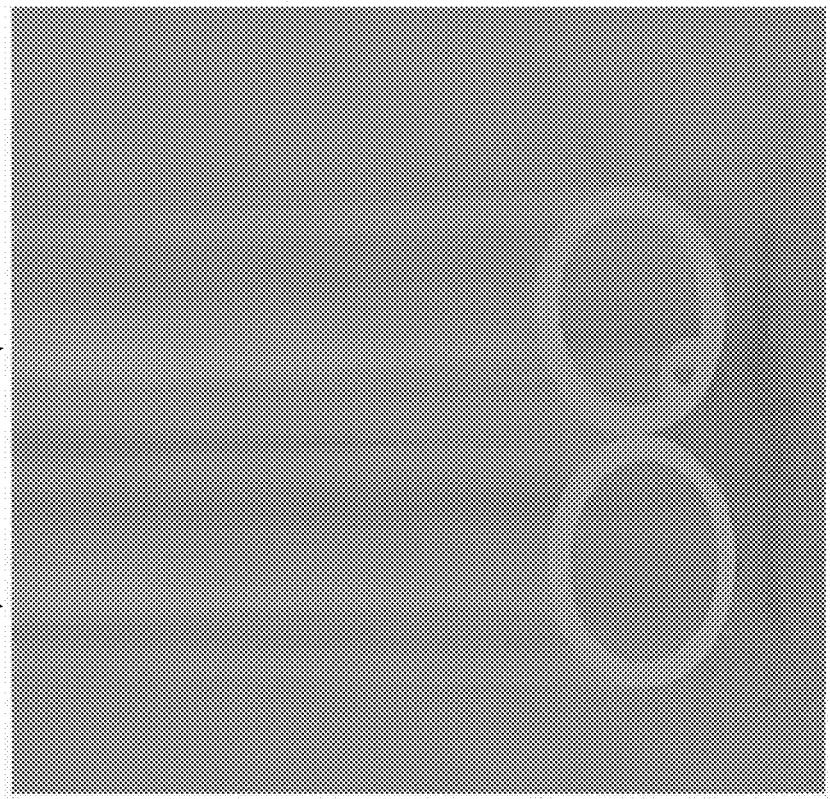
FIG. 49 shows silicone rubber extrusions that can be used to make the outer sheath (or "outer wall," "outer housing," "tube," or "outer tube") of a sensor according to this disclosure.
Figures 50, 51A, 51B:
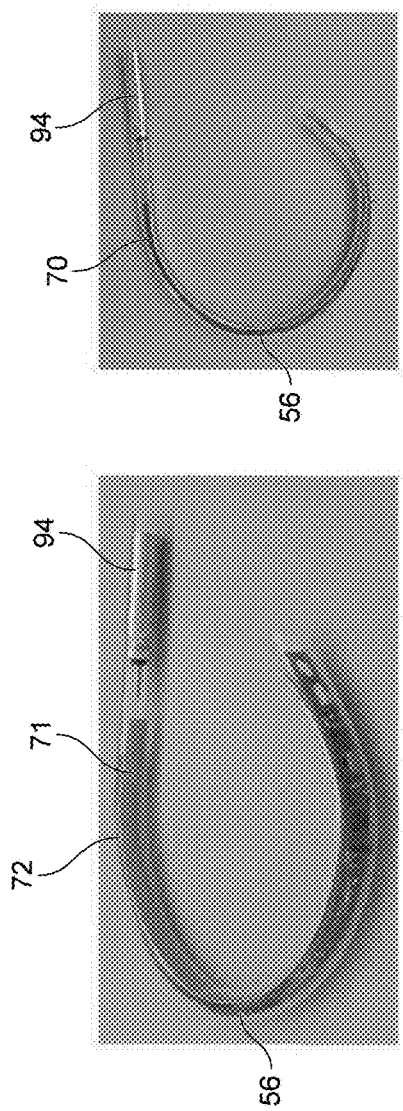
FIG. 50 shows a top, perspective view of a sensor with an outer sheath including the inner electronics and spine of a sensor according to this disclosure.
FIG. 51A is a top view of the sensor of FIG. 50.
FIG. 51B illustrates a spine being inserted into an outer sheath of a sensor.
Figure 58:
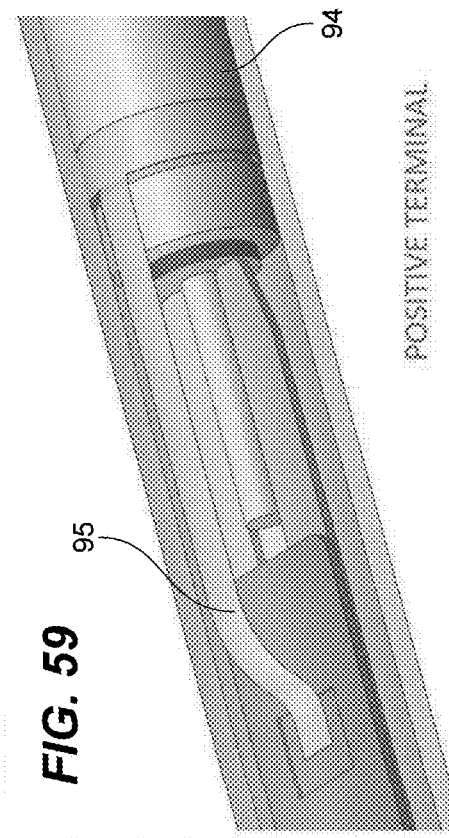
FIGS. 57-59 show cut-away images of a sensor positive electrical contact and negative electrical contact structure to provide power to the internal sensor components.
Figure 59:
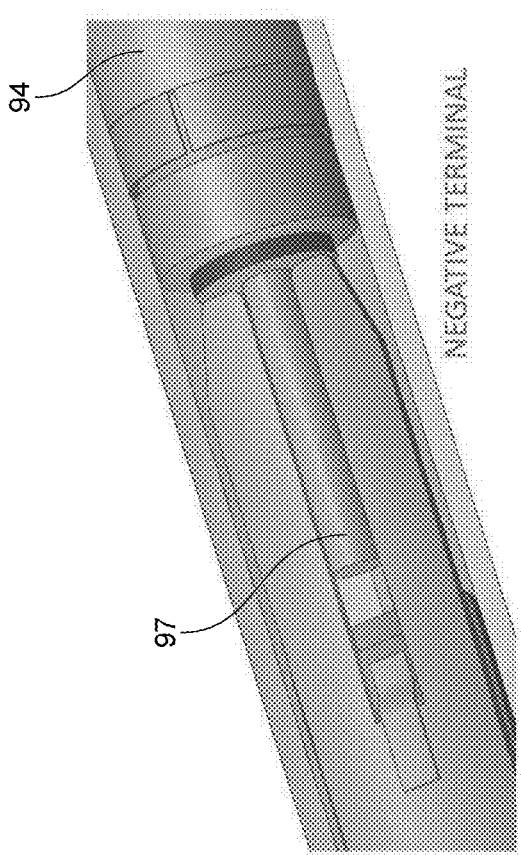
Figure 57:
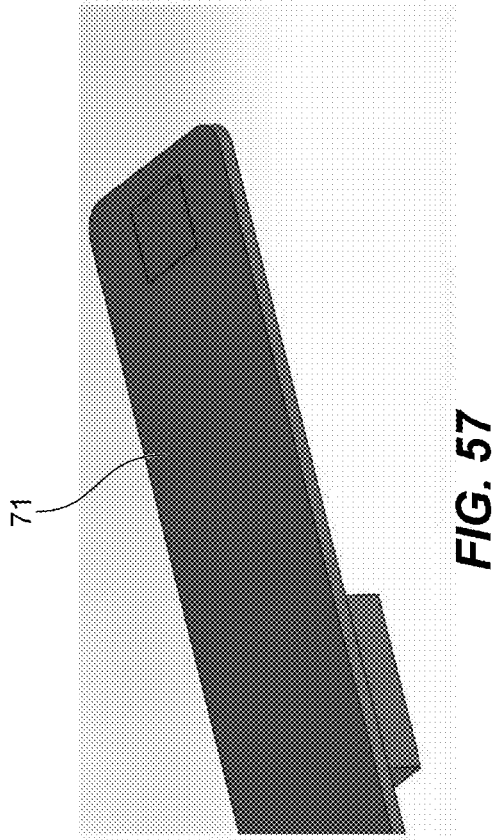
Figure 65:
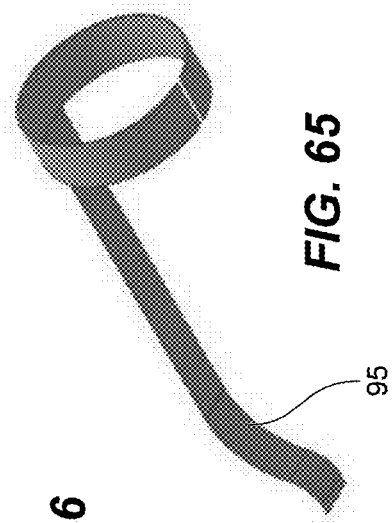
FIGS. 65-68 show various views of a battery connector for a sensor according to this disclosure.
Figure 66:
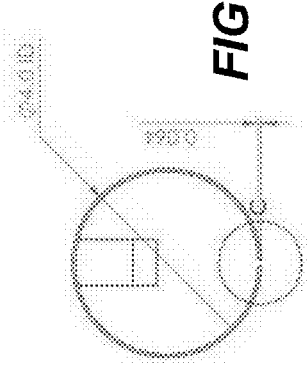
Figure 67:
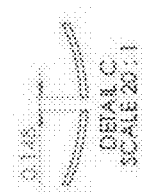
Figure 68:
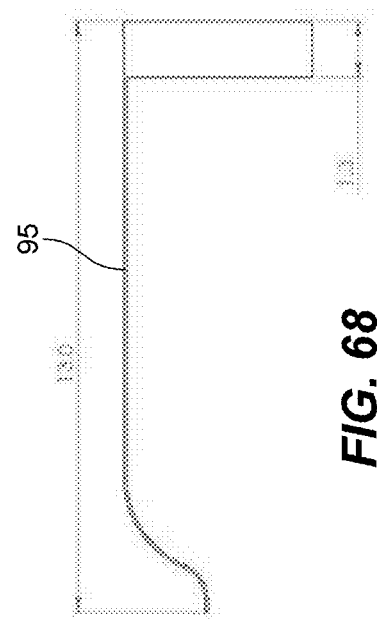

FIGS. 45-48 are views of a sensor 50. FIG. 49 shows silicone rubber extrusions that can be used as the outer sheath for sensor 50. FIGS. 50-51B show prototypes of sensors according to this disclosure showing the spine 72, flexible circuit board 71, and electronics 70 positioned in a tube 56. FIGS. 52-53 show a spine 72. FIG. 57 is a partial image of a spine 71. FIG. 58 shows a positive terminal 95 of battery 94. FIG. 59 shows a negative terminal 97 of battery 94.

FIGS. 60-64 show a possible assembly process of a sensor 50. At FIG. 64 the electronics 70 are connected to the flexible circuit board 71. At FIG. 63 the spine 72 is connected, such as by welding, to flexible circuit board 71. At FIG. 62, battery 94 and positive lead 95 and negative lead 97 are connected. At FIG. 61, the assembled flexible circuit board and spine are inserted into outer sheath 56. At FIG. 60, end caps 74 and 76 are attached and cavity 78 is filled with silicone oil to a pressure greater than atmospheric.

Figure 70:
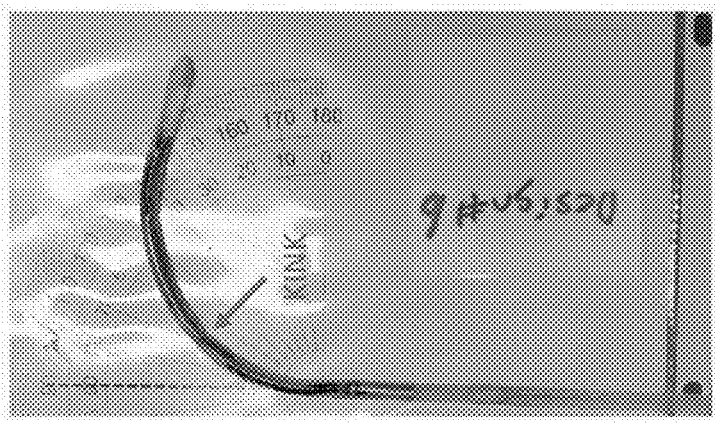
FIGS. 70-72 illustrates the flexibility of different sensor designs.
Figure 71:
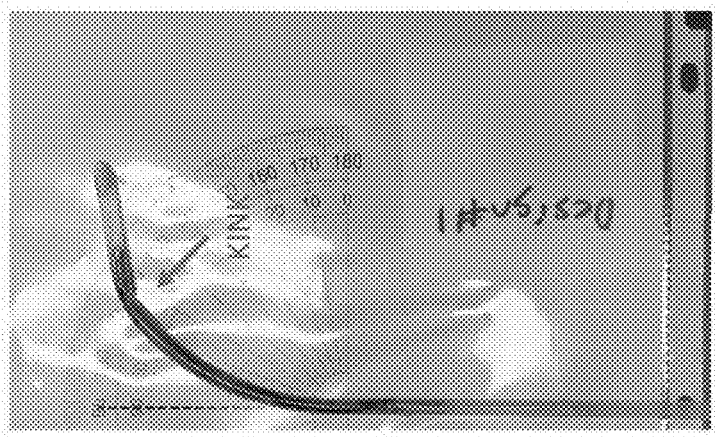
Figure 72:
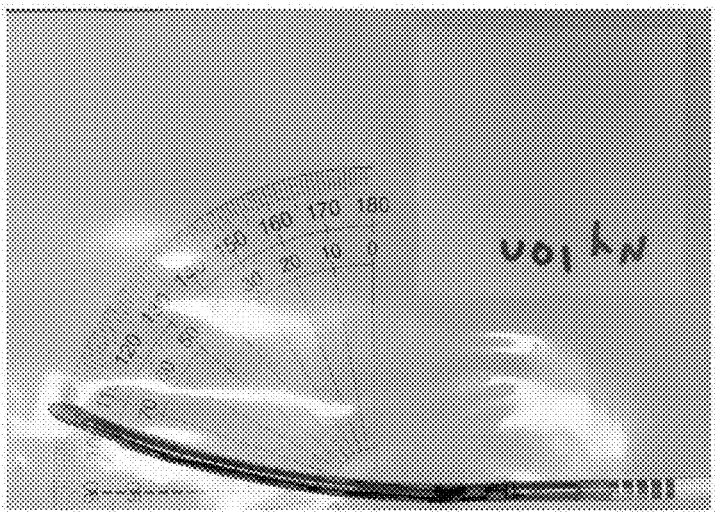
Figure 74:
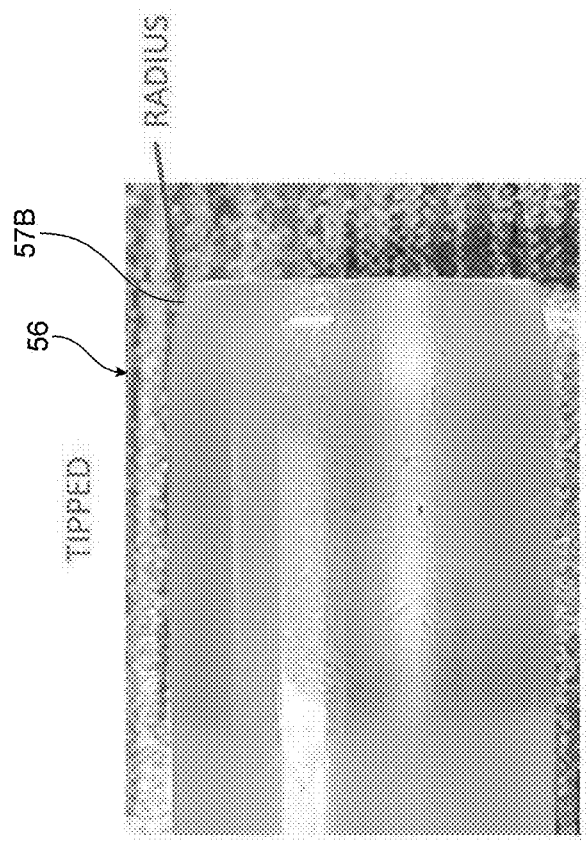
FIGS. 73-74 show partial, side views of a sensor tube with an end that is not tipped versus one that has a radiused tip for eliminating trauma.
Figure 73:
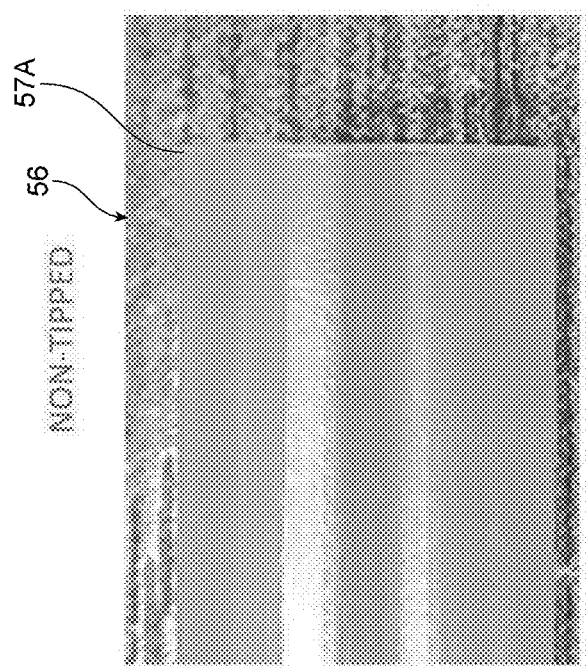
Figure 78:
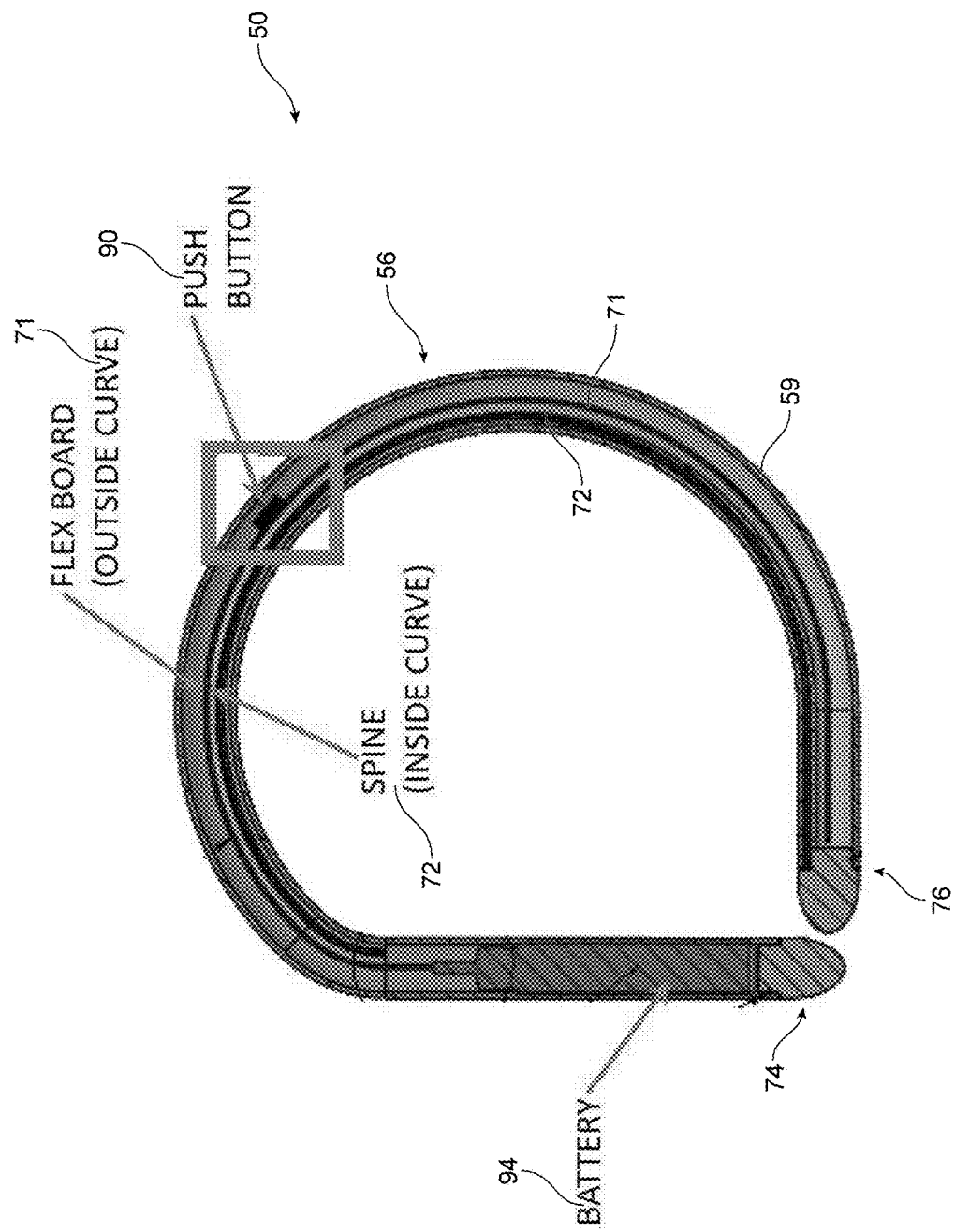
FIG. 78 shows a side view of a sensor according to this disclosure.
Figures 88, 89:
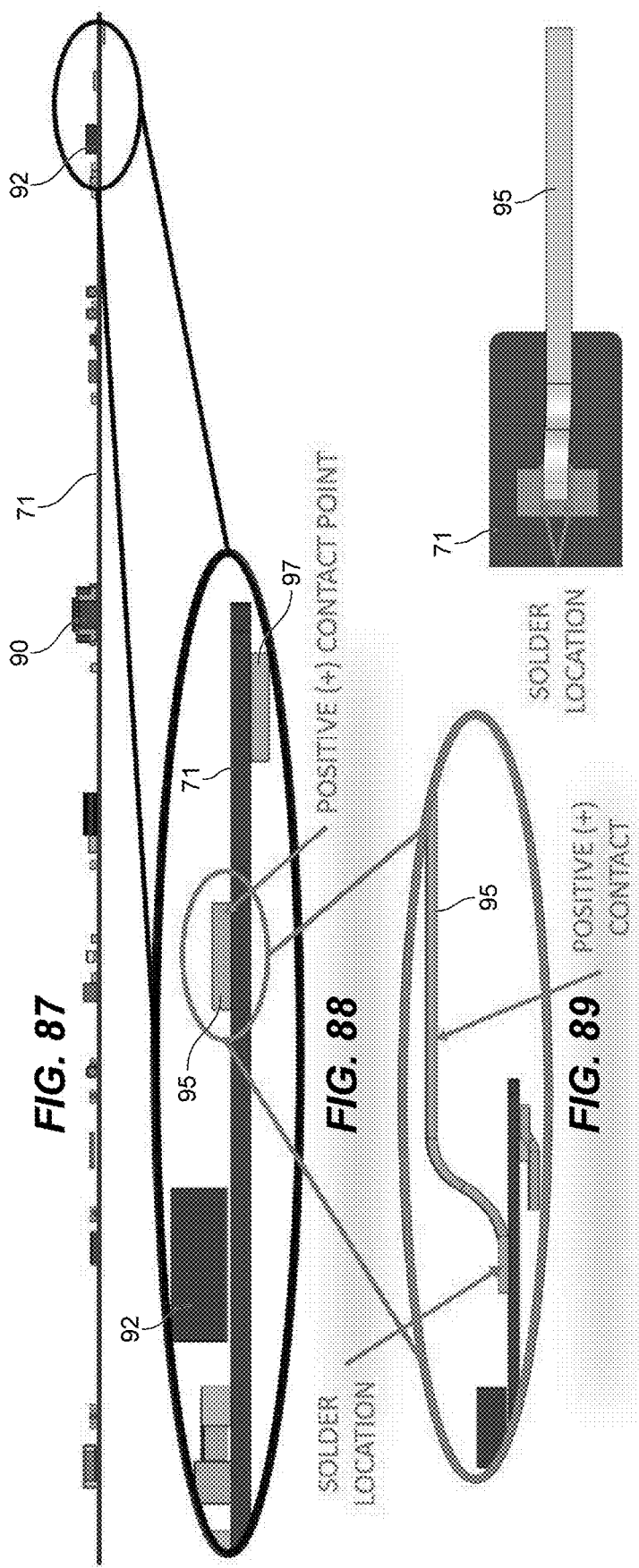
Figure 90:
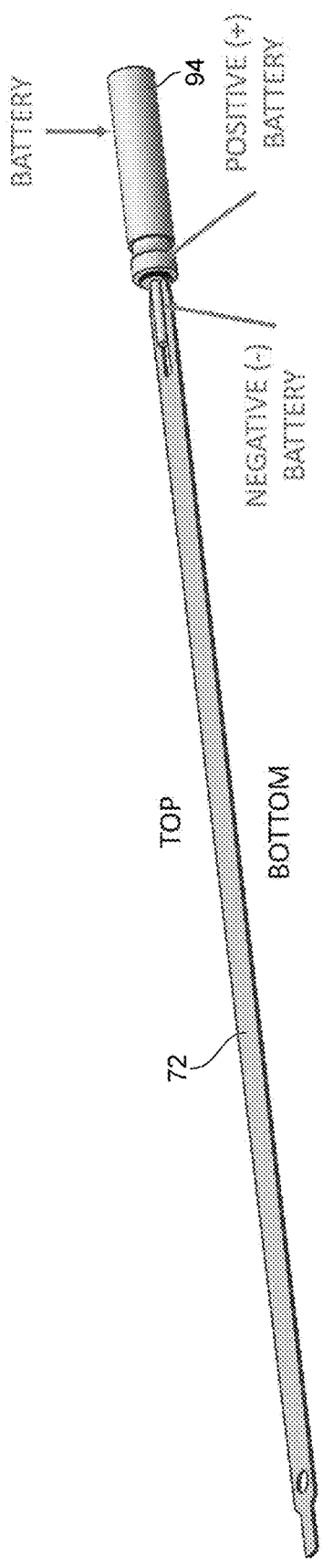
FIGS. 90-92 show side views and a side, perspective view of a battery and spine that indicate where welds are placed.
Figure 91:
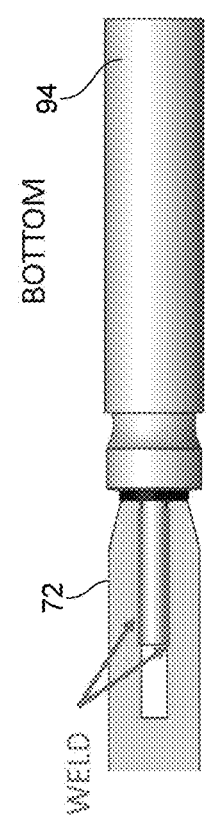
Figure 92:
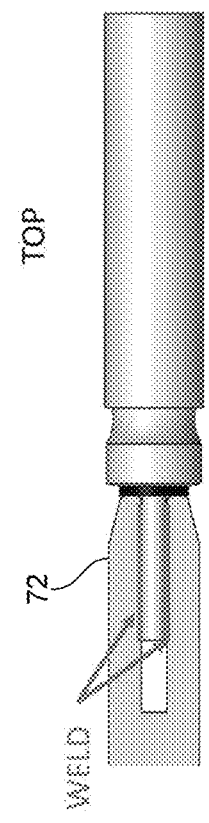

FIGS. 65-68 are of the positive contact for the battery. FIG. 69 shows leakage results for tests using different gauge needles. FIGS. 70-71 show the sensor flexibility of different sensor designs. FIGS. 73-74 show close up means of outer sheath ends that are non-radiused (57A) and radiused (57B).

FIGS. 75-78 are assembly drawings of forming the flexible circuit board 71 with electronic 70, the spine 72, and the battery 94. FIG. 77 is a top view of a sensor 50. FIGS. 79-82 show positive and negative contacts, 95 and 97, respectively, for battery 94. FIGS. 84-91 show various components of flexible circuit board 71.

Figure 93:
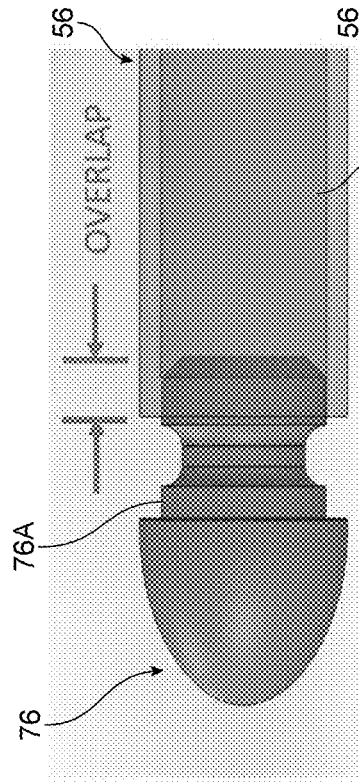
FIGS. 93-95 show side views of a distal end cap being connected to an outer tube of a sensor.
Figure 94:
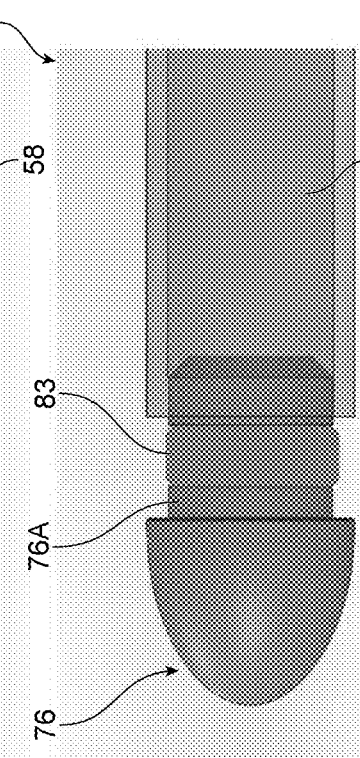
Figure 95:
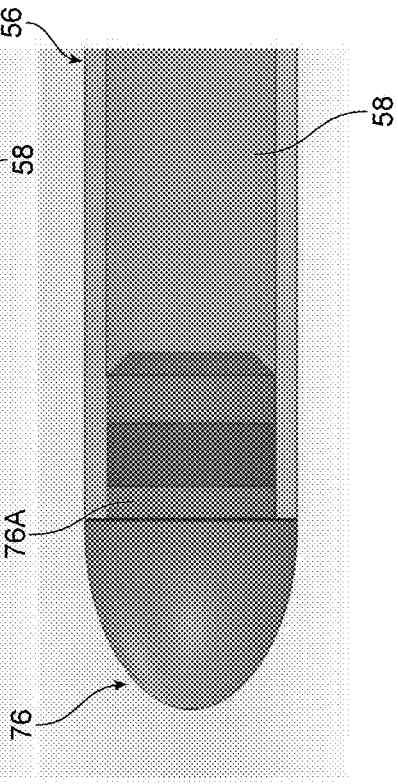
Figure 97:
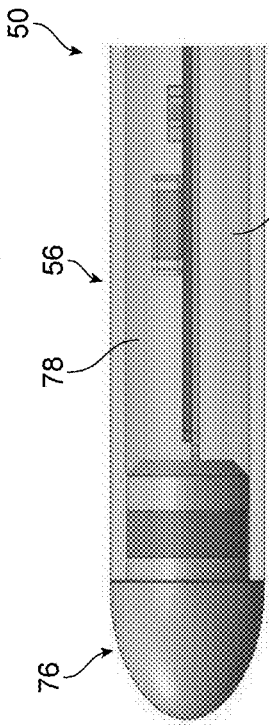
FIGS. 96-97 show partial side views of the distal end of a sensor illustrating needles for filling the sensor with silicone oil and for releasing air.
Figure 96:
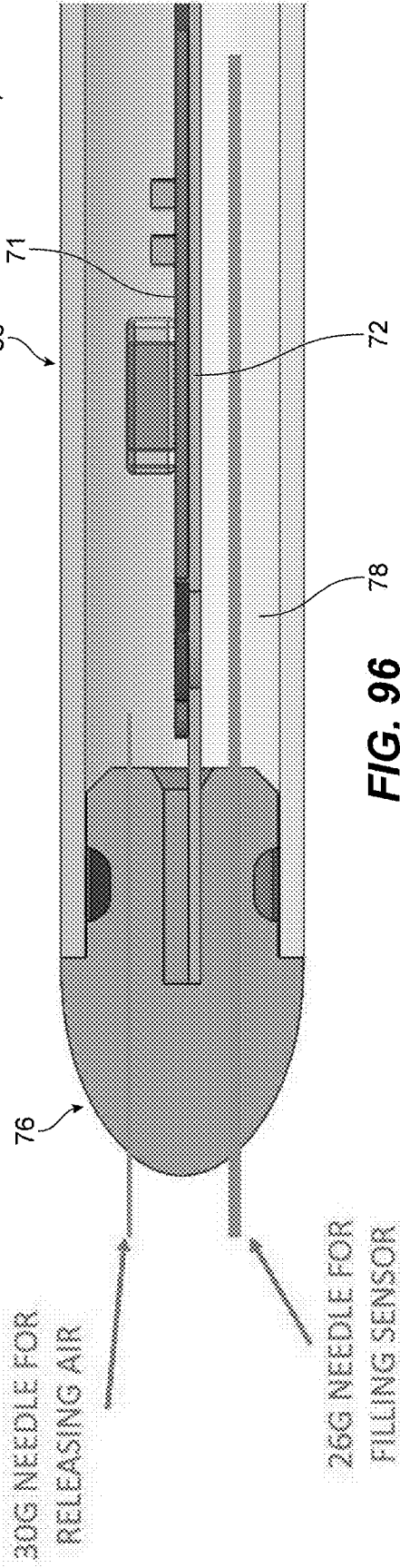

FIGS. 93-95 show the placement of the distal end cap onto outer sheath 56 by using silicone adhesive 83. FIGS. 96-97 illustrate filling the cavity of sensor 50 completely with silicone oil after applying the distal end cap 76.

FIGS. 98-99 illustrate an experiment of adding a septum 300 to a distal end cap 76. FIGS. 100-101 are shown exemplary oils for testing purposes.

Figure 102:
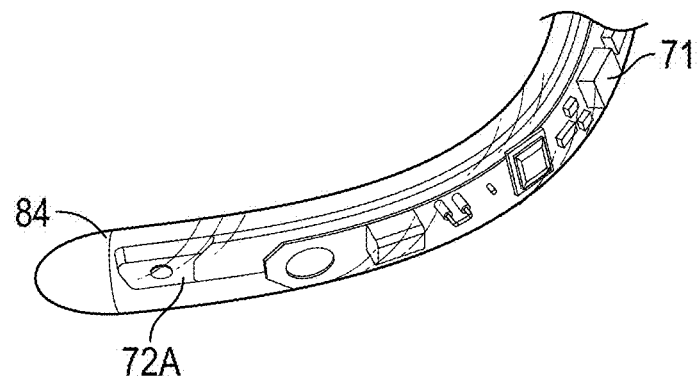
FIG. 102 is a partial, side perspective view of a sensor showing the interaction between the spine and the distal end cap and the end of the spine being encased in a plastic spacer.
Figure 103:
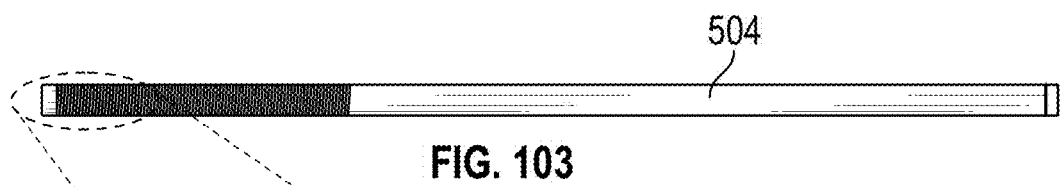
FIGS. 103-105 show side views of an insertion tool that can be used to retain and insert a sensor according to this disclosure.
Figure 104:
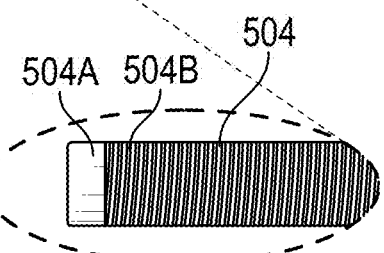
Figure 105:
Figure 106:
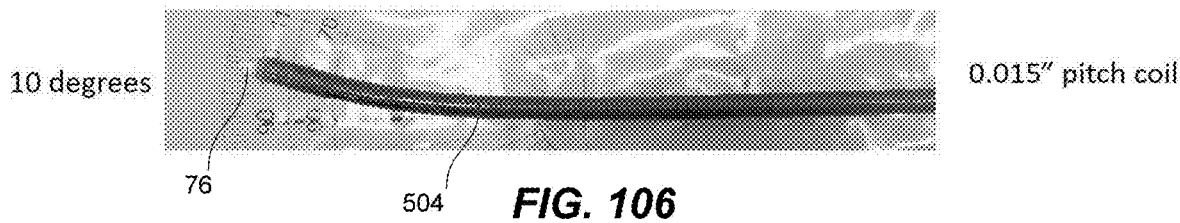
FIGS. 106-107 show side views of a sensor inside of an insertion tool according to this disclosure with an 8° bend and 10° bend.
Figure 107:
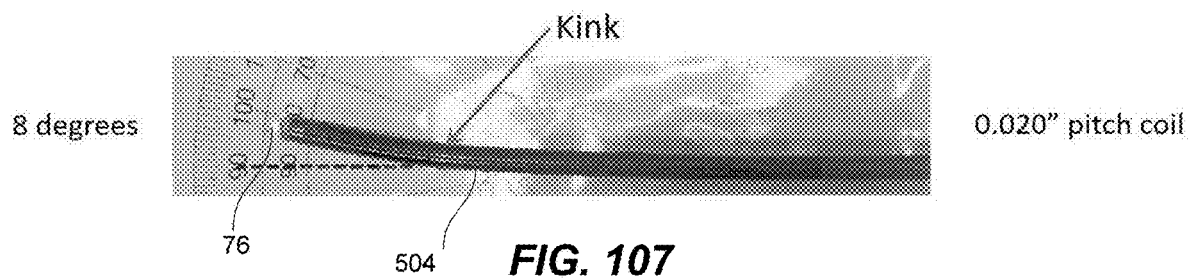
Figure 108:
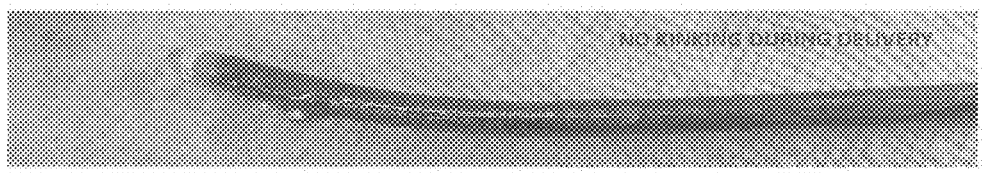
FIG. 108 illustrates the forces required to pull a sensor into an insertion tool and to push a sensor out of the insertion tube.
Figure 109:
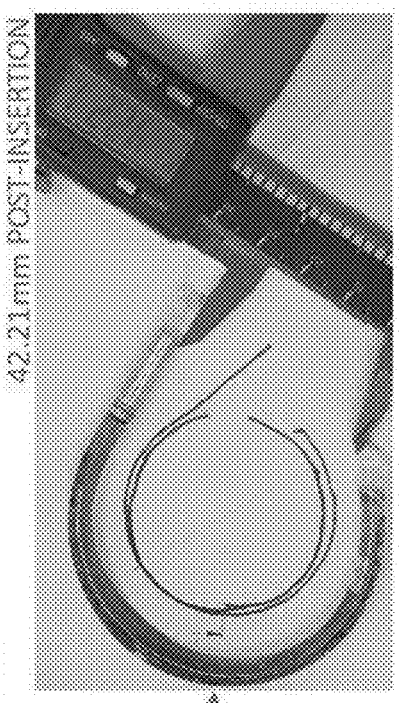
FIGS. 109-112 show side views of sensors in insertion tools and presenting a sensor spine flexion.
Figure 110:
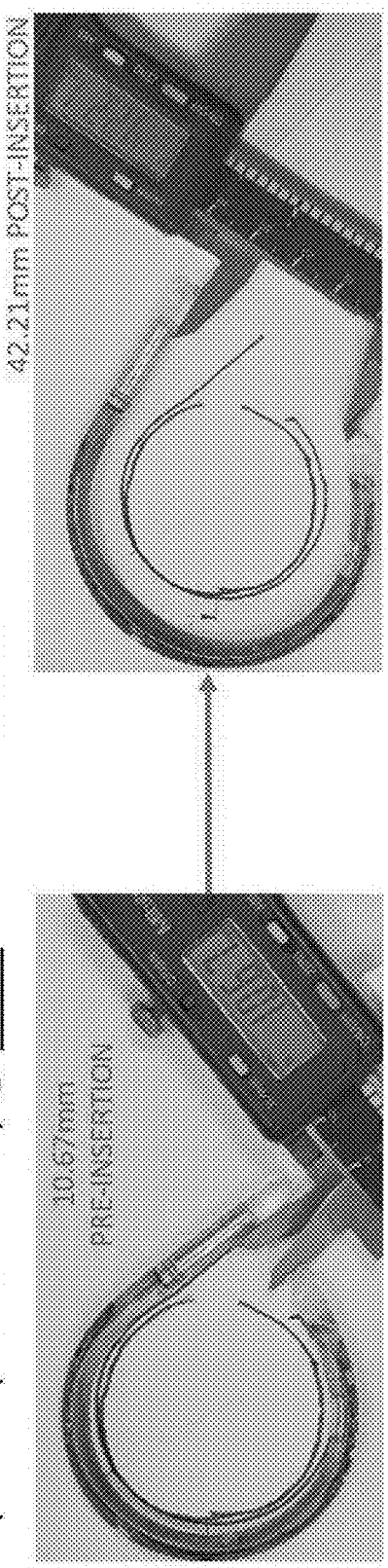
Figure 111:
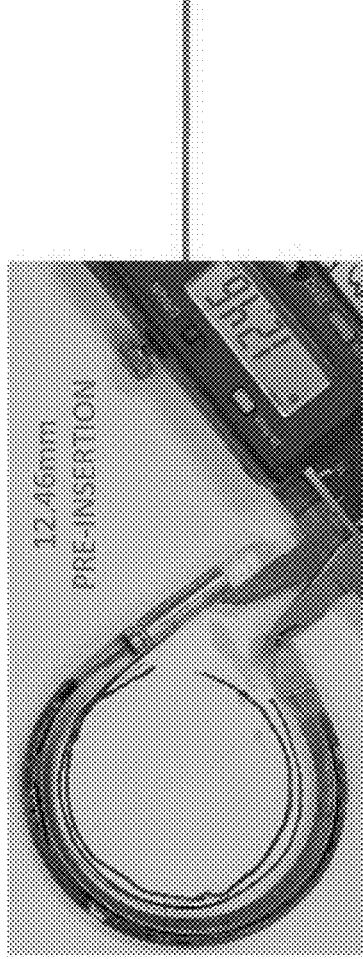
Figure 112:
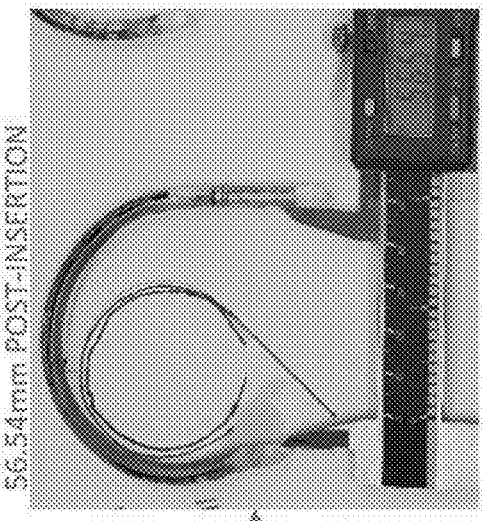
Figure 113:
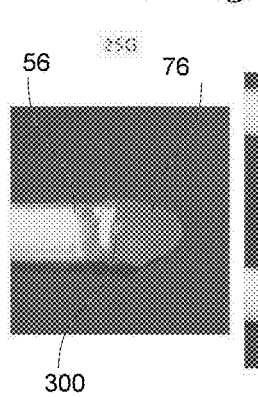
FIGS. 113-117 show partial side views of distal ends of sensors having septas and determining no leakage with an 18G needle.
Figure 114:
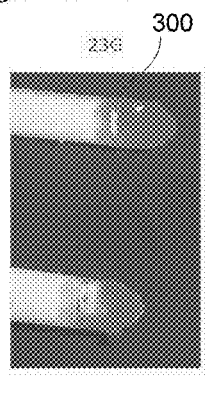
Figure 115:
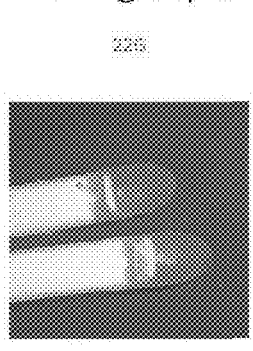
Figure 116:
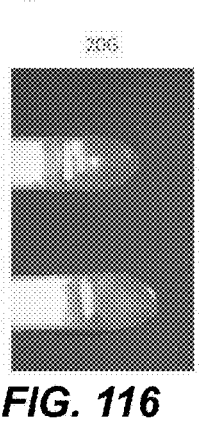
Figure 117:
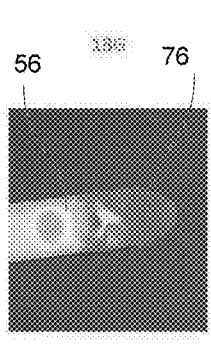

FIG. 102 shows an end 72A of spine 72 embedded in a spacer 84 of soft plastic to prevent end 72A from damaging tube 56. FIGS. 103-105 show a stem 504 of an insertion tool 500. Stem 504 has a plastic inner portion 504A surrounded by braided wire 504B. FIG. 105 shows a sensor inside of a stem 504 and shows the coude distal end cap 76 extending therefrom. FIGS. 106-107 are further examples of sensors 50 inside of a stem 504. FIG. 108 describes the process of pulling a sensor 50 into an insertion tool 500 and the forces required to move sensor 50.

Figure 118:
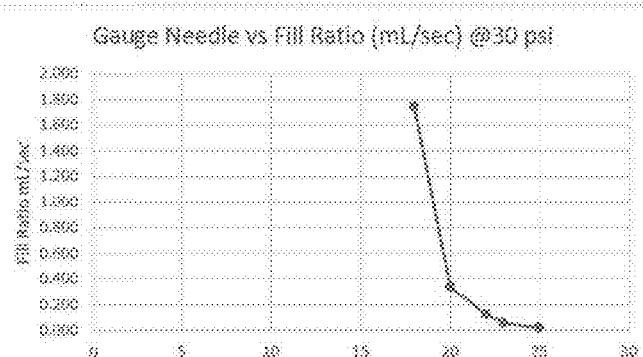
FIG. 118 shows charts of fill analysis of a sensor cavity.

FIGS. 109-112 depict the spine 72 flexion analysis. FIGS. 113-117 show that there was no leakage was found when using needles of 25G, 23G, 32G, 20G, and 18G to completely fill a sensor cavity 58 with silicone oil when a septum 300 was used at the distal end cap 76 of sensor 50. FIG. 118 is a fill analysis using different gauge needles.

Figure 119:
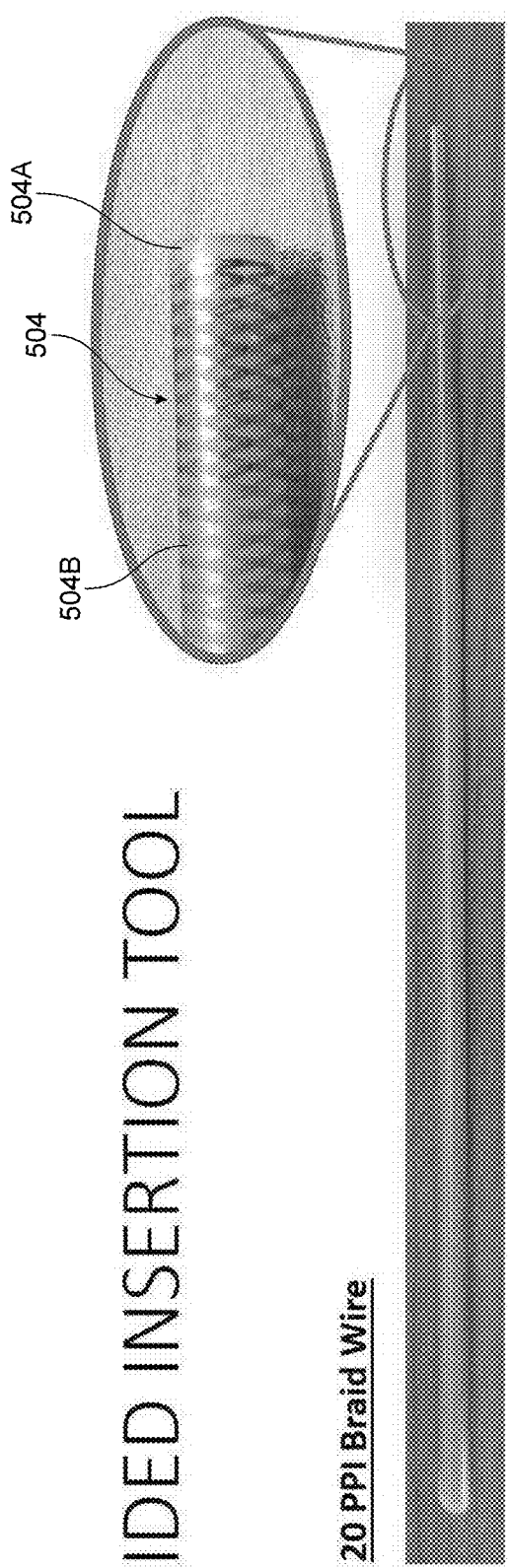
FIGS. 119-120 are side views of insertion tool stems with wire braid over an extruded plastic or silicone rubber tube.
Figure 120:
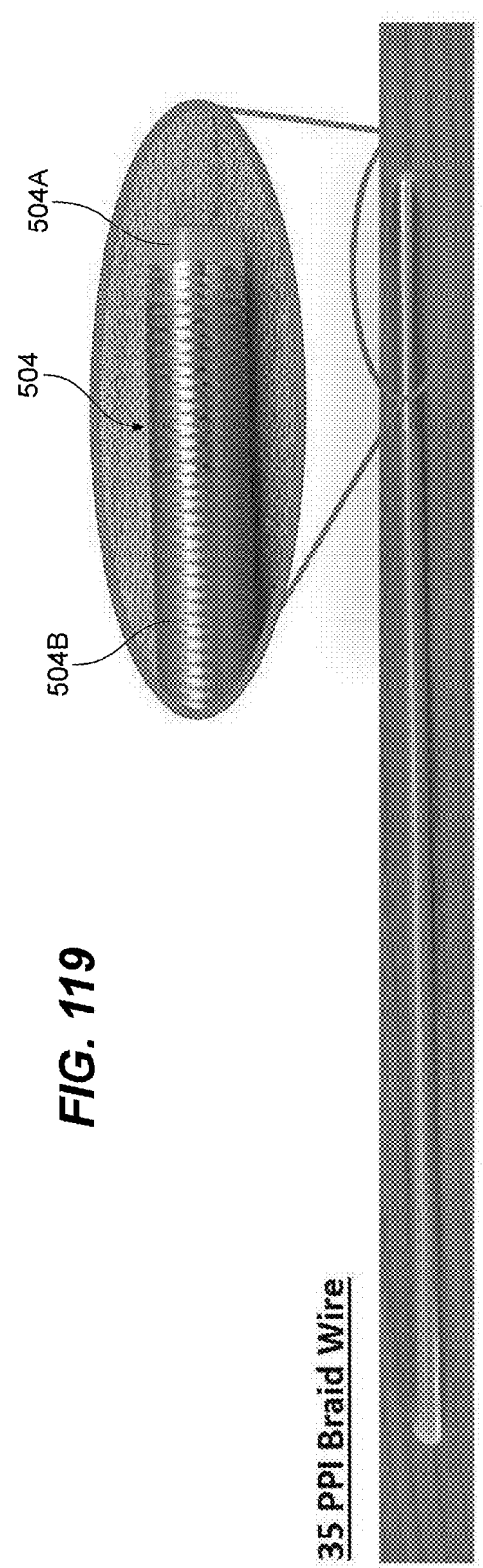

FIGS. 119-120 show additional examples of an insertion tool 500 stem 504 comprised of an inner plastic tube 504A surrounded by a wire braid 504B. FIGS. 122-123 show further examples of a sensor 50 positioned in a stem 504 of an insertion tool 500. FIGS. 123-123A are top views of sensors 50 illustrating that they returned to the correct shape after being flexed.

FIGS. 124-126 show a plastic spacer 84 covering end 72A of spine 72. FIGS. 127-128 show the difference in diameter of a spine 72 after 10 flexation cycles. FIG. 129 shows a material/oil testing chart. FIGS. 130-132 show leakage results when completely filling the cavity 78 of tube 56 using various needles with or without a septum FIG. 133 shows a chart of needle size analysis.

Figure 138:
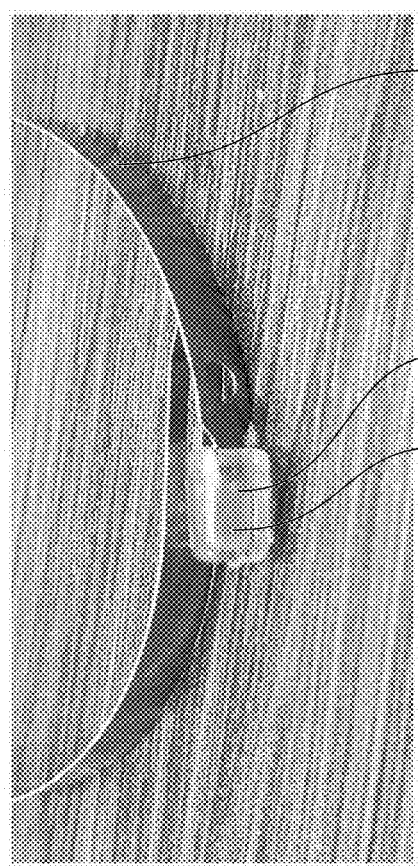
FIGS. 138-140 show top, perspective views of a distal end cap spacer attached to a spine of a sensor according to this disclosure.
Figure 139:
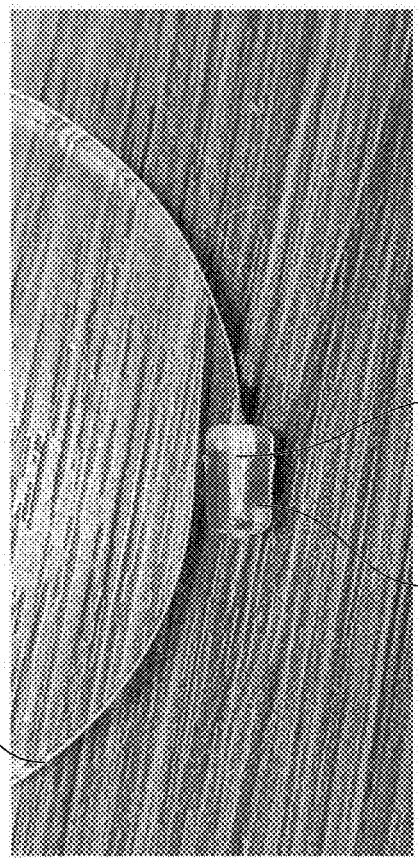
Figure 140:
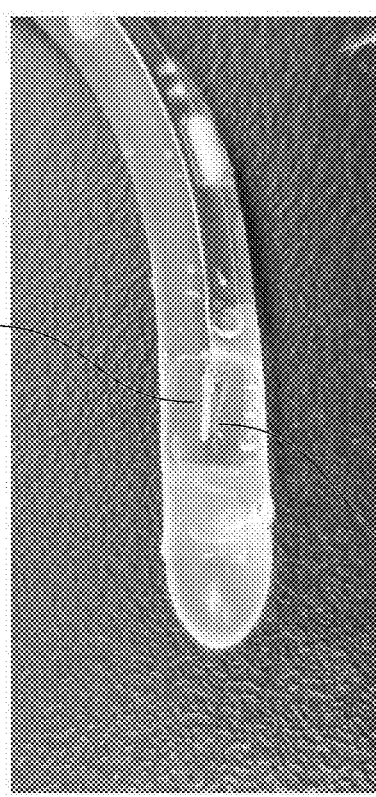
Figure 144:
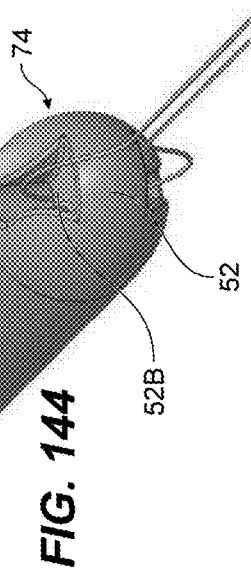
FIGS. 144-147 show a proximal tip that may be used with a sensor according to this disclosure.
Figure 145:
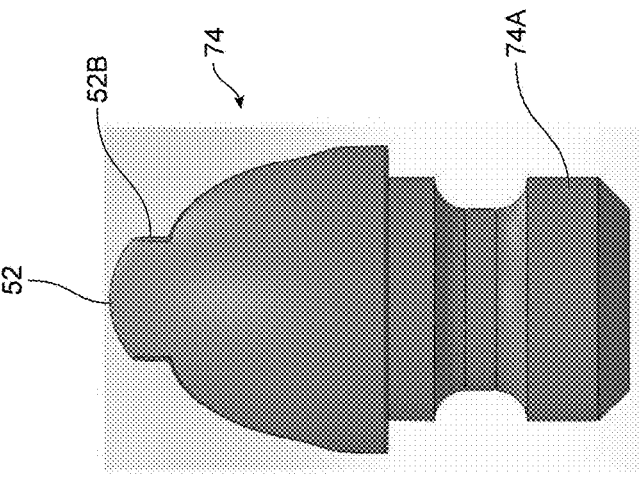
Figure 147:
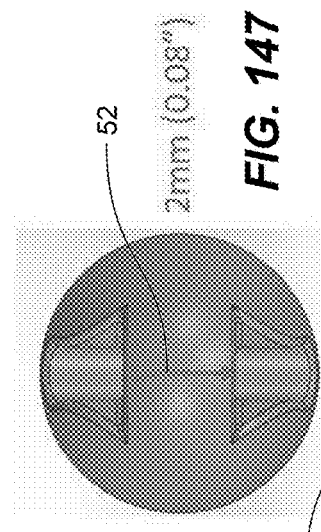
Figure 146:
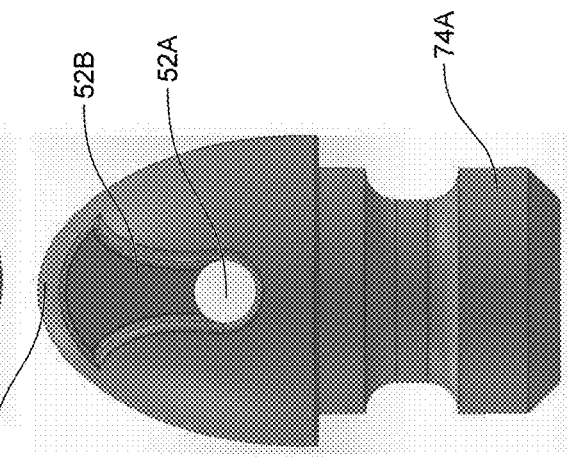

FIGS. 134-137 show a sensor 50 being pulled into an insertion tool 500 and then being pushed out by push rod 530. FIGS. 138-140 illustrate the distal spacer for end 72A of spine 72.

FIGS. 141-142 show packaging for a sensor 50, an insertion tool 500 and a push rod 530. With reference to FIGS. 141-143, a case 400 for retaining and protecting sensor 50, insertion tool 500, and push rod 530. Case 400 can be similar or identical to tray 1200 (discussed further below) in some or many respects. Case 400 (which may also be referred to as a "tray") can include a base 402 that can retain and/or act as a support surface for sensor 50, insertion tool 500, and push rod 530. Case 400 can further include a cover 400 that can be pivotably connected to base 402 and pivotable between an open position (as shown in FIGS. 141-143) and a close position in which cover 404 "covers" sensor 50, insertion tool 500, and push rod 530. As shown, cover 400 can include a first flap 404a and a second flap 404b that are independently connected and pivotable relative to base 402 via hinges 401, 403. In some variants, cover 404 and base 402 are not connected via a hinge, but rather, are independent. Regardless of whether cover 404 and base 402 are connected to one other (e.g., via a hinge), portions of cover 404 and base 402 can be configured to removably secure to one another (for example, via a press-fit arrangement). Base 402 can include a recessed portion 409 that is configured to receive and retain sensor 50. Base 402 can include channels 416a, 416b, 416c configured to receive a sheath 502 of insertion tool 500 and channels 418a, 418b, 418c configured to receive stem 532 of push rod 500. Base 402 can include a cavity 420a configured to receive handle 506 of insertion tool 500 and a cavity 424a configured to receive handle 538 of push rod 500. Cover 404 can include corresponding cavities 420b, 424b which can align with and act in tandem with cavities 420a, 424a to enclose handles 506, 538 when cover 404 (for example, flap 404a) is in a closed position. Cavities 420a, 424a, 420b, 424b can be similar or identical to cavities 1220a, 1224a, 1220b, 1224b described with respect to tray 1200.

Figure 148:
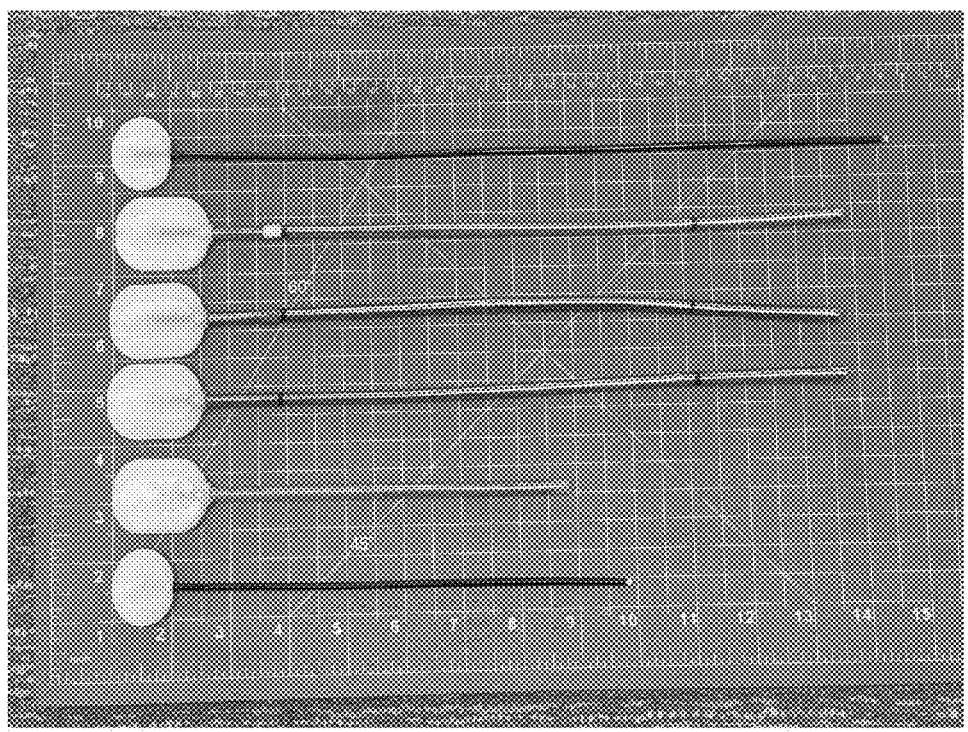
FIG. 148 shows different handles of this disclosure connected to different insertion tools of this disclosure, and push rods of this disclosure having different lengths for a male anatomy, which are longer, and a female anatomy, which are shorter.

FIGS. 144-147 show a proximal cap end 74. FIG. 148 illustrates different insertion tools 500, wherein the top four are for use by males and the bottom two are for use by females.

Figure 149:
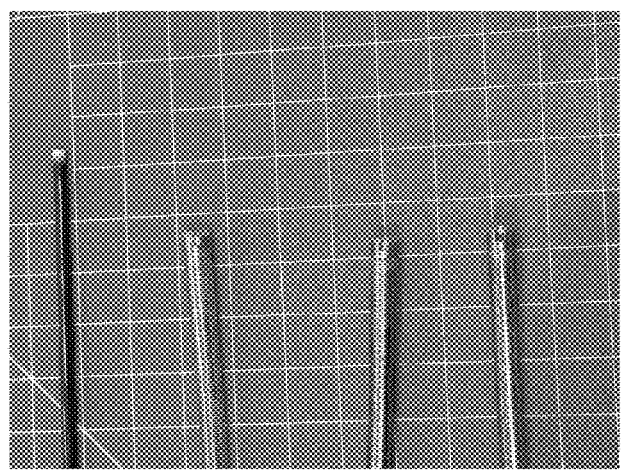
FIG. 149 shows distal ends of insertion tools of this disclosure having keyways configured to receive a key on a distal end of a sensor.
Figure 150:
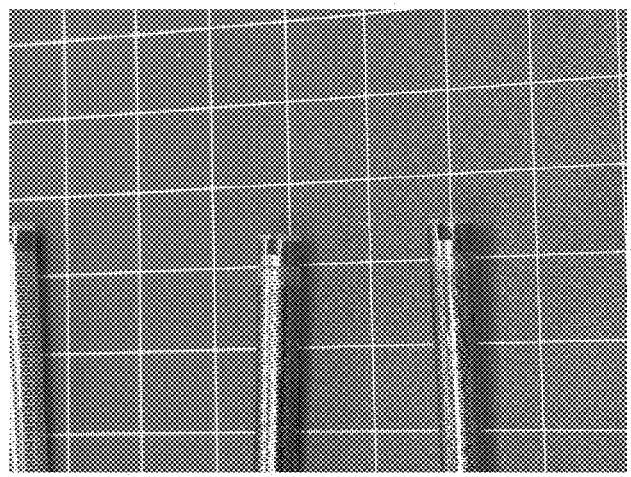
FIG. 150 shows distal ends of insertion tools of this disclosure having keyways configured to receive a key on a distal end of a sensor.

FIGS. 149-150 show the tips 516 of insertion tools and the keyways (or sheath tip inserts) 518.

The sensor distal end cap 76 is preferably a coude-shaped tip and has a key projection (or key) formed therein. The key is configured to be received in a keyway (or slot) at the distal end of the insertion tool sheath. Although any suitable method of manufacture may be used to make the distal tip of the sensor, it can be manufactured by injection molding the distal end cap 76 in 70A durometer silicone rubber to form the desired shape. The insertion tool 500 sheath at its distal end 516 may include a stainless steel ring with the keyway 518 which may be covered in a plastic applied using a reflow process. The keyway 518 in the sheath may, however, be formed in any suitable manner. Integration of the key of the distal end cap 76 with the keyway 518 is done by manually positioning the two structures adjacent to one another and the bend of the coude tip of end cap 76 biases the key into the keyway 518. This mates the key with the keyway 518 so the sensor 50 and insertion tool 500 rotate together, but also permits the sensor 50 to be pushed forward and out of the insertion tool 500 and into the bladder.

The sensor 50 also includes a proximal end (or proximal insert, or proximal endcap) 74 that is inside the lumen of the insertion tool 500 when the sensor 50 is moved into the lumen of the insertion tool 500 sheath 502. The proximal end cap 74 has a shape that engages with a geometric shape of the beginning of the second, proximal section 514 (also called a D-lock) of the insertion tool lumen, so that rotation of the insertion tool 500 translates rotational force to the sensor 50. This enables the proximal endcap 74 of the sensor 50 to provide rotational force to the sensor 50 when the handle 503 or sheath 502 of the insertion tool 500 is rotated. Thus, the sensor 50 can be rotated by a two-point connection with the insertion tool—one at the distal end of the sensor and one at the proximal end of the sensor, although only one connection need be used.

The distal end cap 76 and proximal end cap 74 of the sensor 50 may be attached to the sensor tube (or housing, or tube, or outer sheath, or sheath) 56 by over-molding, gluing, or otherwise attaching rigid or semi-rigid inserts (proximal end cap and distal end cap) 74, 76 into the lumen 78 of the sensor tube 50, or using an extrusion with a custom-shaped die or using reflow with a custom shaped mandrel. The durometer of the proximal endcaps 74, 76 of the sensor 50 is also 70A, although any suitable material, hardness, or shape may be used.

The insertion tool 500 may have a 18 Fr OD and a 16 Fr ID in the first, distal section where the sensor 50 is positioned and have a smaller cross-sectional area in the second, proximal lumen between the sensor 50 and the handle 503. The smaller cross-sectional area is configured to be too small for the proximal end cap 74 of the sensor 50 to pass through.

The combination of both the proximal and distal endcaps 74, 76 in the sensor 50 and insertion tool 500 enable reliable translation of rotational force from the handle 503 (or outer sheath 504) of the insertion tool 500 to the distal end 76 of the sensor 50. The coude, distal tip 54 at the distal end cap 76 aids clinicians in moving the sensor 50 through the urethra and into the bladder. If the clinician is unable to properly orient the sensor 50 including its distal tip 54 by rotating it via rotation of the insertion tool 500, it could result in injury or trauma to the patient's anatomy when trying to deploy the sensor into the bladder, and also prevent the clinician from successful insertion of the sensor into the bladder. This is helpful for both male and female anatomies. The insertion tool 500 may be shorter and stiffer for females due to the differences in anatomy.

The sensor 50 may incorporate a rigid or semi-rigid material such as stainless steel to enable reliable shape memory via a spring 72. This may be a variety of symmetric or asymmetric shape(s) in order to provide the proper spring rate for the application. In some embodiments the spring 72 may be heat treated and/or rolled to create the spring/return rates desired. The spring (or spine) 72 may also be integrated into the circuit board 71 and be welded to the battery 94. At the opposite end the spine 72 may be attached to a plastic spacer 84 to prevent any potential for the spine 72 to puncture the housing 56 of the sensor 50 and maintain patient safety. In this embodiment, linear force can be translated from the proximal end cap 74 of the sensor 50 to the distal end cap 76 of the sensor 50 by using the battery 94, spine 72, and plastic spacer 84.

The design of the sensor materials and components provide reliable integration with the insertion tool. For example, the sensor spine 72 and housing 56 utilize material with properties to enable repeated and reliable memory to maintain the desired shape when in the first position in the bladder so the sensor 50 does not migrate out of the bladder once positioned therein.

The sensor spine 72 is preferably made of 301 stainless steel (SS) and formed using a rolling process, although any suitable material and process may be utilized. The hardness and material of the sensor 50, and of the sensor spine 72 must be such that it rebounds to the desired first, curved or circular shape and does not lose its shape memory after straightening. If the sensor 50 does not maintain the proper shape and orientation, then it may lead to undesirable outcomes such as migration out of the bladder and/or injury to the lower urinary tract.

The sensor 50 uses materials and an assembly process that also provide reliable translation of force linearly when the sensor 50 is straightened. To assemble the sensor 50, a metal contact is laser welded (although any suitable method may be used) to the battery 94 and soldered (although any suitable method may be used) to a flexible electronic circuit board 71. The sensor spine 72 is laser welded (although any suitable method may be used) to the battery contact. The flexible electronic circuit 71 is then attached to the spine 72 for rigidity and support. At the distal end cap 76 of the sensor 50, the sensor spine 72 is attached to a small plastic spacer 84 so the spine 72 will not push through or tear the sensor outer wall (or housing) 56. The distal sensor endcap 76 is preferably attached to the plastic spacer 84 and to the sensor housing 56 such that there is linear translation of force using rigid or semi-rigid components from the proximal endcap 74 to the distal endcap 76.

The materials and processes are selected in order to achieve a desired range of rebound (or memory) and strength of the sensor spine with the strength and rigidity of the insertion tool sheath such that there is a desired level of curvature before the sensor is inserted in the sheath. These structures offer a combination of flexibility and pushability for the clinician to insert the sensor safely and reliably in the bladder.

The insertion tool 500 and sensor 50 may be constructed in a manner to allow for insertion without a pushrod 530. In this embodiment, the mechanical properties of the sheath 56 and sensor 50 may be optimized such that it offers characteristics for insertion through the urethra and into the bladder. This may allow for more ergonomic insertion and safe handling of the device for clinicians because the tool is shorter and has one less component to handle during the insertion process.

In some embodiments the insertion tool 500 sheath 502 may utilize multiple durometers of material (e.g., stiffer at the proximal end and softer at the distal end) as well as reinforcement from braiding or coiling the exterior wall of the insertion tool sheath with different: materials, such as steel, thicknesses, and patterns.

The proximal endcap 74 may also be shaped in a manner that enables quick and easy retrieval of the sensor 50 using standard cystoscopic tools including flexible graspers or forceps. These can be utilized in the event that the removal string 58 connected to the proximal end cap 74 of the sensor fails. Due to the size of the forceps able to be utilized during cystoscopy, a specially designed shelf or rim 52B with reduced thickness can be implemented on the sensor outer sheath 56 or the proximal endcap 74 in some embodiments to enable quick and easy removal of the sensor by any trained urologist using commonly available tools. The design of such an endcap 74 enables quick and reliable retrieval using standard flexible cystoscopes and commonly available tools.

Packaging 700 for the sensor 50 and insertion tool 500 may be designed in a manner to facilitate efficient and safe clinical workflow. This may enable the clinician to insert the sensor into the patient's bladder without touching the sensor body. This requires the packaging 700 to be protective but flexible to enable the push of the sensor button through a packaging barrier in order to activate the sensor. This also requires support for the sensor 50 and the insertion tool 500 so that the string 58 can be preloaded in a reliable and effective manner such that the coude tip 54 of distal end cap 76 is properly aligned in the distal end of the insertion tool 500 for insertion into the bladder. This helps to minimize any potential contamination of the sensor, which may reduce complications such as urinary tract infections and bacterial inoculation of the bladder. The packaging 700 can be designed in a manner to support both the female and male insertion tools with the same shell/tray.

Each key/keyhole feature may be constructed of common materials (silicone, plastic) and also reinforced by rigid or semi-rigid materials (e.g., metal such as stainless steel) to improve the strength of the engagement between the over sheath and sensor. This material can be incorporated into the design such that any metal is covered by soft/flexible plastic such as TPE/TPU to minimize or eliminate any potential trauma to the urethra and bladder during insertion and deployment into the bladder.

In some embodiments, there may be a different insertion tool 500 design for female and male anatomies. In this instance the female tool may be shorter than the male tool 500 in order to accommodate the shorter urethral length and improve ease of insertion.

If a coude or asymmetric sensor tip 54 on end cap 76 is utilized then the sheath handle 503 may have a visual and/or tactile indicator 508 to provide reliable confirmation of the sensor end cap 76 orientation for the clinician to properly insert the sensor 50 into the male or female anatomies.

In both the female and male insertion tools 500 the design of mechanical components may take into account the mechanical properties of the sheath to enable safe and reliable delivery of the sensor 50 into the bladder through the urethra. This includes the materials and properties of the sensor housing 56 (durometer and material), the sensor spine 72 (material and spring rate) when considered with the sheath 502 (material), and sheath construction methods (braiding and/or coiling). In some embodiments, the sheath 502 may include braiding and coiling patterns that differ at different sections. This may offer the clinician more or less stiffness/flexibility to provide the proper characteristics for insertion.

Loading the Sensor into the Insertion Tool

As explained above, the sensor is preferably loaded into the insertion tool by pulling it into the insertion tool lumen using the removal string attached to the proximal end of the sensor. Pulling the removal string pulls the sensor into the first, distal section of the insertion tool lumen. As mentioned previously, the proximal end of the sensor cannot fit through the second, proximal section of the insertion tool lumen so it cannot advance past that point. When fully positioned in the insertion tool, the removal string is outside of the proximal end of the insertion tool sheath, the proximal tip (i.e., the most proximal part of the proximal end) of the sensor is positioned inside the beginning of the second, proximal lumen of the insertion tool, and the distal end of the sensor is positioned outside of the distal end of the insertion tool sheath. The key (if utilized) on the distal end of the sensor is positioned in the keyway of the distal end of the insertion tool, and the geometric structure (preferably rectangular) of the proximal tip of the proximal end of the sensor is received in and engages a mating structure (preferably a rectangular opening) at the beginning of the second, proximal section of the insertion tool lumen.

Advancing (or Push) Rod

The advancing rod 530 is described above and is designed to provide a combination of flexibility and pushability enabling reliable sensor deployment. It is a flexible tube with a handle that has a lumen in the middle enabling urine to flow through the tube. This aids clinicians in confirmation that the device has been deployed in the bladder successfully.

The pushrod 530 may also contain a lumen running the length of the rod and through the handle. This feature is useful to enable urine to flow through the pushrod and out of the pushrod handle which enables clinicians to confirm placement of the sensor into the bladder.

Sensor Performance and Cavity Fill

The sensor uses a combination of silicone rubber for the outer wall (or housing, or tube), adhesive, and silicone oil in the sensor cavity. The silicone oil has properties that minimize the transfer of fluid into and through the silicone outer wall and adhesive. Silicone rubber is a porous material so it absorbs certain materials and allows for transfer of fluid (as used herein, fluid refers to liquid) and gas through the silicone rubber membrane. In order to enable reliable pressure sensing for the bladder sensor, the volume of mass/fluid in the sensor housing (or cavity defined by the silicone rubber tube) should be at a preset amount or else the pressure readings could be affected by the external environment and may cause sensor drift and reduced precision. This volume should be such that when combined with the other components of the sensor there is a pressure achieved in the sensor cavity that is higher than atmospheric pressure with a minimal amount of, or no, air or gas remaining inside the sensor cavity. In this event, the higher pressure of oil inside the sensor cavity will work to push air or gas outside of the sensor cavity in an attempt to reach equilibrium with the external environment (atmospheric pressure). This is desirable as reduction of compressible gas in the sensor cavity will provide a sensor with higher frequency response than otherwise.

Filling the sensor with fluid (most preferably silicone oil, and most preferably fluorosilicone oil that contains hydrophobic properties and molecules that are larger than that of the silicone rubber tube) to a pressure that is below atmospheric (e.g., less than one Bar) will permit air to move into the sensor cavity (or housing) from the outside environment through the porous silicone tube before the sensor is positioned in the bladder. In that case, air will enter the sensor cavity until the cavity eventually reaches an equilibrium pressure (e.g., atmospheric) with the external environment. Thus, the storage of such a sensor before use allows air to enter the sensor housing, which may or may not be desirable because it could dampen pressure readings. This is undesirable in certain applications unless a damping effect is desired, such as for a low-pass filter.

Fluids (i.e., liquids) disposed in the sensor housing cause the sensor to be essentially incompressible whereas gasses such as air cause the sensor to be more readily compressed. So, if air is present in the sensor cavity (or housing), it may serve to dampen the signal from the external environment of the bladder and alter the pressure reading sensed by the internal pressure sensor (which is preferably on the circuit board) in the sensor housing. Air can be used to act as a damping mechanism and filter some aspect of the signal (low pass filter). This feature can be useful if the filtering is desired.

Filling the sensor cavity to a pressure greater than atmospheric level is usually beneficial for sensor performance and manufacturing. This enables simple assembly and reduced manufacturing time because the amount of fluid, such as silicone oil, can easily be measured by volume or mass using tools such as an electronic fluid dispenser and a scale. In this embodiment, the air dampens the signal received by the pressure sensor inside of the sensor housing and decreases the frequency response of the pressure sensor as compared to a similar system in which additional fluid (i.e., liquid) replaces the air. Ultimately, there is a range of pressure/volume that can be utilized in which the pressure sensor will sense pressure at a lower frequency response than a similar system with more fluid. In this range, more air in the sensor housing decreases the frequency response and more fluid in the sensor increases the frequency response. In all embodiments, a sensor with air in the sensor housing will have a decreased frequency response than a sensor at the same pressure with no air and only liquid in the cavity. During manufacturing including more fluid may be valuable because it can enable simple assembly and increase manufacturing yield because there is less precision required and also because there a two-step filling process may be used. In this embodiment, a portion of the sensor cavity may be filled and sealed before a second step to overpressurize the sensor cavity. This can be used to allow for the precise level of air to enter the cavity and enable a specified amount of damping to the system (low/high pass filtering).

Filling the sensor housing with a volume of fluid that is higher than atmospheric pressure (e.g., greater than one Bar) will cause air/gas bubbles to expel from the sensor outer wall (or tube) and the sensor housing will reach a point of pressure equilibrium that may be higher than atmospheric pressure, as long as (1) the mass/volume of fluid in the housing is not escaping through the porous silicone tube, and (2) the mass/volume of air/gas inside the sensor is small enough so that the volume of fluid in the sensor housing is greater than the volume of the sensor cavity. This is helpful in manufacturing to increase yield and reduce the precision required but does require additional components and methods of assembly to ensure a standardized volume of liquid in each sensor housing. In some embodiments improved frequency response is desired so air/gas inside of the sensor housing should be eliminated or minimized. To accomplish this the sensor is filled with a greater volume of fluid than the volume of the sensor cavity to create a pressure in the sensor housing that is higher than atmospheric pressure. In one embodiment the sensor may be manufactured so that the pressure after air/gas is expelled from the cavity is as high as 1250-1400 hPa. In some implementations, pressure within an interior of the sensor (for example, within a tubular housing of the sensor) is greater than 1250 hPa, such as, between 1750 hPa and 2000 hPa. For example, such pressure can be at least 1250 hPa, at least 1300 hPa, at least 1350 hPa, at least 1400 hPa, at least 1450 hPa, at least 1500 hPa, at least 1550 hPa, at least 1600 hPa, at least 1650 hPa, at least 1700 hPa, at least 1750 hPa, at least 1800 hPa, at least 1850 hPa, at least 1900 hPa, or at least 1950 hPa, or any value or range within or bounded by any of these ranges or values. Any of the sensing devices disclosed herein can be pressurized at these values. Sensors that are pressurized at or above this level will not allow air/gas to enter the sensor housing under normal circumstances, and this standardizes the frequency response characteristics of the internal pressure sensor, which provides reliable and predictable pressure sensor readings with little drift and high accuracy.

To accomplish adding a volume of fluid greater than the volume of the sensor cavity, an assembly process using a two-stage fluid fill may be used. First, a volume of fluid is inserted directly into the sensor housing that is less than the final desired volume. The sensor distal endcap is then attached to the sensor tube in any suitable manner, such as with adhesive, which is allowed to dry to seal the distal tip to the sensor tube. The sensor housing can then be filled further using a syringe with a needle to poke through the distal endcap to add additional fluid into the sensor housing. Silicone rubber has self-sealing properties that may support being punctured with a syringe and then sealing afterwards, but for extra reliability the addition of a septa (e.g., a rubber septum) may be used. The septum is typically compression-molded rubber or elastomer and can withstand multiple punctures from syringe needles and self-seal thereafter. This maintains a reliable barrier to prevent the transfer of fluid/gas through the septum and, hence, out of the sensor housing. Using the septum enables the sensor housing to be pressurized with additional fluid in the second stage of assembly to levels that otherwise may not be possible because puncturing silicone rubber with a needle may cause a permanent gap or opening that would allow fluid to escape. In some embodiments, the septum may be integrated with the sensor distal endcap. In some embodiments, the septum may be integrated with both the sensor distal endcap, and also with a plastic spacer. Alternatively, the septum may only be integrated with the plastic spacer or attached to the distal or proximal end of the sensor in any suitable manner.

The material properties of the septum may be selected for use with a specific needle size/shape for precision in filling. In this case, the amount of fluid volume in the sensor housing may not need to be measured because excess pressure will bleed off after reaching a target pressure because of leakage from the septa and/or silicone needle punctures. This may aid in manufacturing and offers a range (for example, between 1250-1400 hPa) of values acceptable which increases yield and reduces time/precision required.

Septas are made by a compression molding technique that creates a "self-healing" feature such that needles may puncture the septa without creating holes that would jeopardize the mechanical integrity of the sensor cavity. In some embodiments a septa may be incorporated into the design for a spine spacer and include multiple filling holes for a syringe to fill the sensor cavity with fluid.

In other embodiments, the septa may be integrated into the sensor spacer and sealed prior to final attachment of the sensor endcap. This may offer improved reliability of sealing and reduce complexity of assembly by reducing the distance that the needle is required to travel through the silicone. In this embodiment, a larger needle size may be utilized to speed the flow of fluid into the sensor cavity.

If the sensor cavity is pressurized to a level that will still maintain a pressure greater than atmospheric level after elimination of any compressible fluids and there is little or no loss of molecules of the remaining fluid (such as silicone oil), then the sensor cavity pressure will remain stable thereby increasing the potential service life and/or shelf life of the sensor. This may be beneficial for any commercial activity and to enhance the supply chain and logistics for the sensor. This may also reduce or eliminate any need for calibration or recalibration of the sensor so that the pressure sensor (or pressure monitor) that is part of the sensor circuitry will produce accurate readings of the bladder pressure.

In one embodiment, the sensor may actively transmit the pressure of the sensor cavity to aid in manufacturing. In another embodiment, the method of filling the sensor with fluid may be automated such that a closed loop is created by software that receives a signal from the pressure sensor and fills the cavity with fluid until the sensor cavity reaches a pressure threshold that may slow or cease the fluid filling in the sensor cavity.

If desired, some embodiments of the sensor may incorporate the use of compressible fluids, such as air. This may be valuable to act as a low-pass filter and remove undesired artifact from signal from the sensor's internal pressure sensor. This damping effect is correlated to the amount of air in the sensor and pressure of the sensor cavity and will decrease the frequency response of the system Conversely, greater pressures in the sensor cavity may work to increase the frequency response of the system, which is desirable in certain situations.

The sensor can sense conditions inside of the bladder and electronically communicate the data, preferably by wireless communications, to a computing device having a processor and software configured to receive the data, analyze the data, compare the data to relevant data, display the data, and/or store the data.

Additional Sensing Devices

Figure 151A:
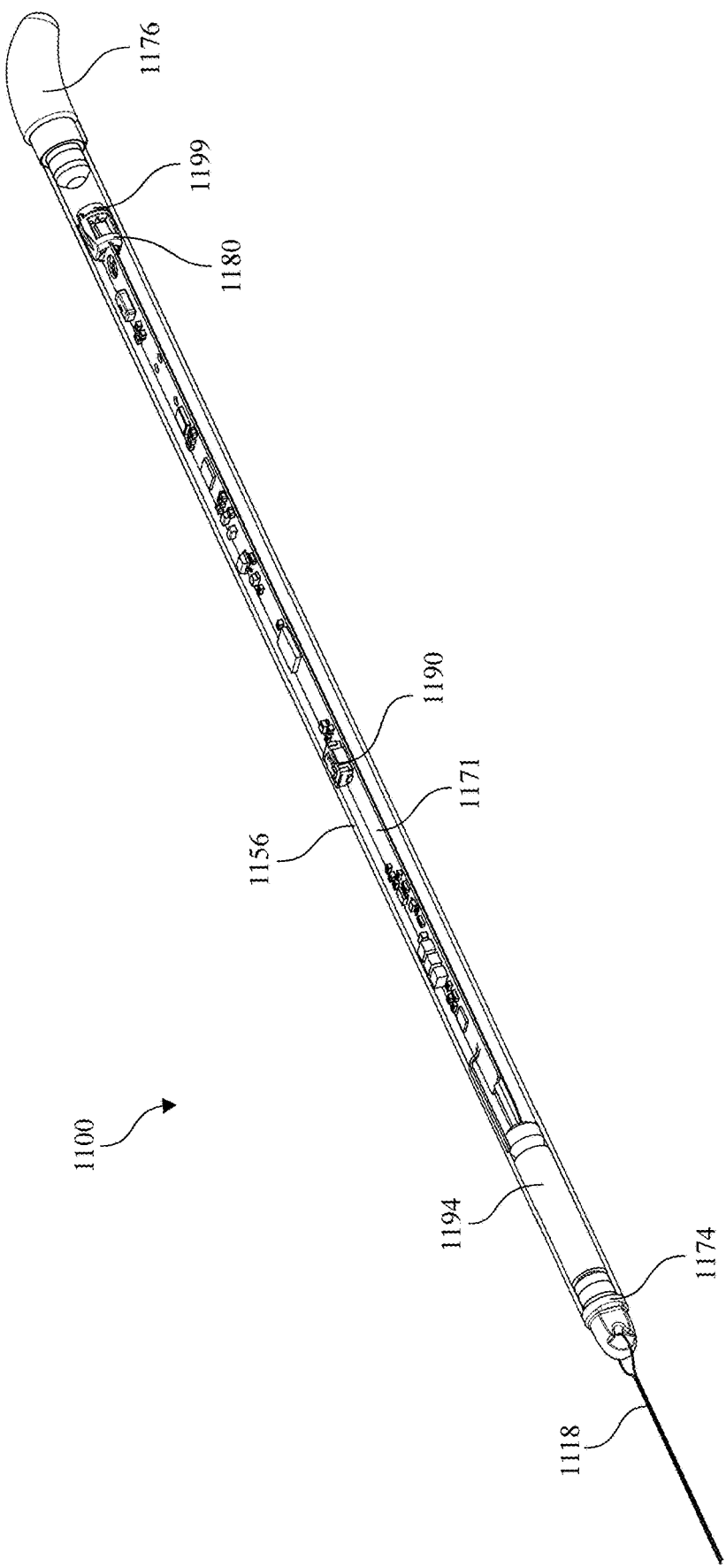
FIGS. 151A-151B illustrate top and bottom perspective views of a sensing device.
Figure 151B:
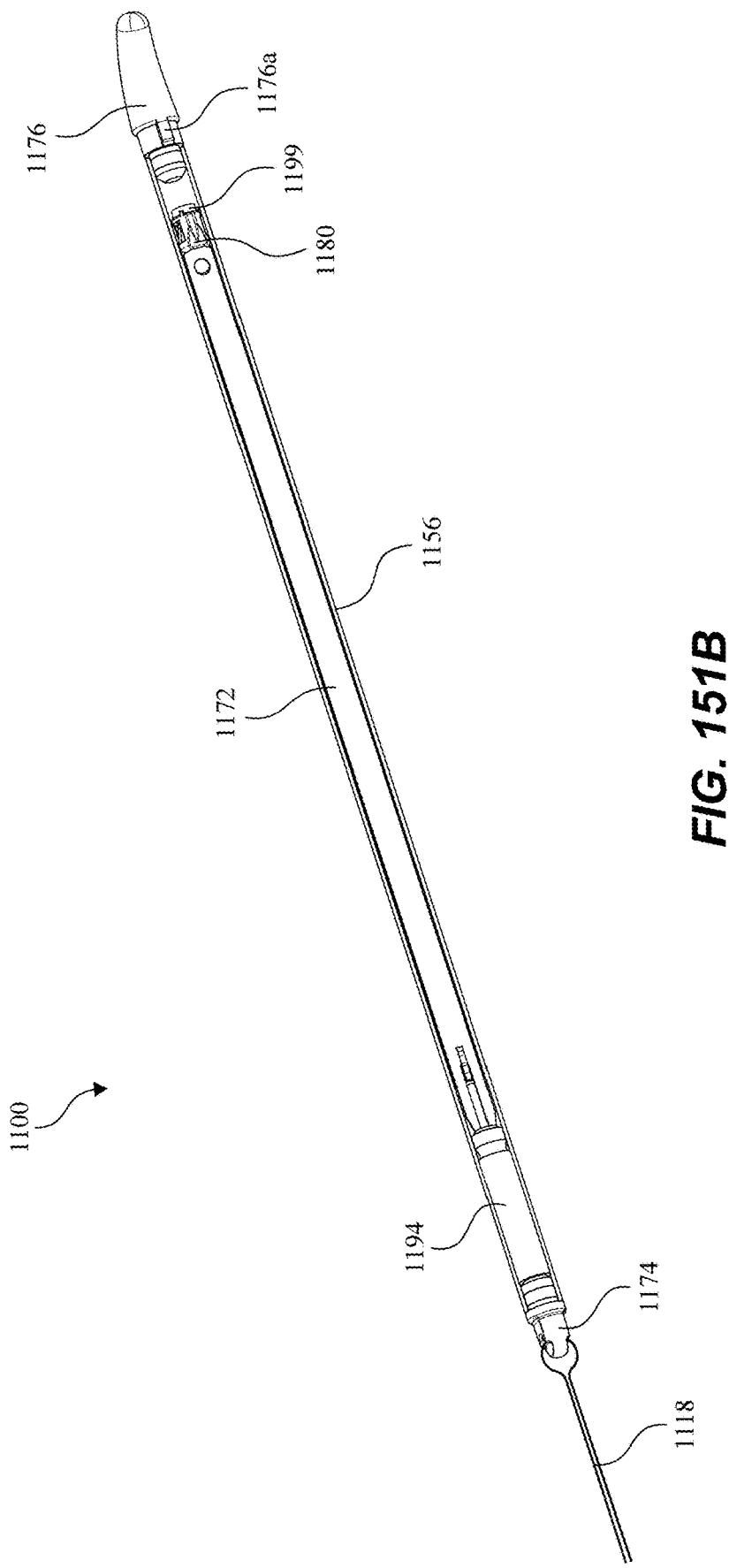

FIGS. 151A-151B illustrate top and bottom perspective views of a sensing device 1100 (which may also be referred to as a "sensor" or "device"). Sensing device 1100 can be similar in some or many respects to any of the sensors described and/or illustrated herein, such as sensor 10 and/or sensor 50. Any of the features or components described with respect to sensing device 1100 below may be incorporated into sensor 10 and/or sensor 50. Additionally, any of the features or components described herein with respect to sensor 10 and/or sensor 50 can be incorporated into sensing device 1100. Sensing device 1100 can be utilized in a manner similar to that described herein with respect to sensor 10 and/or sensor 50. Sensing device 1100 can be utilized as part of a urodynamics system such as any of those described herein. Sensing device 1100 can be utilized with an insertion tool, such as any of the insertion tools described herein (such as insertion tool 500), for deployment into a body cavity of a subject (for example, through a subject's urethra and into the subject's bladder).

Sensing device 1100 can include a body 1156 which can be similar or identical to body 56 of sensor 50 described herein. Body 1156 can comprise a tubular housing, for example, made of any of the materials described herein with respect to body 56. Body 1156 can house any of the components described as being positioned within body 56 of sensor 50. Body 1156 can comprise a transparent material as illustrated in FIGS. 151A-151B, which can allow components of sensing device 110 arranged within an interior cavity of body 1156 to be visible. Sensing device 1100 can include, among other things, a flexible circuit board 1171, a spine 1172, a battery 1194, and a button 1190 positioned within body 1156. Circuit board 1171, spine 1172, battery 1194, and button 1190 can be similar or identical to circuit board 71, spine 72, battery 94, and button 90 (respectively) in some or many respects. Sensing device 110 can additionally include a septum 1199 as described further below with respect to FIGS. 152A-152C. Sensing device 1100 can include a pressure sensor, a memory, a processor (for example, a microprocessor), an LED, and/or an antenna, each of which can be similar or identical (respectively) to pressure sensor 92, memory 88, microprocessor 86, LED 84, and antenna 82. Although FIGS. 151A-151B illustrate sensing device 1100 in a straight configuration, sensing device 1100 can be configured to transition between such straight configuration (in which it may be insertable through a urethra of a subject, for example, via insertion tool 500) and another state in which sensing device 1100 is at least partially curled, as described and/or shown herein with respect to sensor 10 and/or sensor 50. Spine 1172 can be configured to bias sensing device 1100 to such at least partially curled configuration in a similar or identical manner as that described herein with respect to spine 72. Sensing device 1100 can be filled with any of the fluid described herein for any of the purposes described herein. For example, oil (such as fluorosilicone oil) or another fluid can be arranged within an interior cavity of body 1156 at any of the pressures described herein (for example, at least 1250 hPa).

With continued reference to FIGS. 151A-151B, sensing device 1100 can include a distal end cap 1176 and a proximal end cap 1174. Distal end cap 1176 can be similar or identical to distal end cap 76 in some, many, or all respects. As shown in FIG. 151B, at least a portion of distal end cap 1176 can have a coude shape, similar to that described with respect to distal end cap 76 herein. As also shown, distal end cap 1176 can include a projection 1176a that can be received in sheath key/tip insert 518 in a manner similar or identical to that described herein with respect to distal end cap 76. Proximal end cap 1174 can be similar or identical in some or many respects as proximal end cap 74 described herein. Proximal end cap 1174 is further described below with respect to FIGS. 154A-154D. As also shown in FIGS. 151A-151B, sensing device 1100 can include a string 1118 connected to proximal end cap 1174 (or another portion of sensing device 1100). String 1118 can be similar or identical to any of the other strings described herein, such as string 18 or string 58. String 1118 can allow sensing device 1100 to be pulled to facilitate loading of at least a portion of sensing device 1110 into a portion of insertion tool 500 (for example, sheath 502), as described herein with respect to sensor 50. String 1118 can also be utilized to remove sensing device 1100 from the subject's bladder as described herein with respect to string 18 or string 58.

Sensing device 1100 can include a spacer 1180, as shown in FIGS. 151A-151B. Spacer 1180 can be positioned within body 1156 and can serve a similar purpose as spacer 80 described herein. Spacer 1180 can advantageously secure to and/or cover an end of spine 1172 to inhibit such end of spine 1172 from contacting body 1156 (and, for example, causing damage to body 1156 when spine 1172 biases sensing device 1100 to an at least partially curled state). In some implementations, spacer 1180 can secure to and/or cover an end of flexible circuit board 1171. FIGS. 152A-152B illustrate an enlarged view of an end of flexible circuit board 1171 and an end 1172a of spine 1172 secured to spacer 1180, and FIG. 152C illustrates an exploded view of the end of circuit board 1171 and end 1172a of spine 1172 along with spacer 1180 and septum 1199. Septum 1199 can be similar or identical to any of the septa described herein. FIGS. 153A-153I illustrate various views of spacer 1180.

Figure 153I:
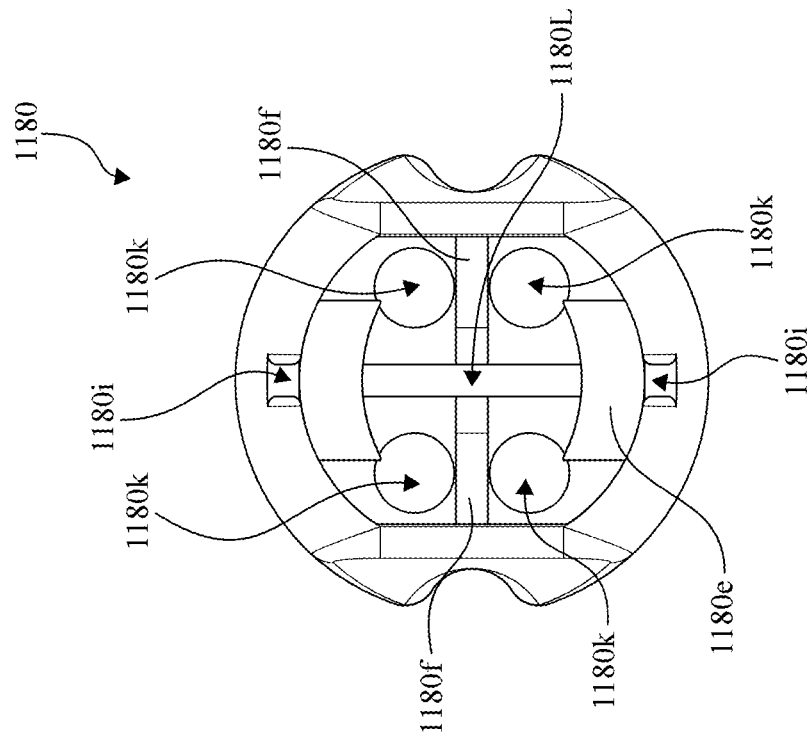
Figure 153H:
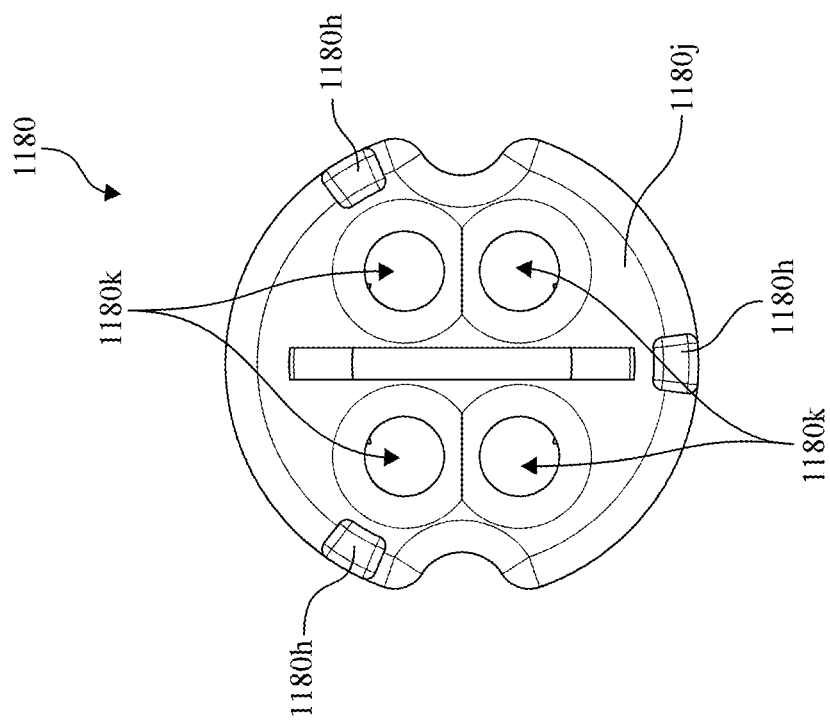

FIGS. 153A-153B illustrate top perspective views, FIG. 153C illustrates a bottom perspective view, FIGS. 153D-153E illustrate front and rear views (respectively), FIGS. 153F-153G illustrate side views (respectively), and FIGS. 153H-153I illustrate top and bottom views (respectively), of spacer 1180. Spacer 1180 can include a first end 1180a, a second end 1180b, and an outer wall 1180c extending between the first and second ends 1180a, 1180b. Spacer 1180 can include an opening 1180m that can allow an end 1172a of spine 1172 to pass into an interior of spacer 1180 defined at least partially within outer wall 1180c. Spacer 1180 can include openings 1180d (for example, on sides of outer wall 1180c of spacer 1180) and fingers 1180e which may be configured to flex as further described below.

With reference to FIG. 153C, spacer 1180 can include a pair of inner walls 1180f extending within an interior of spacer 1180 (for example, inward from outer wall 1180c) and spaced from one another by a gap 1180g. Gap 1180g can be sized and/or shaped to correspond to a thickness of an end 1172a of spine 1172 (see FIG. 152C) so that end 1172a is received between walls 1180f. Inner walls 1180f and gap 1180g can facilitate alignment and/or positioning of end 1172a such that end 1172a engages fingers 1180e of spacer 1180 when end 1172a is inserted into the interior of spacer 1180. In some implementations (such as that illustrated in the figures), fingers 1180e are biased inwards toward an interior of spacer 1180. End 1172a can be configured to engage fingers 1180e and cause fingers 1180e to be pushed outward (for example, away from one another and/or away from an interior of spacer 1180) when end 1172a is inserted into the interior of spacer 1180. With reference to FIGS. 152A-152B, fingers 1180e can be configured to return to or toward a neutral position after end 1172a passes a free end of fingers 1180e. For example, fingers 1180e can be configured to move inward (towards an interior of spacer 1180) after end 1172a passes a free end of fingers 1180e. In some implementations, end 1172a has tapered sides that facilitate smooth movement of end 1172a passed ends of fingers 1180e (see FIG. 152C). In some implementations, end 1172a comprises an arrowhead shape with a blunt tip (see FIG. 152C). Fingers 1180e can be connected to outer wall 1180c at and/or within openings 1180d, which advantageously allows fingers 1180e to flex inward and outward when engaged by end 1172a of spine 1172. Fingers 1180e can include a smaller width and/or height than openings 1180d (see FIGS. 153F-153G). With reference to FIGS. 152A-152B and 153C, spacer 1180 can include notches 1180i that can help guide and/or align end 1172a of spine 1172 into the interior of spacer 1180 (for example, toward and into gap 1180g). Notches 1180i can be arranged along end 1180b proximate opening 1180m. Notches 1180i can be aligned with one another. Notches 1180i can have a width that corresponds to a thickness of end 1172a of spine 1172. With reference to at least FIG. 152C and FIG. 153C, portions of inner walls 1180f can be tapered inward toward and interior of spacer 1180 in order to facilitate guiding of end 1172a within gap 1180g.

With reference to FIGS. 153A-153B and 153H, spacer 1180 can include a top wall 1180j. Top wall 1180j can be perpendicular to an axis that extends through a center of spacer 1180 (for example, along a height of spacer 1180). Spacer 1180 can further include one or a plurality of tabs 1180h extending from wall 1180j (for example, extending perpendicular relative to wall 1180j). In some implementations, spacer 1180 includes a plurality of tabs 1180h (for example, three tabs 1180h), and such tabs 1180h are arranged along a perimeter of wall 1180j spaced from one another. Although the figures illustrate three tabs 1180h, and alternative number of tabs 1180h is possible. For example, spacer 1180 can include two, four, five, or six or more tabs 1180h. Tabs 1180h can be configured to align septum 1199 and/or hold septum 1199 in place, for example, adjacent wall 1180j. Spacer 1180 can include one or a plurality of holes 1180k extending through wall 1180j. Holes 1180k can allow a needle to pass through spacer 1180 to inject fluid into an interior of sensing device 1100. With reference to FIGS. 151A-151B which illustrate sensing device 1100 in an assembled state, spacer 1180 and septum 1199 can be sealed within body 1156, for example, after an interior of sensing device 1100 is filled with a certain quantity of fluid (such as any of the fluids described herein). After spacer 1180 and septum 1199 are secured within body 1156 (for example, via any of the methods described herein), additional fluid can be inserted into the interior of sensing device 1100 by inserting a fluid delivery needle through septum 1199 and through one of holes 1180k. In some instances, it may be necessary to carry out multiple fluid insertion steps with such needle to add a desired amount of fluid thereby pressurizing the interior of sensing device 1100 (for example, to any of the pressure values disclosed herein). Advantageously, spacer 1180 can include a plurality of holes 1180k which can allow for such multiple fluid insertion steps without requiring that septum 1199 be pierced in the same location. This in turn preserves the integrity of septum 1199 and septum's ability to self-seal. Spacer 1180 can include, two, three, or four or more holes 1180k. In some implementations, and as illustrated in at least FIGS. 153A-153B, spacer 1180 includes a slot 1180L extending through wall 1180j. Slot 1180L can be sized and/or shaped to receive at least a portion of end 1172a of spine 1172 when spine 1172 is secured to spacer 1180 (see FIGS. 152A-152B).

FIGS. 154A-154D illustrate various views of proximal end cap 1174. As mentioned previously, proximal end cap 1174 can be similar or identical to proximal end cap 74 in some or many respects. Proximal end cap 1174 can include a first end 1174a and a second end 1174b. Proximal end cap 1174 can include a first portion 1174c that is configured to be positioned within and secured to body 1156 of sensing device 1100, for example, in a similar or identical manner as that described with respect to any of the end caps described herein (such as end cap 74). Proximal end cap 1174 can include a second portion 1174d that is configured to be positioned outside body 1156 of sensing device 1100 when end cap 1174 is secured to body 1156 (for example, when sensing device is in an assembled state). Proximal end cap 1174 can include a rim 1174h (which may also be referred to as an "abutment") that can be configured to engage an end of body 1156 of sensing device 1100. Second portion 1174d of end cap 1174 can have narrowed tip 1174g and a body portion 1174f, each of which can include two planar (flat) surfaces proximate curved/rounded surfaces. Narrowed tip 1174g can advantageously facilitate grasping of proximal end cap 1174 (and thus, the sensing device 1100) by a cystoscope (such as forceps) to allow sensing device 1100 to be removed from a subject's bladder, if removable in such manner is desired and/or needed. Body portion 1174f can be sized and/or shaped to match a size and/or shape of a locking feature within insertion tool 500, such as D-lock 514 described herein. Mating of body portion 1174f and such locking feature can inhibit rotation of insertion tool 500 and sensing device 1100 relative to one another, which can advantageously allow a user to manipulate sensing device 1100 during an insertion procedure through a subject's urethra and into the subject's bladder, as described elsewhere herein. Such mating of body portion 1174f with such locking structure of insertion tool 500 can be utilized alone or in combination with a mating of projection 1176a of end cap 1176 with sheath key insert 518. With reference to FIG. 154D, tip 1174g can have a smaller width $w_2$ than a width $w_1$ of body portion 1174f and/or can have a smaller height $h_2$ than a height $h_1$ of body portion 1174f. As also shown, end cap 1174 can include an opening 1174e that can facilitate connection of string 1118 with end cap 1174.

Figure 155A:
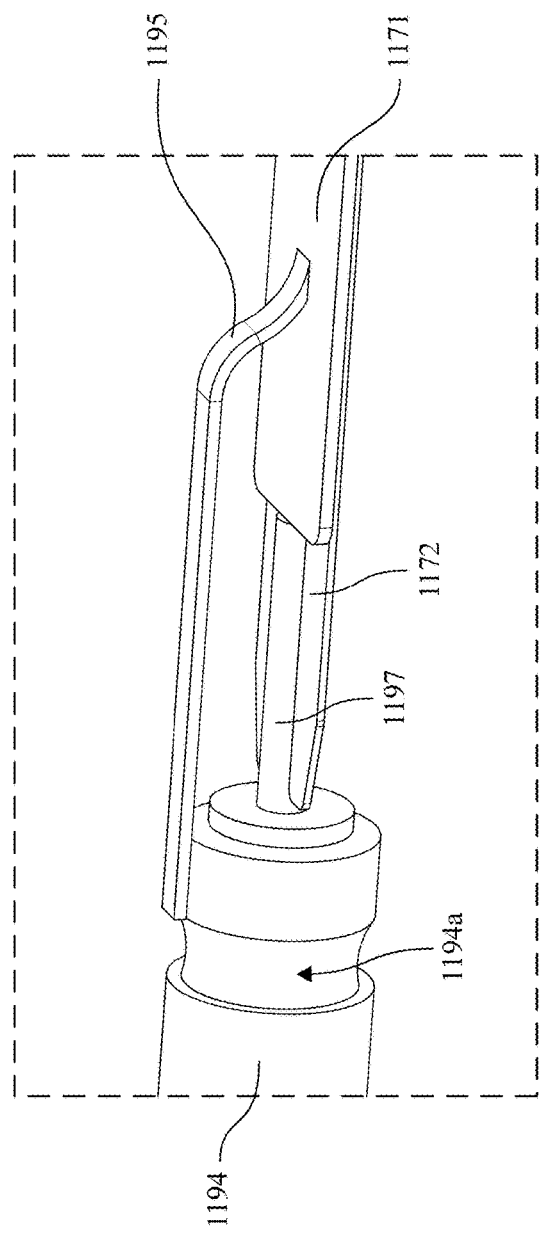
FIG. 155A illustrates an enlarged view of a battery, spine, and flexible circuit board of a sensing device.
Figure 155D:
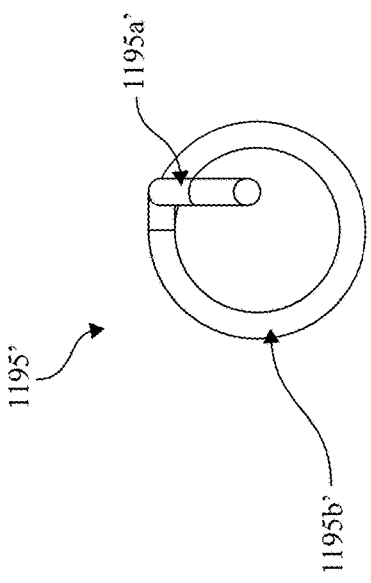
FIGS. 155B-155D illustrate a positive terminal connection device.
Figure 155B:
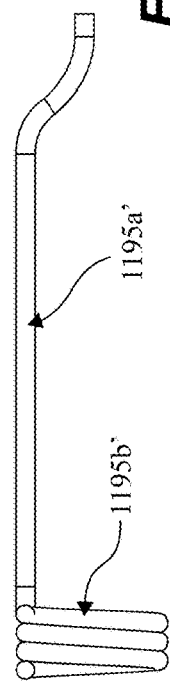
Figure 155C:
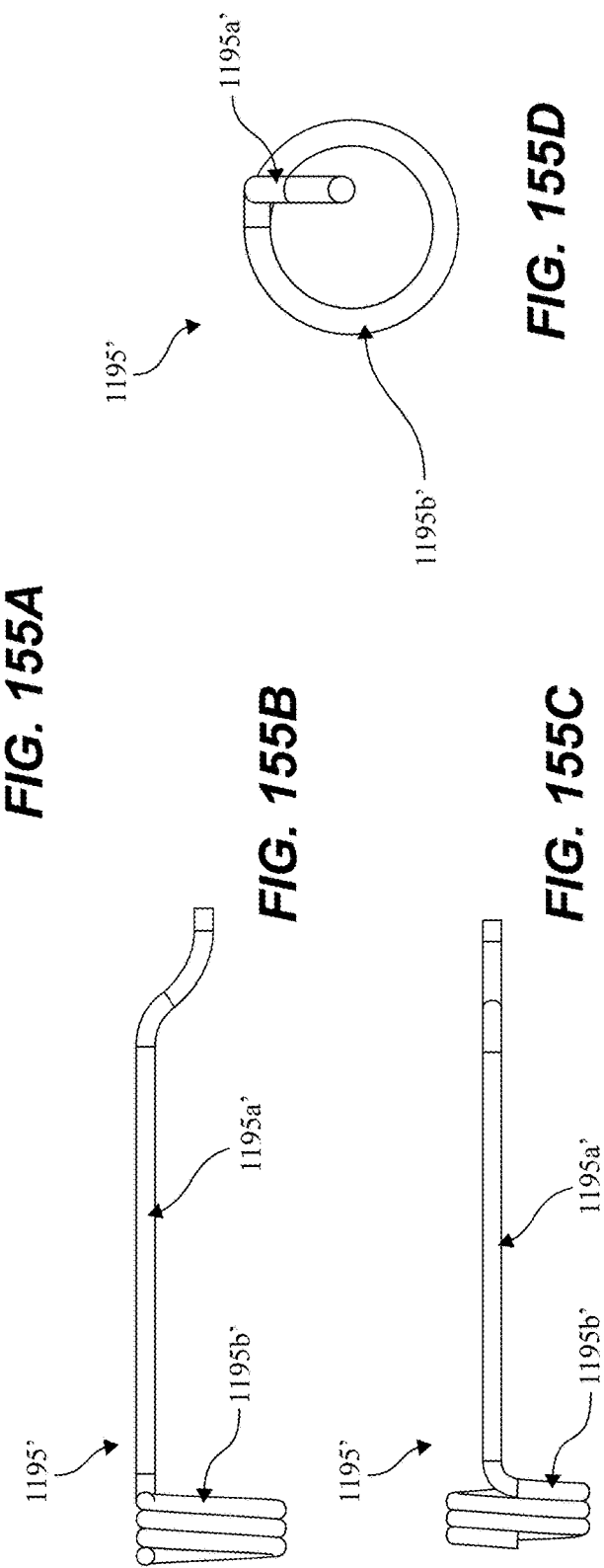

FIG. 155A illustrates an enlarged view of portions of battery 1194, spine 1172, and flexible circuit board 1171. FIG. 155A also illustrates an example of how battery 1194 can be electrically connected to circuit board 1171 via a positive terminal connection 1195 and a negative terminal connection 1197, which can be similar or identical to any of the positive or negative terminal connections described herein. FIGS. 155B-155D illustrate an alternative positive terminal connection device 1195' that can be utilized. Device 1195' includes a body portion 1195a' and a coiled portion 1195b' that can include one or a plurality of coils. Coiled portion 1195b' can be arranged at an end of device 1195'. Device 1195' can advantageously be connected to battery 1194 via positioning of coiled portion 1195b' within a peripheral groove 1194a of battery 1194 (which can extend around an entire circumference of a cross-section of battery 1194). Such method of connection between device 1195' to battery 1194 is advantageous in that it can obviate the need for welding, which can be difficult where battery 1194 comprises aluminum. In some implementations, coiled portion 1195b' is sized and/or shaped such that, when positioned within groove 1194a, coiled portion 1195b' is substantially flush with an outer surface of battery 1194. An end of device 1195' (for example, an end opposite the end which includes coiled portion 1195b') can be connected to circuit board 1171 as described and/or shown herein.

Example Packaging Assemblies

Figure 156A:
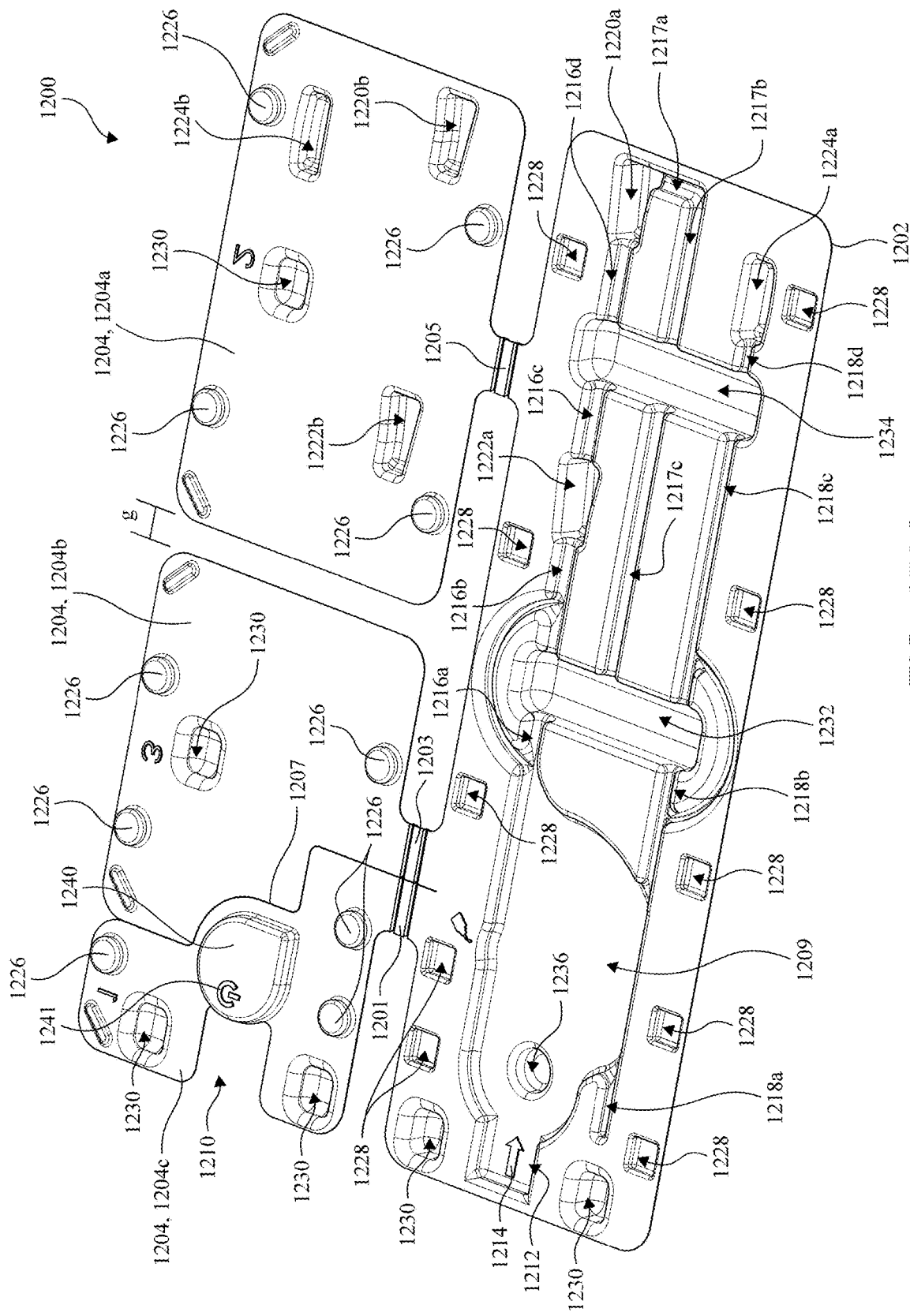
FIGS. 156A-156B illustrate top perspective views of a packaging tray in accordance with aspects of the disclosure.
Figure 156B:
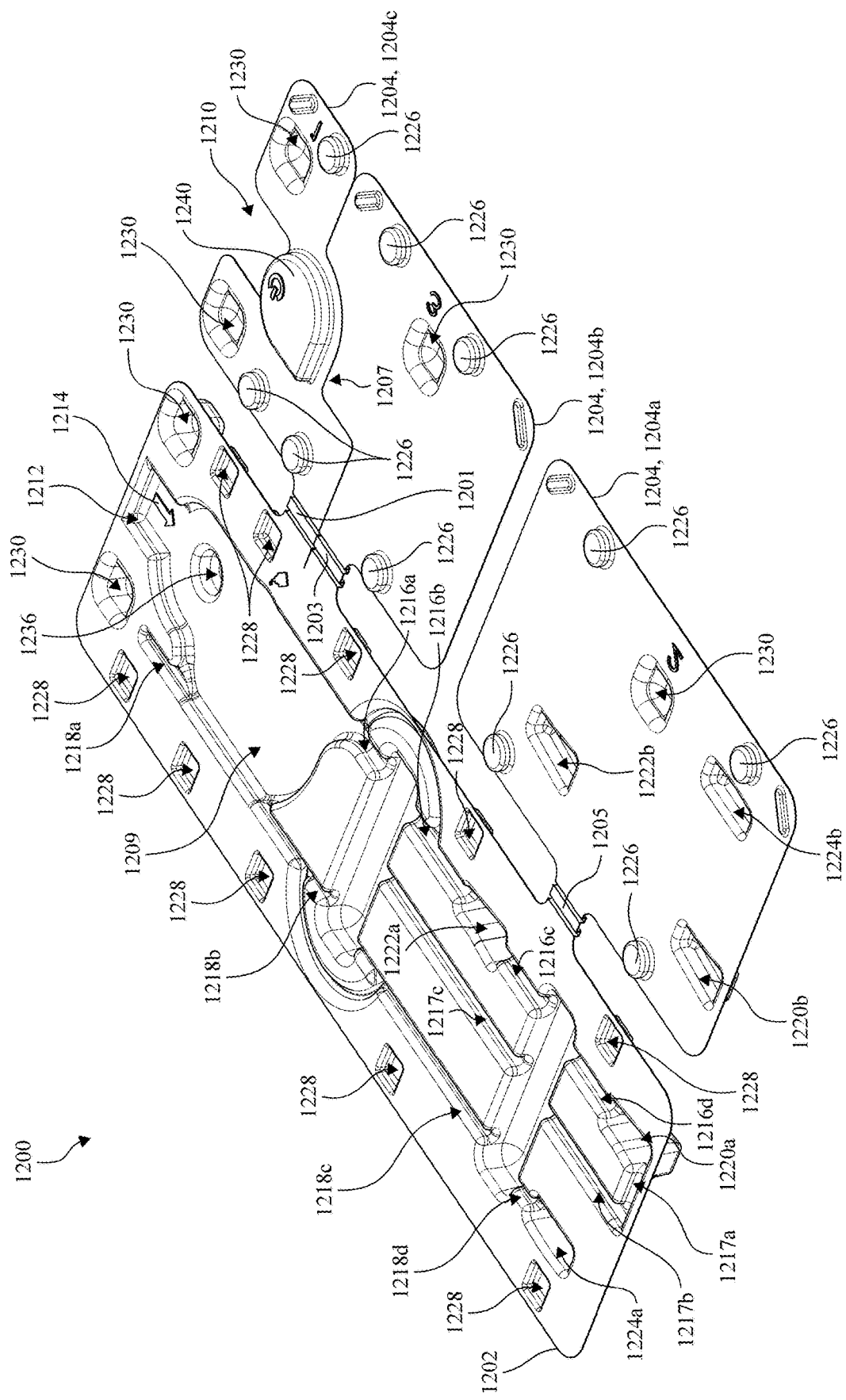
Figure 156C:
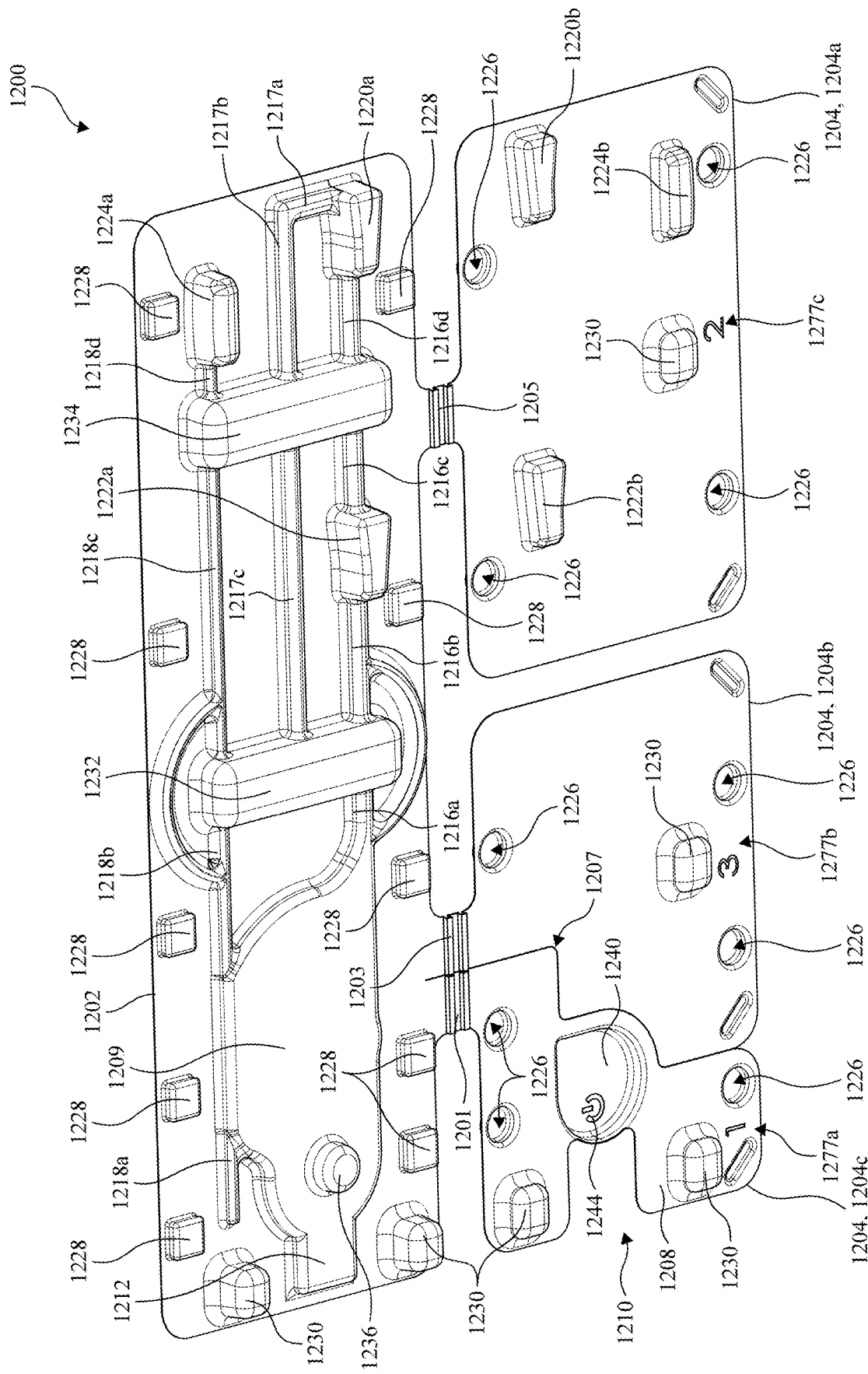
FIG. 156C illustrates a bottom perspective view of the packaging tray of FIGS. 156A-156B in accordance with aspects of the disclosure.
Figure 156D:
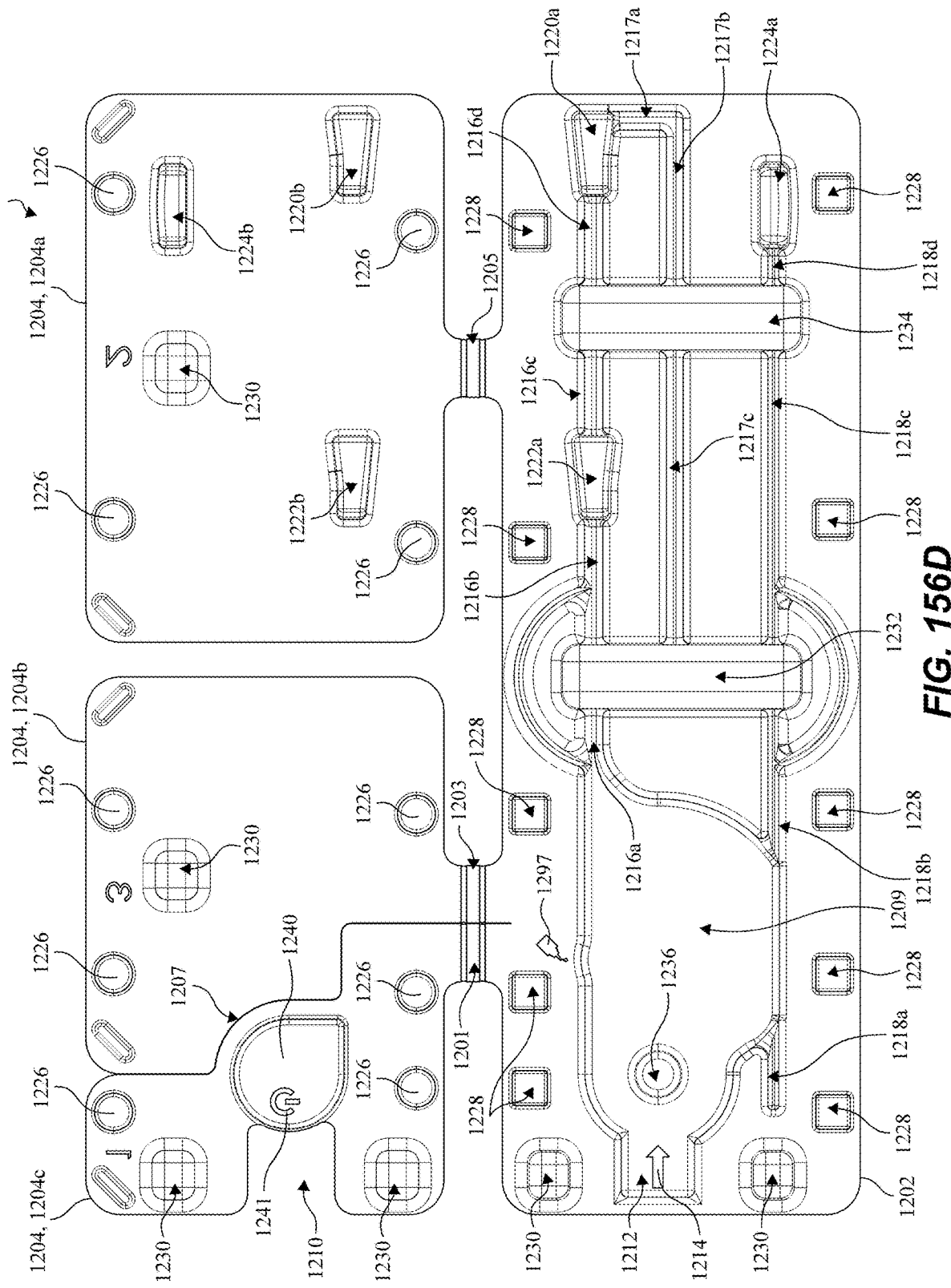
FIG. 156D illustrates a top view of the packaging tray of FIGS. 156A-156B in accordance with aspects of the disclosure.
Figure 156E:
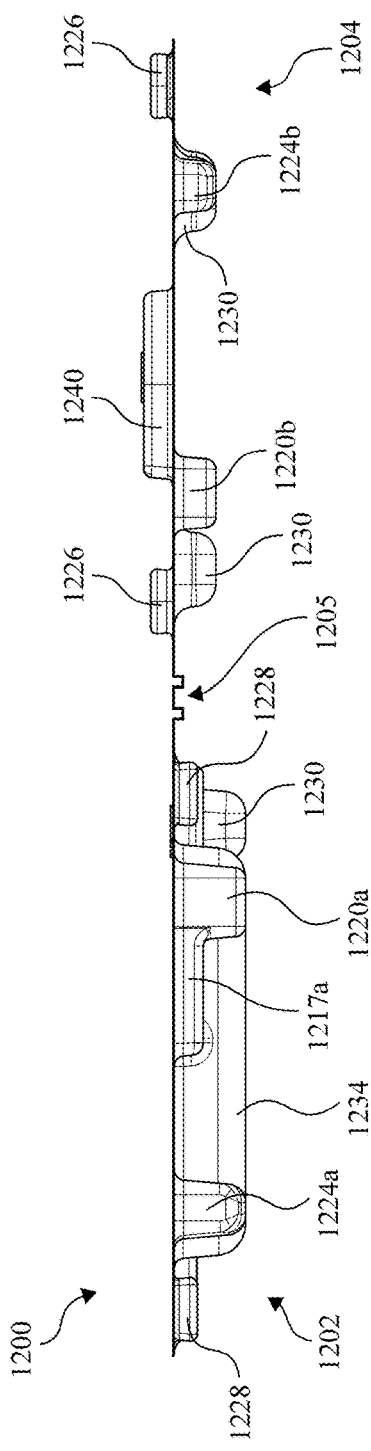
FIG. 156E illustrates a front view of the packaging tray of FIGS. 156A-156B in accordance with aspects of the disclosure.
Figure 156F:
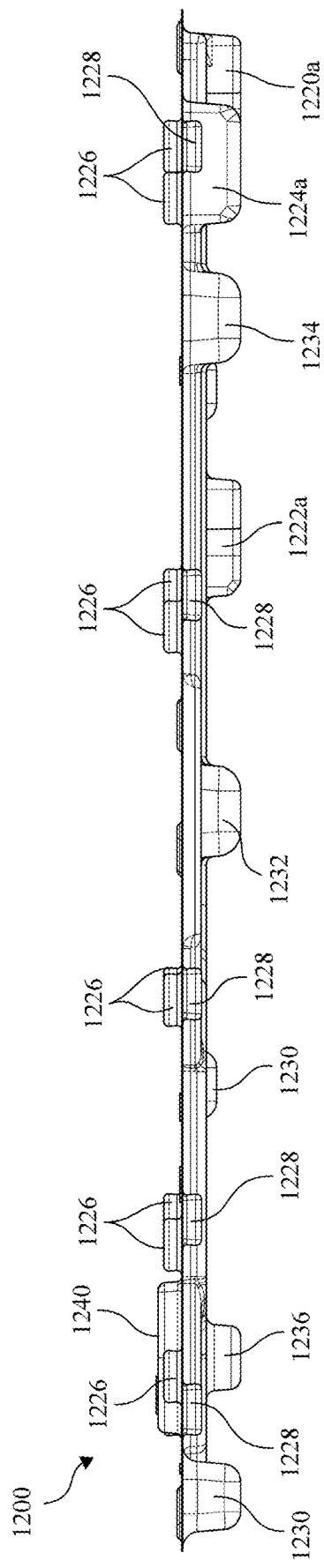
FIG. 156F illustrates a side view of the packaging tray of FIGS. 156A-156B in accordance with aspects of the disclosure.

FIGS. 156A-156F illustrate various views of a packaging tray 1200 (also referred to herein as "tray") that can be used to at least partially retain, enclose, and/or protect sensing device 1100 (or sensors 10, 50), insertion tool 500, and/or push rod 530. Tray 1200 (which can also be referred to herein as a "case") can advantageously facilitate efficient preparation of sensing device 1100, insertion tool 500, and push rod 530 prior to an insertion procedure, for example, an insertion procedure whereby sensing device 1100 is inserted into a body cavity of a subject (for example, inserted through a subject's urethra and into the subject's bladder as described elsewhere herein). Additionally, tray 1200 can advantageously allow sterility to be maintained prior to such procedure. For example, in some implementations, tray 1200 can facilitate loading of sensing device 1100 into insertion tool 500 without requiring a user (for example, a doctor, nurse, technician, or other caregiver) to grab or otherwise contact sensing device 1100 (with or without a glove). As will be described further below, tray 1200 can be configured to retain insertion tool 500 while at least a portion of sensing device 1100 is pulled into sheath 502 of insertion tool 500, for example, via string 1118. Tray 1200 can be utilized in combination with a bag 1298 (to form a packaging assembly) as shown and described further below with respect to FIGS. 157A-157C. FIGS. 156A-156B illustrate top perspective views of tray 1200 and FIG. 156C illustrates a bottom perspective view of tray 1200. FIG. 156D illustrates a top view of tray 1200. FIG. 156E illustrates a front view of tray 1200 and FIG. 156F illustrates a side view of tray 1200.

Tray 1200 can be configured to at least partially retain and enclose sensing device 1100, insertion tool 500, and/or push rod 530. Tray 1200 can include a base 1202 that can rest atop a surface. Tray 1200 can also include a cover 1204 connected to base 1202 and configured to at least partially enclose sensing device 1100, insertion tool 500, and/or push rod 530 when retained by tray 1200. Cover 1204 can be pivotably connected to base 1202 and configured to pivot between a closed position in which cover 1204 at least partially encloses sensing device 1100, insertion tool 500, and/or push rod 530 and an open position in which cover 1204 does not cover sensing device 1100, insertion tool 500, and/or push rod 530. Cover 1204 can be connected to base 1202 via one or more hinges, such as one or more living hinges integrally formed from the same material as cover 1204 and base 1202. In some variants, cover 1204 and base 1202 are not connected via a hinge, but rather, are independent. Regardless of whether cover 1204 and base 1202 are connected to one other (e.g., via a hinge), portions of cover 1204 and base 1202 can be configured to removably secure to one another (for example, via a press-fit arrangement).

Tray 1200 can be configured to retain sensing device 1100 while at the same time allowing a portion of sensing device 1100 to be accessible. For example, tray 1200 can be configured to enclose only a portion of sensing device 1100 thereby allowing a portion of sensing device 1100 to be accessible. In some implementations, tray 1200 is configured to enclose a majority of sensing device 1100 yet still allow a portion of sensing device 1100 to be accessible. Such configurations can advantageously allow a user to access a button of sensing device 1100, for example, to transition sensing device 1100 from a non-operational state to an operational state when sensing device 1100 is retained and partially enclosed by tray 1200. In implementations of sensing device 1100 where such button is contained within an interior of a housing of sensing device 110, the tray 1200 can be configured to allow access to a portion of the housing proximate the button. In implementations where tray 1200 includes base 1202 and cover 1204, a portion of either or both of the base 1202 and cover 1204 can be configured to provide access to such button of sensing device 1100 (and/or a portion of a housing of sensing device 1100 proximate such button) while sensing device 1100 is retained and partially enclosed by the base 1202 and cover 1204. In some implementations, such portion(s) of tray 1200 (e.g., of base 1202 and/or cover 1204) is arranged at an end of tray 1200 (for example, an end of base 1202 and/or cover 1204). For example, cover 1204 can include an opening that allows a user to access a button of sensing device 1100 (for example, to transition sensing device 1100 from a non-operational state to an operational state) when cover 1204 is in the closed position in which the cover 1204 at least partially covers and/or protects sensing device 1100, insertion tool 500, and/or push rod 530. Such opening can advantageously also allow a user to access such button when tray 1200 is positioned within an interior of bag 1298 as described further below. Such opening can be, for example, opening 1210 as illustrated in at least FIGS. 156A-156F. In some implementations, cover 1204 comprises a plurality of flaps, such as flaps 1204a, 1204b, and/or 1204c illustrated in FIGS. 156A-156F. In some implementations, flaps 1204a, 1204b, and/or 1204c are independently movable relative to one another. In some variants, cover 1204 comprises only two of flaps 1204a, 1204b, 1204c. In some variants, flap 1204b and 1204c are integral with one another (for example, form a single flap). In some variants, flaps 1204a and 1204b are integral with one another (for example, form a single flap). In some variants, cover 1204 is a single piece member that includes the structure shown and/or described with respect to flaps 1204a, 1204b, 1204c.

Flap 1204a can be pivotably connected to base 1202 via a hinge 1205, flap 1204b can be pivotably connected to base 1202 via a hinge 1203, and/or flap 1204c can be pivotably connected to base 1202 via a hinge 1201. In some implementations, hinges 1201, 1203, 1205 are living hinges formed out of the same material as the base 1202 and flaps 1204a, 1204b, 1204c. Flaps 1204a, 1204b, 1204c can be pivotable about base 1202 independently from one another. This can advantageously allow for different portions of base 1202 to be exposed when preparing sensing device 1100 for an insertion procedure, as described further below with respect to FIGS. 157D-157I. Flap 1204c can be pivoted between a closed position in which flap 1204c at least partially covers sensing device 1100 and an open position in which flap 1204c does not cover sensing device 1100 (see FIGS. 157D-157E). Each of flaps 1204a, 1204b can be pivoted between a closed position in which flaps 1204a, 1204b at least partially cover insertion tool 500 and push rod 530 and an open position in which flaps 1204a, 1204b do not cover insertion tool 500 and push rod 530 (see FIGS. 157D-157I). FIGS. 156A-156D illustrate a seamline 1207 between flaps 1204c and 1204b. In some implementations, flaps 1204a, 1204b are spaced from one another by a gap g (see FIG. 156A). In some variants, flaps 1204a, 1204b are not separated by such gap g and join at a seamline similar to seamline 1207.

Base 1202 can include one or more recessed portions, cavities, and/or channels for retaining sensing device 1100, insertion tool 500, and/or push rod 530. With reference to FIGS. 156A-156B and 156D, base 1202 can include a recessed portion 1209 that can be configured to receive sensing device 1100 and a portion of insertion tool 500 (see also FIGS. 157E and 157I). Recessed portion 1209 can be recessed from a top surface of base 1202 by a depth that is equal to or greater than a cross-section of sensing device 1100. As shown, base 1202 can include cavities 1220a, 1222a, 1224a. Cavity 1220a can be configured to receive handle 506 of insertion tool 500 and cavity 1224a can be configured to receive handle 538 of push rod 530 (see FIG. 157G). In some implementations, base 1202 includes cavity 1222a, which is configured to receive a handle of another insertion tool that is shorter than insertion tool 500 (for example, an insertion tool intended for use for a female). Inclusion of both of cavities 1222a and 1220a thus allow base 1202 to accommodate either of two insertion tools intended for male and female anatomies. In some implementations, flap 1204a includes cavities 1220b, 1222b, 1224b which are configured to align with cavities 1220a, 1222a, 1224a of base 1202 (respectively) when flap 1204a is in a closed position, such as that shown in FIGS. 157D-157F. In such implementations, cavities 1220a and 1220b can retain and enclose handle 506 and cavities 1224a and 1224b can retain and enclose handle 538 when flap 1204a is in a closed position. Where an alternative insertion tool is retained in tray, such as a female version that is shorter in length (as discussed above), the handle of such female version can be retained and enclosed by cavities 1222a and 1222b when flap 1204a is in a closed position. Cavity 1220a can be configured to limit rotation of handle 506. For example, cavity 1220a can be configured to limit a degree of rotation of handle 506 (and therefore insertion tool 500) about an axis of insertion tool 500 (for example, extending through sheath 502 and/or handle 506) to less than or equal to about 90 degrees, about 85 degrees, about 80 degrees, about 75 degrees, about 70 degrees, about 65 degrees, about 60 degrees, about 55 degrees, about 50 degrees, about 45 degrees, less than or equal to about 40 degrees, less than or equal to about 35 degrees, less than or equal to about 30 degrees, less than or equal to about 25 degrees, less than or equal to about 20 degrees, less than or equal to about 15 degrees, less than or equal to about 10 degrees, or less than or equal to about 5 degrees. Limitation of rotation of handle 506 (and therefore insertion tool 500) can advantageously facilitate alignment of a mating feature on sensing device 1100 (for example, projection 1176a on end cap 1176) with a corresponding mating feature of insertion tool 500 (for example, slot 518 illustrated in FIGS. 25-26 and 28). Engagement between such mating features can inhibit relative rotation of insertion tool 500 and sensing device 1100, which can provide benefits such as those described herein with respect to sensor 50 and insertion tool 500. With continued reference to FIGS. 156A-156B and 156D, base 1202 can include channels 1216a, 1216b, 1216c, 1216d for accommodating insertion tool 500 (for example, sheath 502) and/or channels 1218a, 1218b, 1218c, 1218d for accommodating stem 532 of push rod 530. In some implementations, base 1202 includes channel 1217a, 1217b, and/or 1217c. Channels 1217a, 1217b, 1217c can be used to retain string 1118 when string 1118 extends through sheath 502 and handle 506 (see FIG. 157G).

Base 1202 and cover 1204 can include one or more engagement features that allow base 1202 and cover 1204 to be secured to one another when cover 1204 is in a closed position. In implementations where cover 1204 includes flaps 1204a, 1204b, 1204c, base 1202 and flaps 1204a, 1204b, 1204c can include one or more engagement features that allow base 1202 and flaps 1204a, 1204b, 1204c to be secured to one another when flaps 1204a, 1204b, 1204c are in a closed position. For example, base 1202 can include one or a plurality of indents 1228 configured to receive (for example, removably receive) protrusions 1226 on flaps 1204a, 1204b, 1204c, for example, via a press-fit arrangement. Base 1202 can include a one or plurality of protruding portions 1230, 1232, 1234, 1236 (which may be referred to as "legs" or "feet") that can act to support base 1202 on a surface (see FIG. 156C), alone or in combination with cavities 1224a, 1220a, 1222a (see FIGS. 156C and 156E-156F). Protruding portions 1230, 1232, 1234, 1236 and/or cavities 1224a, 1220a, 1222a can terminate along a same plane and/or be arranged to allow base 1202 to retain sensing device 1100, insertion tool 500, and push rod 530 in a non-inclined manner, for example, relative to a plane of a surface on which base 1202 and/or tray 1200 rests. This can, among other things, advantageously inhibit sensing device 1100, insertion tool 500, and push rod 530 from inadvertently falling onto such support surface (for example, a table) that may not be sterile. With reference to FIGS. 156A and 157I, cavities formed at the top surface of base 1202 of protruding portions 1232, 1234 can aid a user in removing insertion tool 500 (e.g., sheath 502) and push rod 500 (e.g., stem 532) from base 1202 as they can provide a space in which the user's fingers can be inserted to grasp the tool 500 and rod 500 (for example, while wearing gloves).

Figure 157D:
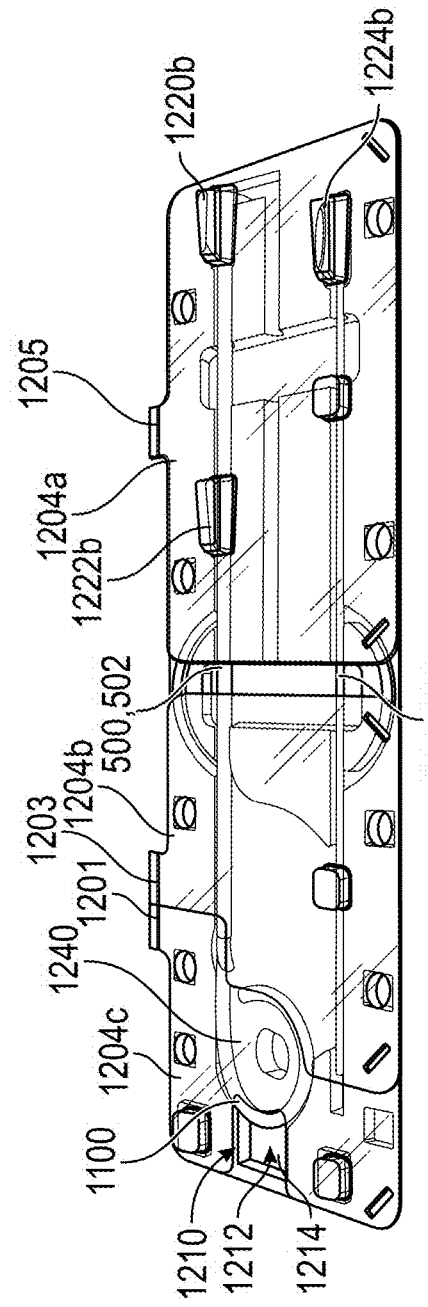
Figure 157E:
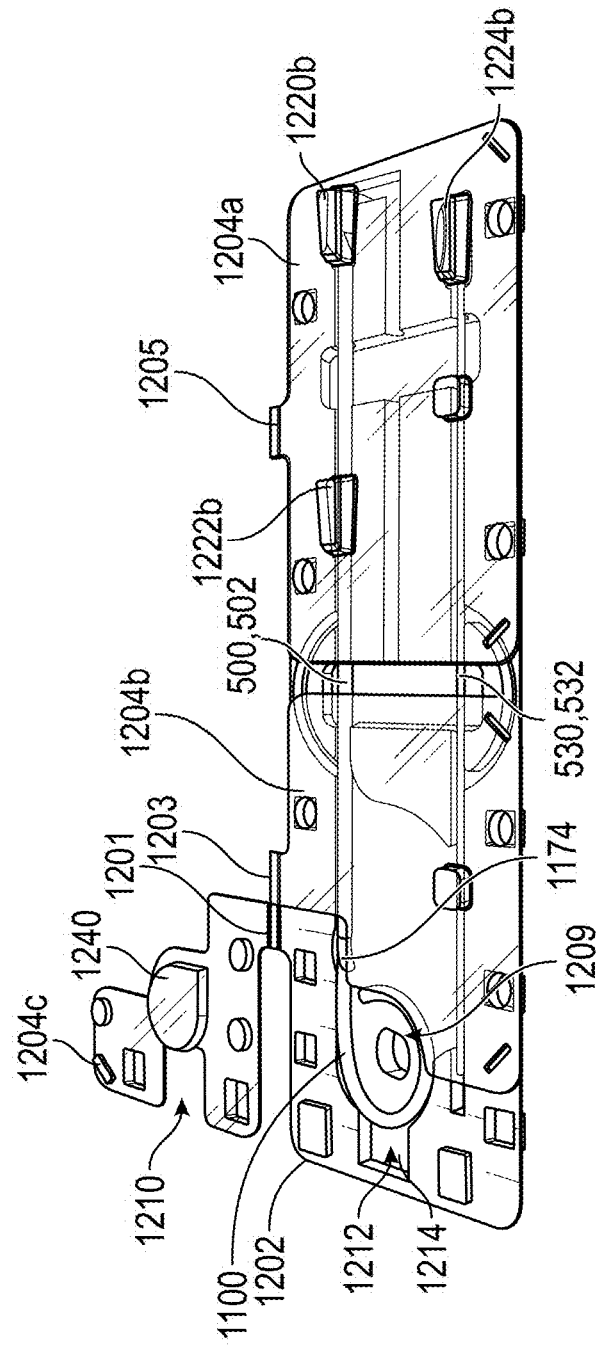

As mentioned above, tray 1200 can include an opening (for example, in cover 1204) that allows a user to engage a button of sensing device 1100 (for example, button 1190) when sensing device 1100 is retained by tray 1200. An implementation of such opening is opening 1210 in flap 1204c. Opening 1210 can be arranged on an end of flap 1204c and/or an end of tray 1200 or cover 1204 where flap 1204c is arranged at an end of tray 1200 or cover 1204. In some implementations, flap 1204c includes a protrusion 1240 that is configured to retain sensing device 1100 in an at least partially curled configuration when sensing device 1100 is retained and enclosed by tray 1200. FIG. 157D illustrates flap 1204c in a closed position and sensing device 1100 curled around protrusion 1240. Protrusion 1240 can have an at least partially circular shape that facilitates positioning of sensing device 1100 in such curled position. Retaining sensing device 1100 in such position can advantageously allow end cap 1174 of sensing device 1100 to be operably positioned relative to an end of sheath 502 of insertion tool 500 so as to facilitate insertion of sensing device 1100 inside sheath 502 during loading (see FIG. 157E).

Base 1202 can be configured to allow access to a portion of sensing device 1100 (for example, at or near a button of sensing device 1100) when sensing device 1100 is retained by base 1202. For example, with reference to at least FIGS. 156A-156B and 156D, in some implementations, base 1202 includes a recessed portion 1212 that facilitates access to button 1190 of sensing device 1100 (see also FIGS. 157D-157E). Recessed portion 1212 can be positioned adjacent (for example, below) opening 1210 when flap 1204c is in the closed position and can be positioned adjacent sensing device 1100 and recessed portion 1209. In some implementations, base 1202 includes a visual indicator 1214 (for example, an arrow) in recessed portion 1212 to aid a user in locating a button of sensing device 1100. With reference to FIGS. 156A and 156C, in some implementations, cover 1205 includes a visual indicator 1241 on a portion of protrusion 1240 that is configured to aid a user in locating the button. Such indicator 1241 can be arranged along a portion of a perimeter of protrusion 1240 that is configured to be positioned adjacent button 1190 of sensing device 1100 when sensing device 1100 is positioned in recessed portion 1209.

FIGS. 157A-157I illustrate an example method of preparing sensing device 1100 for insertion into a body cavity of a subject (for example, a bladder) in a manner that preserves sterility, using a bag 1298 and tray 1200. The methods described below may be utilized in the context of inserting sensing device 1100 into a subject's bladder or in other contexts as well. Maintaining sterility prior to and during a sensor insertion procedure, for example, within the subject's bladder, is important to minimize the risk of infections. However, it is often difficult to maintain sterility during such procedures, especially when a caregiver needs to interact with other electronic patient monitoring devices in order to wirelessly pair the sensing device (to allow transmission of physiological data). Indeed, in some cases, caregivers wear multiple gloves on each hand and sequentially remove each glove when a non-sterile object is touched in order to preserve sterility during a sensor insertion procedure. The methods and packaging assemblies described herein advantageously allow a sensing device (such as sensing device 1100) to be prepared for insertion in an efficient and convenient manner that avoids breaking sterility.

With reference to FIG. 157A, tray 1200 can be packaged within an interior of bag 1298. The interior of bag 1298 can be sealed in order to preserve sterility. In some implementations, tray 1200 is more rigid than bag 1298. Sensing device 1100, insertion tool 500, and push rod 530 can be at least partially retained and enclosed by tray 1200 as shown in FIG. 157D, which illustrates tray 1200, sensing device 1100, insertion tool 500, and push rod 530 outside of bag 1298. As discussed above, sensing device 1100 can include a button 1190 configured to allow sensing device 1100 to be transitioned from a non-operational state to an operational state. In some implementations, when sensing device 1100 is in such operational state, sensing device 1100 is able to wirelessly communicate with one or more separate devices (such as a patient monitoring device or mobile phone or tablet). In some implementations, when sensing device 1100 is in such operational state, a pressure sensor of sensing device 1100 is activated, thereby allowing the sensing device 1100 to obtain pressure data that can be used for urodynamic monitoring and/or analysis as described elsewhere herein. In some implementations, when sensing device 1100 is in such non-operational state, sensing device 1100 does not wireless communicate with separate devices and/or does not obtain pressure data (or other data that can be utilized to assess physiological conditions or characteristics of a subject).

Bag 1298 and tray 1200 can advantageously be configured to allow a user to activate button 1190 of sensing device 1100 (to transition sensing device 1100 to such operational state) while sensing device 1100 and tray 1200 are positioned within a sterile interior of bag 1298. As discussed above, and with reference to FIG. 157B, tray 1200 can include opening 1210 that facilitates access to button 1190 of sensing device 1100. Additionally, as also discussed above, tray 1200 (for example, base 1202 of tray 1200) can include recessed portion 1212 that can also facilitate access to button 1190. In some implementations, tray 1200 includes visual indicator 1214 and/or visual indicator 1241 to aid a user in locating button 1190. With reference to FIG. 157C, bag 1298 can be made of a material that allows the user to engage button 1190 by pressing a portion of bag 1298 against button 1190 (e.g., a portion of sensing device 1100 which houses button 1190). Such portion of bag 1298 can be transparent to allow the user to more easily locate and engage button 1190, opening 1210, recessed portion 1212, and/or indicators 1214, 1241. Accordingly, as illustrated in FIGS. 157A-157C, a user can advantageously transition sensing device 1100 to an operational state while sensing device 1100 (and tray 1200) is positioned inside a sealed, sterile interior of bag 1298. With continued reference to FIG. 157A, in some implementations, tray 1200 includes an identification tag 1299 that includes information associated with sensing device 1100. Such identification tag 1299 can allow a user to wirelessly pair sensing device 1100 with a patient monitoring device. Such identification tag 1299 can be or include a QR code, for example. In some implementations, tray 1200 is more rigid than bag 1298.

A method of preparing sensing device 1100 for insertion into a body cavity of a subject (for example, a bladder) to preserve sterility can include obtaining bag 1298 and tray 1200 positioned within the interior of bag 1298, as illustrated in FIG. 157A. Tray 1200 can at least partially retain and enclose sensing device 1100, insertion tool 500, and/or push rod 530, as discussed above. The method can further include transitioning sensing device 1100 from a non-operational state to an operational state. Transitioning sensing device 1100 to such operational state can be performed: without removing tray 1200 and/or sensing device 1100 from the interior of the bag 1298; without opening bag 1298; without wearing a glove; and/or without directly contacting sensing device 1100 (with or without a glove). For example, as illustrated and described with respect to FIGS. 157B-157C, transitioning sensing device 1100 to such operational state can be performed by pressing a portion of the bag 1298 against button 1190 (or a portion of sensing device 1100 that houses button 1190) via opening 1210 and/or recessed portion 1212. For example, transitioning sensing device 1100 to such operational state can be performed by pressing a portion of bag 1298 against a portion of housing 1156 to engage button 1190, via opening 1210 and/or recessed portion 1212. In some implementations, button 1190 is engaged by pressing a transparent portion of bag 1298 against button 1190 or against a portion of housing 1156 to engage button 1190. In some implementations, visual indicator 1214 and/or visual indicator 1241 is utilized to locate button 1190. In some implementations, visual indicator 1214 and/or visual indicator 1241 aligns with button 1190 when sensing device 1100 is retained by tray 1200. In some implementations, after button 1190 is engaged and sensing device 1100 is transitioned to the operational state, the method further includes wirelessly pairing sensing device 1100 with a separate electronic device, such as a patient monitoring device. Sensing device 1100 can be configured for communication with any of the components described herein with respect to system 1400. In some implementations, identification tag 1299 is utilized (for example, electronically scanned) by such patient monitoring device or a mobile device configured for communication with such patient monitoring device in order to provide information related to the sensing device 1100 to the patient monitoring device.

After sensing device 1100 is transitioned to the operational state (and, in some implementations, wirelessly paired with a patient monitoring device), the method can further include opening bag 1298 and emptying tray 1200 onto a surface (for example, a table). In some implementations, opening bag 1298 includes opening an end of bag 1298 and/or breaking a seal of bag 1298. In some implementations, opening an end of bag 1298 and/or breaking a seal of bag 1298 is performed without wearing a glove. In some implementations, emptying tray 1200 onto the surface includes causing tray 1200 to fall out of bag 1298 onto the surface without touching tray 1200 with a bare hand and/or without touching tray 1200 with a glove. In some implementations, sensing device 1100, insertion tool 500, and/or push rod 530 are retained by tray 1200 (for example, held in place by tray 1200) when tray 1200 is emptied onto the surface. Such surface may be a sterile or non-sterile surface. FIG. 157D illustrates a top perspective view of tray 1200 in an example orientation in which tray 1200 rests atop a support surface.

Figure 157F:
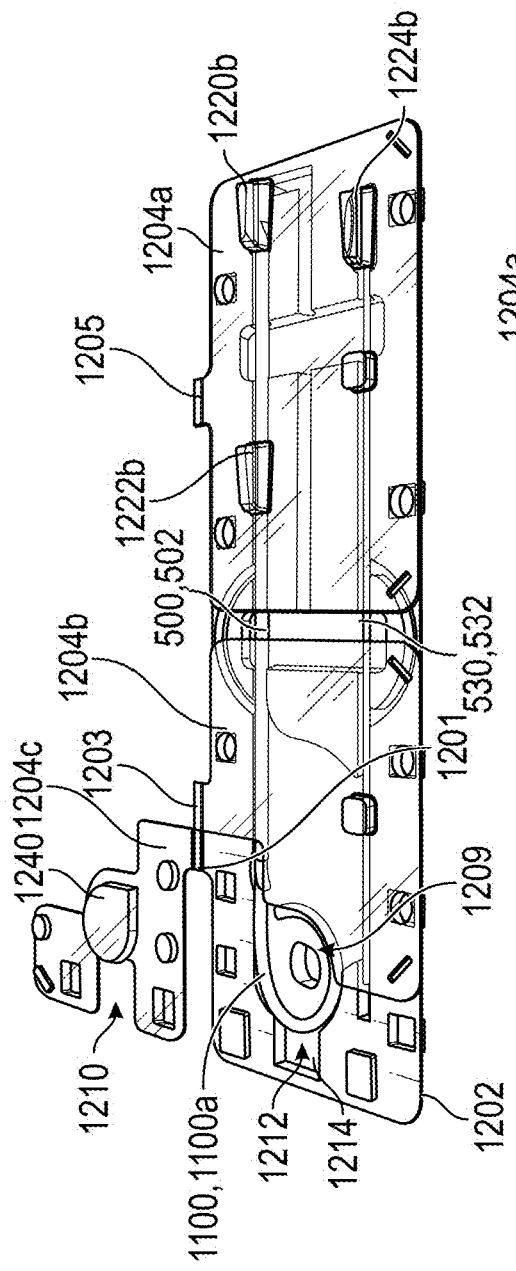

The method can further include opening cover 1204 of tray 1200 or a portion of cover 1204 in order to expose sensing device 1100, insertion tool 500, and/or push rod 530. In some implementations, tray 1200 includes at least two flaps, one flap configured to cover at least a portion of sensing device 1100 and another flap configured to cover at least a portion of insertion tool 500 and/or push rod 530. For example, in implementations in which cover 1204 includes flap 1204c, the method can include pivoting flap 1204c from a closed position (see FIG. 157D) to an open position (see FIG. 157E), thereby exposing sensing device 1100. With reference to FIG. 157F, the method can further include applying a lubricating material 1100a (for example, lubricating jelly) to all or a portion of sensing device 1100. In some implementations, applying the lubricating material 1100a to all or a portion of sensing device 1100 is performed without contacting sensing device 1100 (via a bare hand or with a glove). For example, lubricating material 1100a can be applied to all or a portion of sensing device 1100 by squeezing a container including lubricating material 1100a from a location above sensing device 1100 such that the lubricating material 1100a falls on portions of the sensing device 1100 under the force of gravity. With reference to FIG. 156D, in some implementations, tray 1200 includes a visual indicator 1297 for indicating which portion of sensing device 1100 to be lubricated and/or reminding a user to apply the lubricating material 1100a. Visual indicator 1297 can be arranged proximate a location of tray 1200 where sensing device 1100 is retained (for example, on a portion of a top surface of base 1202 proximate recessed portion 1209).

Figure 157G:
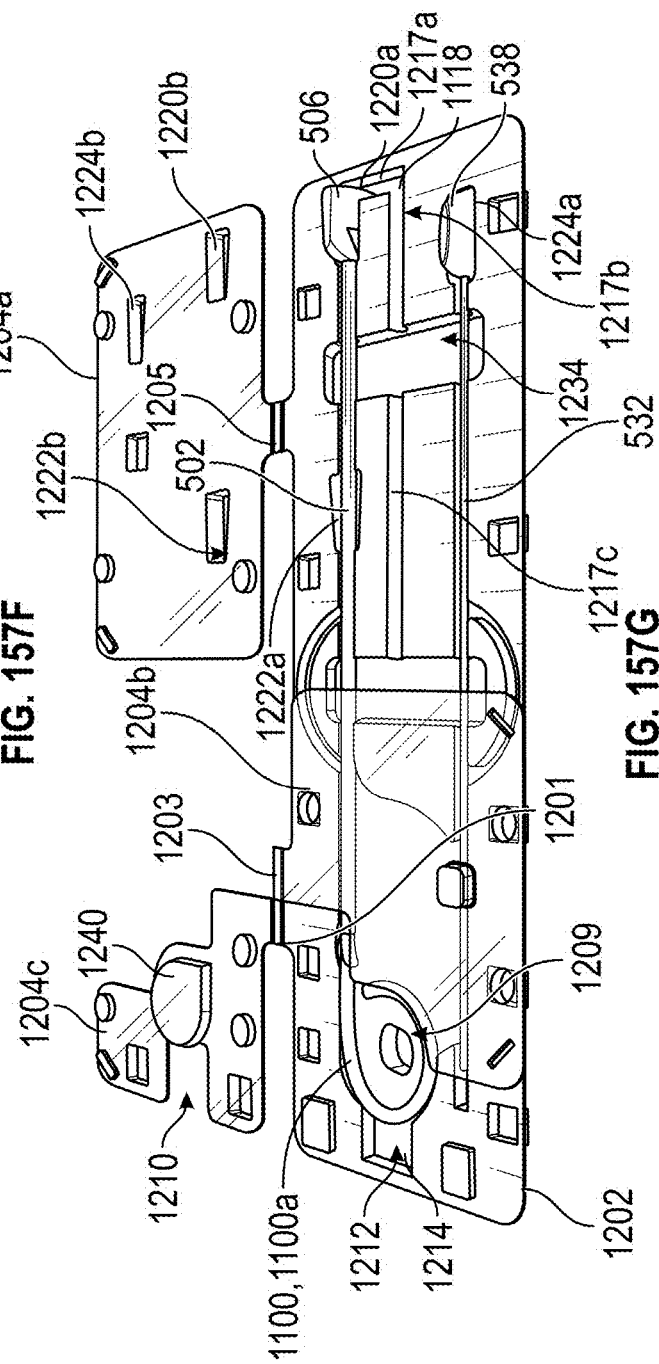

The method can further include pivoting flap 1204a from a closed position (see FIG. 157F) to an open position (see FIG. 157G). After flap 1204a is pivoted to such open position, at least a portion of sensing device 1100 can be inserted into sheath 502, for example, by pulling string 1118 that extends from sensing device 1100 through sheath 502 and handle 506 (see FIG. 157H). With reference to FIG. 157G, in some implementations, string 1118 can be positioned in channel 1217a, 1217b, and/or 1217c or cavity 1234, when sensing device 1100, insertion tool 500, and string 1118 are in a packaged configuration within tray 1200 (for example, prior to an insertion procedure). In such implementations, the method can include removing string 1118 from channel 1217a, 1217b, and/or 1217c or cavity 1234 such that it can be pulled as illustrated in FIG. 157H.

As mentioned previously, lubricating material 1100a can be applied to sensing device 1100. The lubricating material 1100a can advantageously facilitate insertion of sensing device 1100 into sheath 502. In some implementations, at least a portion of sensing device 1100 is inserted into sheath 502 without requiring a user to grasp or otherwise contact sensing device 1100 and/or without requiring a user to grasp or otherwise contact sheath 502. Tray 1200 can be configured to hold insertion tool 500 in place while sensing device 1100 is pulled into sheath 502, for example, via string 1118 (see FIGS. 157G-157H). For example, cavity 1220a of base 1202 can be configured to hold handle 506 (and thus, insertion tool 500) in place while sensing device 1100 is pulled into sheath 502 via string 1118. In some implementations, the method further includes engaging a mating feature of sensing device 1100 (for example, projection 1176a) with a mating feature of insertion tool 500 (for example, slot 518) such that rotation of the sensing device 1100 relative to insertion tool 500 is prevented or inhibited (for example, about an axis extending through sheath 502 and/or handle 506). In some implementations, sensing device 1100 is inserted into sheath 502 until only end cap 1176 (or a portion thereof) is exposed (see FIG. 157I). In some implementations, inserting at least the portion of sensing device 1100 into sheath 502 comprises inserting sensing device 1100 such that sensing device 1100 (for example, proximal end cap 1174) abuts a stop located within sheath 502. In some implementations, sensing device 1100 is inserted into sheath 502 until proximal end cap 1174 engages a locking feature within sheath 502, such as D-lock 514 described herein.

In some implementations in which tray 1200 includes flap 1204b, the method can further include pivoting flap 1204b from a closed position (see FIG. 157H) to an open position (see FIG. 157I). After flaps 1204a, 1204b, 1204c are pivoted to their respective open positions, sensing device 1100, insertion tool 500, and push rod 530 can be utilized to insert sensing device 1100 through a subject's urethra and into the subject's bladder, as described elsewhere herein. With reference to FIG. 156C, flaps 1204a, 1204b, 1204c can include visual indicators 1277a, 1277b, 1277c that can advantageously indicate a proper sequence of opening flaps 1204a, 1204b, 1204c. Each visual indicator 1277a, 1277b, 1277c can comprise a different number, as shown.

Figure 158A:
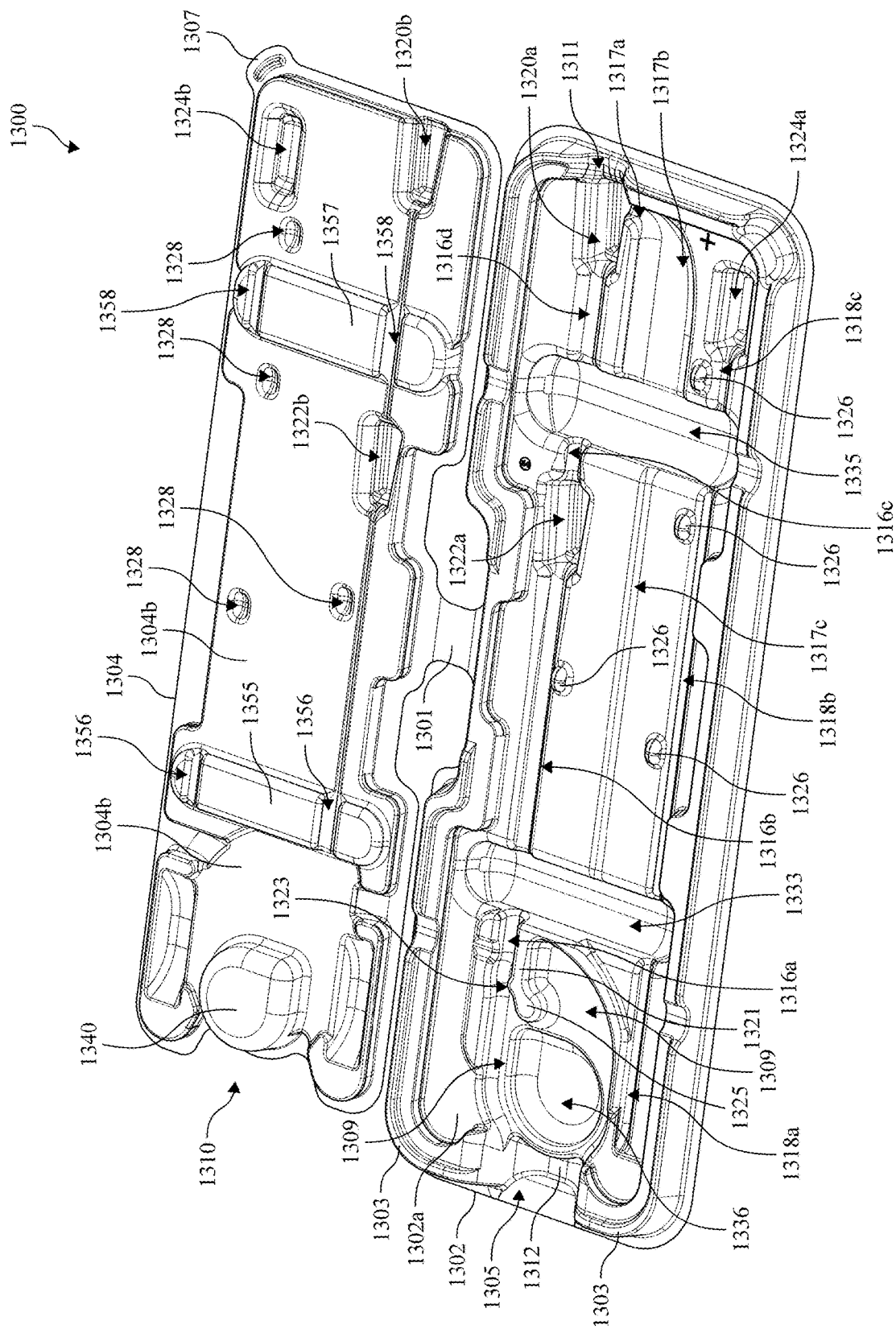
FIGS. 158A-158B illustrate top perspective views of a packaging tray in accordance with aspects of the disclosure.
Figure 158B:
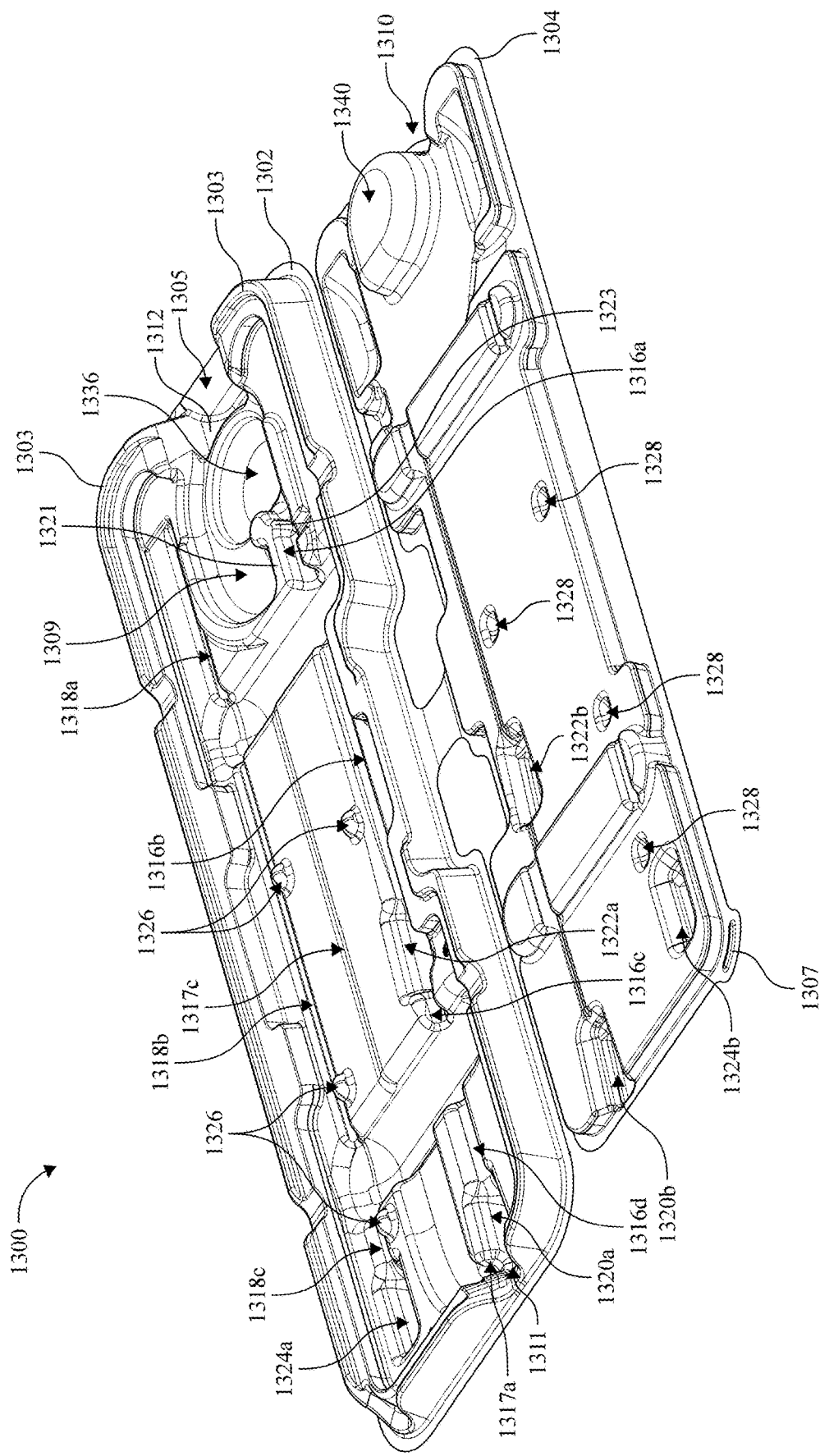
Figure 158C:
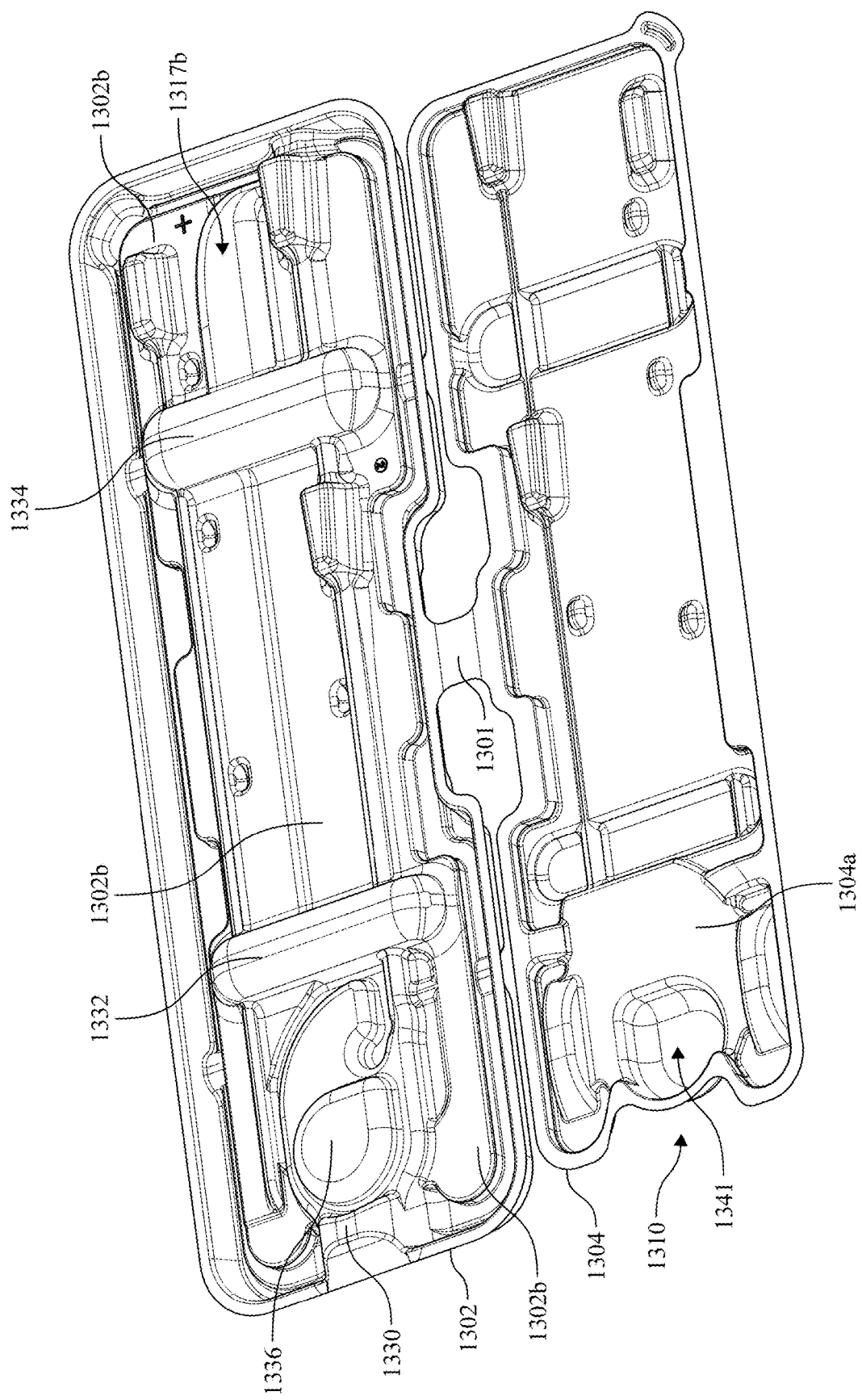
FIG. 158C illustrates a bottom perspective view of the packaging tray of FIGS. 158A-158B in accordance with aspects of the disclosure.
Figure 158D:
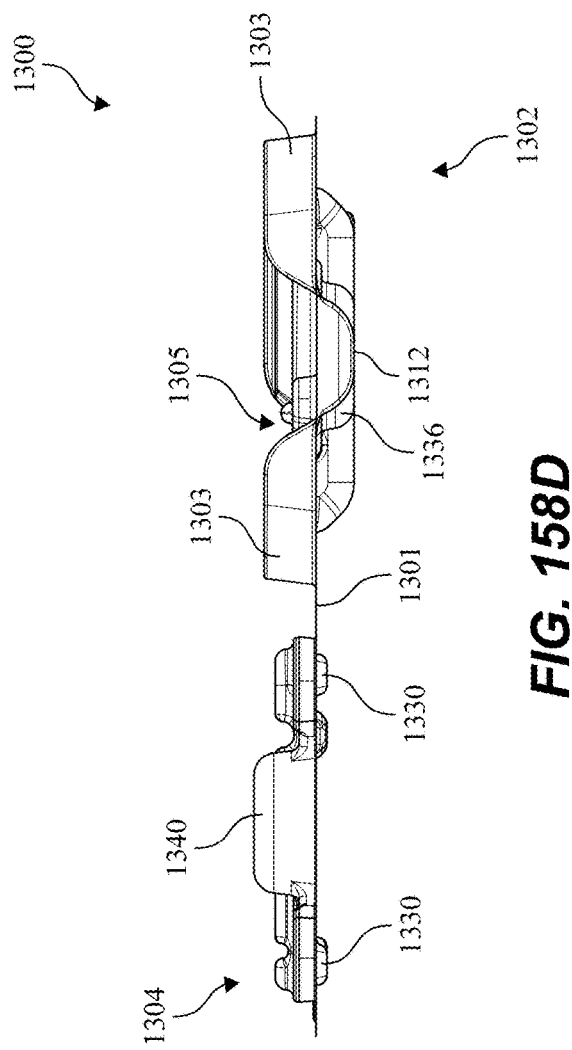
FIGS. 158D-158E illustrate front and rear views of the packaging tray of FIGS. 158A-158B in accordance with aspects of the disclosure.

FIGS. 158A-158I illustrate various views of a packaging tray 1300 (also referred to herein as "tray") that can be used to at least partially retain, enclose, and/or protect sensing device 1100 (or sensors 10, 50), insertion tool 500, and/or push rod 530. Tray 1300 (which can also be referred to herein as a "case") can advantageously facilitate efficient preparation of sensing device 1100, insertion tool 500, and push rod 530 prior to an insertion procedure wherein sensing device 1100 is inserted into a body cavity of a subject (for example, inserted through a subject's urethra and into the subject's bladder as described elsewhere herein). Additionally, tray 1300 can advantageously allow sterility to be maintained prior to such procedure. For example, in some implementations, tray 1300 can facilitate loading of sensing device 1100 into insertion tool 500 without requiring a user (for example, a doctor, nurse, technician, or other caregiver) to grab or otherwise contact sensing device 1100 (with or without a glove). As will be described further below, tray 1300 can be configured to retain insertion tool 500 while at least a portion of sensing device 1100 is pulled into sheath 502 of insertion tool 500, for example, via string 1118. Tray 1300 can be utilized in combination with a bag 1298 (to form a packaging assembly) as shown and described further below with respect to FIGS. 159A-159C. FIGS. 158A-158B illustrate top perspective views of tray 1300 and FIG. 158C illustrates a bottom perspective view of tray 1300. FIG. 158D-158I illustrate a front view, a rear view, a top view, a bottom view, a first side view, and a second side view, (respectively) of tray 1300.

Tray 1300 can be configured to at least partially retain and enclose sensing device 1100, insertion tool 500, and/or push rod 530. Tray 1300 can include a base 1302 that can rest atop a surface. Tray 1300 can also include a cover 1304 connected to base 1302 and configured to at least partially enclose sensing device 1100, insertion tool 500, and/or push rod 530 when retained by tray 1300. Cover 1304 can be pivotably connected to base 1302 and configured to pivot between a closed position in which cover 1304 at least partially encloses sensing device 1100, insertion tool 500, and/or push rod 530 and an open position in which cover 1304 does not cover sensing device 1100, insertion tool 500, and/or push rod 530. Cover 1304 can be connected to base 1302 via one or more hinges, such as one or more living hinges integrally formed from the same material as cover 1304 and base 1302. For example, base 1302 and cover 1304 can be connected via hinge 1301. In some variants, cover 1304 and base 1302 are not connected via a hinge, but rather, are independent. Regardless of whether cover 1304 and base 1302 are connected to one other (e.g., via a hinge), portions of cover 1304 and base 1302 can be configured to removably secure to one another (for example, via a press-fit arrangement).

Tray 1300 can be configured to retain sensing device 1100 while at the same time allowing a portion of sensing device 1100 to be accessible. For example, tray 1300 can be configured to enclose only a portion of sensing device 1100 thereby allowing a portion of sensing device 1100 to be accessible. In some implementations, tray 1300 is configured to enclose a majority of sensing device 1100 yet still allow a portion of sensing device 1100 to be accessible. Such configuration can advantageously allow a user to access a button of sensing device 1100, for example, to transition sensing device 1100 from a non-operational state to an operational state when sensing device 1100 is retained and partially enclosed by tray 1300. In implementations of sensing device 1100 where such button is contained within an interior of a housing of sensing device 1100, the tray 1300 can be configured to allow access to a portion of the housing proximate the button. In implementations where tray 1300 includes base 1302 and cover 1304, a portion of either or both of the base 1302 and cover 1304 can be configured to provide access to such button of sensing device 1100 (and/or a portion of a housing of sensing device 1100 proximate such button) while sensing device 1100 is retained and partially enclosed by the base 1302 and cover 1304. In some implementations, such portion(s) of tray 1300 (e.g., of base 1302 and/or cover 1304) is arranged at an end of tray 1300 (for example, an end of base 1302 and/or cover 1304). With reference to at least FIGS. 158A-158C and 158F, cover 1304 can include an opening 1310 that allows a user to access a button of sensing device 1100 (for example, to transition sensing device 1100 from a non-operational state to an operational state) when cover 1304 is in a closed position in which the cover 1304 at least partially covers and/or protects sensing device 1100, insertion tool 500, and/or push rod 530. Such opening 1310 can advantageously also allow a user to access such button when tray 1300 is positioned within an interior of a bag 1298 as described further below. As shown, opening 1310 can be formed at an end of cover 1304. However, opening 1310 can be formed at an alternative location of cover 1304. Base 1302 can include a top surface 1302a (see FIGS. 158A and 158F), a bottom surface 1302b (see FIGS. 158C and 158G), and a wall 1303 extending above at least a portion of the top surface 1302a and along or near a perimeter of the base 1302. With reference to at least FIGS. 158A-158B and 158D, wall 1303 can include an opening 1305 configured to provide access to the button of sensing device 1100, for example, when cover 1304 is in a closed position. In some implementations, tray 1300 includes both opening 1310 and opening 1305. In some implementations, only one of opening 1310 and opening 1305 is included. In some implementations, opening 1310 and opening 1305 are arranged proximate one another so as to facilitate access to a portion of sensing device 1100 (and the button) when sensing device 1100 is retained by tray 1300. With reference to at least FIGS. 158A-158B and 158D, in some implementations base 1302 includes a recessed portion 1312 proximate opening 1310 and/or 1305 and configured to provide additional access to a portion of sensing device 1100 (and the button) when sensing device 1100 is retained by tray 1300. Opening 1310, opening 1305, and recessed portion 1312 can advantageously allow a user to locate and access (for example, "press") a portion of the sensing device 1100 where button is housed.

Base 1302 can include one or more recessed portions, cavities, and/or channels for retaining sensing device 1100, insertion tool 500, and/or push rod 530. With reference to FIGS. 158A-158B and 158F, base 1302 can include a recessed portion 1309 that can be configured to receive sensing device 1100 and a portion of insertion tool 500 (see also FIGS. 159E and 159F). Recessed portion 1309 can be recessed from top surface 1302a of base 1302 by a depth that is equal to or greater than a cross-section of sensing device 1100. As shown, recessed portion 1309 can be arranged proximate opening 1305 in wall 1303, recessed portion 1312, and/or opening 1310 of cover 1304 when cover 1304 is in a closed position (see FIG. 159D). As shown, base 1302 can include cavities 1320a, 1322a, 1324a (see FIG. 158A). Cavity 1320a can be configured to receive handle 506 of insertion tool 500 and cavity 1324a can be configured to receive handle 538 of push rod 530 (see FIG. 159E). In some implementations, base 1302 includes cavity 1322a, which is configured to receive a handle of another insertion tool that is shorter than insertion tool 500 (for example, an insertion tool intended for use for a female). Inclusion of both of cavities 1322a and 1320a thus allow base 1302 to accommodate either of two insertion tools intended for male and female anatomies. With continued reference to FIG. 158A, in some implementations, cover 1304 includes cavities 1320b, 1322b, 1324b which are configured to align with cavities 1320a, 1322a, 1324a of base 1302 (respectively) when cover 1304 is in a closed position, such as that shown in FIG. 159D. In such implementations, cavities 1320a and 1320b can retain and enclose handle 506 and cavities 1324a and 1324b can retain and enclose handle 538 when cover 1304 is in a closed position. Where an alternative insertion tool is retained in tray, such as a female version that is shorter in length (as discussed above), the handle of such female version can be retained and enclosed by cavities 1322a and 1322b when cover 1304 is in a closed position. Cavity 1320a can be configured to limit rotation of handle 506. For example, cavity 1320a can be configured to limit a degree of rotation of handle 506 (and therefore insertion tool 500) about an axis of insertion tool 500 (for example, extending through sheath 502 and/or handle 506) to less than or equal to about 90 degrees, about 85 degrees, about 80 degrees, about 75 degrees, about 70 degrees, about 65 degrees, about 60 degrees, about 55 degrees, about 50 degrees, about 45 degrees, less than or equal to about 40 degrees, less than or equal to about 35 degrees, less than or equal to about 30 degrees, less than or equal to about 25 degrees, less than or equal to about 20 degrees, less than or equal to about 15 degrees, less than or equal to about 10 degrees, or less than or equal to about 5 degrees. Limitation of rotation of handle 506 (and therefore insertion tool 500 and sheath 502) can advantageously facilitate alignment of a mating feature on sensing device 1100 (for example, projection 1176a on end cap 1176) with a corresponding mating feature of insertion tool 500 (for example, slot 518 on sheath 502 illustrated in FIGS. 25-26 and 28). Engagement between such mating features can inhibit relative rotation of insertion tool 500 and sensing device 1100, which can provide benefits such as those described herein with respect to sensor 50 and insertion tool 500. With continued reference to FIGS. 158A-158B and 158F, base 1302 can include channels 1316a, 1316b, 1316c, 1316d for accommodating sheath 502 of insertion tool 500 and/or channels 1318a, 1318b, 1318c for accommodating stem 532 of push rod 530. In some implementations, base 1302 includes channel 1317a and/or recessed portion 1317b for retaining string 1118 when string 1118 extends through sheath 502 and handle 506 (see FIG. 159E).

Figure 158E:
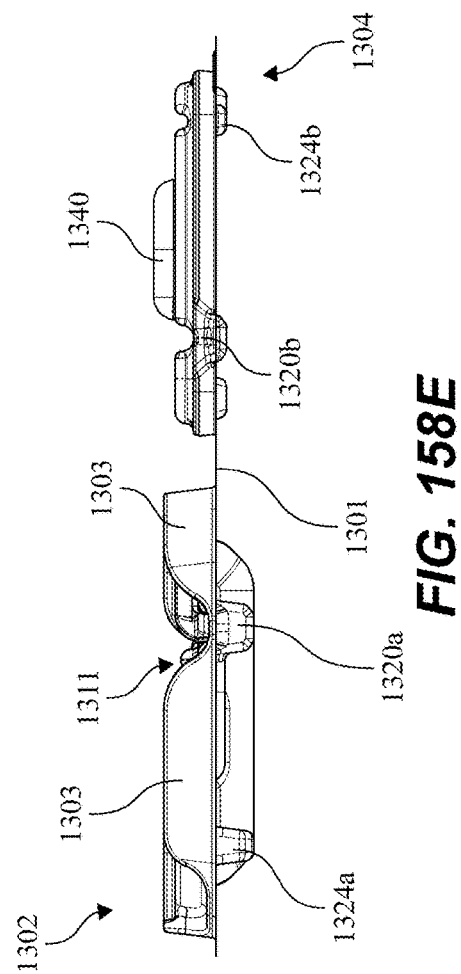
Figure 158F:
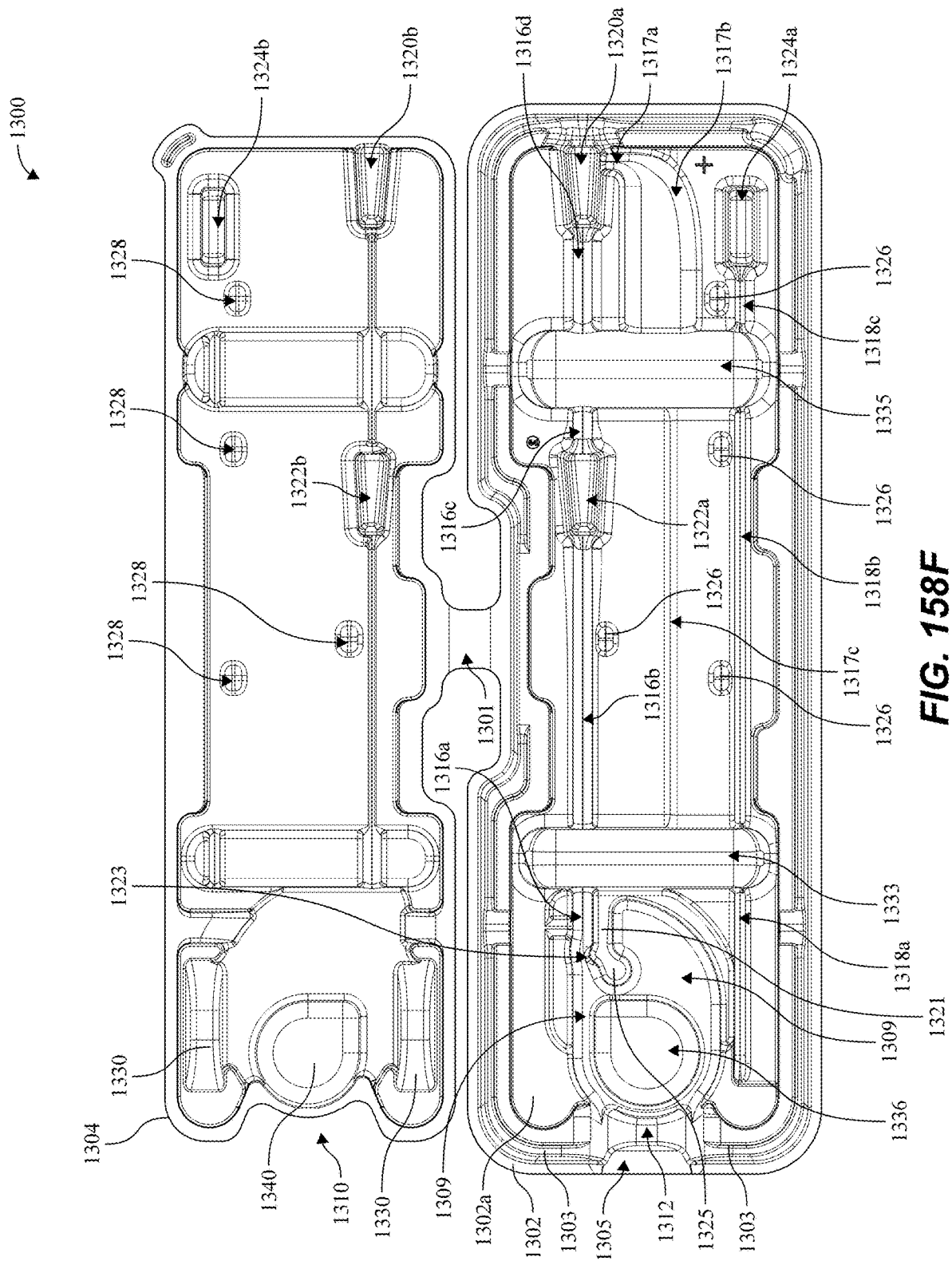
FIGS. 158F-158G illustrate top and bottom views of the packaging tray of FIGS. 158A-158B in accordance with aspects of the disclosure.
Figure 158G:
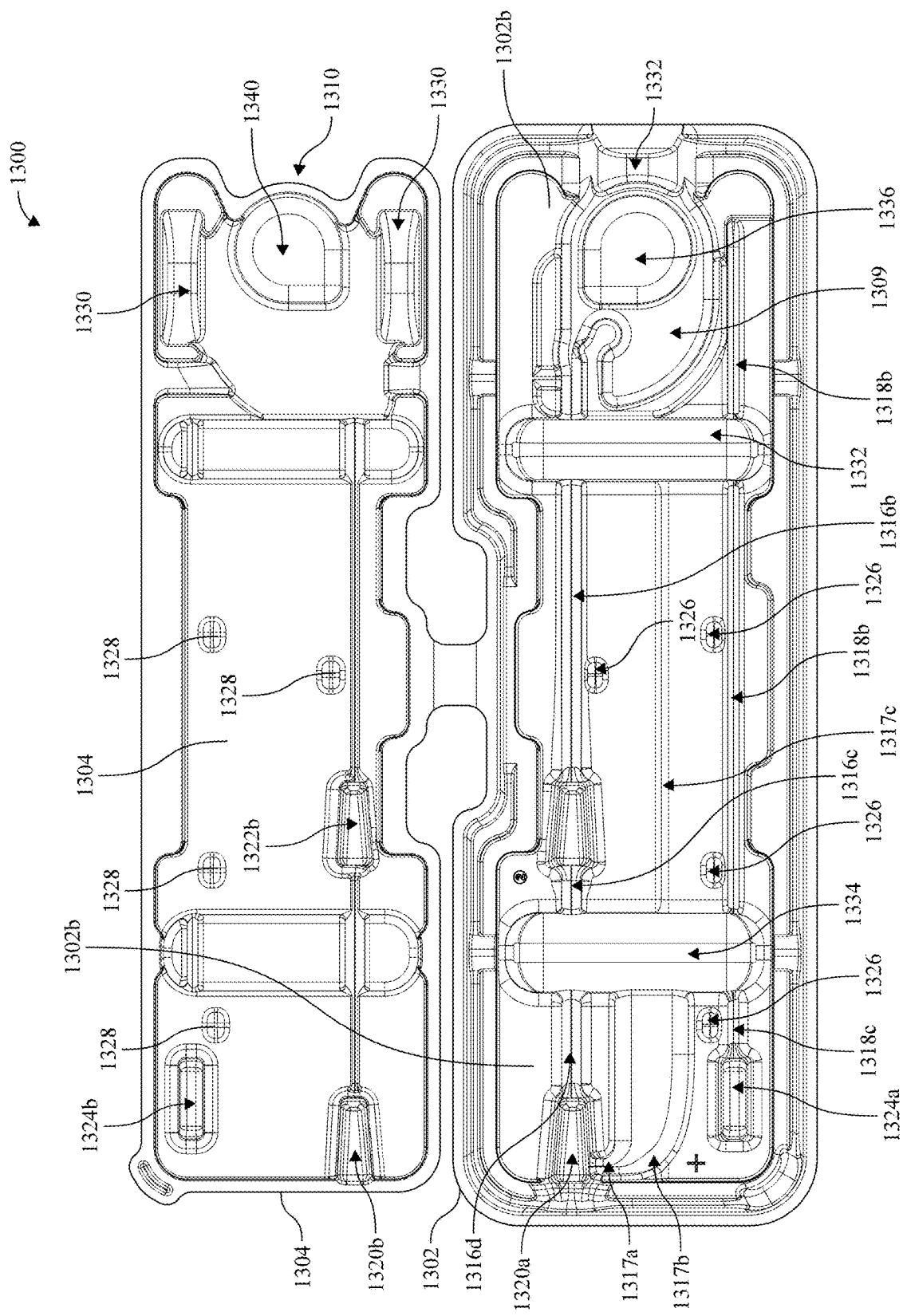
Figure 158H:
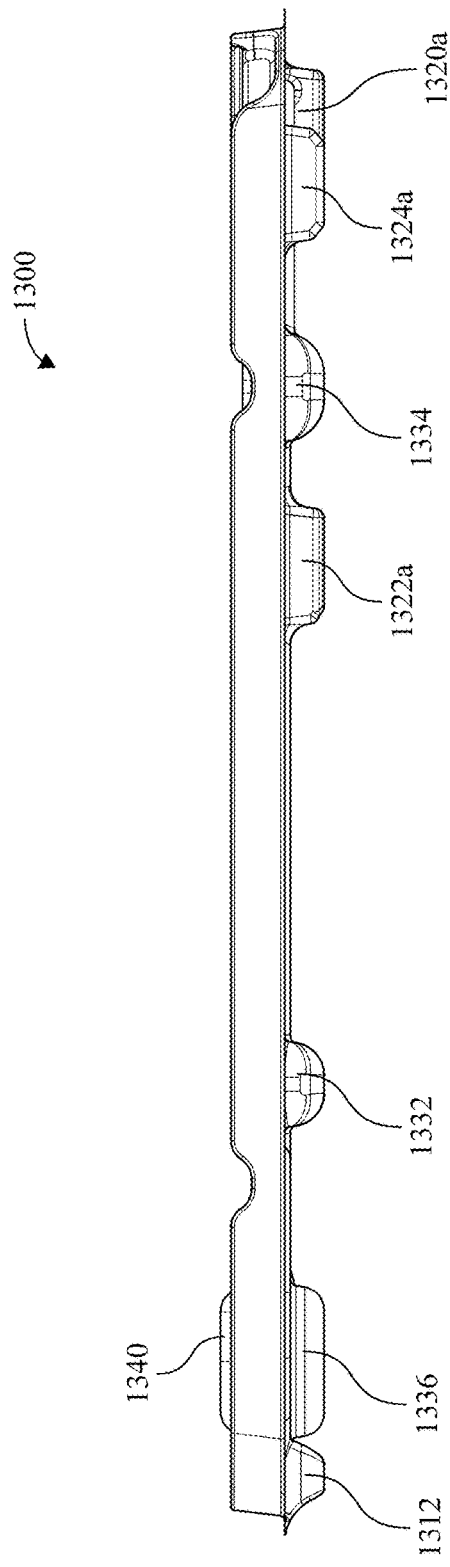
FIGS. 158H-158I illustrate side views of the packaging tray of FIGS. 158A-158B in accordance with aspects of the disclosure.
Figure 158I:
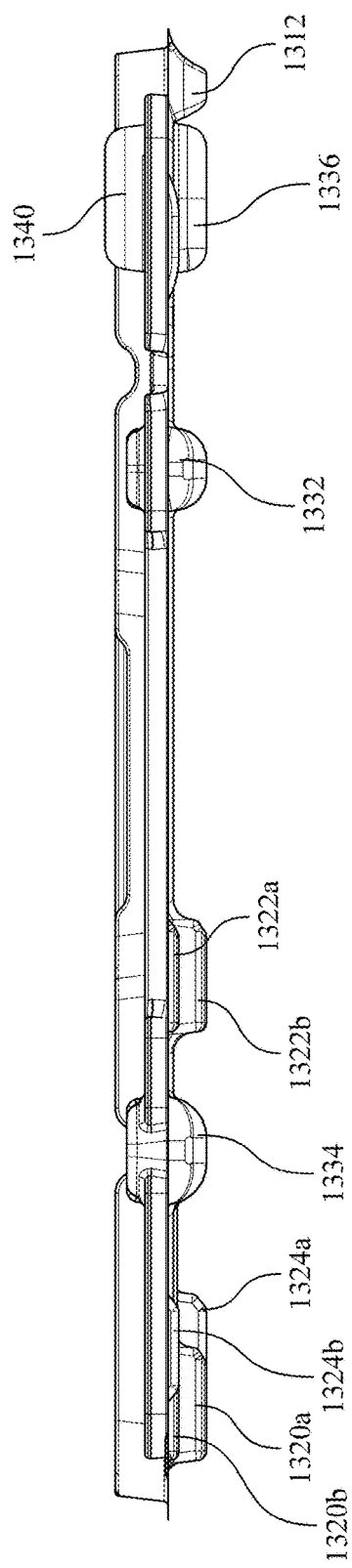

With reference to FIGS. 158A-158B and 158E, in some implementations, wall 1303 of base 1302 includes an opening 1311 proximate cavity 1320a. Opening 1311 (which can be formed by a low point of wall 1303) can allow for inspection of handle 506 and/or sheath 502, and/or inspection or accommodation of string 1118.

Figure 159D:
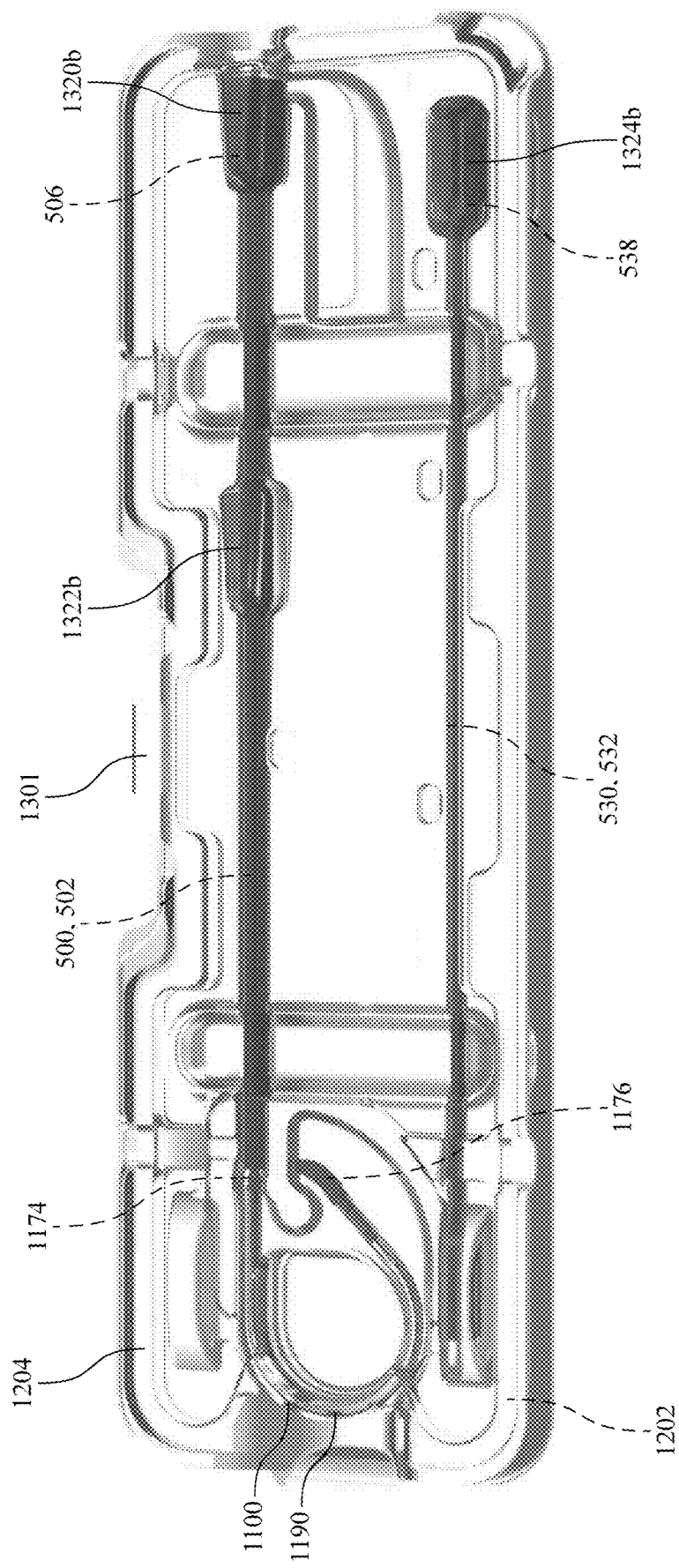
Figure 159E:
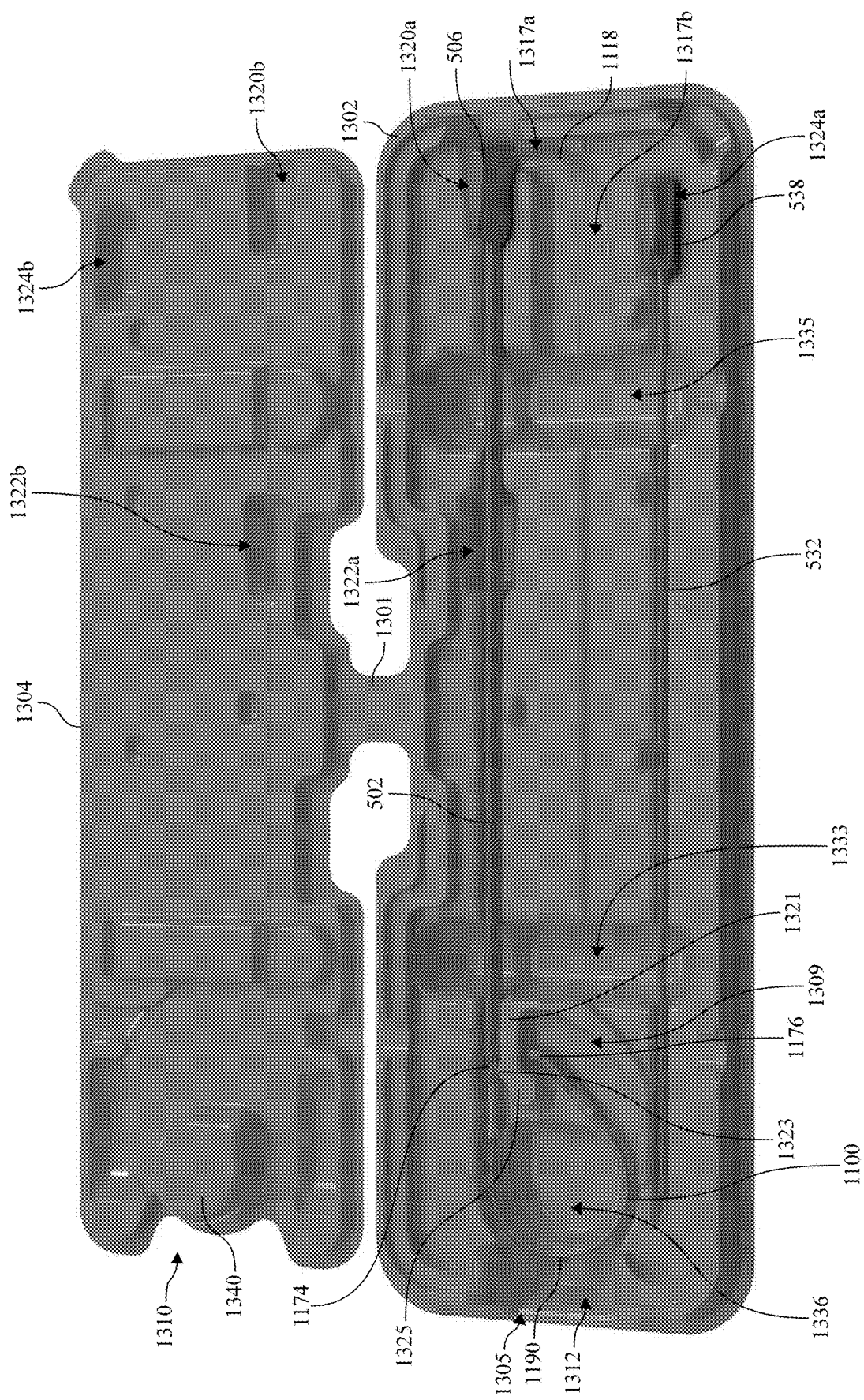
Figure 159F:
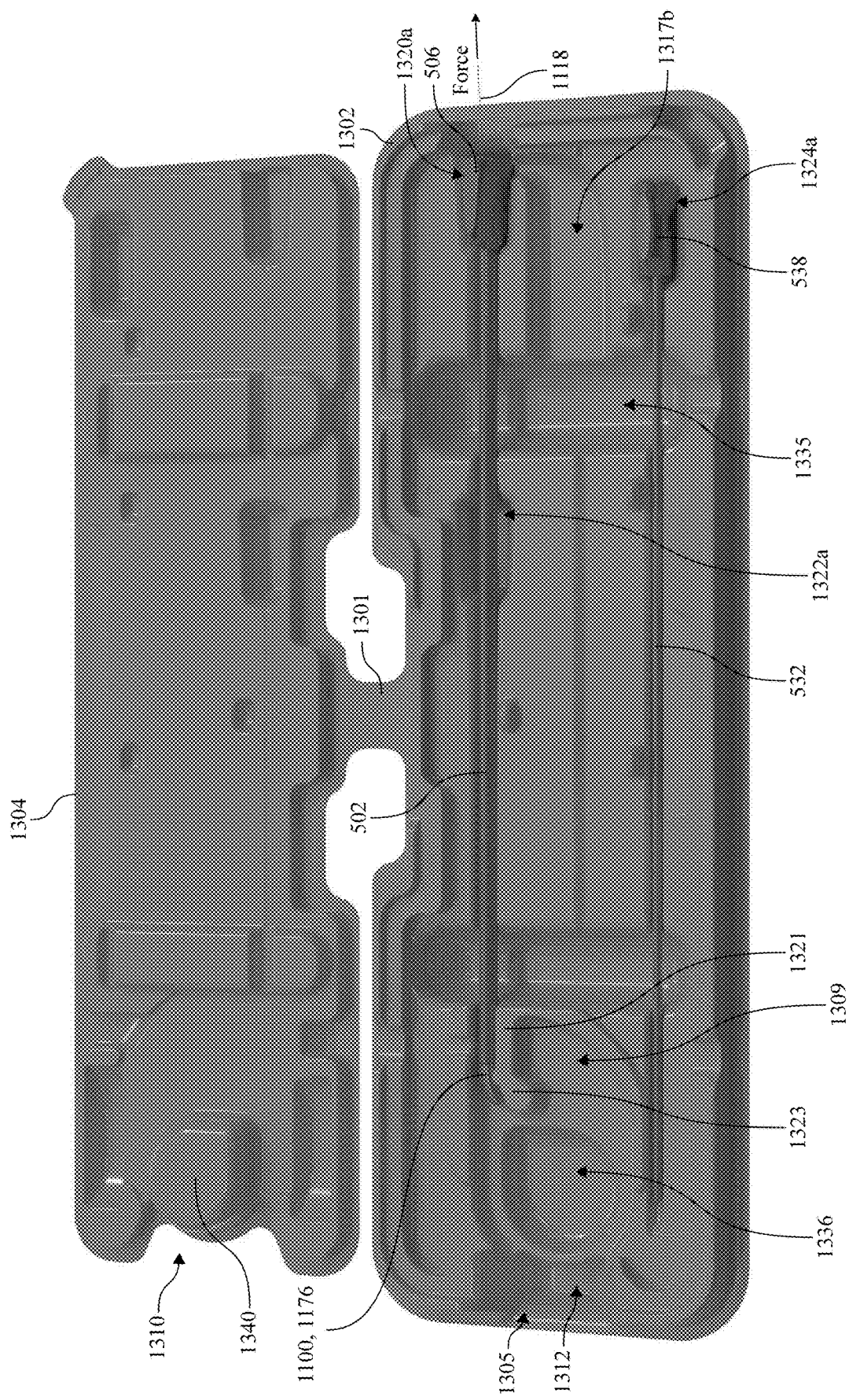

Base 1302 and cover 1304 can include one or more engagement features that allow base 1302 and cover 1304 to be secured to one another when cover 1304 is in a closed position. In some implementations, a bottom of the cover 1304 is sized and/or shaped to engage (e.g., via a press-fit arrangement) a size and/or shape of wall 1303 of base 1302. Additionally or alternatively, in some implementations base 1302 includes one or a plurality of engagement protrusions 1326 configured to engage (e.g., via a press-fit arrangement) indent(s) 1328 of cover 1304 (see FIGS. 158A-158B). With reference to FIGS. 158A-158B, cover 1304 can include a tab 1307 configured to aid detachment of cover 1304 from base 1302. With reference to FIGS. 158C, 158D-158E, and 158H-158I, base 1302 can include a one or plurality of protruding portions 1330, 1332, 1334, 1336 (which may be referred to as "legs" or "feet") that can act to support base 1302 on a surface (see FIGS. 158C and 158H-158I), alone or in combination with cavities 1320a, 1322a, 1324a (see FIGS. 158C, 158E, and 158H-158I). Protruding portions 1330, 1332, 1334, 1336 and/or cavities 1320a, 1322a, 1324a can terminate along a same plane and/or be arranged to allow base 1302 to retain sensing device 1100, insertion tool 500, and push rod 530 in a non-inclined manner, for example, relative to a plane of a surface on which base 1302 and/or tray 1300 rests. This can, among other things, advantageously inhibit sensing device 1100, insertion tool 500, and push rod 530 from inadvertently falling onto such support surface (for example, a table) that may not be sterile. With reference to FIGS. 158A and 159F, cavities formed at the top surface of base 1302 of protruding portions 1333, 1335 can aid a user in removing insertion tool 500 (e.g., sheath 502) and push rod 500 (e.g., stem 532) from base 1302 as they can provide a space in which the user's fingers can be inserted to grasp the tool 500 and rod 500 (for example, while wearing gloves).

Sensing device 1100 can be biased toward an at least partially curled configuration as described herein. Tray 1300 can be configured to retain sensing device 1100 in an at least partially curled configuration, for example, as illustrated in FIGS. 159D-159E. As mentioned previously, base 1302 can include a recessed portion 1309 configured to receive sensing device 1100, and such recessed portion 1309 can be sized and/or shaped to retain sensing device 1100 in an at least partially curled configuration. With reference to at least FIGS. 158A-158B, cover 1304 can include a protrusion 1340 configured to retain sensing device 1100 in such curled configuration. Protrusion 1304 can extend from a bottom surface 1304b of cover 1304. In some implementations, protrusion 1304 is at least partially surrounded by sensing device 1100 when sensing device 1100 arranged in recessed portion 1309. Protrusion 1340 can have an at least partially cylindrical shape. As shown in FIGS. 158A-158B, in some implementations base 1302 includes a cavity 1336 that can receive protrusion 1340 when cover 1304 is in a closed position. In some implementations, cavity 1336 is sized and/or shaped to conform to a size and/or shape of protrusion 1340. With reference to FIG. 158C, protrusion 1340 can form a cavity 1341 on a top surface 1304a of cover 1304 (see FIG. 158C). In some implementations, protrusion 1340 and cavity 1341 are arranged proximate opening 1310 of cover 1304, opening 1305 of wall 1303, and/or recessed portion 1312 of base 1302. In some implementations, tray 1300 is configured to retain sensing device 1100 in a manner that positions a button of sensing device 1100 proximate opening 1310 of cover 1304, opening 1305 of wall 1303, and/or recessed portion 1312 of base 1302 (see FIG. 159D-159E). In such implementations, protrusion 1340 and cavity 1341 can advantageously aid a user in engaging a button of sensing device 1100 when sensing device 1100 is retained by tray 1300. For example, such configurations can allow a user to position a first finger in cavity 1341 and a second finger in the space defined by opening 1310, opening 1305, and/or recessed portion 1312, and thereafter press a portion of sensing device 1100 including the button against protrusion 1340. FIG. 159C illustrates an example of such process where a portion of a bag is used to contact the cover 1304 and sensing device 1100. Base 1302 and/or cover 1304 can include one or more visual indicators to aid a user in locating the button of sensing device 1100, for example, similar to visual indicators 1241, 1214 described with respect to tray 1200.

As mentioned previously, base 1302 can include a channel 1316a that can receive sheath 502 of insertion tool 500. With reference to at least FIGS. 158A-158B, base 1302 can include an inner wall 1321 that at least partially defines channel 1316a. Inner wall 1321 can be spaced from a perimeter of base 1302, for example, spaced from wall 1303. In the illustrated implementation, inner wall 1321 is arranged proximate recessed portion 1309 and forms part of recessed portion 1309. As shown in FIGS. 159D-159E, when sensing device 1100 is retained by base 1302, endcap 1174 of sensing device 1100 is arranged within a portion of channel 1316a along with an end of sheath 502. As described herein, in some implementations, sheath 502 includes a mating feature (for example, slot 518) configured to engage a mating feature of endcap 1176 of sensing device 1100 (for example, projection 1176a) when sensing device 1100 is received within sheath 502. Further, as described herein, sensing device 1100 can be inserted into sheath 502 via endcap 1174. In some implementations, base 1302 comprises bump 1323 arranged on inner wall 1321 at and/or within channel 1316a configured to align endcap 1174 with lumen 510 of sheath 502. Bump 1323 can extend from inner wall 1321 partially across and/or in front of channel 1316a. In some implementations, bump 1323 is configured to contact endcap 1174 when sensing device 1100 is inserted into lumen 510 of sheath 502. In implementations where sheath 502 includes slot 518 at an end thereof, bump 1323 can advantageously inhibit or prevent interference of endcap 1174 with slot 518, for example, prevent endcap 1174 from entering slot 518, which could disrupt insertion of sensing device 1100 within lumen 510 (for example, via string 1118). With reference to FIGS. 158A and 158F, in some implementations, inner wall 1321 comprises a bent end 1325 that is angled and/or curved relative to a remainder of inner wall 1321. Such bent end 1325 can engage with endcap 1176 of sensing device 1100 help retain sensing device 1100 in recessed portion 1309 of base 1302 (see FIG. 159D-159E). For example, bent end 1325 can inhibit or prevent sensing device 1100 from further curling when retained by base 1302.

Protruding portions 1332, 1334 can extend from bottom surface 1302*b* of base 1302 as shown in FIG. 158C. With reference to FIG. 158A, such protruding portions 1332, 1334 can form cavities 1333, 1335 on top surface 1302*a* of base 1302. Such cavities 1333, 1335 can be configured to receive protrusions 1355, 1357 extending from bottom surface 1304*a* of cover 1304. In some implementations, protrusions 1355, 1357 include channels 1356, 1358 configured to receive portions of sheath 502 of insertion tool 500 and stem 538 of push rod 530 when cover 1204 is in a closed position.

FIGS. 159A-159F illustrate an example method of preparing sensing device 1100 for insertion into a body cavity of a subject in a manner that preserves sterility, using a bag 1298 and tray 1300. The methods described below may be utilized in the context of inserting sensing device 1100 into a subject's bladder or in other contexts as well. Maintaining sterility prior to and during a sensor insertion procedure is important to minimize the risk of infections. However, it is often difficult to maintain sterility during such procedures, especially when a caregiver needs to interact with other electronic patient monitoring devices in order to wirelessly pair the sensing device (to allow transmission of physiological data). Indeed, in some cases, caregivers wear multiple gloves on each hand and sequentially remove each glove when a non-sterile object is touched in order to preserve sterility during a sensor insertion procedure. The methods and packaging assemblies described herein advantageously allow a sensing device (such as sensing device 1100) to be prepared for insertion in an efficient and convenient manner that avoids breaking sterility.

With reference to FIG. 159A, tray 1300 can be packaged within an interior of bag 1298. The interior of bag 1298 can be sealed in order to preserve sterility. In some implementations, tray 1300 is more rigid than bag 1298. Sensing device 1100, insertion tool 500, and push rod 530 can be at least partially retained and enclosed by tray 1300 as shown in FIG. 159D, which illustrates tray 1300, sensing device 1100, insertion tool 500, and push rod 530 outside of bag 1298. As discussed above, sensing device 1100 can include a button 1190 configured to allow sensing device 1100 to be transitioned from a non-operational state to an operational state. In some implementations, when sensing device 1100 is in such operational state, sensing device 1100 is able to wirelessly communicate with one or more separate devices (such as a patient monitoring device or mobile phone or tablet). In some implementations, when sensing device 1100 is in such operational state, a pressure sensor of sensing device 1100 is activated, thereby allowing the sensing device 1100 to obtain pressure data that can be used for urodynamic monitoring and/or analysis as described elsewhere herein. In some implementations, when sensing device 1100 is in such non-operational state, sensing device 1100 does not wireless communicate with separate devices and/or does not obtain pressure data (or other data that can be utilized to assess physiological conditions or characteristics of a subject).

Bag 1298 and tray 1300 can advantageously be configured to allow a user to activate button 1190 of sensing device 1100 (to transition sensing device 1100 to such operational state) while sensing device 1100 and tray 1300 are positioned within a sterile interior of bag 1298. As discussed above, cover 1304 can include opening 1310, base 1302 can include opening 1305 in wall 1303, and/or base 1302 can include recessed portion 1312, each of which are illustrated in FIGS. 159B-159C. Bag 1298 can be made of a material that allows the user to engage button 1190 by pressing a portion of bag 1298 against button 1190 (e.g., a portion of sensing device 1100 which houses button 1190). Such portion of bag 1298 can be transparent to allow the user to more easily locate button 1190, opening 1310, opening 1305, and/or recessed portion 1312. Accordingly, as illustrated in FIGS. 159A-159C, a user can advantageously transition sensing device 1100 to an operational state while sensing device 1100 and tray 1300 are positioned inside a sealed, sterile interior of bag 1298. In some implementations, tray 1300 includes an identification tag that includes information associated with sensing device 1100, similar or identical to identification tag 1299 described and illustrated elsewhere herein.

FIG. 159D illustrates tray 1300 along with sensing device 1100, insertion tool 500, and push rod 530 retained therein. In FIG. 159D, cover 1304 is illustrated in a closed position, whereas in FIGS. 159E-159F, cover 1304 is illustrated in an open position. In FIGS. 159D-159F, portions of base 1302 and/or cover 1304 are shown in transparent or non-transparent for the purpose of better illustrating portions of sensing device 1100, insertion tool 500, and push rod 530. It is to be understood that both or either of base 1302 and cover 1304 can be transparent.

A method of preparing sensing device 1100 for insertion into a body cavity of a subject (for example, a bladder) to preserve sterility can include obtaining bag 1298 and tray 1300 positioned within the interior of bag 1298, as illustrated in FIG. 159A. Tray 1300 can at least partially retain and enclose sensing device 1100, insertion tool 500, and/or push rod 530, as discussed above. The method can further include transitioning sensing device 1100 from a non-operational state to an operational state. Transitioning sensing device 1100 to such operational state can be performed: without removing tray 1300 and/or sensing device 1100 from the interior of the bag 1298; without opening bag 1298; without wearing a glove; and/or without directly contacting sensing device 1100 (with or without a glove). For example, as illustrated and described with respect to FIGS. 159B-159C, transitioning sensing device 1100 to such operational state can be performed by pressing a portion of bag 1298 against button 1190 (or a portion of sensing device 1100 that houses button 1190) via opening 1310, opening 1305, and/or recessed portion 1312. For example, transitioning sensing device 1100 to such operational state can be performed by pressing a portion of bag 1298 against a portion of housing 1156 to engage button 1190, via opening 1310, opening 1305, and/or recessed portion 1313. In some implementations, button 1190 is engaged by pressing a transparent portion of bag 1298 against button 1190 or against a portion of housing 1156 to engage button 1190. In some implementations, tray 1300 includes one or more visual indicators similar or identical to visual indicator 1314 and/or visual indicator 1341. In such implementations, such visual indicators can be utilized to locate button 1190. In some implementations, after button 1190 is engaged and sensing device 1100 is transitioned to the operational state, the method further includes wirelessly pairing sensing device 1100 with a separate electronic device, such as a patient monitoring device. Sensing device 1100 can be configured for communication with any of the components described herein with respect to system 1400. In some implementations, an identification tag of tray 1300 (such as tag 1299) is utilized (for example, electronically scanned) by such patient monitoring device or a mobile device configured for communication with such patient monitoring device in order to provide information related to the sensing device 1100 to the patient monitoring device.

After sensing device 1100 is transitioned to the operational state (and, in some implementations, wirelessly paired with a patient monitoring device), the method can further include opening bag 1298 and emptying tray 1300 onto a surface (for example, a table). In some implementations, opening bag 1298 includes opening an end of bag 1298 and/or breaking a seal of bag 1298. In some implementations, opening an end of bag 1298 and/or breaking a seal of bag 1298 is performed without wearing a glove. In some implementations, emptying tray 1300 onto the surface includes causing tray 1300 to fall out of bag 1298 onto the surface without touching tray 1300 with a bare hand and/or without touching tray 1300 with a glove. In some implementations, sensing device 1100, insertion tool 500, and/or push rod 530 are retained by tray 1300 (for example, held in place within tray 1300) when tray 1300 is emptied onto the surface. Such surface may be a sterile or non-sterile surface. FIG. 159D illustrates a top perspective view of tray 1300 in an example orientation in which tray 1300 rests atop a support surface.

The method can further include opening cover 1304 of tray 1300 or a portion of cover 1304 in order to expose sensing device 1100, insertion tool 500, and/or push rod 530. As discussed previously, in some implementations cover 1304 is pivotably connected to base 1302 via one or more hinges (such as hinge 1301). In such implementations, opening cover 1304 includes pivoting cover 1304 from a closed position (see FIG. 159D) to an open position (see FIG. 159E). The method can further include applying a lubricating material to all or a portion of sensing device 1100. Such lubricating material can be similar or identical to lubricating material 1100a shown and/or described above with respect to FIGS. 157F-157G. In some implementations, applying the lubricating material to all or a portion of sensing device 1100 is performed without contacting sensing device 1100 (via a bare hand or with a glove). For example, lubricating material can be applied to all or a portion of sensing device 1100 by squeezing a container including lubricating material from a location above sensing device 1100 such that the lubricating material 1100a falls on portions of the sensing device 110o under the force of gravity. In some implementations, tray 1300 includes a visual indicator (e.g., similar or identical to visual indicator 1297) for indicating which portion of sensing device 1100 to be lubricated and/or reminding a user to apply the lubricating material. Visual indicator 1297 can be arranged proximate a location of tray 1300 where sensing device 1100 is retained (for example, on a portion of base 1302 proximate recessed portion 1309).

With reference to FIGS. 159E-159F, the method can further include inserting at least a portion of sensing device 1100 into sheath 502 of insertion tool 500, for example, by pulling string 1118 that extends from sensing device 1100 through sheath 502 and handle 506. With reference to FIG. 159E, in some implementations, string 1118 can be positioned in channel 1317a, 1317b, and/or cavity 1335, when sensing device 1100, insertion tool 500, and string 1118 are in a packaged configuration within tray 1300 (for example, prior to an insertion procedure). In such implementations, the method can include removing string 1118 from channel 1317a, 1317b, and/or cavity 1335 such that it can be pulled as illustrated in FIG. 159F.

As mentioned previously, lubricating material can be applied to sensing device 1100. The lubricating material can advantageously facilitate insertion of sensing device 1100 into sheath 502. In some implementations, at least a portion of sensing device 1100 is inserted into sheath 502 without requiring a user to grasp or otherwise contact sensing device 1100 and/or without requiring a user to grasp or otherwise contact sheath 502. Tray 1300 can be configured to hold insertion tool 500 in place while sensing device 1100 is pulled into sheath 502, for example, via string 1118 (see FIGS. 159E-159F). For example, cavity 1320a of base 1302 can be configured to hold handle 506 (and thus, insertion tool 500) in place while sensing device 1100 is pulled into sheath 502 via string 1118. In some implementations, the method further includes engaging a mating feature of sensing device 1100 (for example, projection 1176a) with a mating feature of insertion tool 500 (for example, slot 518) such that rotation of the sensing device 1100 relative to insertion tool 500 is prevented or inhibited (for example, about an axis extending through sheath 502 and/or handle 506). In some implementations, sensing device 1100 is inserted into sheath 502 until only end cap 1176 (or a portion thereof) is exposed (see FIG. 159F). In some implementations, inserting at least the portion of sensing device 1100 into sheath 502 comprises inserting sensing device 1100 such that sensing device 1100 (for example, proximal end cap 1174) abuts a stop located within sheath 502. In some implementations, sensing device 1100 is inserted into sheath 502 until proximal end cap 1174 engages a locking feature within sheath 502, such as D-lock 514 described herein.

As described above, base 1302 can include a channel 1316a within which a portion of sheath 502 and endcap 1174 of sensing device 1100 are arranged. As also described above, in some implementations, base 1302 includes a bump 1323 arranged on inner wall 1321 and located at, near, and/or within channel 1316a. In some implementations, the method further includes abutting (or otherwise contacting) endcap 1174 with bump 1323 to: align endcap 1174 (and sensing device 1100) with lumen 510 of sheath 502; and/or inhibit endcap 1174 from engaging slot 518 of sheath 502.

After at least a portion of sensing device 1100 is loaded into sheath 502 of insertion tool 500, insertion tool 500 and push rod 530 can be utilized to insert sensing device 1100 into a body cavity of a subject. For example, insertion tool 500 and push rod 530 can be utilized to insert sensing device 1100 through a subject's urethra and into the subject's bladder, as described elsewhere herein.

Computer System

Figure 160:
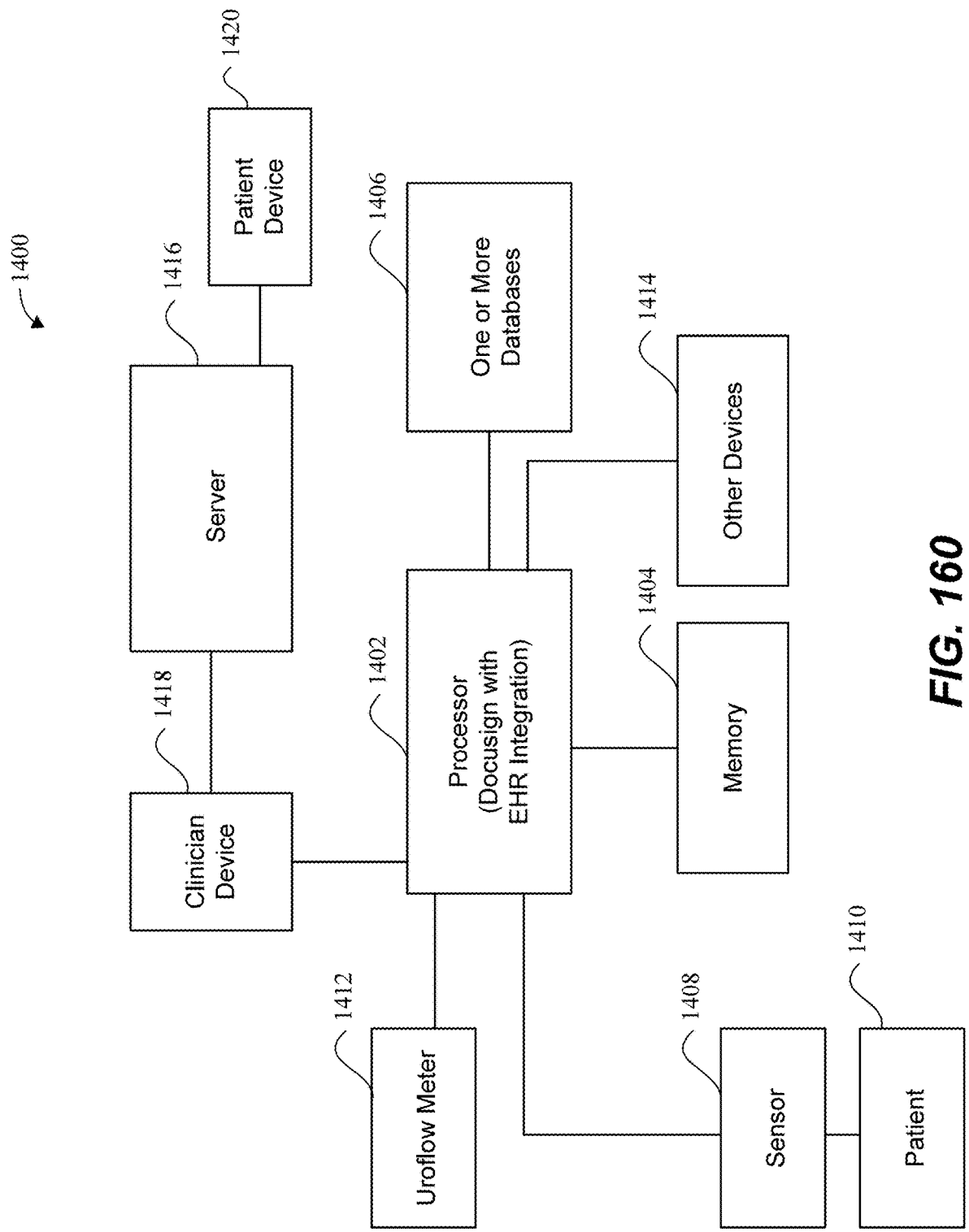
FIG. 160 is a block diagram of a computer system that may be utilized with aspects of this disclosure.

FIG. 160 shows a computer system 1400 according to this disclosure. Computer system 1400 has a processor 1402 having a memory 1404, and in communication with one or more databases 1406. Databases 1406 can store any urological data for any number of patients. This data can be accessed by processor 1402 for comparison to data for patient 1410 for any purpose, such as to examine trends or determine if patient 1410's data is unusual or deviates from normal.

Processor 1402 is in communication with a sensor 1408, which is any sensor resident in the bladder of patient 1410, such as any of the sensors described in this disclosure. Sensor 1408 provides urological data regarding patient 1410 to processor 1402 for analysis. Processor 1402 may also be in communication with a uroflowmeter 1412, which either weighs or determines the volume of urine for a voiding episode. The data from uroflowmeter 1412 can be included with data from sensor 1408 or analyzed separately.

Data from sensor 1008 and/or uroflowmeter 1412 may be compared to and/or added to data from one or more databases 1406, and stored in memory 1404 and/or one or more databases 1406.

Other devices 1414 are one or more other devices that may provide information from processor 1002 or receive information from processor 1402.

A clinician device 1418 is any suitable computing device, such as a tablet, desk top computer, or cellular phone. Clinician device 1418 may communicate directly with processor 1402 or indirectly with processor 1402 through server 1416. Clinician device 1418 receives data from processor 1402 and displays it in any manner depicted herein such that the data is easily organized and simple to interpret. Clinician device 1418 is configured to pre-populate reports with the urological data of patient 1410, which leads to significant time savings. Using the clinician device 1418, a clinician can review a report and electronically sign or verify it using the DocuSign (or electronic signature) function of processor 1402 and the report can then be stored as an electronic health record (EHR) in either memory 1404 or one or more databases 1406.

A patient device 1420 is in indirect communication with processor 1002 and clinician device 1418 via server 1416. Patient device 1420 is any suitable device such as a computer or cellular phone. Patient device 1020 may receive urological information from clinician device 1418 or processor 1402 and present it to patient 1410 in any suitable manner, such as those shown in this disclosure.

As used herein, the terms application and module and the like can refer to computer program instructions, encoded on computer storage medium for execution by, or to control the operation of, data processing apparatus. Alternatively or additionally, the program instructions can be encoded on an artificially-generated propagated signal, e.g., a machine-generated electrical, optical, or electromagnetic signal, which is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of the substrates and devices. Moreover, while a computer storage medium is not a propagated signal, a computer storage medium can be a source or destination of computer program instructions encoded in an artificially-generated propagated signal. The computer storage medium is non-transitory and can also be, or be included in, one or more separate physical components or media (e.g., solid-state memory that forms part of a device, disks, or other storage devices).

As used herein, "database" refers to any suitable database for storing information, electronic files or code to be utilized to practice embodiments of this disclosure. As used herein, "server" refers to any suitable server, computer or computing device for performing functions utilized to practice embodiments of this disclosure.

As used herein, "processor" refers to a data-processing apparatus configured to execute computer program instructions, encoded on computer storage medium, wherein the instructions control the operation of the engine. Alternatively or additionally, the program instructions can be encoded on an artificially-generated propagated signal, e.g., a machine-generated electrical, optical, or electromagnetic signal, which is generated to encode information for transmission to suitable receiver apparatus for execution by a data processing apparatus.

A "storage" or "memory" can be, or be included in, a computer-readable storage device, a computer-readable storage substrate, a random or serial access memory array or device, or a combination of one or more of the substrates and devices. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., solid-state memory that forms part of a device, disks, or other storage devices). In accordance with examples of the disclosure, a non-transient computer readable medium containing program can perform functions of one or more methods, modules, engines and/or other system components as described herein.

A computer system 1400 with software, such as a patient and/or clinician application designed to be used on any suitable computing device, such as a server, mobile device (tablet/phone) or computer. The software may operate on a processor that may or may not be resident on a server. The processor has or is in communication with a memory and one or more databases, wherein the processor is configured to store data and run software applications. Some aspects of the computer system 1400 include:

(1) The ability to integrate and synchronize data from the sensor, uroflowmeter, and software, specifically, the ability to align this information in time with high precision. Devices connected to the server (which may be on a mobile device (tablet or phone) synchronize using any suitable wired connection (if the sensor is outside of the body) or wireless connection (such as Wi-Fi, cellular, or Bluetooth).

(2) Visual data handling techniques that help clinicians review and analyze data may include one or more of the following:

(a) An analyze function, which means the ability to view/analyze/note findings for any one filling/voiding cycle. Because the system/device standardizes reporting and reduces operator variability a repository may be used to develop algorithms to identify characteristics of the data presented to aid a clinician in diagnosis of the waveforms. The waveforms specifically depicting of wireless, catheter-free urodynamics data from a human or animal patient.

(b) An overlay function, which is the ability to overlay two or more filling/voiding cycles to help view/identify trends. This may include a global analysis within the patient to analyze key metrics such as average voids per day, number of leaks per day, and number of nocturia events. Artificial intelligence/machine learning (AI/ML), statistical, and/or mathematical algorithms can be used to highlight a variety of trends including detrusor underactivity (DU), detrusor overactivity (DO), detrusor/sphincter dyssynergia (DSD), leakage, incontinence, and other aspects of bladder filling/storage/voiding dysfunction.

(c) A compare function, which means the ability to directly compare two or more filling/voiding cycles to determine similarities and differences. This may also be used to generate a proprietary scoring mechanism to understand and quantify intra-patient variability across multiple voiding cycles.

(d) A patient versus repository comparison function, which means the ability to analyze a filling/voiding cycle from a patient that can be compared with the data repository to help categorize and identify if any specific forms of bladder dysfunction exist. This information may be provided as a suggestion to the clinician to aid in diagnosis of the patient and save time for the clinician. It may also help to standardize metrics by utilizing reporting from other patients, potentially including patients in other locales or other countries.

(e) An intra-patient comparison function, which is the ability to analyze two or more filling/voiding cycles from the same patient to determine the similarities and differences in the filling/voiding cycles. With multiple cycles this could prove valuable to confirm or deny potential diagnoses through extended monitoring and repeated measurements. The system of this disclosure has the ability to do this during one urodynamics evaluation, or from the same patient but at different times or periods of urodynamics evaluation.

An intra-clinic or intra-clinician comparison function, which is the ability to analyze the data from a clinic or clinician and compare the analysis with aggregated data in a data repository using algorithms to determine a variety of factors including: clinic proficiency, clinician proficiency, adherence to training and other metrics. This type of data could also identify trends through analysis to determine the prevalence of certain urological conditions within certain geographical regions, or types of individuals (such as by age, ethnicity, or lifestyle). When such data is overlayed with aggregated health records through electronic health records (EHR) integration this may support trend analysis for population health management and risk profiles for insurers. The systems, devices, and methods of this disclosure are not limited to the above functions and they can perform any suitable function or provide any suitable data.

Integration and generation of reports through the incorporation of data from a patient's medical records through EHR integration and also data from event detection algorithms from data collected during the urodynamics exam. Use of this information may aid in improving efficiency by pre-populating notes and assessment plans for clinicians. This may be accomplished using templates and advanced signal processing or data science (AI/ML) techniques or using generative AI functionality (such as Chat GPT).

The software (or "App" or "application") is resident on the processor (patient and/or clinician) that can directly or indirectly wirelessly communicate with a server to send/receive information, enable AI/ML, support algorithm development, and facilitate use of cloud-based software applications.

The server or processor can run software designed to integrate with various EHR platforms to streamline clinical workflow. In some embodiments, these algorithms may incorporate natural language processing (NLP) techniques to generate a report including suggested report notes for integration into EHR. In other embodiments, this may also incorporate patient history through various means of analysis to include NLP.

The computer system 1400 can also enable distributed and/or remote patient monitoring by collecting data from patients, who may be at home or otherwise be remote to a hospital or health care provider. The data obtained can then be shared with clinicians who may or may not be collocated with the patient to support tele-health or remote care.

The sensor 50 is designed to communicate with the clinician and patient software application (or simply "software" or "App"), which is resident on a server or processor of a computing device. The software may be run on a processor of a computing device to allow clinicians and patients to use the system.

The clinician App allows the clinician to communicate with the sensor wirelessly and prepare it for insertion in the bladder. Once the sensor 50 is removed from the bladder, data can be wirelessly downloaded from the memory in the sensor or downloaded via a wired connection. Further, data may be transmitted by the sensor while it is in the bladder. One means of wireless communications is Bluetooth.

The clinician App also allows clinicians to manually input data such as voiding events, leakage events, urgency, and other patient reported symptoms or events, or any relevant information.

The clinician App allows the clinician to visually observe on a computing device screen and analyze data collected by the sensor, both the patient App and clinician app, and the uroflowmeter. This may be used in a manner that leverages methods of visualizing data including the use of artificial intelligence and machine learning (AI/ML).

The clinician App may also be used in conjunction with any specified clinical protocol to log data pertaining to the patient's behavior. The clinician App will enable the clinician to provide a window by entering the type of event as well as "start" and "stop". This creates a data entry that enables aggregation and analysis of events across patients and intra patient to help develop and train any ML models. These events may include urological events (such as leakage) or other physiological events (such as jumping, standing, coughing, climbing stairs). This enables refinement and enhancement of precision for ML models developed from the dataset.

The clinician App and Web App may also incorporate a feature to simplify the reporting and analysis of urological events. This may appear similar to other quick signing platforms such as DocuSign where the report for clinicians is prepared and pre-populated with anticipated voiding events that are either confirmed, rejected, or modified by the clinician reading the report. In this manner, this input aids in "training" any ML models being utilized by the company generating the report.

The clinician App and Web App also incorporate inputs from multiple devices that are synchronized in the cloud which can be utilized to streamline workflow and improve clinic efficiency. This is accomplished visually through the depiction of relevant information and providing pre-populated input which may generate the impetus for a clinical response or intervention (such as a patient report awaiting interpretation). The ability to sort and filter these parameters will allow for some customization of the interface such that each clinician may be able to observe this data consistently.

This Web App may also incorporate direct connections to Electronic Health Records (EHR) systems to provide a comprehensive interface for the patient data. This may include past history, notes, exams, diagnostic labs, and messaging activity.

The clinician Apps may also enable automation and measurement of key urodynamic parameters including but not limited to # of voids per day, # of leakage events, and other events. This may be utilized in conjunction with other visual features, such as shading or coloring, to help simplify interpretation by clinicians.

If the clinician App is connected via EHR, the use of NLP techniques may aid in obtaining clinical insight from past patient notes and history to aid in comprehensive analysis using ML models.

The clinician App may automatically create a report for Clinicians urodynamic evaluation that can be outputted directly into EHR or logged as a PDF file or printed. In some embodiments the reporting feature may use AI and/or ML to generate text for reporting that may be copied and pasted into EHR or automatically populate the notes if enabled. Specifically, templates may be pre-populated using the metrics obtained from the EHR integration and also the algorithms for analysis of the current urodynamics exam or using a generative AI platform with LLMs such as Chat GPT.

The clinician App may also integrate valuable communications methods to enable the clinician to communicate with the patient by conducting a voice call, video call, text message, email, or other method of secure communication.

The patient App enables patients to log any fluid inputs and symptoms the patient experiences and is similar to a digital voiding diary. Other urodynamic parameters may be cataloged by the patient using the App.

Both Apps can communicate with the sensor and with the uroflowmeter using Bluetooth or other wireless protocol and send data to a server for storage, analysis, display, and/or other purposes using any appropriate wireless communications methods such as Bluetooth, Wi-Fi, or cellular.

The clinician web App will enable clinicians to observe and analyze patient data from the examination through the use of a cloud-based server housing data. This enables simple and reliable access for clinicians via any web browser to streamline reporting and ease of use for the clinician to generate the report from any urodynamics evaluation. This App may also incorporate various features to aid in clinical decision making including AI/ML, statistical, and/or mathematical algorithms.

Uroflowmeter

The uroflowmeter 600 is designed to measure the volume of urine voided and changes to the volume voided (i.e., flow).

This data may be stored locally on the device for some period and can also be transmitted wirelessly to the device(s) Apps for analysis, review, display, and/or storage. Once the data is received by one or more Apps it may be sent wirelessly to a server or processor for storage, analysis, display, and/or for other purposes. In some embodiments, the uroflowmeter and sensor may possess a cellular, Wi-Fi, or other antenna that enables direct communication and upload of data to a device, such as a server without the requirement for the clinician App or patient App. The uroflowmeter may use any relevant means of wireless communications including Bluetooth, Wi-Fi, and or cellular.

Wireless Telemetry

The sensor 50 may be designed to wirelessly transmit data in real-time through the body while the sensor is in the bladder. This could be accomplished using a variety of suitable wireless communications and done either continuously, intermittently, or in response to a command. In some embodiments, this may be done by the sensor communicating directly with a smartphone, computer, or similar device. In other embodiments, this may be done using a wireless relay to receive the signal from the sensor in the body and then transmit this signal to another device, such as one that includes the clinician App or patient App.

Volume Sensing

Other methods of volume sensing modalities for the sensor 50 include the following:

Impedance, which uses electrodes to measure conductance of the fluid in the bladder.

Vibration, which uses a shockwave or pressure pulse to be sent from the sensor into the fluid in the bladder and then the volume is sensed using the same or a different sensor.

Optical methods, wherein various light waves are sent from the sensor in the bladder into the bladder and received by sensors on the circuit of the sensor. The light waves could utilize infrared (IR) or visible light.

Lasers, wherein a laser beam would detect the level of fluid and the volume of the bladder and based on that information, the volume of fluid in the bladder is calculated.

Acoustic (audio), which is similar to or the same as sonar and can map the bladder structure and volume of fluid.

Ultrasound, wherein its method of operation is known to those skilled in the art.

Pressure, wherein the pressure sensing signal is processed and input features are identified to incorporate into a ML/AI algorithm to predict volume of fluid.

Each of these modalities may be used in isolation or in combination with other modalities to accomplish the goal of providing reliable fluid volume estimation of the bladder.

Use of AI/ML, statistical, and/or mathematical algorithms to enable volume measurement by evaluating the measurement of area under the curve of a urodynamics trace, derivative of urodynamics pressure waveform, and other aspects of the waveform to enable volume estimation from pressure measurement in the bladder and volume/flow from external uroflowmeter. These algorithms may be developed to utilize one or more of the any combination of the signals from sensing modalities listed above, in conjunction with, or totally separate from, pressure measurements.

Thus, disclosed is the use of a single sensor in the bladder and advanced signal processing techniques to identify and characterize the intra-abdominal pressure waveform. This can then enable the removal of intra-abdominal pressure from the vesical pressure to provide the detrusor pressure. This method can then be used to reconstruct the intra-abdominal pressure waveform with high levels of accuracy. This eliminates the need for the use of a rectal or vaginal catheter to measure intra-abdominal pressure.

Use of the sensor to measure forces exerted on the sensor from the bladder walls can be used to estimate the volume of urine in the bladder. This can be used to estimate post-void residual volume and also time to fill the bladder. This signal may also be utilized with or without advanced signal processing techniques to estimate or derive specific and well validated urodynamic parameters including but not limited to Bladder Contractility Index (BCI), Bladder Wall Thickness (BWT), Detrusor Contraction Index, and other parameters.

The geometric shape and diameter of the sensor may be sized to function at different volumes of urine in the bladder such that the forces of the bladder walls may allow for volume estimation regardless of the volume. One example is that a smaller diameter and/or longer length sensor could enable higher resolution in a smaller bladder whereas a larger diameter and/or longer length sensor would be ideal for measurement of a larger bladder.

The use of a software application and signal processing techniques may be used to identify the offset of a pressure sensor and automatically calibrate the results to accommodate this from one or more filling/voiding cycles. This would streamline the interpretation process for clinicians and improve reliability of analysis.

Additional Considerations and Terminology

Although this disclosure has been described in the context of certain examples, it will be understood by those skilled in the art that the present disclosure extends beyond the specifically disclosed examples to other alternative examples and/or uses of the disclosure and obvious modifications and equivalents thereof. In addition, while a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the examples may be made and still fall within the scope of the disclosure. Accordingly, it should be understood that various features and aspects of the disclosure can be combined with or substituted for one another in order to form varying modes of the disclosed.

Features, materials, characteristics, or groups described in conjunction with a particular aspect, or example are to be understood to be applicable to any other aspect, or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing examples of devices or systems. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that the actual steps taken in the processes illustrated and/or disclosed may differ from those shown in the figures. Depending on the system, certain of the steps described above may be removed, others may be added. Furthermore, the features and attributes of the specific examples disclosed above may be combined in different ways to form additional examples of systems, all of which fall within the scope of the present disclosure. Also, the separation of various system components in the implementations described above should not be understood as requiring such separation in all implementations, and it should be understood that the described components and systems can generally be integrated together in a single product or packaged into multiple products.

Conditional language used herein, such as, among others, "can," "could," "might," "may," "e.g.," and the like, unless specifically stated otherwise, or otherwise understood within the context as used, is generally intended to convey that certain features, elements, and/or steps are optional. Thus, such conditional language is not generally intended to imply that features, elements, and/or steps are in any way required or that one or more embodiments necessarily include logic for deciding, with or without other input or prompting, whether these features, elements, and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each" as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 10 degrees, 5 degrees, 3 degrees, or 1 degree. As another example, in certain embodiments, the terms "generally perpendicular" and "substantially perpendicular" refer to a value, amount, or characteristic that departs from exactly perpendicular by less than or equal to 10 degrees, 5 degrees, 3 degrees, or 1 degree.

While the above detailed description has shown, described, and pointed out novel features, it can be understood that various omissions, substitutions, and changes in the form and details of the devices or systems illustrated can be made without departing from the spirit of the disclosure. As can be recognized, certain portions of the description herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A kit including a sensing device and a packaging assembly for preserving sterility of the sensing device prior to insertion into a body cavity of a subject, wherein:
   the sensing device is configured for sensing one or more physiological conditions inside the subject's body cavity and comprises a housing, one or more electronic components contained within the housing, and a button arranged within the housing and configured to transition the sensing device from a non-operational state to an operational state in which the sensing device can be paired with a separate electronic device, the housing comprising a transparent and flexible material to allow the button to be located and engaged via a portion of the housing; and the packaging assembly comprises:
- a bag comprising an interior, the bag at least partially comprising a transparent material; and
- a tray positioned within the interior of the bag and configured to retain and protect the sensing device, wherein the tray is further configured to enclose only a portion of the sensing device to allow a portion of the bag to be pressed directly against the portion of the housing to engage the button, thereby allowing the sensing device to be transitioned to said operational state while retained by the tray and positioned within the interior of the bag.

2. The kit of claim 1, wherein:
the tray comprises a base and a cover that is pivotably connected to the base via one or more hinges and configured to pivot between an open position and a closed position; and
the tray comprises an opening configured to allow the portion of the housing and the button to be engaged via the portion of the bag when the cover is in said closed position.

3. The kit of claim 2, wherein the cover comprises said opening.

4. The kit of claim 2, wherein the base comprises a perimeter and a wall extending along at least a portion of said perimeter, and wherein the wall comprises said opening of the tray.

5. The kit of claim 2, wherein the opening of the tray is defined by a portion of the cover and a portion of the base.

6. The kit of claim 2, wherein:
the cover comprises:
- a top surface and a bottom surface, the bottom surface configured to face toward the base when the cover is in the closed position; and
- a protrusion extending from the bottom surface and forming a cavity on the top surface, the protrusion having an at least partially cylindrical shape and being at least partially surrounded by the sensing device when the sensing device is retained by the tray;

the protrusion is arranged adjacent said opening of the tray; and
the opening of the tray and the cavity formed by the protrusion of the cover provide access for fingers of a user to press the portion of the housing and the button against the protrusion, thereby allowing the sensing device to be transitioned to said operational state.

7. The kit of claim 1, wherein:
the kit further comprises:
- an insertion tool configured to facilitate insertion of the sensing device into the subject's body cavity, the insertion tool comprising a sheath configured to receive a portion of the sensing device; and
- a string coupled to the sensing device and configured to extend through the sheath, the string configured to allow the portion of the sensing device to be pulled into the sheath; and the tray is further configured to retain and limit movement of the insertion tool when the portion of the sensing device is pulled into the sheath via the string.

8. The kit of claim 7, wherein:
the insertion tool further comprises a handle connected to the sheath;
the tray comprises a cavity configured to receive at least a portion of the handle; and
the cavity is configured to limit movement of the handle, and in turn the sheath, when the portion of the sensing device is pulled into the sheath via the string.

9. The kit of claim 8, wherein the tray comprises a base and a cover that is pivotably connected to the base and configured to pivot between an open position and a closed position, and wherein the base comprises said cavity.

10. The kit of claim 8, wherein:
the sheath of the insertion tool further comprises a first mating feature and the sensing device further comprises a second mating feature, the first and second mating features configured to engage one another and inhibit rotation of the sensing device relative to the insertion tool when the portion of the sensing device is positioned within the sheath; and
the cavity is configured to limit rotation of the handle, and in turn, the sheath, when the at least the portion of the sensing device is pulled into the sheath via the string, thereby facilitating alignment of the first and second mating features with one another.

11. The kit of claim 10, wherein said cavity is configured to limit a degree of rotation of the handle to be less than 45 degrees relative to an axis extending through the handle and the sheath.

12. The kit of claim 7, wherein:
the sheath of the insertion tool comprises a first end, a second end, and a sheath lumen extending between the first and second ends and configured to receive the portion of the sensing device;
the string is configured to allow the portion of the sensing device to be pulled through the first end of the sheath and into the sheath lumen; and
the tray comprises a channel configured to receive and operably position the first end of the sheath when the portion of the sensing device is pulled through the first end of the sheath and into the sheath lumen.

13. The kit of claim 12, wherein:
the insertion tool further comprises a first mating feature arranged at the first end of the sheath;
the sensing device comprises a first endcap secured to a first end of the housing, a second endcap secured to a second end of the housing, and a second mating feature arranged on the first endcap;
the first and second mating features are configured to engage one another and inhibit rotation of the sensing device relative to the insertion tool when the portion of the sensing device is positioned within the sheath lumen;
the tray comprises an inner wall at least partially defining said channel and a bump arranged on said inner wall within said channel; and
said bump is configured to contact the second endcap of the sensing device when the sensing device is pulled through the first end of the sheath to align the second endcap with the sheath lumen, thereby inhibiting interference of the second endcap with the first mating feature at the first end of the sheath.

14. A packaging assembly for preserving sterility of a sensing device prior to insertion into a body cavity of a subject, the packaging assembly comprising:
a bag comprising an interior, the bag at least partially comprising a transparent material; and a tray configured to be positioned within the interior of the bag and configured to retain and protect the sensing device, wherein the tray comprises an opening configured to allow a portion of the bag to be pressed directly against a portion of a housing of the sensing device to engage a button of the sensing device, thereby allowing the sensing device to be transitioned from a non-operational state to an operational state when retained by the tray and positioned within the interior of the bag.

15. The packaging assembly of claim 14, wherein the tray comprises a base and a cover that is pivotably connected to the base via one or more hinges and configured to pivot between an open position and a closed position, and wherein said opening is configured to allow the button to be engaged via the portion of the bag when the cover is in said closed position.

16. The packaging assembly of claim 15, wherein the cover comprises said opening.

17. The packaging assembly of claim 15, wherein the base comprises a perimeter and a wall extending along at least a portion of said perimeter, and wherein the wall comprises said opening of the tray.

18. The packaging assembly of claim 15, wherein the opening of the tray is defined by a portion of the cover and a portion of the base.

19. The packaging assembly of claim 15, wherein:
the cover comprises:
a top surface and a bottom surface, the bottom surface configured to face toward the base when the cover is in the closed position; and
a protrusion extending from the bottom surface and forming a cavity on the top surface, the protrusion having an at least partially cylindrical shape and being at least partially surrounded by the sensing device when the sensing device is retained by the tray;
the protrusion is arranged adjacent said opening of the tray; and
the opening of the tray and the cavity formed by the protrusion of the cover provide access for fingers of a user to engage the button of the sensing device and a portion of the protrusion, thereby allowing the sensing device to be transitioned to said operational state.

20. The packaging assembly of claim 15, wherein the base of the tray comprises a channel configured to receive a sheath of an insertion tool, the insertion tool configured to receive a portion of the sensing device.

21. The packaging assembly of claim 20, wherein:
the tray comprises an inner wall at least partially defining said channel and a bump arranged on said inner wall within said channel; and
said bump is configured to contact and align an end of the sensing device with a lumen of the sheath when the portion of the sensing device is inserted into the sheath.

22. The packaging assembly of claim 15, wherein the base of the tray comprises a cavity configured to receive at least a portion of a handle of an insertion tool that is configured to receive a portion of the sensing device, said cavity configured to limit movement of the insertion tool when the portion of the sensing device is inserted into the insertion tool.

23. A method of preparing a sensing device for insertion into a body cavity of a subject to preserve sterility, the method comprising:
obtaining a bag and a tray positioned within an interior of the bag, wherein said sensing device is retained by the tray, said sensing device configured for sensing one or more physiological conditions inside the subject's body cavity and comprising a housing, one or more electronic components contained within the housing, and a button arranged within the housing and configured to transition the sensing device from a non-operational state to an operational state, wherein the tray comprises an opening;
pressing a portion of the bag directly against a portion of the housing via said opening to engage the button, thereby transitioning the sensing device to said operational state; and
wirelessly pairing the sensing device with a patient monitoring device after the sensing device is transitioned to said operational state.

24. The method of claim 23, further comprising opening the bag and emptying the tray onto a surface without touching the tray after the sensing device is wirelessly paired to the patient monitoring device.

25. The method of claim 23, wherein said tray is further configured to retain an insertion tool that is configured to facilitate insertion of the sensing device into the subject's body cavity, and wherein the method further comprises inserting at least a portion of the sensing device into a sheath of the insertion tool.

* * * * *